US008299210B2

(12) United States Patent
Jungbluth et al.

(10) Patent No.: US 8,299,210 B2
(45) Date of Patent: Oct. 30, 2012

(54) METHODS FOR PURIFYING PERTUSSIS TOXIN AND PEPTIDES USEFUL THEREFOR

(75

U.S. PATENT DOCUMENTS

| | | |
|---|---|---|
| 6,429,300 B1 | 8/2002 | Kurz et al. |
| 6,436,665 B1 | 8/2002 | Kuimelis |
| 6,602,685 B1 | 8/2003 | Lohse |
| 6,623,926 B1 | 9/2003 | Lohse et al. |
| 6,696,065 B1 | 2/2004 | Fahim et al. |

OTHER PUBLICATIONS

Ota, M et al, Biopolymers, vol. 46, pp. 65-73, 1998, Synthesis, Characterization, and Sweetness-Suppressing activities of Gurmarin Analogues Mssing One Disulfide Bond.*

Bogdan, et al. Identification of Peptides That Mimic the Pertussis Binding Site on Bovine Fetuin. Appln. Env. Microb. 69(10): 6272-6279 (2003).

Kurz, et al. cDNA-Protein Fusions: Covalent Protein-Gene Conjugates for the In Vitro Selection of Peptides and Proteins. Chembiochem: A European J. Chem. Biol. 2(9): 666-672 (2001).

Liu, et al. Optimized Synthesis of RNA-Protein Fusions for in Vitro Protein Selection. Methods Enzymol. 318: 268-293 (2000).

Sekura, et al. Pertussis Toxin. Affinity Purification of a New ADP-Ribosyltransferase. J. Biol. Chem. 258:14647-14651 (1983).

* cited by examiner

FIGURE 19
pp26/15
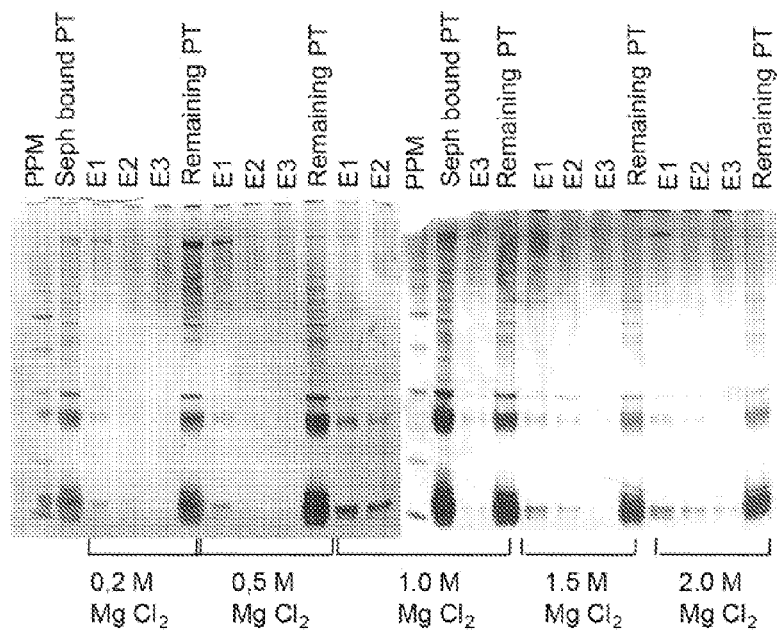
Gurmarin/9
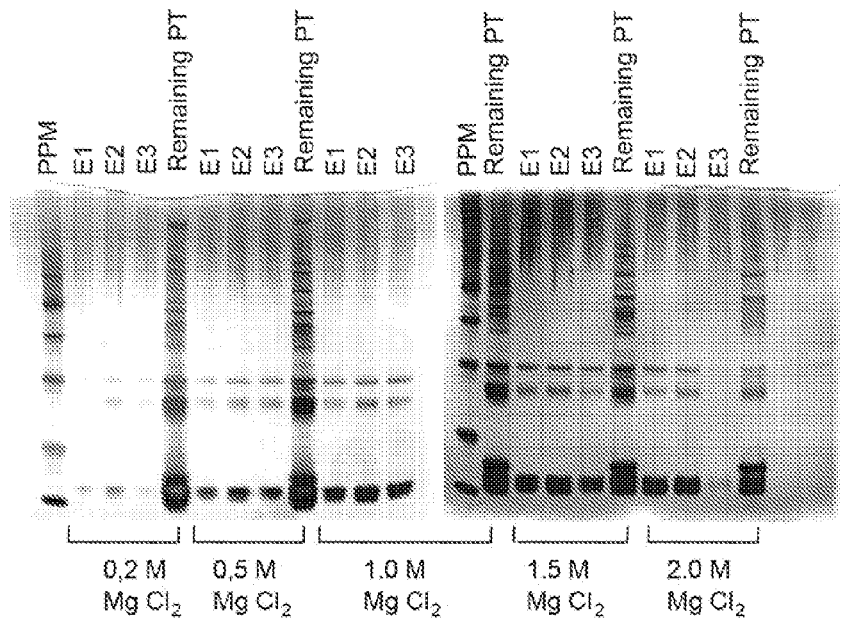

FIGURE 20
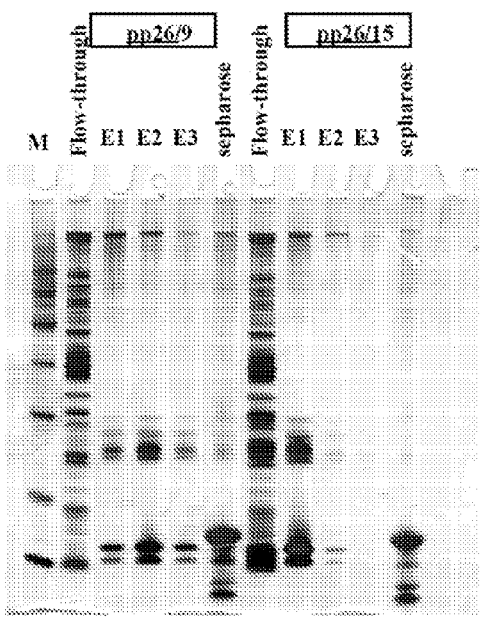
Elution with glycin pH 2.5
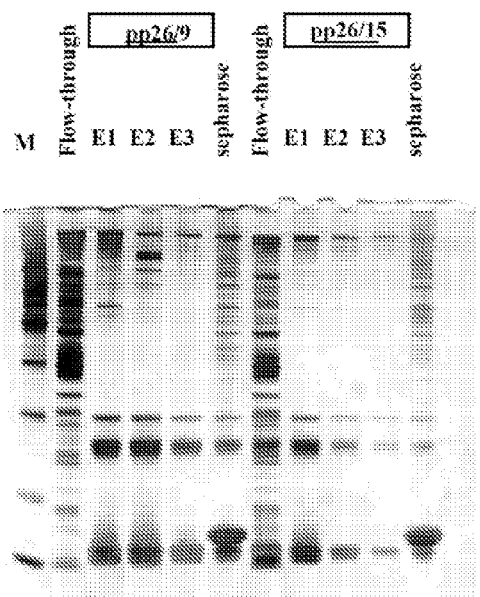
Elution with carbonate pH 10.5
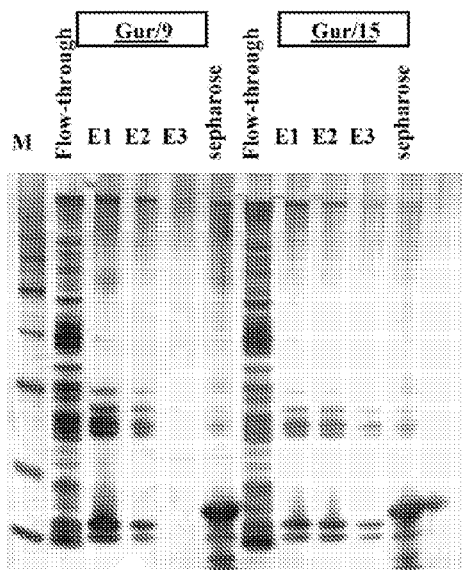
Elution with glycin pH 2.5
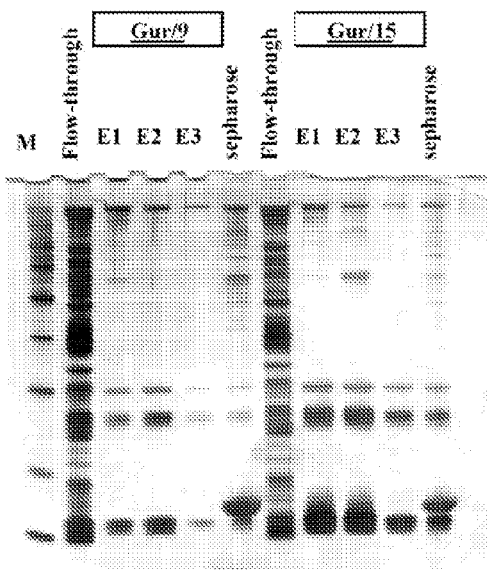
Elution with carbonate pH 10.5

METHODS FOR PURIFYING PERTUSSIS TOXIN AND PEPTIDES USEFUL THEREFOR

RELATED APPLICATIONS

This application is the National Stage Application under 35 U.S.C. §371 of International Application No. PCT/US2004/038700 filed Nov. 18, 2004, which claims priority to U.S. Provisional Application No. 60/523,881 filed Nov. 20, 2003.

FIELD OF THE INVENTION

The present invention relates to reagents and methods for purifying pertussis toxin (PT).

BACKGROUND OF THE INVENTION

Pertussis toxin (PT) is produced by *Bordetella pertussis* is a main component in all vaccines against whooping cough. PT is typically combined with tetanus and diphtheria toxoids. Industrial production of PT is typically achieved by cultivating *B. pertussis* in defined media. PT is then isolated from the supernatant and purified by using the well-known techniques (i.e., U.S. Pat. Nos. 6,399,076; 5,877,298; and, Sekura, et al. J. Biol. Chem. 258:14647-14651, 1983; Bogdan, et al. Appl. Env. Micro. 69(10): 6272-6279, October 2003). The majority of known methods each require the use of matrix-bound bovine fetuin (BF) or asialofetuin, the source and purity of which is critical. The use of bovine-derived reagents has led to some concern over bovine-related diseases such as bovine spongioform encephalopathy (BSE).

Those of skill in the art have therefore desired a method for purifying PT that does not rely on BF. One such method is described by Bogdan, et al. (Appl. Env. Micro. 69(10): 6272-6279, October 2003) Peptides having the ability to mimic the glycosidic moiety of bovine fetuin by binding to PT were identified using a phage display system. Three peptides (3G5: NGSFSGF (SEQ ID NO: 1); 3G8: NGSFSGC (SEQ ID NO: 2); and, 3G2: DGSFSGF (SEQ ID NO: 3) having the consensus sequence XGSFSGX (X is any amino acid: SEQ ID NO: 4) were identified as having PT-binding capacity. 3G2 was also utilized in an affinity column to purify PT from a partially purified PT preparation.

Additional methods for designing and utilizing peptides to purify PT in the absence of bovine products are desired by those of skill in the art. Provided herein are reagents and methodologies for affinity purification of PT without the use of fetuin in any form.

BRIEF DESCRIPTION OF THE DRAWINGS

Figure 3:
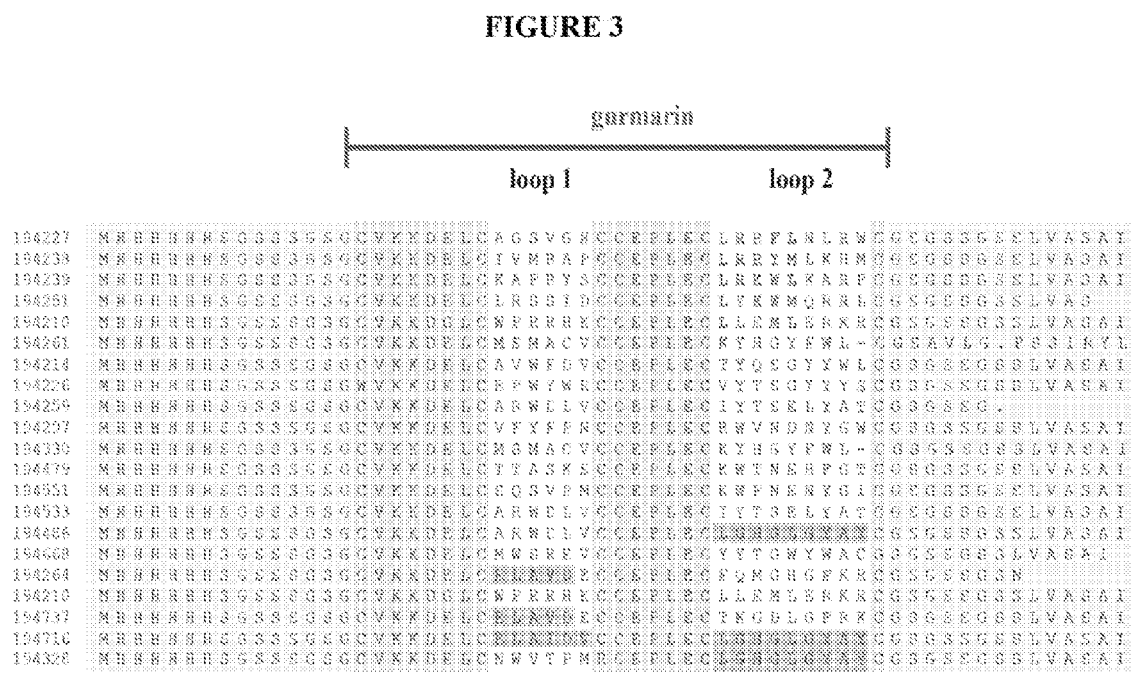

FIG. 3. Selected gurmarin variants that should be tested for binding activity towards PT. Conserved sequence motifs are highlighted. The variants listed are, from top to bottom, SEQ ID NOS. 81-101.

Figure 4:
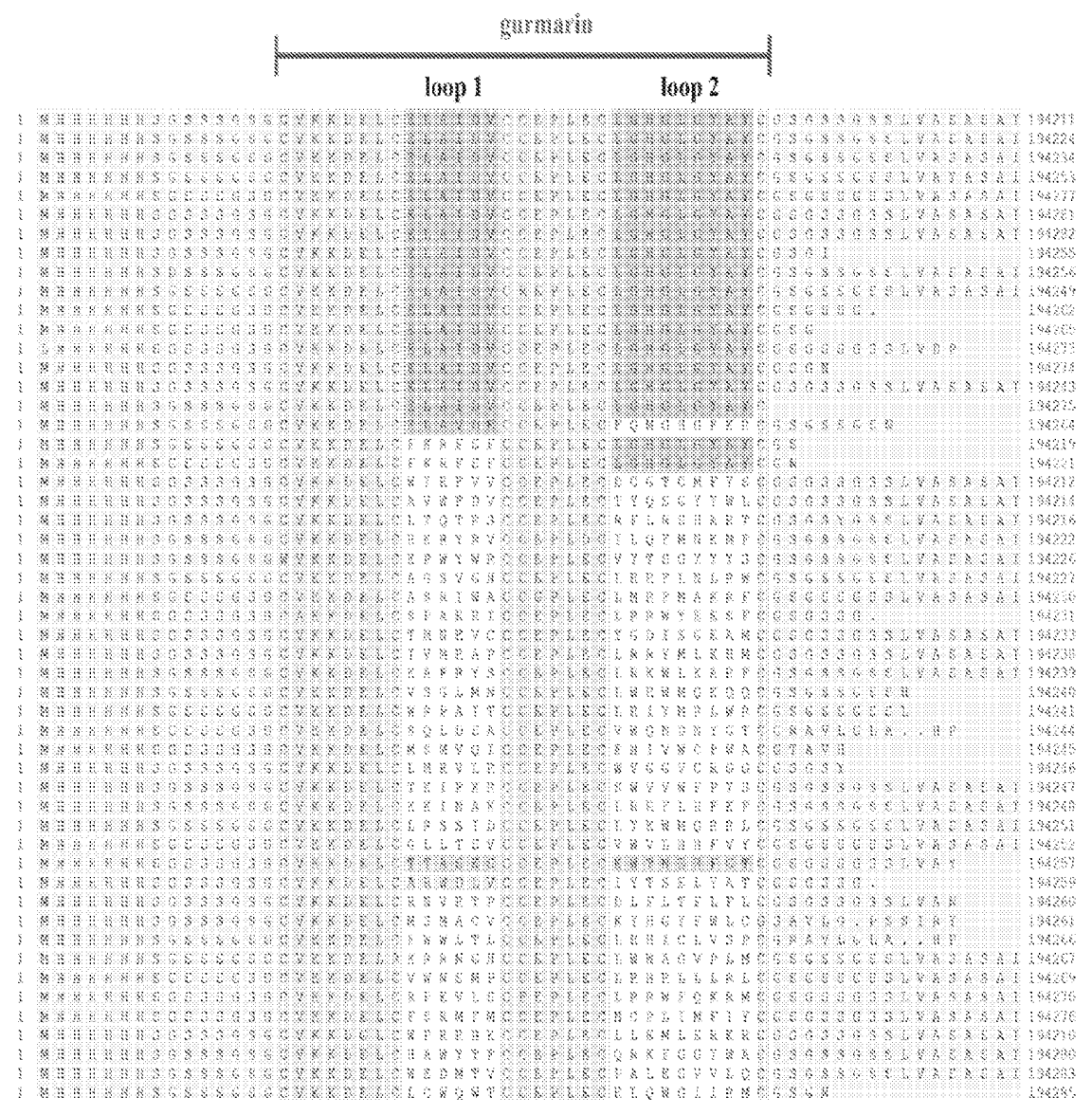

FIG. 4. Sequence analysis of the gurmarin selection round 4 against PT. The amino acid sequence of individual variants is shown in the single letter amino acid code. Constant, flanking regions of the library and constant regions of the gurmarin scaffold are indicated. The position of the randomized loops 1 and 2 are indicated. The variants are listed from top to bottom in the following order: SEQ ID NOS. 102 (3), 103, 102 (3), 104-110, 102, and 111-147.

Figure 5:
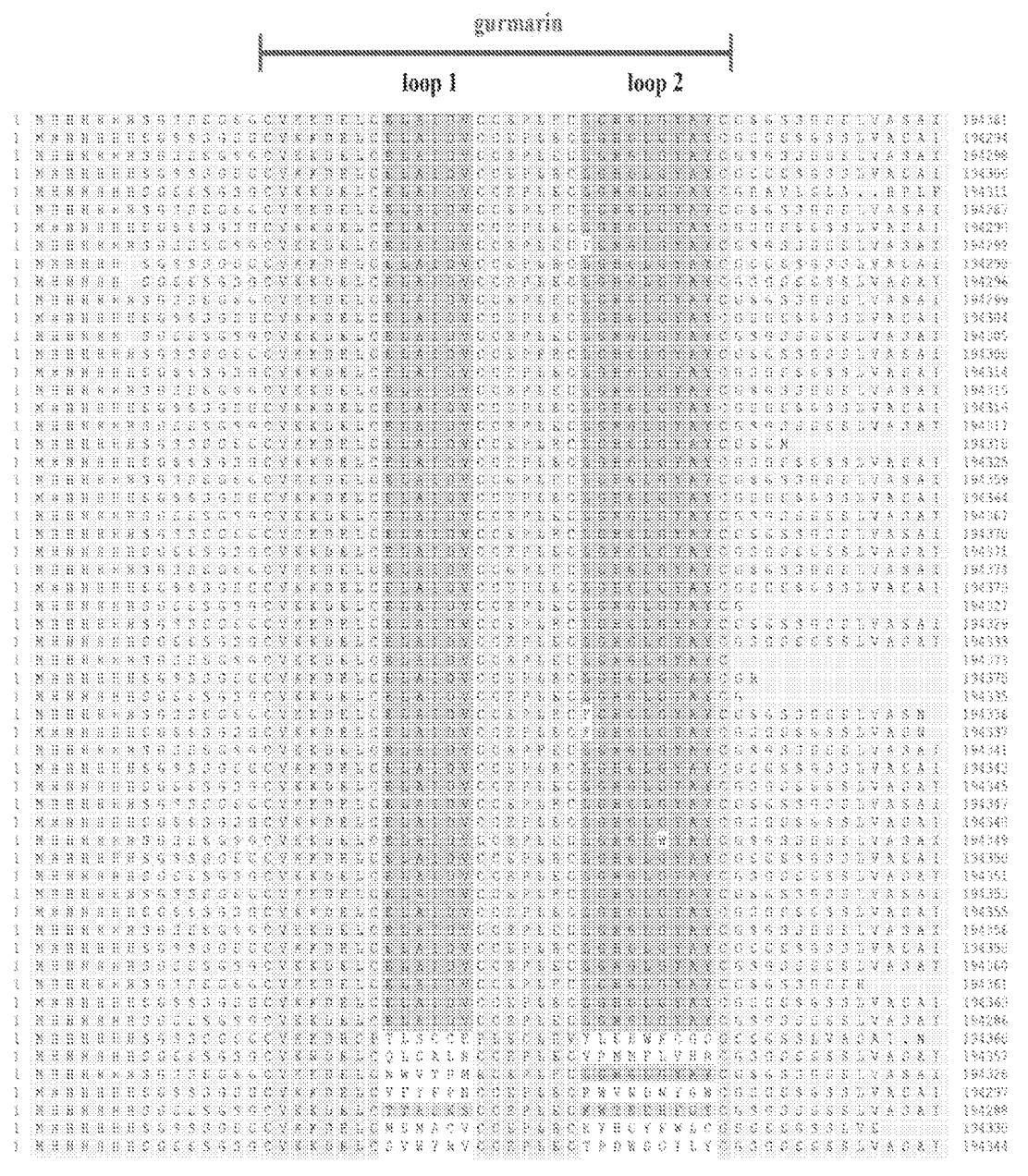

FIG. 5. Sequence analysis of the gurmarin selection round 5a against PT (epoxy). The amino acid sequence of individual variants is shown in the single letter amino acid code. Constant, flanking regions of the library and constant regions of the gurmarin scaffold are indicated. The position of the randomized loops 1 and 2 are indicated. The variants are listed from top to bottom in the following order: SEQ ID NOS. 148 (3), 149, 148 (2), 150, 151 (2), 148, 152, 151, 148 (5), 153, 148, 154, 148 (4), 154, 148, 155, 148 (2), 156, 157, 155, 158 (2), 159, 148 (4), 160, 148 (2), 161, 148 (4), 162, 148 (2), and 163-169.

FIG. 9. Selected PP26 variants that will be tested for binding activity towards PT. Conserved sequence motifs are highlighted as colored letters. The variants, listed from top to bottom, are SEQ ID NOS. 253-269.

Figure 10:
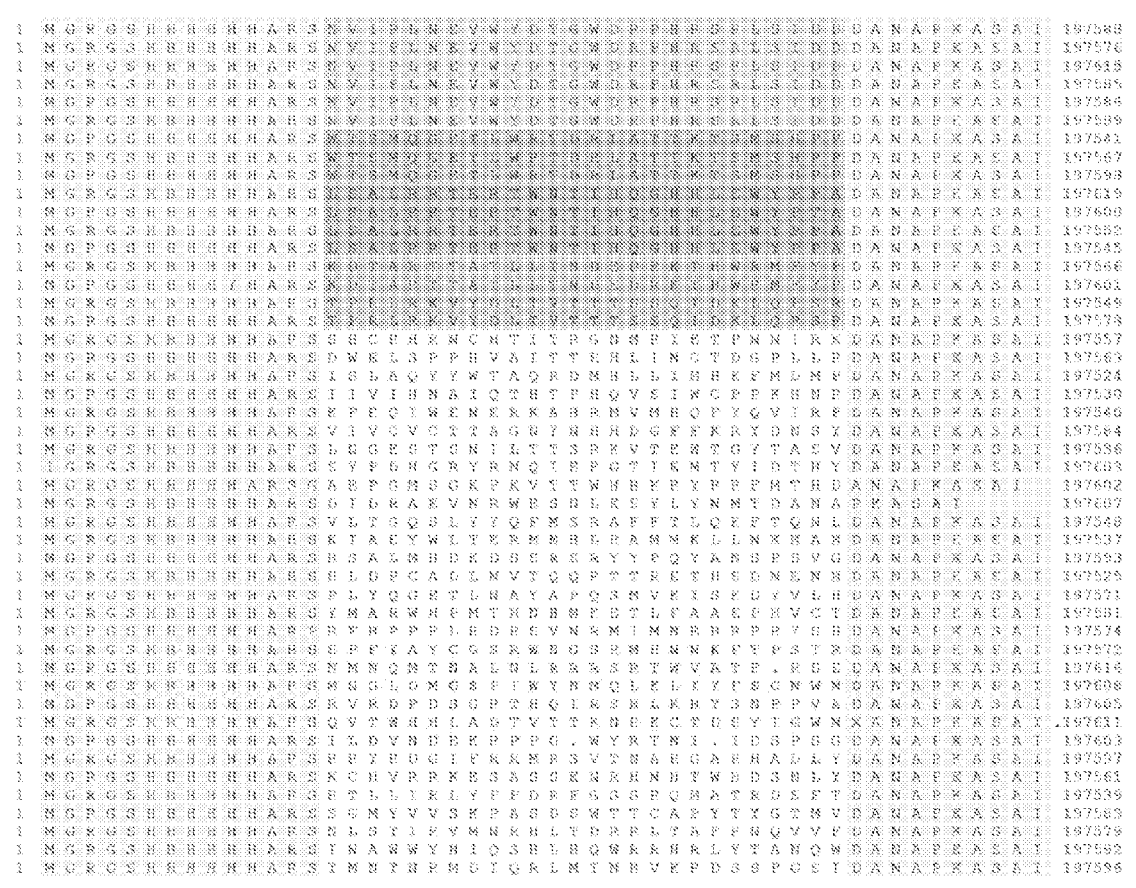

FIG. 10. Sequence analysis of the PP26 selection round 4 against PT. The amino acid sequence of individual variants is shown in the single letter amino acid code. Constant, flanking regions of the library are indicated. The variants are listed from top to bottom in the following order: 253 (6), 270 (3), 271, 272, 271 (2), 273, 274, 275 (2), and 276-305.

Figure 12:
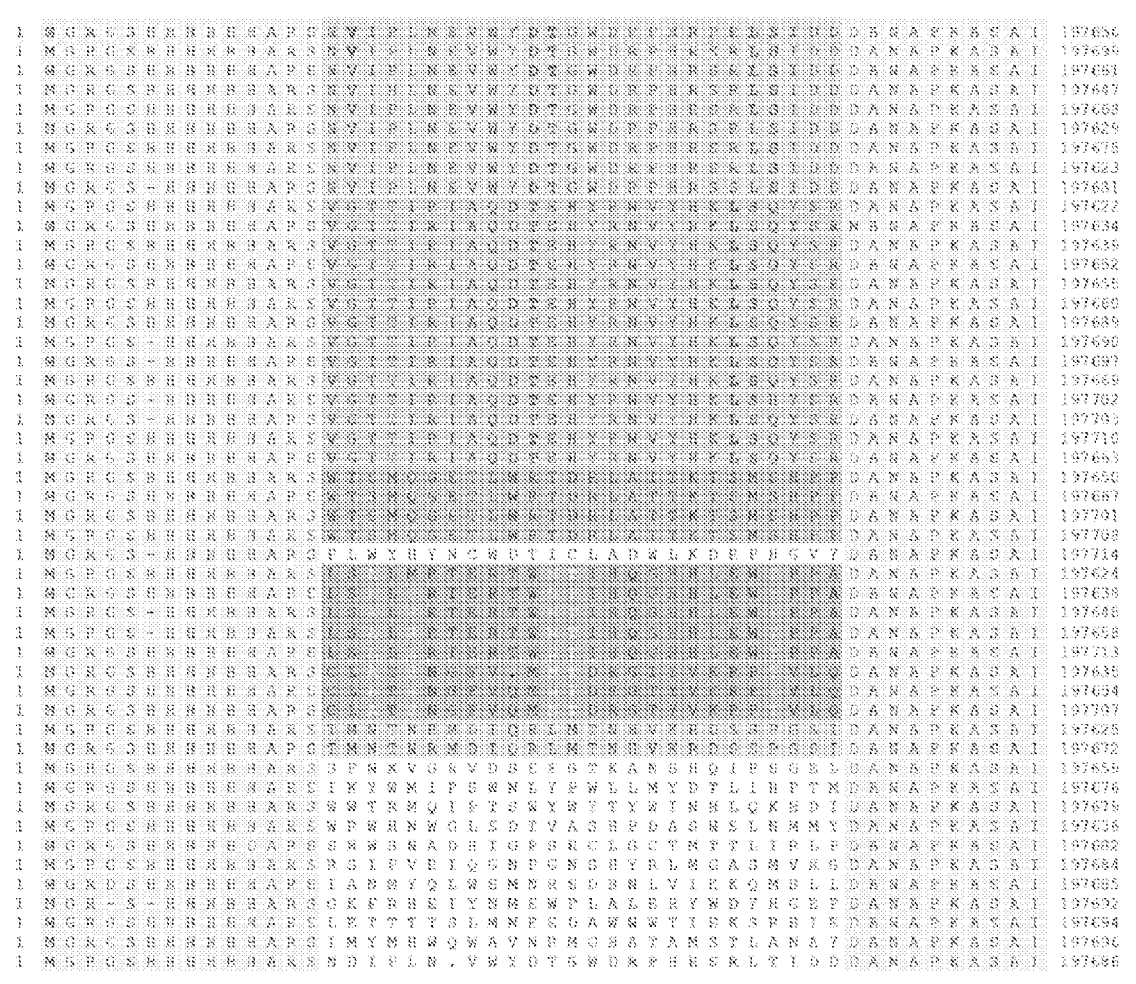

FIG. 12. Sequence analysis of the PP26 selection round 5b against PT (strep). The amino acid sequence of individual variants is shown in the single letter amino acid code. Constant, flanking regions of the library are indicated. Conserved sequence motifs are highlighted. The variants are listed from top to bottom in the following order: 343 (7), 344-346, 345 (5), 347 (2), 345, 348, 347, 345 (2), 349 (4), 350-354, 355 (2), 356 (2), and 357-367.

Figure 13:
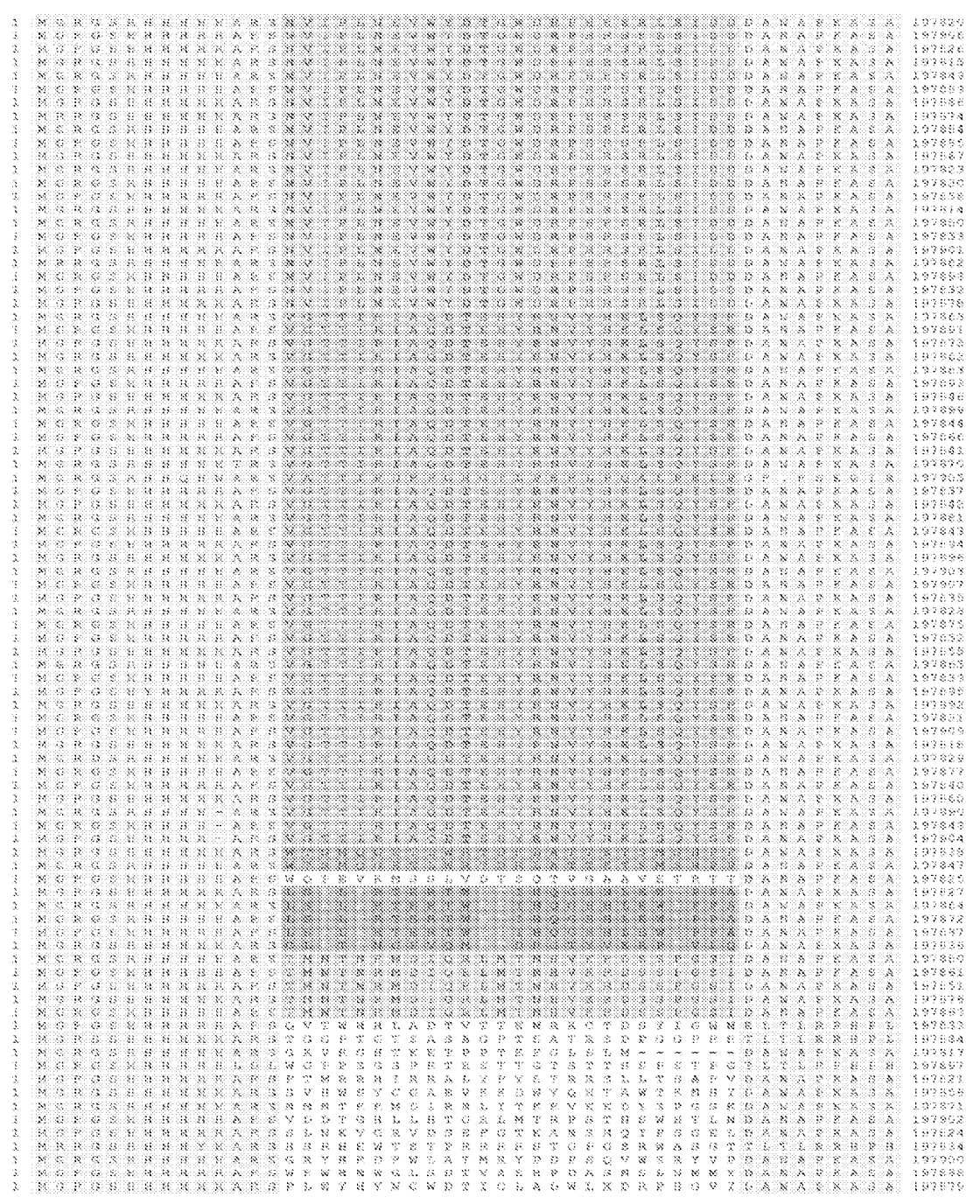

FIG. 13. Sequence analysis of the PP26 selection round 6a against PT. The amino acid sequence of individual variants is shown in the single letter amino acid code. Constant, flanking regions of the library are indicated. Conserved sequence motifs are highlighted. The variants are listed from top to bottom in the following order: 368 (18), 369, 368 (3), 370 (11), 371, 372, 373 (15), 374, 373 (8), 375 (2), 376 (2), 377, 378 (4), 379, 380 (5), and 381-393.

FIG. 19. Elution of PT from peptide streptavidin sepharose with 0.2 to 2.0 MMgCl$_2$ in 50 mM Tris/HCl. Peptide bound PT was displaced from the peptide-streptavidin sepharose by three consecutive washes with the indicated elution buffers (20 µl each). Remaining material was subsequently eluted with gel loading buffer. All elutions were analyzed on 12% Bis Tris gels (1×MES running buffer) and visualized by silver staining.

FIG. 20. Elution of PT from peptide streptavidin sepharose under acidic (50 mM glycine, pH 2.5) or basic (100 mM carbonat boffer, pH 10.5) conditions. Peptide bound PT was displaced from the peptide streptavidin sepharose (20 µl containing ~200 pmol of one peptide) by three consecutive washes with with the indicated elution buffers (40 µl each). Remaining material was subsequently eluted with gel loading buffer. All elutions were analyzed on 12% Bis Tris gels (1×MES running buffer) and visualized by silver staining. 1/40 volume of the flow through after peptide streptavidin sepharose incubation with sample A was analyzed was analyzed on the same gel for each peptide.

FIG. 24. PT yield as function of varying amounts of input material (sample B) per µl peptide streptavidin sepharose or 6.85 µl asialofetuin sepharose. The amount of eluted PT was calculated on the basis of direct comparison to defined amounts of purified PT on the same gel and listed in the Table 12.

FIG. 25. Reutilization of peptide sepharose for repeated PT binding and elution. Bound PT to streptavidin sepharose were 4 times eluted with 100 mM Carbonate buffer at pH 10.5 and the cloumn matrix was regenerated with 10 mM HCl.

FIG. 26. PT elution fractions after FPLC-column purification on pp26/9 peptide streptavidin sepharose (0.5 ml) from sample B. The elution fractions (0.5 µl of each 500 µl elution) were analyzed by PAGE (12% Bis-Tris-Gel, MES running buffer) and silver staining. Defined amounts of purified PT were seperated on the same gel for direct comparision. Concentration of PT was determined by measuring the absorbance of the elution fractions at 280 nm ($A_{280}$) and compared to purified PT standards (see table).

SUMMARY OF THE INVENTION

The present invention relates to methods for purifying pertussis toxin (PT). In one embodiment, a method for generating a DNA-protein fusion by covalently bonding a nucleic acid reverse-transcription primer bound to a peptide acceptor to an RNA, translating the RNA to produce a peptide product such that the protein product is covalently bound to the primer, reverse transcribing the RNA to produce a DNA-protein fusion, and testing the fusion product to identify those containing PT binding peptides. The sequence of the peptide is then identified by sequencing. In other embodiments, peptides are provided that have PT-binding capacity and are useful for purifying PT from complex biological fluids. Also provided are peptides bound to solid supports and/or chromatographic media for use in purifying PT from complex biological fluids and methods for carrying out such purifications.

DETAILED DESCRIPTION

The present invention provides reagents and methodologies for a new method for purifying pertussis toxin (PT). As described above, one such method has been demonstrated by Bogdan, et al. In that method, phage display was utilized to identify PT-binding peptides. For the purposes of practicing the present invention, PT includes naturally expressed PT as well as PT detoxified genetically or otherwise (see, for example, U.S. Pat. Nos. 6,399,076; 6,168,928; 6,018,022; 5,977,304; 5,965,385; 5,856,122; 5,877,298; 5,433,945; 5,358,868; 5,332,583; 5,244,657; 5,221,618; 5,085,862; 4,997,915). In most cases, chemical detoxification is performed following purification of PT. Within this application, all cited references, patents, and patent applications are incorporated herein by reference.

The present invention also relates to the use of recombinant technology to identify PT-binding peptides. The present invention provides advantages over methods already known in the art. In addition, novel peptides useful in purifying PT are provided herein. In one embodiment, a method for generating a DNA-protein fusion by covalently bonding a nucleic acid reverse-transcription primer bound to a peptide acceptor to an RNA, translating the RNA to produce a peptide product such that the protein product is covalently bound to the primer, reverse transcribing the RNA to produce a DNA-protein fusion, and testing the fusion product to identify those containing PT binding peptides. The sequence of the peptide is then identified by sequencing. In certain embodiments, the RNA moiety may be removed from the complex by treatment with an RNA-degrading compound such as RNase H. Photo-crosslinking reagents and peptide acceptors are also useful in practicing the present invention. This system and related reagents have been described elsewhere in, for example, U.S. Pat. Nos. 6,416,950 (Lohse, et al); 6,429,300 (Kurz, et al.); 6,436,665 (Kuimelis, et al.); 6,602,685 (Lohse, et al); and, 6,623,926 (Lohse, et al).

In practicing the invention, a reagent such as a nulceic acid, peptide, fusion, ligand, affinity complex, or the like may be non-diffusively bound or attached to a solid support. In order to be non-diffusively bound or attached, the reagent is chemically or physically combined with the solid support such that the reagent does not move in the presence of liquid from a region of high concentration of reagent to a region of low concentration of reagent. A solid support is any column (i.e., unpacked or packed chromatographic media, column material), bead, test tube, microtiter dish, solid particle (i.e., agarose or sepharose), microchip (i.e., silicon, silicon-glass, or gold chip), membrane (i.e., the membrane of a liposome or vesicle), or other medium to which a reagent may be bound or attached, either directly or indirectly (for example, through other binding partner intermediates such as an antibody, Protein A, Protein G, streptavidin, biotin).

In preferred embodiments, the reagent is a substance or compound having the ability to bind PT. More preferably, the reagent is a substance or compound having the ability to reversibly bind PT. Even more preferably, the reagent is a peptide having the ability to at least bind, and preferably reversibly bind PT within a liquid containing components other than PT. A reagent that reversibly binds PT is one that binds PT under certain conditions (adsorption), and releases PT under other conditions (desorption). For example, the reagent may bind PT when exposed to conditions of neutral pH and release PT following exposure to conditions of acidic or basic pH. Thus, the ability of the reagent to bind PT (i.e., the equilibrium dissociation constant or $K_d$) may be manipulated by altering the conditions under which the reagent is in contact with PT. Other conditions may also be changed, including temperature, ionic strength (i.e., salt concentration), solvent concentration, presence or absence of a competitor reagent/free ligand/analogue, polar properties, among others as is known in the art.

In certain embodiments, an affinity matrix (i.e., a PT-binding peptide bound to a solid support) is utilized to separate a desired component (i.e., PT) from a complex mixture found within a liquid, biological or otherwise. In certain cases, it may be desirable to purify PT from a complex bioloigcal fluid such as a bacterial lysate or other composition in which PT does not comprise the majority of components within the fluid (as determined by SDS-PAGE, for example). In other cases, PT may be isolated from a comopsition that has been partially purified for PT such that the majority of the components within the fluid is represented by PT (a composition consisting of approximately greater than or equal to 50% PT). For example, a composition in which PT consists of about 50% or more of the total protein in the composition as determined by SDS-PAGE would under most circumstances be considered partially purified.

To purify PT, a composition containing PT may be placed into contact with a PT-binding reagent, preferably a reversibly binding PT-binding reagent, that is bound to a solid support for a sufficient period of time such that PT and the PT-binding reagent bind to one another to form a complex. Non-PT components are then washed away. One or more conditions (i.e., pH) are then changed such that the $K_d$ of the PT—PT binding reagent bond increases, and PT is released from the complex. Released PT is then collected and prepared for further use. Such a separation may be termed affinity purification and products so purified referred to as being affinity purified.

Chromatographic techniques that are generally considered by those of skill in the art to be less selective than affinity purification techniques may also be used in practicing the present invention. As is known in the art, such techniques may include, for example, size-exclusion chromatography, ion-exchange chromatography, reverse-phase chromatography, and hydrophobic-interaction chromatography. Any of these techniques (including affinity purification) may be carried out using the proper solid support in a low pressure chromotography (LPC), high pressure liquid chromotography (HPLC), or fast protein liquid chromotography (FPLC) setting, for example. Suitable solid supports and equipment for carrying out such techniques are widely available in the art. In practicing the present invention, both affinity chromatography and the more generalized techniques may be combined as needed to either partially purify a starting material (i.e., complex biological fluid such as a bacterial lysate), purify material, or further purify affinity- or otherwise-purified material (i.e., affinity purified PT).

Peptides have been identified that bind PT and are described herein. Certain peptides have been found to bind PT with high affinity. Such preferred PT binding peptides include:

```
RSSHCRHRNCHTITRGNMRIETPNNIRKDA
(pp26-5; SEQ ID NO: 5);

STMNTNRMDIQRLMTNHVKRDSSPGSIDA
(pp26-6; SEQ ID NO: 6);
```

Figure 1:
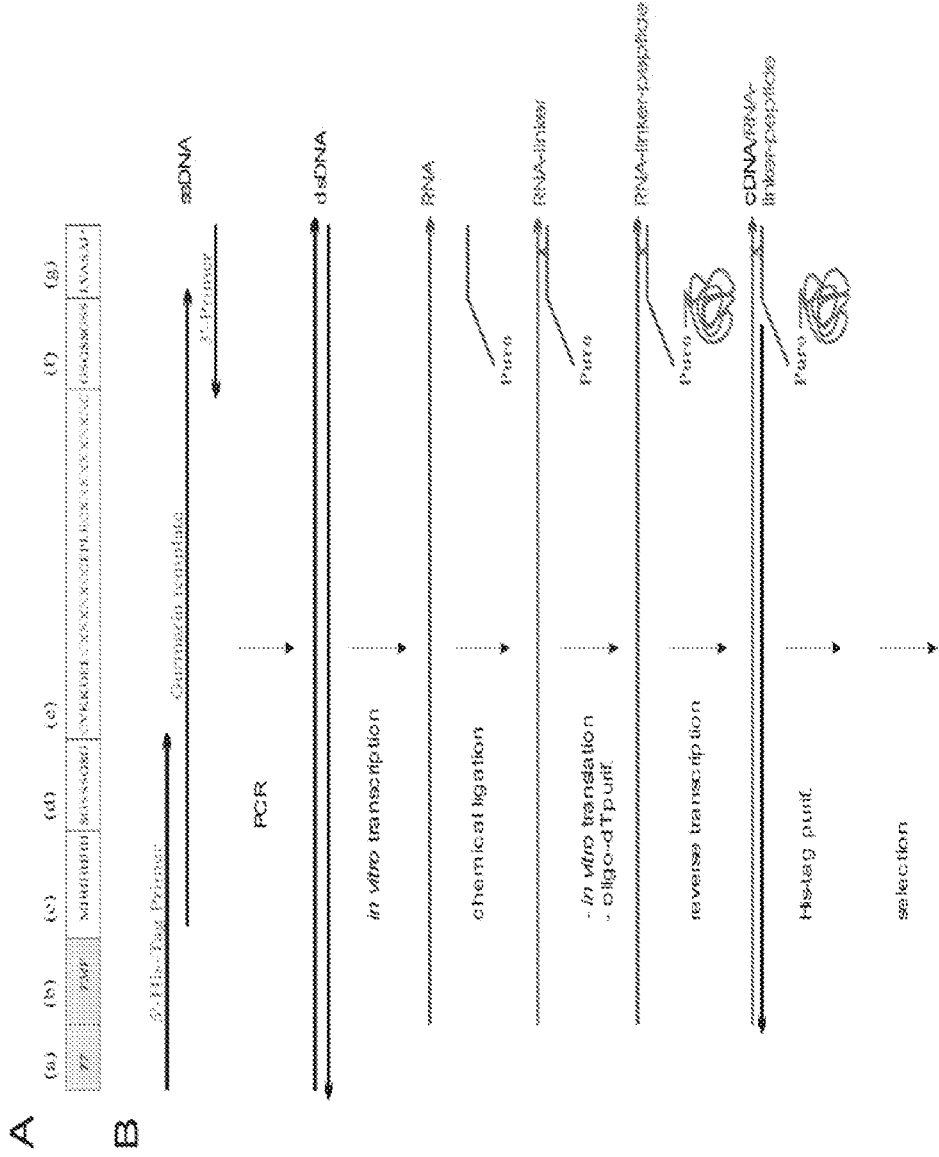
FIG. 1. A) Schematic representation of the gurmarin library. Positions of the library that are translated to an amino acid sequence are indicated by boxes in light yellow. The sequence of the protein portion (59 amino acids in length) is shown in the single letter amino acid code, where X represents any amino acid. Portions of the library that are not translated are indicated as gray boxes. (a) T7-promoter for optimal in vitro transcription of library, (b) TMV—Tabaco Mosaic Virus translation initiation sequence for perfect in vitro translation of library, (c) $His_6$-tag for efficient affinity purification of PROfusion™ library, (d) structural, flexible linker, (e) gurmarin core with two randomized loops containing 5 and 9 amino acids respectively, (f) structural, flexible linker and (g) optimized linker for efficient coupling with puromycin-acceptor-molecule. B) The construction of the gurmarin PROfusion™ library is a multi-step process comprising the following reactions: PCR, in vitro transcription, chemical ligation of RNA with puromycin-oligonucleotide linker, in vitro translation, oligo-dT purification, reverse transcription and His-tag purification.

```
RSNVIPLNEVWYDTGWDRPHRSRLSIDDDA
(pp26-9; SEQ ID NO: 7);

RSWRDTRKLHMRHYEPLAIDSYWDHTLRDA
(pp26-15; SEQ ID NO: 8);

SGCVKKDELCARWDLVCCEPLECIYTSELYATCG
(G-9; SEQ ID NO: 9);

SGCVKKDELCELAVDECCEPLECFQMGHGFKRCG
(G-10; SEQ ID NO: 10);

SGCVKKDELCSQSVPMCCEPLECKWFNENYGICGS
(G-15; SEQ ID NO: 11);
and,

SGCVKKDELCELAIDECCEPLECTKGDLGFRKCG
(G-19; SEQ ID NO: 12).
```

Of these, especially preferred peptides include:

```
RSNVIPLNEVWYDTGWDRPHRSRLSIDDDA
(pp26-9; SEQ ID NO: 7);
and,

SGCVKKDELCSQSVPMCCEPLECKWFNENYGICGS
(G-15; SEQ ID NO: 11).
```

Further contemplated are related peptides such as, for example, fragments, variants orthologs, homologues, and derivatives, for example, that possess at least one characteristic or activity (i.e., activity, antigenicity) of the peptide. A fragment comprises a truncation of the sequence (i.e., nucleic acid or polypeptide) at the amino terminus (with or without a leader sequence) and/or the carboxy terminus of the peptide. Fragments may also include variants, orthologs, homologues, and other variants having one or more amino acid additions or substitutions or internal deletions as compared to the parental sequence. In preferred embodiments, truncations and/or deletions comprise about one amino acid, two amino acids, five amino acids, 10 amino acids, 20 amino acids, 30 amino acids, 40 amino acids, 50 amino acids, or more. A variant is a sequence having one or more sequence substitutions, deletions, and/or additions as compared to the parental sequence. Variants may be naturally occurring or artificially constructed. Such variants may be prepared from the corresponding nucleic acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table I.

TABLE I

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A component such as PT may be said to be purified when it has been separated from at least about 50% of the proteins, lipids, carbohydrates, or other materials with which it is originally found (i.e., a bacterial lysate). It is preferred that the component be separated from at least about 95-100%, 90-95%, 80-90%, 70-80%, 60-70% or 50-60% of the total protein content of a composition. In certain embodiments, a purified component is one that is useful in inducing an immune response in a host to whom the component has been administered, either alone or in combination with other agents. The immune response may include the production of antibodies that bind to at least one epitope of PT or *Bordetella pertussis*, for example, and/or the generation of a cellular immune response against cells expressing PT. The response may be an enhancement of a current immune response by, for example, causing increased antibody production, production of antibodies with increased affinity for the antigen, or an increased cellular response (i.e., increased T cells). Other measures of an immune reponse are known in the art and would be suitable in determining whether or not an immune response has occurred.

PT isolated using the methods described herein may be prepared as pharmaceutical compositions. Preferred pharmaceutical compositions include, for example, PT in a liquid preparations such as a suspensions, syrups, or elixirs. Preferred injectable preparations include, for example, peptides suitable for parental, subcutaneous, intradermal, intramuscular or intravenous administration such as sterile suspensions or emulsions. For example, PT may be prepared as a composition in admixture with a suitable carrier, diluent, or excipient such as sterile water, physiological saline, glucose or the like. The composition may also be provided in lyophilized form for reconstituting, for instance, in isotonic aqueous, saline buffer. Such compositions may also be prepared and utilized as a vaccine as described in, for example, U.S. Pat. Nos. 5,877,298 and 6,399,076 (Vose, et al.) as well as International App. No. PCT/CA96/00278. PT prepared as indicated herein may also be combined with other antigens from disease-causing organisms such as Corynbacterium (i.e., diphtheria), Clostridium (i.e., tetanus), polio virus (i.e., IPV, OPV), hepatitis virus, Neisseria (i.e., meningitis), Streptococcus, Hemophilus, or other pertussis antigens (i.e., filamentous hemagglutinin, pertactin, and agglutinogens), among others as is known in the art.

A better understanding of the present invention and of its many advantages will be had from the following examples, given by way of illustration.

EXAMPLES

Materials and Methods

A. Pertussis Toxin (PT)

PT is a heterooligomeric protein complex with a MWr. of 109 kD (consists of the 6 subunits S1, S2, S3, 2x S4, S5). A high purity (>99.99%) preparation, formulated as an ammonium sulfate precipitate, was utilized. A PT-specific ligand (asialofetuin) recognizing the native hexameric complex was also utilized. Asialofetuin is available in a solubilized and in sepharose immobilized form.

B. Cumarin Library Selection

Gurmarin is a 35-residue polypeptide from the Asclepiad vine *Gymnea sylvestre*. It has been utilized as a pharmacological tool in the study of sweet-taste transduction because of its ability to selectively inhibit the neural response to sweet tastants in rats. It has no apparent effect in humans. It has been suggested that the taste-suppressing of gurmarin might be due to the peptide either by binding directly to a sweet-taste receptor or interacting with a downstream target in the sweet-taste-transduction system.

Gurmarin belongs to the family of "knottins", a group of structurally related proteins, typically less than 40 residues in length. Knottins bind to a diverse range of molecular targets that includes proteins, sugars and lipids but share a common scaffold comprising a small triple-stranded antiparallel β-sheet and disulphide bound framework.

A specialized gurmarin-library was designed with 15 randomized amino acid positions, as shown below:

```
Wild-type gumarin:
qqCVKKDELCIPYYLDCCEPLECKKVNWWDHKCig    (SEQ ID NO: 13)

Gumarin core:
CVKKDELCXXXXXXXCCEPLECXXXXXXXXXXC      (SEQ ID NO: 14)
```

Within the gumarin core sequence, X represents any amino acid. This library was validated to yield high affinity binders against protein targets. The gurmarin library combines a set of advantages that makes it the best choice for a selection against the PT-toxin for at least the following reasons: limited flexibility makes up for high entropic cost in conforming to target topology; theoretically fewer amino acids for higher affinities than in linear libraries; resistant to proteases; and susceptibility to redox-elution conditions in downstream applications. The gumarin library was constructed using process shown in FIG. 1.

1. PCR of Starting Oligonucleotides

Three gel-purified oligos were used to construct the gurmarin library with two randomized loops. 1 nmole of gurmarin template ($\approx$ca. $6\cdot10^{14}$ sequences) 5'-AGT GGC TCA AGC TCA GGA TCA GGC TGC GTC AAG AAA GAC GAG CTC TGC NNS NNS NNS NNS NNS NNS TGC TGT GAG CCC CTC GAG TGC NNS NNS NNS NNS NNS NNS NNS NNS NNS TGC GGC AGC GGC AGT TCT GGG TCT AGC-3' (SEQ ID NO: 15), was amplified for 6 rounds of PCR (94° C., 1 min; 65° C., 1 min; 72° C., 1 min) using 1 µM of the 5'-His-Tag Primer 5'-TAA TAC GAC TCA CTA TAG GGA CAA TTA CTA TTT ACA ATT ACA ATG CAC CAT CAC CAT CAC CAT AGT GGC TCA AGC TCA GGA TCA-3' (SEQ ID NO: 16) and 1 µM of the 3'-Primer 5'-TTT TAA ATA GCG GAT GCT ACT AGG CTA GAC CCA GAA CTG CCG CT-3' (SEQ ID NO: 17) using Taq-polymerase and analyzed on a 2% agarose gel, which indicated a representative library had been constructed.

2. In Vitro Transcription dsDNA was transcribed into RNA using the RiboMax Express In vitro transcription kit from Promega. After incubation for 45 min at 37° C., DNase I was added and the incubation at 37° C. continued for an additional 15 minutes. This mixture was subjected to a phenol/chloroform extraction. Excess of NTPs was removed by NAP-5 gel filtration (Pharmacia). RNA was analyzed on a 6%-TBU-gel, and incidacted that the dsDNA had been efficiently transcribed.

3. Chemical Coupling of RNA and Puromycin-Oligonucleotide Linker

Purified RNA will be annealed (85° C., 1 min cool down to 25° C. at a ramp of 0.3° C./s) to a 1.5-fold excess of puromycin-oligonucleotide linker PEG2A18: 5'-psoralen-UAG CGG AUG C $A_{18}$ (PEG-9)$_2$ CC puromycin (SEQ ID NO: 18; nucleotides shown in italics represent 2'-O-methyl-derivatives). The covalent coupling is performed by illumination for 15 min at RT (RT) with UV-light (365 nm). The reaction product was analyzed on 6%-TBU gel and indicated the linking reaction had proceeded efficiently.

4. In Vitro Translation

Ligated RNA was translated using the rabbit reticulocyte lysate from Promega in the presence of 15 µCi $^{35}$S-methionine (1000 Ci/mmole). After a 30 min incubation at 30° C., KCl and MgCl$_2$ were added to a final concentration of 530 mM and 150 mM respectively and a sample was analyzed on 4-20% Tris/glycine-SDS-PAGE. The gel indicated that the translation reaction was successful.

5. Oligo-dT Purification

Molecules (mRNA-protein fusions) were isolated by incubation with oligo dT magnetic beads (Miltenyi) in incubation buffer (100 mM Tris-HCl pH 8.0, 10 mM EDTA, 1 mM NaCl and 0.25% Triton X-100) for 5 min at 4° C. PROfusion™ molecules were isolated by filtration through MiniMACS-columns (Miltenyi), washing with incubation buffer and elution with water. A sample was analyzed on 4-20% Tris/glycine-SDS-PAGE, and indicated that the reaction was successful.

6. Reverse Transcription

A corresponding cDNA strand was generated by reverse transcription with SuperScript II Reverse Transcriptase (Gibco BRL) under the manufacture's recommended conditions using a 5-fold excess of 3'-Primer. A sample was analyzed on 4-20% Tris/glycine-SDS-PAGE, and indicated that the reaction was successsul.

7. His-tag Purification

Reverse transcribed PROfusion™ molecules were mixed with Ni-NTA-agarose (50 µl/10 pmole PROfusion™) (QIAGEN) in HBS buffer (20 mM HEPES pH 7.0, 150 mM NaCl, 0.025% Triton X-100, 100 µg/ml sheared salmon sperm DNA, 1 mg/ml BSA) and incubated for 60 min at RT under gentle shaking. Ni-NTA was then filtrated, washed with HBS/5 mM imidazole and PROfusions™ were eluted with HBS/150 mM imidazole. A sample was analyzed on 4-20% Tris/glycine-SDS-PAGE, and indicated that the purification was successful. 20 pmole ($\approx$ca. $1\cdot10^{13}$ sequences) of PROfusion™ molecules will be used as input for each selection.

B. Linear Peptide Library PP26 for Selection

A specialized linear peptide library PP26 with 26 randomized amino acid positions was also designed using the following construct: T7-TMV-MGRGS-HHHHHH-ARS-XXXXXXXXXXXXXXXXXXXXXXXXXX-DANAPK-ASAI (SEQ ID NO: 19). The sequence of the protein portion (50 amino acids in length) is shown in the single letter amino acid code, where X represents any amino acid. Portions of the library that are not translated include: (a) T7: the T7-promoter for optimal in vitro transcription of library; and, (b) TMV: the Tabaco Mosaic Virus translation initiation sequence for perfect in vitro translation of library. MGRGS represents a structural, flexible linker. HHHHHH (SEQ ID NO: 20) represents a $His_6$-tag for efficient affinity purification of PROfusion™ library. ARS represents a second structural, flexible linker. DANAPK (SEQ ID NO: 21) represents a third structural, flexible linker. ASAI represents an optimized linker for efficient coupling with puromycin-acceptor-molecule.

1. PCR of Starting Oligonucleotides

Three gel-purified oligos were used to construct the gurmarin library with two randomized loops. 1 nmole of PP26 template ($\approx$ca. $6 \cdot 10^{14}$ sequences) 5'-AGC GGA TGC CTT CGG AGC GTT AGC GTC SNN SNN SNN SNN SNN SNN SNN SNN SNN SNN SNN SNN SNN SNN SNN SNN SNN SNN SNN SNN SNN SNN SNN AGA TCT AGC ATG ATG ATG ATG A-3' (SEQ ID NO: 22), was amplified for 6 rounds of PCR (94° C., 1 min; 65° C., 1 min; 72° C., 1 min) using 1 μM of the 5'-His-Tag Primer 5'-TAA TAC GAC TCA TAG GGA CAA TTA CTA TTT ACA ATT ACA ATG GGA CGT GGC TCA CAT CAT CAT CAT CAT CAT GCT AGA TCT-3' (SEQ ID NO: 23) and 1 μM of the 3'-Primer 5'-AA TTA AAT AGC GGA TGC CTT CGG AGC GTT AGC-3' (SEQ ID NO: 24) using Taq-polymerase and confirmed by analysis on a 2% agarose gel.

2. In Vitro Transcription dsDNA was transcribed into RNA using the RiboMax Express In vitro transcription kit from Promega. After incubation for 45 min at 37° C., DNase I was added and the incubation at 37° C. continued for an additional 15 minutes. This mixture was subjected to a phenol/chloroform extraction. Excess of NTPs was removed by NAP-5 gel filtration (Pharmacia). Transcription of RNA was confirmed by analysis on a 6%-TBU-gel.

3. Chemical Coupling of RNA and Puromycin-Oligonucleotide Linker

Purified RNA will be annealed (85° C., 1 minΔcool down to 25° C. at a ramp of 0.3° C./s) to a 1.5-fold excess of puromycin-oligonucleotide linker PEG2A18: 5'-psoralen-UAG CGG AUG C $A_{18}$ (PEG-9)$_2$ CC puromycin (SEQ ID NO: 18; nucleotides shown in italics represent 2'-O-methyl-derivatives). The covalent coupling is performed by illumination for 15 min at RT (RT) with UV-light (365 nm). The reaction product was analyzed on 6%-TBU gel and indicated the linking reaction had proceeded efficiently.

4. In Vitro Translation

Ligated RNA was translated using the rabbit reticulocyte lysate from Promega in the presence of 15 μCi $^{35}$S-methionine (1000 Ci/mmole). After a 30 min incubation at 30° C., KCl and $MgCl_2$ were added to a final concentration of 530 mM and 150 mM respectively and translation confirmed by analysis on 4-20% Tris/glycine-SDS-PAGE.

5. Oligo-dT Purification

Molecules (mRNA-protein fusions) were isolated by incubation with oligo dT magnetic beads (Miltenyi) in incubation buffer (100 mM Tris-HCl pH 8.0, 10 mM EDTA, 1 mM NaCl and 0.25% Triton X-100) for 5 min at 4° C. PROfusion™ molecules were isolated by filtration through MiniMACS-columns (Miltenyi), washing with incubation buffer and elution with water. A sample was analyzed to confirm the reaction on 4-20% Tris/glycine-SDS-PAGE.

6. Reverse Transcription

A corresponding cDNA strand was generated by reverse transcription with SuperScript II Reverse Transcriptase (Gibco BRL) under the manufacture's recommended conditions using a 5-fold excess of 3'-Primer. A sample was analyzed to confirm transcription on 4-20% Tris/glycine-SDS-PAGE.

7. His-tag Purification

Reverse transcribed PROfusion™ molecules were mixed with Ni-NTA-agarose (50 μl/10 pmole PROfusion™) (QIAGEN) in HBS buffer (20 mM HEPES pH 7.0, 150 mM NaCl, 0.025% Triton X-100, 100 μg/ml sheared salmon sperm DNA, 1 mg/ml BSA) and incubated for 60 min at RT under gentle shaking. Ni-NTA was then filtrated, washed with HBS/5 mM imidazole and PROfusions™ were eluted with HBS/150 mM imidazole. A sample was analyzed to confirm the reaction on 4-20% Tris/glycine-SDS-PAGE. 20 pmole ($\approx$ca. $1 \cdot 10^{13}$ sequences) of PROfusion™ molecules will be used as input for each selection.

C. Target Preparation

In the PROfusion™ technology highly diverse substance libraries, which are composed of up to $10^{13}$ different PROfusion™ molecules (mRNA-Protein fusions), are selected against a wanted target (protein, sugar or lipid) for high affinity binding. In this process the targets will typically be immobilized to solid phases. These solid phase are preferentially magnetic beads that allow fast and efficient handling during the selection process and give low background.

1. Test Targets for Nuclease Activity

Targets—5 μg PRP and 0.5 μg PT—were contacted with 0.12 pmole radioactive labeled PROfusion™ library molecules at 4° C. and RT (RT) followed by an incubation for 1 h and 16 h respectively. The integrity of PROfusion™ molecules after incubation was confirmed by 4-20% Tris/glycine SDS-PAGE and subsequent autoradiography. Degradation of PROfusion™ molecules was not detected, thus demonstrating that the targets are free of nucleases.

2. Test Targets for Protease Activity

Targets—5 μg PRP and 0.5 μg PT—were contacted with 1 μg purified GST-protein at 4° C. and RT followed by an incubation for 1 h and 16 h respectively. The integrity of GST-protein after incubation was analyzed by 4-20% Tris/glycine SDS-PAGE and subsequent Coomassie Brilliant Blue staining. Degradation of GST-protein was not detected, thus demonstrating that the targets are free of proteases.

D. Immobilization of PT

1. Reconstitution of PT

500 μl of the precipitate (2.26 mg/ml) as delivered by Aventis Pasteur were centrifuged at 21.400×g for 45 min at RT. The supernatant was discarded; the pellet was dissolved in 1100 μl CTW-buffer (0.286 g $NaHCO_3$, 0.170 g $Na_2CO_3$, 50 μl Tween-80, add to 50 ml MilliQ $H_2O$). To check the quality of this PT preparation a dilution series (250 ng, 500 ng, 1 μg, 2.5 μg, 5 μg and 15 μg) was separated on a 4-12% BisTris SDS-PAGE, run in MES-buffer). At least 4 bands could be clearly separated, corresponding to the subunits S1 (28 kD), S2 (23 kD), S3 (22 kD) and S4 (11.7 kD). The smallest protein S5 (9.3 kD) in the PT-complex could not be seen. Probably, this band co-migrates in this gel system with the only slightly larger S4 subunit.

2. Coupling Strategy

Several methods were established for immobilization of proteins to magnetic particles. In principle two major strategies are used: primary amino groups and sulfhydryl groups of the target protein are tethered covalently to epoxy-activated magnetic beads (Dynal) forming stabile amide or thioether bounds. This reaction is performed in the presence of ammonium sulfate to promote the reaction and typically results in a very efficient coupling of the target protein. Anyhow, certain proteins seem to undergo structural changes under these conditions resulting in a bound but not native and/or inactive conformation; and, primary amino groups and sulfhydryl groups of the target protein are tethered covalently to NHS-ester activated biotin derivatives (Pierce) subsequently followed by an immobilization of now biotinylated protein to streptavidin magnetic beads (Dynal).

Typically, covalent coupling of a target protein to epoxy beads is preferred if reaction conditions are suitable for a given target since this method guarantees that only the target is presented on the beads. In the case of a biotin/streptavidin coupling the beads also present streptavidin that could lead to the enrichment of anti-streptavidin binder during a selection. Therefore, Phylos has established specialized methods to preclear PROfusion™ libraries for streptavidin binders to get high quality results for a given target. But in total a covalent coupling typically results in a faster enrichment of target specific binders. In the specific case of PT it is most reasonable to start with a covalent coupling strategy since it is known that ammonium sulfate incubation does not influence the functionality of the PT-protein.

3. Optimization of Coupling Conditions to Epoxy Beads (Dynal)

The coupling conditions for PT were optimized in several independent experiments (different ammonium sulfate concentrations (0.5-2.0 M) and different beads/target-ratios were applied, as well as time- and temperature dependency (2 min-16 h; 8° C.-RT). Best results were observed for the following reaction condition: A final volume of 300 µl, consisting of 100 µg PT, 3.3·10$^8$ beads and a final ammonium sulfate concentration of 1M was incubated in a time course for 2 min to 60 min at RT in a 2 ml Eppendorf tube. After incubation the tube was placed in a magnet for 4 min to pull down the beads and the supernatant was stored for subsequent gel analysis. The beads were washed once with 1 ml HEPES-buffer (20 mM HEPES pH 7.0, 150 mM NaCl, 0.025% Triton X100) and an aliquot of beads (5% of the beads) were analyzed on a 4-12% BisTris SDS-PAGE to determine the amount of associated protein. It was found that coupling of PT to epoxy beads occurs very efficiently even after only a two minute reaction.

4. Semi-Preparative Coupling of PT to Epoxy Beads 2.6 mg dry epoxy-activated beads (M-270, Dynal) (~1.7·10$^8$ beads) were resuspended in 1 ml phosphate buffer (19 mM NaH$_2$PO$_4$, 81 mM Na$_2$HPO$_4$, pH 7.4) and equilibrated for 10 min. The equilibration was repeated two times with fresh phosphate buffer. Subsequently the beads were directly used in a coupling reaction with 480 pmole reconstituted PT (1 µg/µl in CTW buffer) in 1 M ammonium sulfate (final volume 157 µl). After incubation at RT for 15 min under continuos agitation the beads were washed with 300 µl HBS-buffer, followed by three washing steps with HEPES-buffer and finally resuspended in 240 µl HEPES-buffer and stored in aliquots at 4° C. The effectiveness of the coupling reaction was checked by a SDS-polyacrylamidgel-analysis of all wash fractions, the supernatant of the coupling reaction and the fraction of PT which was removable from the washed beads by SDS-loading-buffer.

5. Analysis of Epoxy-Bead Immobilized PT for its Binding to Asialofetuin

40 µl of the PT-derivatized beads were incubated with 320 pmole asialofetuin in HEPES-buffer (20 mM HEPES pH 7.0, 150 mM NaCl, 0.025% Triton-X 100) for 1 h at RT (final reaction volume 200 µl), washed 2-7 times with 200 µl HEPES-buffer and finally resuspended in 30 µl HEPES-buffer. 50% of the beads were analyzed on SDS-PAGE to confirm the reaction.

Tests of these PT-derivatized beads after one week of storage at 4° C. showed a reduced asialofetuin binding capacity indicating that the material looses its performance by long term storage. Thus, PT-derivatized beads have to be prepared fresh and quality controlled for each selection round. Since this procedure is quite time consuming, an alternative immobilization strategy involving a biotinylation of PT was evaluated.

6. Semi-Preparative Biotinylation of PT

A biotinylation reaction was performed by incubation of 0.4 mg (~3.65 nmole) reconstituted PT (1 µg/µl in CTW buffer) with 25 µg EZ-link-sulfo-NHS-LC-LC-biotin (PIERCE) in a final volume of 740 µl 50 mM HEPES, 150 mM NaCl, 0.2% Triton-X100. After an incubation period of 2 h on ice under permanent agitation the biotinylation reaction was quenched by addition of 74 µl 1M Tris/HCl pH 7.0. Subsequently, the protein was dialyzed against HEPES-buffer (20 mM HEPES pH 7.0, 150 mM NaCl, 0.025% Triton X100) at 4° C. using a Slide-a-lyzer cassette (PIERCE, 3500 MWCO 0.5-3 ml) to remove the excess of biotinylation reagent. The biotinylated PT was removed from the dialysis cassette and stored in aliquots at −20° C.

7. Quality Control of Biotinylated PT Using a BIAcore Instrument

The quality of the biotinylation reaction was controlled by analysis of the interaction of biotinylated PT with a BIAcore streptavidin chip using BIAcore instrument (BIAcore 2000). It was also possible to detect the binding of asialofetuin to chip immobilized biotinylated PT (binding signal of ~400 RU to immobilized PT; unspecific binding of ~100 RU to the control cell).

F. Analysis of Biotinylated PT for Binding to Streptavidin Magnetic Beads and to Asialofetuin 1. Binding of Biotinylated PT to Streptavidin Magnetic Beads 20 µl streptavidin magnetic beads (Dynal), were incubated with 20 pmole of biotinylated PT in 1×HBS-buffer (20 mM HEPES pH 7.0, 150 mM NaCl, 1 mg/ml BSA, 10 µg/ml salmon sperm DNA, 0.025% Triton-X100) for 1 h at RT, washed 3× with HEPES-buffer (20 mM HEPES pH 7.0, 150 mM NaCl, 0.025% Triton X100) and resuspended in 16 µl SDS-gel-loading buffer. 8 µl were analyzed by SDS-PAGE to confirm conjugation. In a negative control experiment under comparable conditions, free PT (not biotinylated) did not interact with streptavidin magnetic beads.

2. Binding of Asialofetuin to Bead Immobilized Biotinylated PT

20 µl streptavidin magnetic beads (Dynal) were incubated with 20 pmole of biotinylated PT in 1×HBS-buffer for 1 h at RT, washed 4× with HEPES-buffer (20 mM HEPES pH 7.0, 150 mM NaCl, 0.025% Triton X100). Subsequently, beads with immobilized biotinylated PT were incubated with 40 pmole asialofetuin in HEPES-buffer for 1 h at RT. After 4 washes with HEPES-buffer beads were resuspended in 16 µl SDS-gel-loading buffer. 8 µl were analyzed by SDS-PAGE to confirm binding. A simultaneous incubation of biotinylated PT and asialofetuin to the streptavidin magnetic beads instead of serial incubations resulted as well in binding of asialofetuin to biotinylated PT. In a comparable control experiment, it was determined that asialofetuin did not interact with the streptavidin magnetic beads non-specifically. Similar quality controls with biotinylated PT that has been stored for one week at −20° C. showed no significant decrease in streptavidin and/or asialofetuin binding competence. Therefore, biotinylated PT was used as standard target in subsequent selections.

TABLE 1

| Target: Pertussis toxin | | Library: Gurmarin | | | | |
|---|---|---|---|---|---|---|
| | | R1 | R2 | R3 | R4 | Epoxy-PT R5a |
| 1. | PCR | | | | | |
| 1.1. | Analytical RT-PCR | | | | | |
| | specific signal after x rounds of PCR | | 18 | 24 | 24 | 24 |
| | control signal after y rounds of PCR | | 21 | 27 | 24 | 27 |
| 1.2. | Preparative PCR | | | | | |
| | done with z rounds of PCR | | 36 | 30 | 30 |

TABLE 1-continued

| Target: Pertussis toxin | | Library: Gurmarin | | |
|---|---|---|---|---|
| 5. | in vitro Translation and PROfusion ™ formation | | | |
| | input | | 3 nmol | 3 nmol |
| | RNA/200 µl lysate | | 260 pmol | 250 pmol |
| | salt incubation at −20° C. | | over night | over night |
| 6. | Oligo(dT) purification | | | |
| | purified on x coloumns | | 4 | 4 |
| | efficiency | | 3.3% | 2.7% |
| | yield | | 97.6 pmol | 81.1 pmol |
| 7. | Reverse transcription | | | |
| | conditions | | 1 mM DTT | 1 mM DTT |
| | input | | 40 pmol | 50 pmol |
| 8. | His-Tag purification | | | |
| | input | | 35 pmol RT + 15 pmol | 43 pmol RT + 19 pmol |
| | efficiency | | 36% | 43% |
| | yield | | 18 pmol | 26.4 pmol |
| | in volume of | | 450 µl | 450 µl |
| 9. | selection | | | |
| | selection volume | 1 ml | 1 ml | 1 ml |
| | input | 5 pmol | 5 pmol | 5 pmol |
| | final concentration of immidazol | 11.4 mM | 18.8 mM | 21.5 mM |
| | preclear | 3 × 100 µl HBS blocked, biotin saturated streptavidin beads | 3 × 100 µl HBS blocked, biotin saturated streptavidin beads | 3 × 100 µl HBS blocked, biotin saturated streptavidin beads |
| | first preclear binding | 80/50/32 dpm | 37/33/34 dpm | 72/30/37 dpm |
| | beads saturated with a puis of biotin | yes | yes | yes |
| | effective concentration of PT | 100 nM (50 nM) | 100 nM (50 nM) | 100 nM (50 nM) |
| | conditions | 90 min at RT | 90 min at RT | 90 min at RT |
| | specific binding % | 5.2% | 0.4% | 11.6% |

Example 2

Isolation of Peptides Selective for PT or PRP

Figure 2:
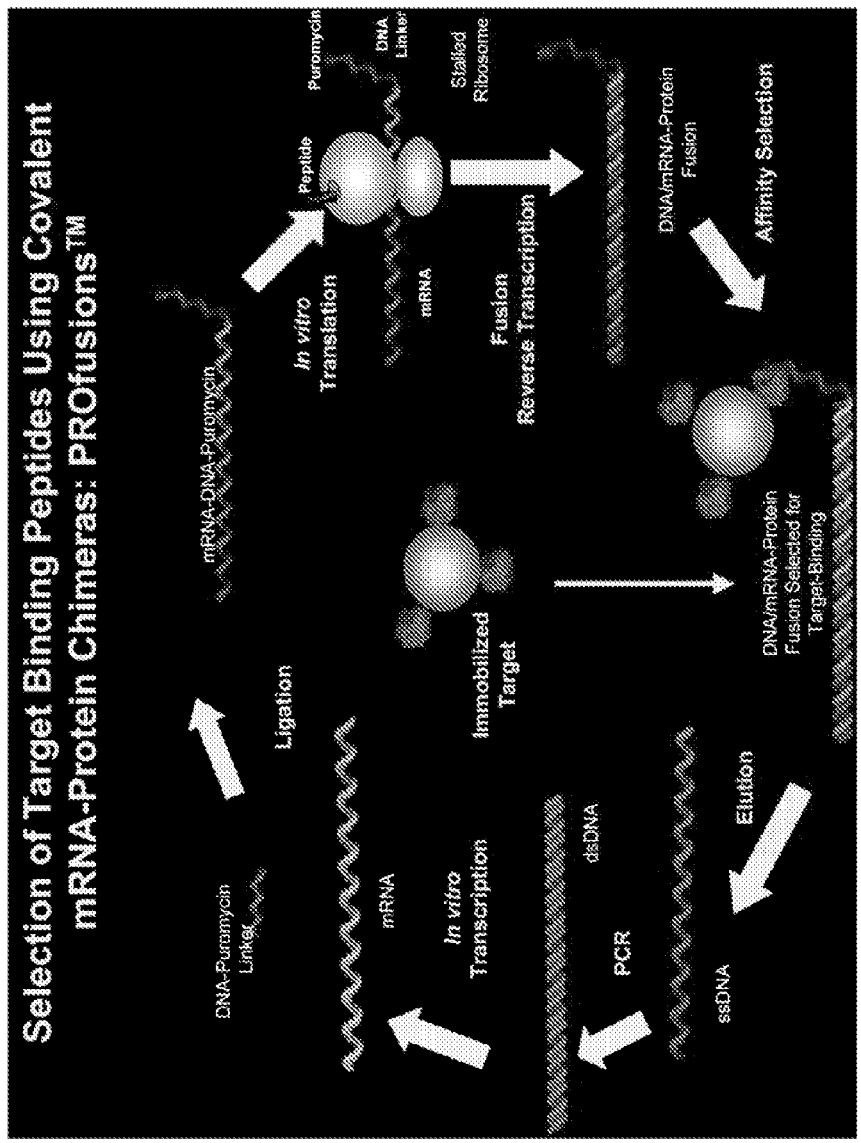
FIG. 2. Schematic representation of a PROfusion™ selection cycle.
Figure 6:
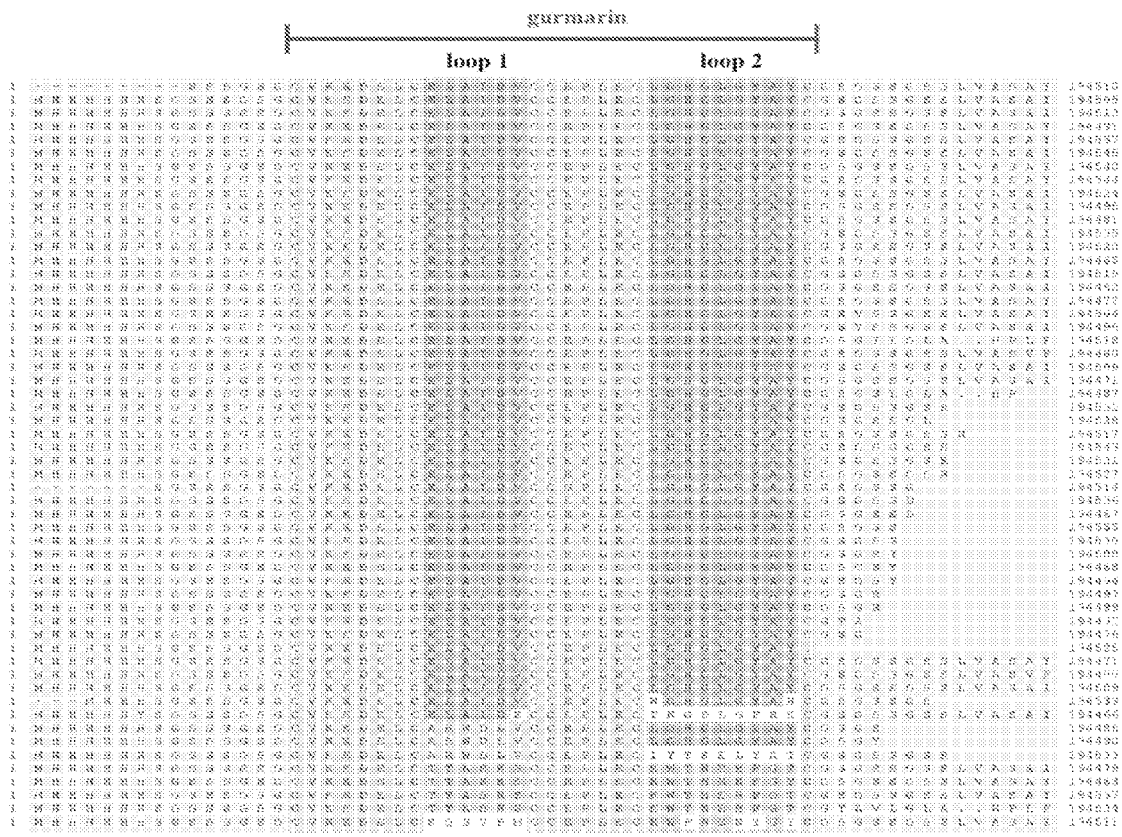
FIG. 6. Sequence analysis of the gurmarin selection round 5b against PT (strep). The amino acid sequence of individual variants is shown in the single letter amino acid code. Constant, flanking regions of the library and constant regions of the gurmarin scaffold are indicated. The position of the randomized loops 1 and 2 are indicated. The variants are listed from top to bottom in the following order: SEQ ID NOS. 170, 171 (16), 172, 173, 174, 171 (2), 175-181, 182 (2), 183 (2), 184, 185 (2), 186 (2), 187-195, 196 (3), 197, and 198.
Figure 7:
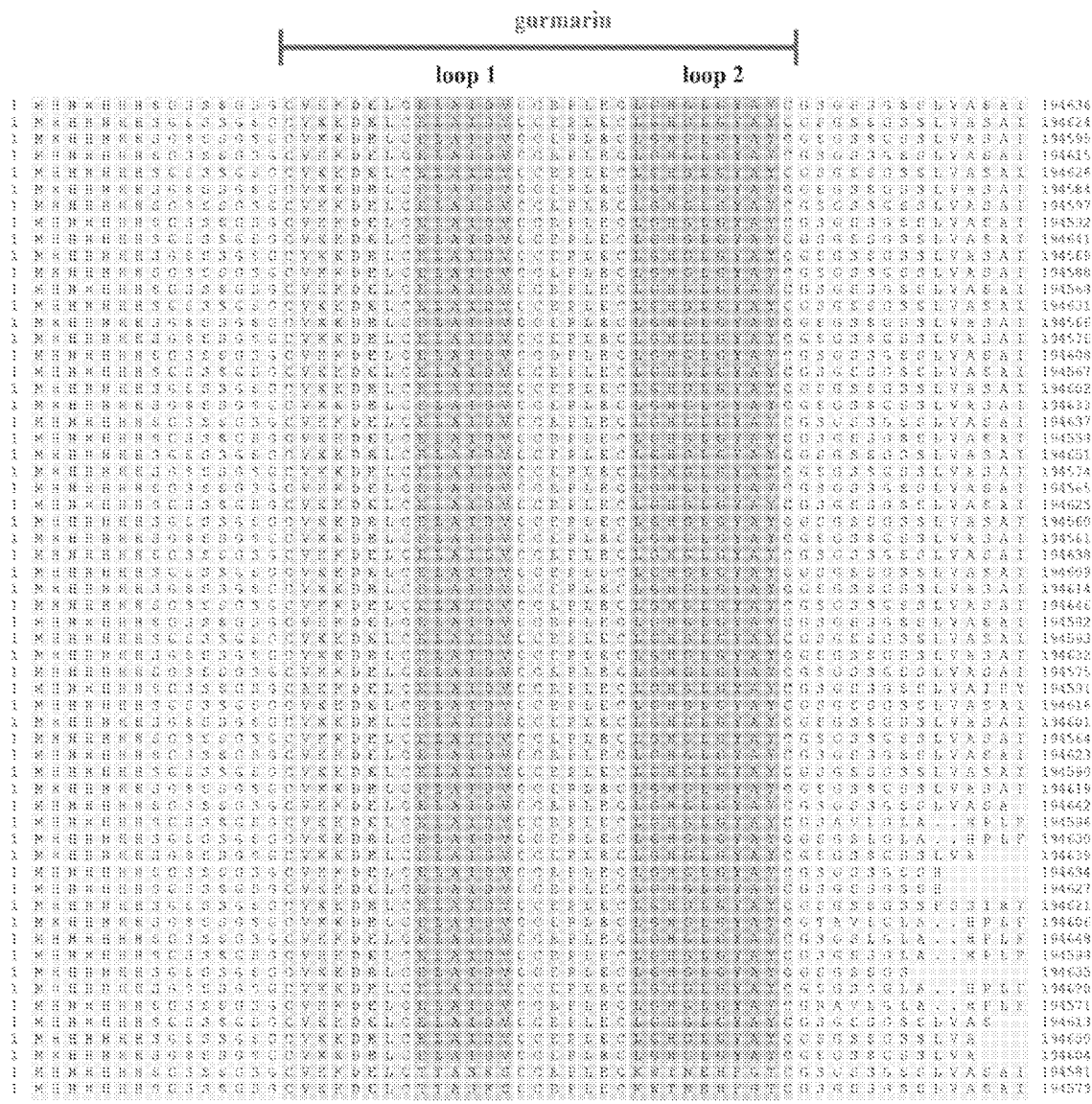
FIG. 7. Sequence analysis of the gurmarin selection round 6a against PT (strep). The amino acid sequence of individual variants is shown in the single letter amino acid code. Constant, flanking regions of the library and constant regions of the gurmarin scaffold are indicated. The position of the randomized loops 1 and 2 are indicated. The variants are listed from top to bottom in the following order: SEQ ID NOS. 199 (15), 200, 199 (19), 201, 199 (6), 202, 203 (2), 204, 205 (2), 206, 207, 203, 208, 209, 203, 210, 211, 204, and 212.
Figure 8:
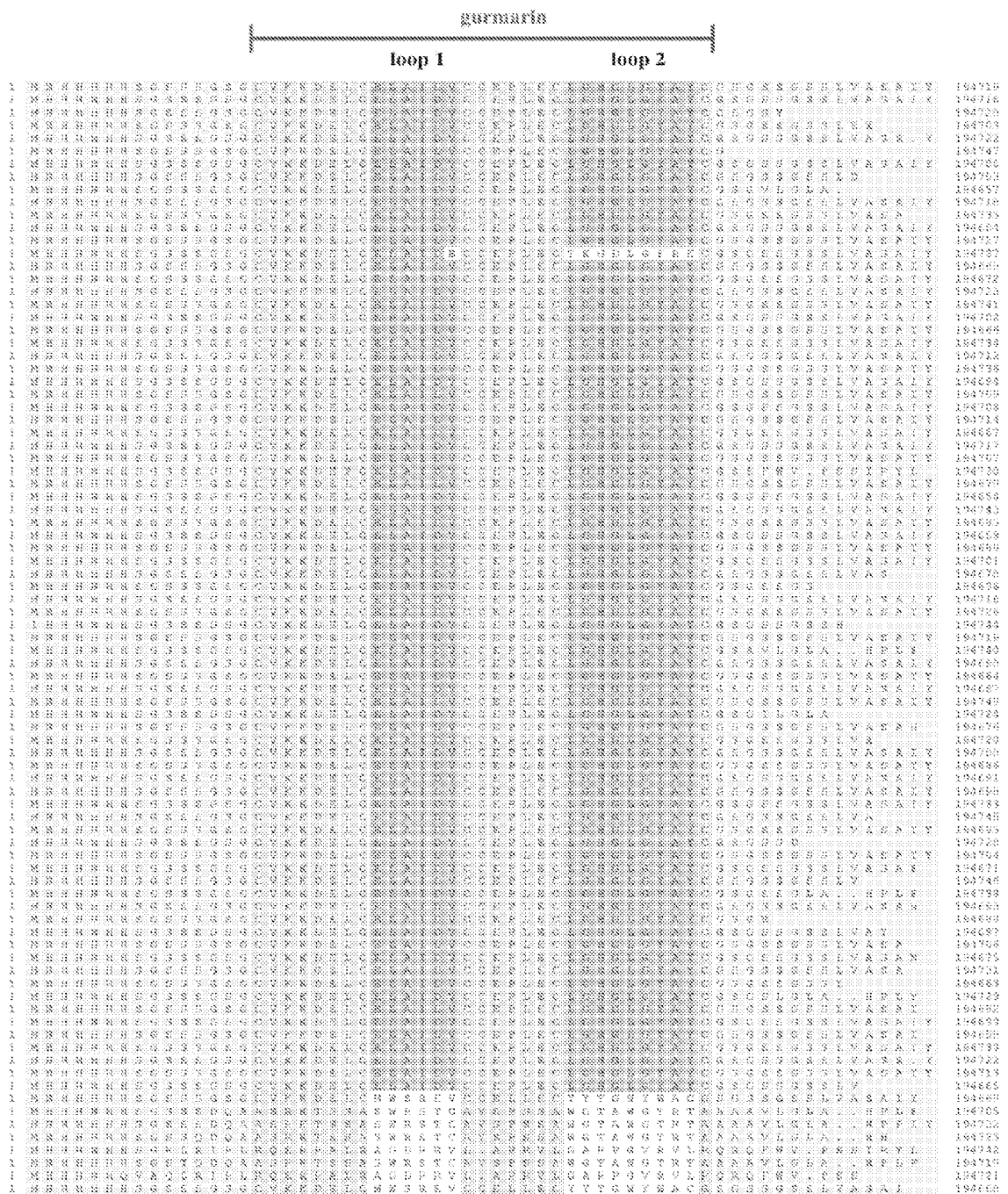
FIG. 8. Sequence analysis of the gurmarin selection round 6b against PT (strep). The amino acid sequence of individual variants is shown in the single letter amino acid code. Constant, flanking regions of the library and constant regions of the gurmarin scaffold are indicated. The position of the randomized loops 1 and 2 are indicated. The variants are listed from top to bottom in the following order: SEQ ID NOS. 213 (2), 214-217, 213, 218, 219, 213, 220, 213 (2), 221, 213 (16), 222, 213 (7), 223, 224, 213 (2), 225, 213, 226, 213 (4), 227-229, 213 (5), 229, 213, 231-242, 213, 242, 213, 243, 213, and 244-252.
Figure 11:
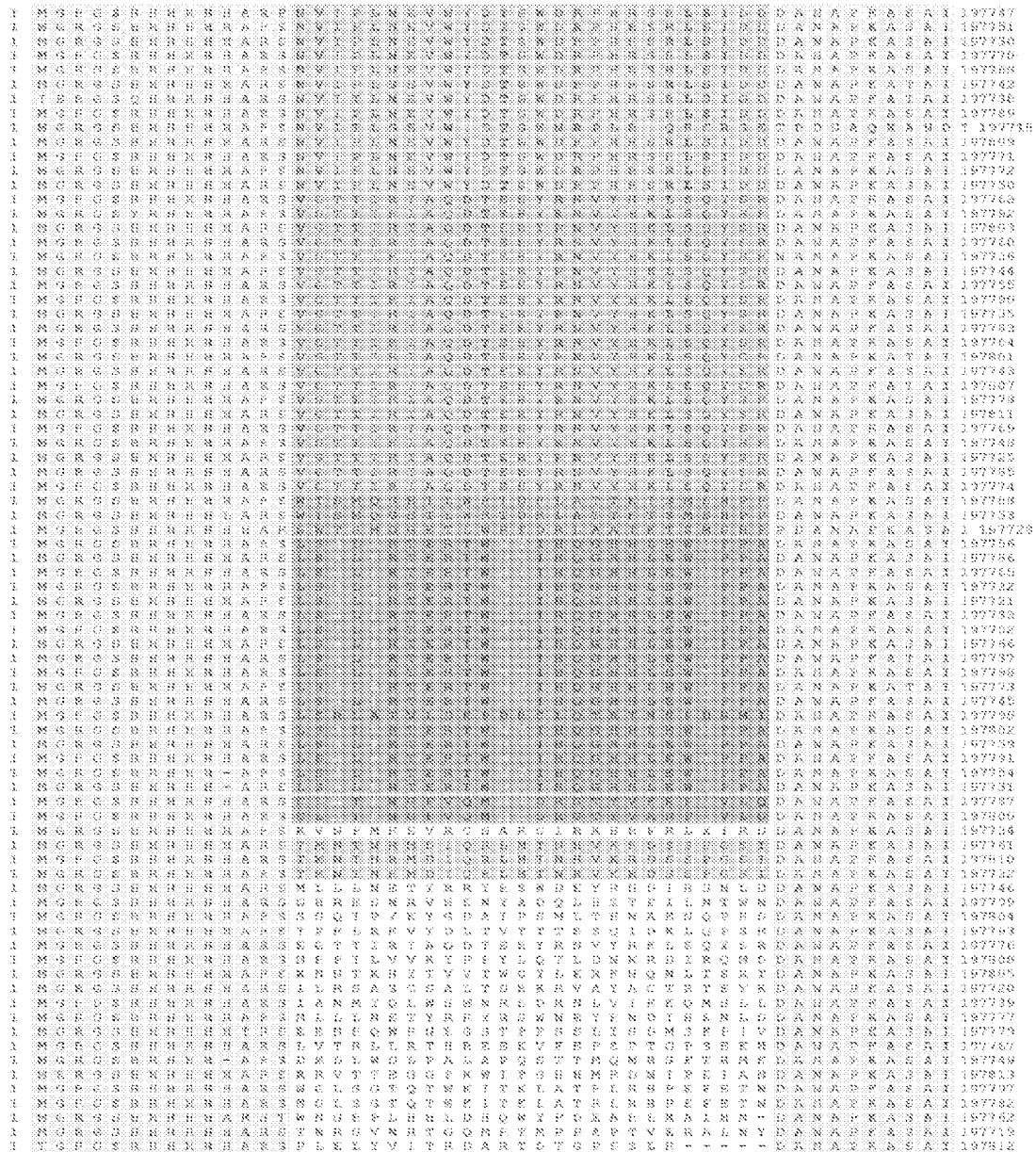
FIG. 11. Sequence analysis of the PP26 selection round 5a against PT (epoxy). The amino acid sequence of individual variants is shown in the single letter amino acid code. Constant, flanking regions of the library are indicated by light yellow boxes. Conserved sequence motifs are highlighted. The variants are listed from top to bottom in the following order: 306, 307 (4), 308-311, 307 (3), 312-315, 312 (6), 316, 312, 316, 312 (7), 317-320, 415, 320 (3), 321 (2), 322 (2), 323, 324 (3), 325-338, 339 (2), 341, and 342.
Figure 14:
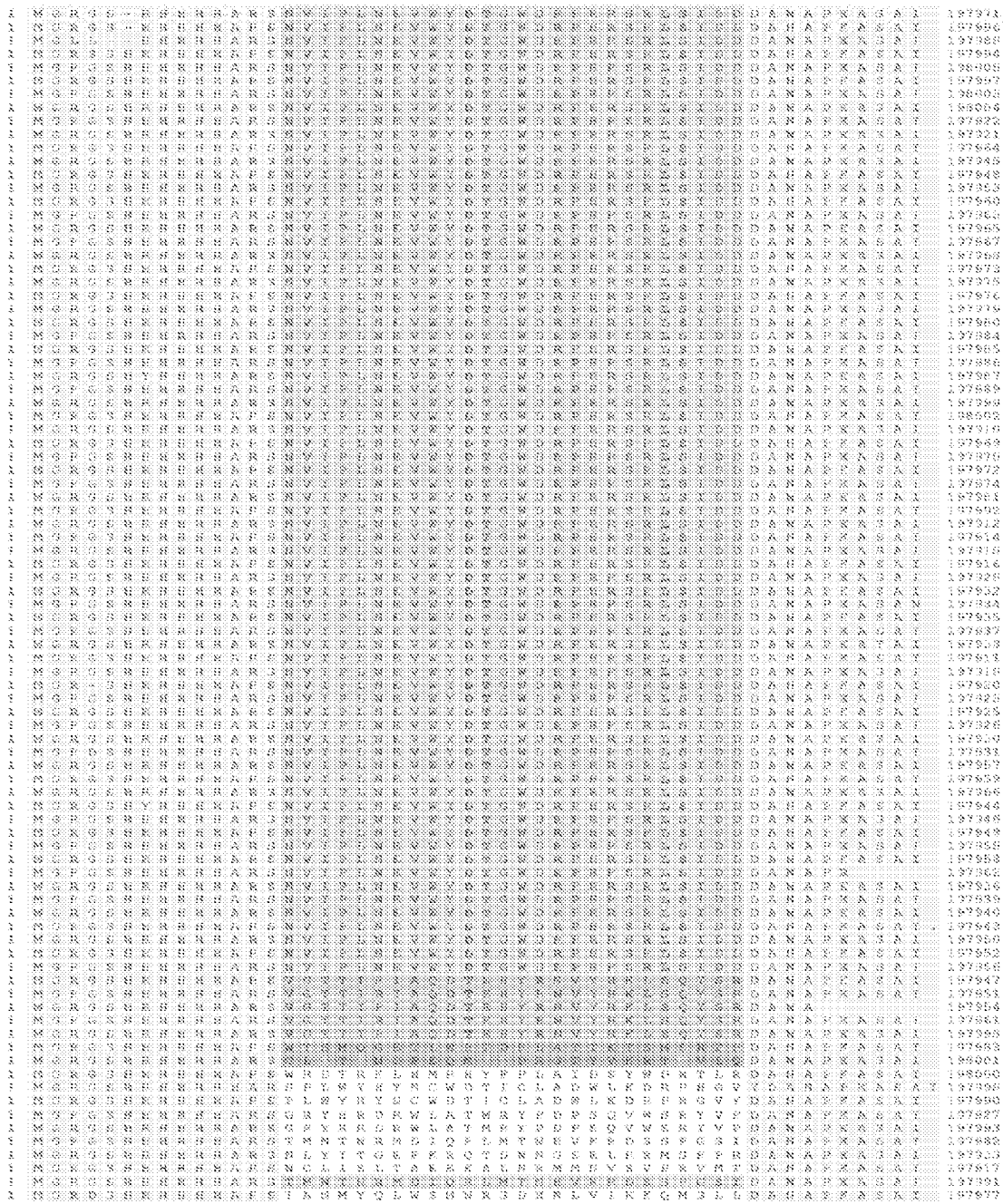
FIG. 14. Sequence analysis of the PP26 selection round 6b against PT. The amino acid sequence of individual variants is shown in the single letter amino acid code. Constant, flanking regions of the library are indicated. The variants are listed from top to bottom in the following order: 394, 395, 396, 397 (40), 398, 399 (5), 400, 399 (13), 401, 399 (7), 400 (2), 401, 402 (2), 403-414.
Figure 15:
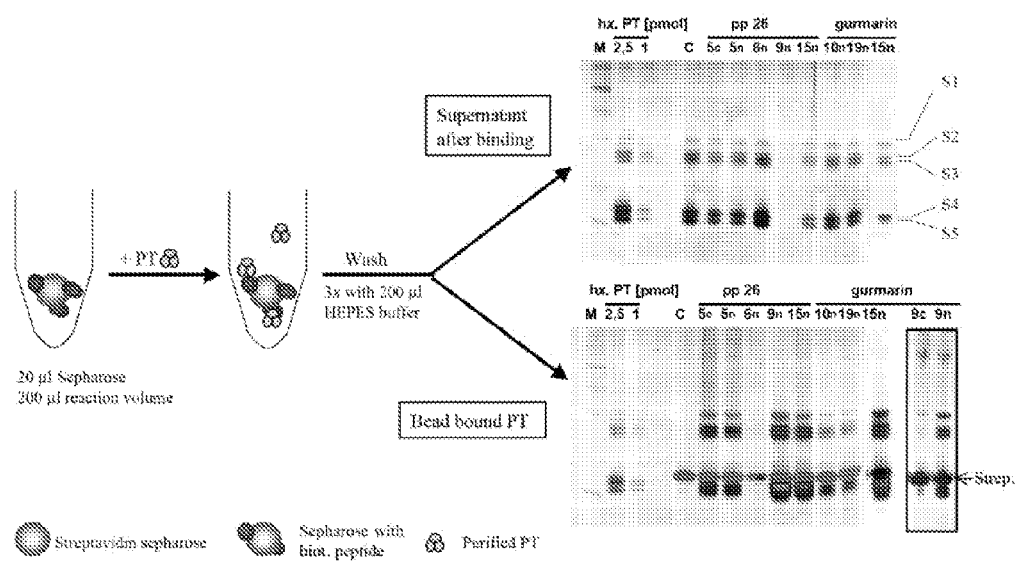
FIG. 15. Immobilization of synthetic biotinylated core peptides to Streptavidin sepharose and verification of binding to purified PT. The unbound fraction of PT was analyzed by separation of 1/40 volume of the supernatant after binding on a 12% NuPage gel with MES running-buffer (upper gel). To analyze sepharose bound PT 50% of the eluate was separated on 12% NuPage gel with MES running-buffer (lower gel). Detection was performed by silver staining. Defined amounts of purified PT were used as standard for quantification, except for the gurmarin peptides 15 and 9.
Figure 16:
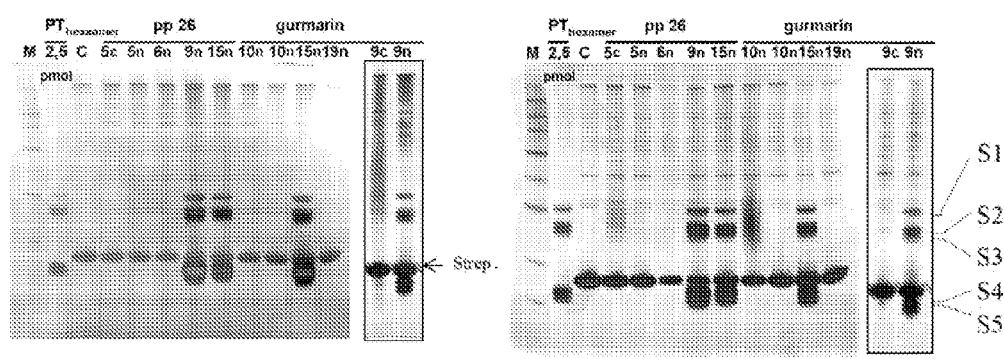
FIG. 16. Purification of PT out of Sample A (left gel) and Sample B (right gel). To analyze sepharose bound PT 50% of the eluate was separated on 12% NuPage gel with MES running-buffer (lower gel). Detection was performed by silver staining. Defined amounts of purified PT were used as standard for quantification, except for the gurmarin peptide 9.
Figure 17:
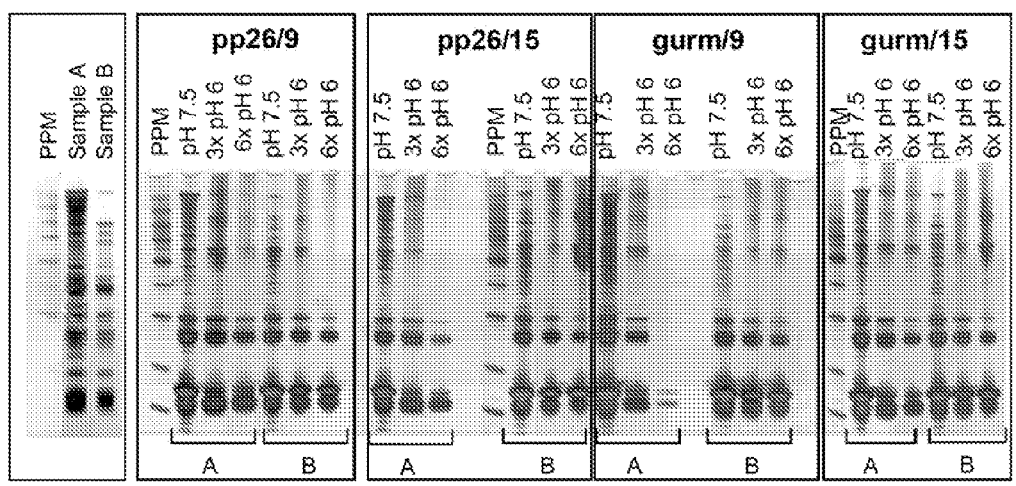
FIG. 17. Optimization of the washing conditions of bound PT out of sample A or B to immobilized peptides pp26 clone 9 and 15 and gurmarin clone 9 and 15 using 3 washes of 50 mM Tris/HCl, pH 7.5 or 50 mM acetate, pH 6. The PT were analyzed on 12% Bis Tris gels and visualized by silver staining. PPM: protein perfect marker.
Figure 18:
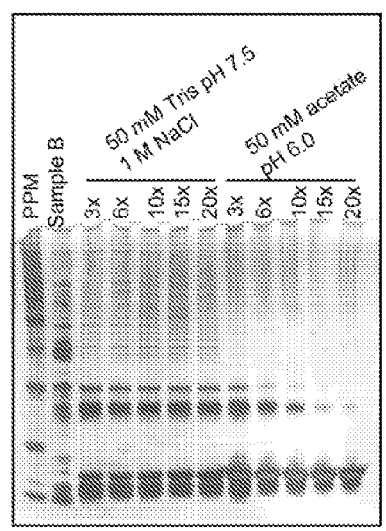
FIG. 18. Optimization of washing conditions of bound PT out of sample B to immobilized peptides pp26 clone 9 using 3 to 20 washes of 50 mM Tris/HCl, pH 7.5 or 50 mM acetate, pH 6. The PT was analyzed on 12% Bis Tris gels and visualized by silver staining.
Figure 21:
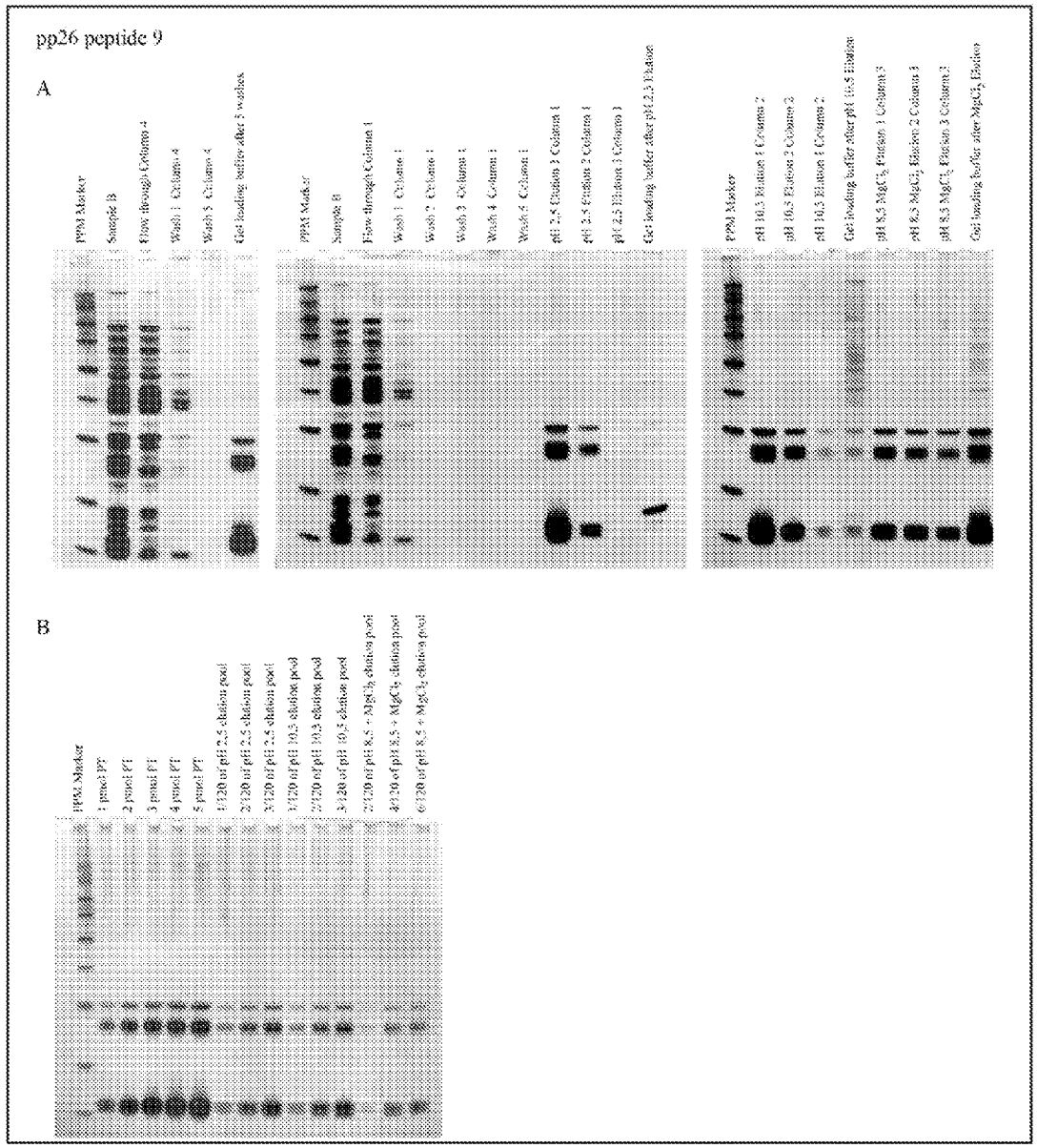
FIG. 21. Small scale column purification of PT from sample B on streptavidin sepharose with immobilized pp26 peptide 9 as affinity ligand (A) an gel estimation of the yield of purified PT (B).
Figure 22:
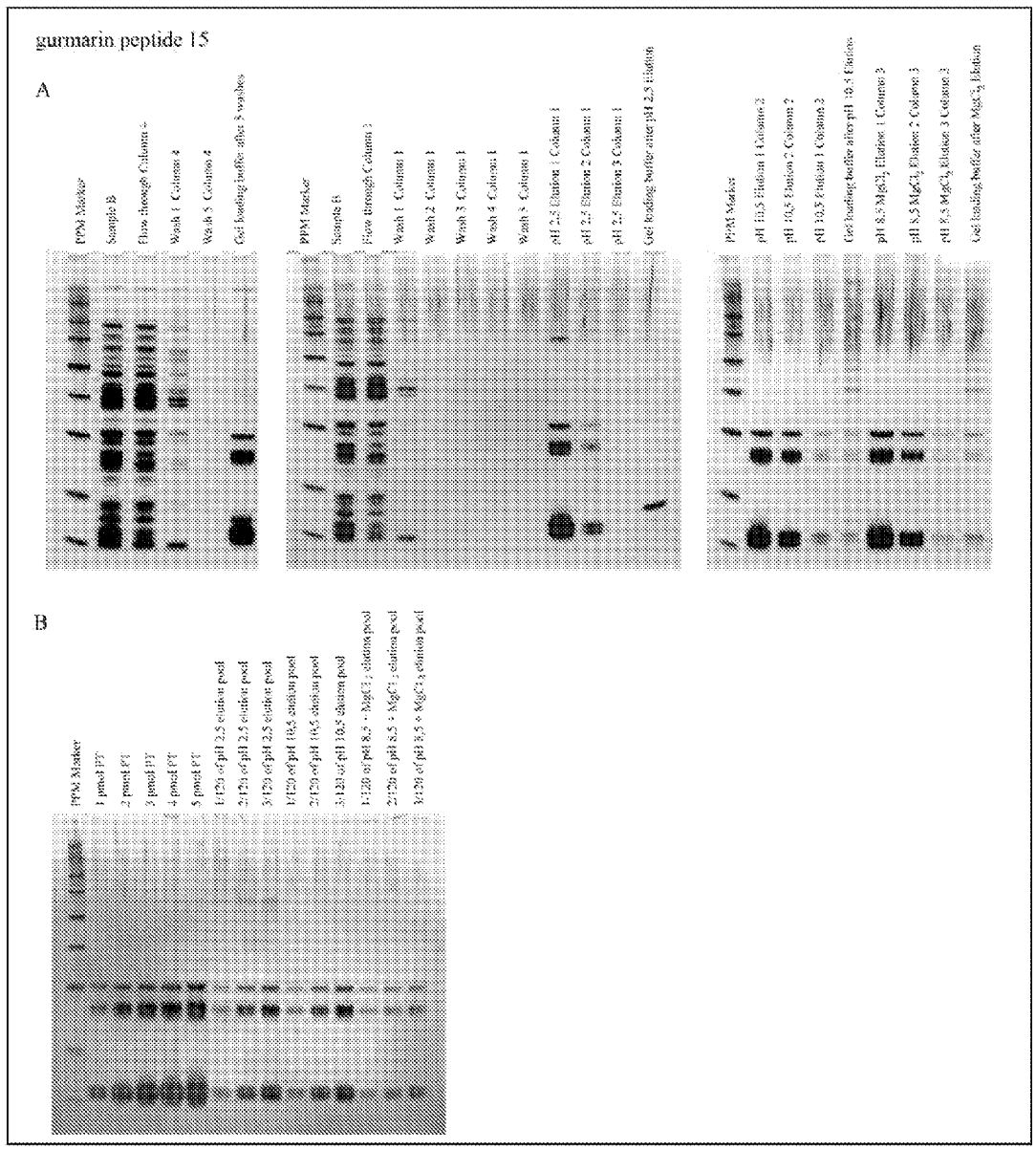
FIG. 22. Small scale column purification of PT from sample B on streptavidin sepharose with immobilized gurmarin peptide 15 as affinity ligand (A) an gel estimation of the yield of purified PT (B).
Figure 23:
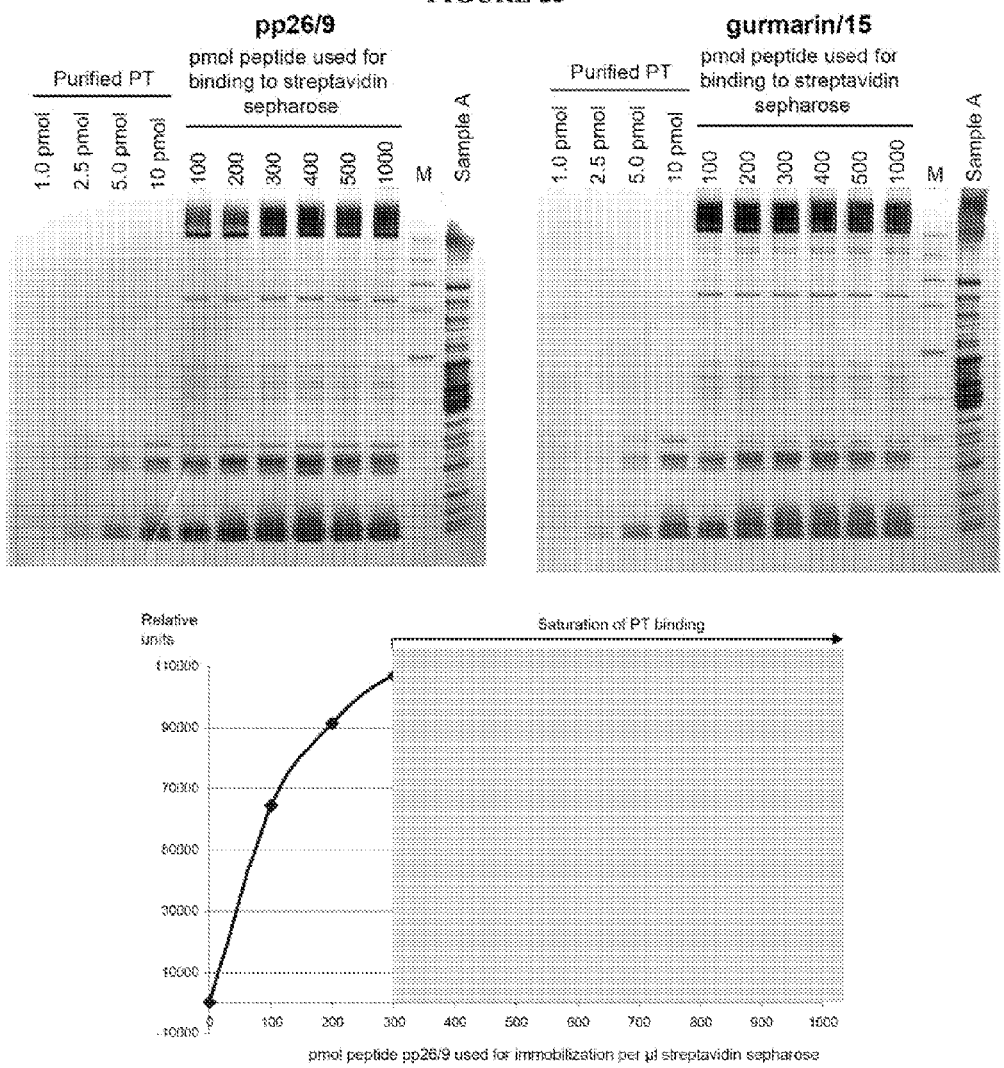
FIG. 23. PT binding to peptide streptavidin sepharose in dependence of varying amounts of peptide (as indicated) used for immobilzation on streptavidin sepharose (per 1 ml). Amount of bound PT was quantified by direct comparison to defined amounts of purified PT on the same gel. As an example, pp26/9 is plotted against the amount of peptide used for immobilization per ml of streptavidin sepharose. Maximal binding was estimated at approximately 100-150 pmol PT.

The gurmarin PROfusion™ library and the targets PT and PRP immobilized to magnetic beads were then contacted under strictly controlled stringency conditions. These conditions allow predominately those variants of the PROfusion™ library showing elevated affinity for PT or PRP, respectively, to bind to the targets. After extensive washes that dilute unwanted, non-specific binding variants, the bound PROfusion™-molecules are eluted from the beads and are subjected to a new PROfusion™-formation cycle as shown in (FIG. 2). By successive rounds of selection and re-amplification along with a fine adaptation of stringency conditions a population of highly specific binding molecules to the given target is enriched (10). Subsequently the DNA-portion of this population is cloned into an E. coli plasmid vector to isolate individual variants that can be analyzed in detail by sequencing.

Six successive selection rounds against immobilized PT have been performed with the gurmarin PROfusion™-library. According to the perception described above, biotinylated PT immobilized to streptavidin beads has been used in these selections (Table 1). In selection round 4, a low background binding of the gurmarin pool to streptavidin beads has been observed which might indicate a starting enrichment of bead and/or streptavidin binding gurmarin variants. Therefore, in the following fifth selection round two individual selections were performed using biotin/streptavidin immobilized PT as target and epoxy bead coupled PT, respectively. In both selections, a clear background corrected enrichment of target binding was observed (Table 1). This trend has been confirmed in the sixth selection round using biotin/streptavidin immobilized PT, clearly indicating an accumulation of PT-binding variants (Table 1).

A. Cloning of Selected Gurmarin Binder Pools

The gurmarin DNA-pools resulting from selection rounds R4, R5 and R6 were cloned into the pCR®2.1-TOPO®-vector using the TOPO TA Cloning® kit (Invitrogen). The gurmarin DNA was ligated to the pCR®2.1-TOPO®-vector in different concentrations. For 6 µl reactions, 0.5 µl, 2 µl and 4 µl of the gurmarin pool DNA were used respectively. The ligation was performed according to the manufacturer's instructions.

Two (2) µl of these ligations were transformed into 20µl of the E. coli Top 10 F' competent cells (Invitrogen) and spread out on LB plates containing 50 µg/ml Kanamycin and 0.5% Glucose. From each of these transformations 150 single colonies were picked to a masterplate containing 50 µg/ml Kanamycin and 0.5% Glucose to repress T7 dependent protein expression and a second plate containing X-Gal and IPTG for a blue white screening. For each transformation, 96 of the colonies from the repressed masterplate corresponding to the white colonies from the blue white test were used to inoculate a 96 well LB agar plate and 500 µl liquid cultures (LB containing 50 µg/ml Kanamycin and 0.5% Glucose). The 96 well agar plates were sent out for commercial sequencing service. The liquid cultures were mixed with 500 µl 40% Glycerol, frozen in liquid nitrogen and stored at −80° C.

TABLE 2

Selection overview of PP26 selection against immobilized PT
Target: Pertussis toxin　　　　　　　　　　　　　　Library: PP26

| | | R1 | R2 | R3 | R4 | epoxy bead Imm. PT R5a | biot PT R5b | biot PT R6a | biot PT R6b |
|---|---|---|---|---|---|---|---|---|---|
| 1. | PCR | | | | | | | from R5a | from R5b |
| | 1.1 Analytical RT-PCR | | | | | | | | |
| | specific signal after x rounds of PCR | | 18 | 18 | 24 | 24 | | | |
| | control signal after y rounds of PCR | | 21 | 24 | 24 | 24 | | | |
| | 1.2 Preparative PCR | | | | | | | | |
| | done with z rounds of PCR | | 36 | 30 | 30 | 32 | | | |
| | quality | | | single band | single band | single band | | | |
| 2. | In vitro transcription | | | | | | | | |
| | scale | | 2 × 500μ | 1 × 500μ | 1 × 500μ | 1 × 500μ | | | |
| | DNase digestion done | | no | no | yes | yes | | | |
| | quality | | | | | | | | |
| 3. | NAP5 gel filtration | | | | | | | | |
| | Inp/E1/E2/E3 | | 500/500/400/200 | | 500/300/400/200 | 500/300/400/200 | | | |
| | yield purified RNA in pooled E2 (OD260) | | 28 nmol | 16 nmol | 6.3 nmol | 12.4 nmol | | | |
| 4. | Linker coupling | | | | | | | | |
| | Linker type | | PEG2 | PEG2 | PEG2 | PEG2 | | | |
| | input | | 6 nmol | 4.5 nmol | 5 nmol | 5 nmol | | | |
| | coupling efficiency | | 70% | 70% | 70% | 70% | | | |
| | yield linker coupled RNA | | 4.2 nmol | 3.15 nmol | 3.5 nmol | 3.5 nmol | | | |
| | quality | | | | | | | | |
| 5. | In vitro Translation and Fusagen formation | | | | | | | | |
| | input | | 4.2 nmol | 3.15 nmol | 3 nmol | 3 nmol | | | |
| | RNA/200 | | 260 pmol | 260 pmol | 250 pmol | 250 pmol | | | |
| | salt inclubation at 20° C. | over weekend | over night | over night | over night | over night | | | |
| 6. | Oligo(dT) purification | | | | | | | | |
| | purified on x columns | | ? | 4 | 4 | 4 | | | |
| | efficiency | 8% | 2.1% | 1.89% | 2.16% | 5.8% | | | |
| | yield | | 88 pmol | 56.7 pmol | 64.9 pmol | 175 pmol | | | |
| 7. | Reverse transcription | | | | | | | | |
| | conditions | | 1 mM DTT | 1 mM DTT | 1 mM DTT | 1 mM DTT | | | |
| | input | | 66 pmol (¾) | 42.5 pmol (¾) | 40.3 pmol (¾) | 50 pmol (¾) | | | |
| | efficiency of RT | | | | | | | | |
| | yield of RT-RNA | | | | | | | | |
| | portion of reverse transcribed Fusagens | | | | | | | | |
| 8. | His-Tag purification on Ni-NTA agarose | | | | | | | | |
| | conditions: endoconcentration of DTT from RT | | 0.75 mM | 0.7 mM | 0.52 mM | 0.5 mM | | | |
| | input | | 88 pmol | 42.5 pmol (RT Ansatz, ohne nicht-RT) | 47 pmol (¾ RT + ¼ OdT | 45 pmol RT + 21 pmol RNA | | | |
| | efficiency | 34% | 25% | 30.6% | 35% | 41% | | | |
| | yield | 55 pmol[17-2] | 19.7 pmol | 12.2 pmol | 16.5 pmol | 27.6 pmol | | | |
| | in volume of | Oligo(dT) purification | 450μ | 300μ | 450μ | 450μ | | | |
| 9. | Selection | | | | | | | | |
| | selection volume | 1 ml | 1 ml | 1 ml | 1 ml | 1 ml | 1 ml | 1 ml | 1 ml |
| | input | 18 pmol | 5 pmol | 5.3 pmol | 5 pmol | 5 pmol | 5 pmol | 5 pmol | 5 pmol |
| | final concentration of immidazol | 25 mM | 18 mM | 19.5 mM | 6 mM | 12.3 mM | 11.4 mM | 24 mM | 34.3 mM |
| | preclear | 5 × 100 streptavidin beads | 5 × 100 streptavidin beads | 3 × 100 epoxy beads | | 2 × 100 blocked epoxy beads bioEirt | 3 × 100 blocked, biotin saturated streptavidin beads | 3 × 100 blocked, biotin saturated streptavidin beads | 3 × 100 blocked, biotin saturated streptavidin beads |

TABLE 2-continued

Selection overview of PP26 selection against immobilized PT
Target: Pertussis toxin    Library: PP26

|  | R1 | R2 | R3 | R4 | epoxy bead Imm. PT R5a | biot PT R5b | biot PT R6a | biot PT R6b |
|---|---|---|---|---|---|---|---|---|
| first preclear binding % | 0% | 0.5% | background | 0.5% | 42 dpm | 0.3% | 278/214/208 dpm | 72/30/37 dpm |
| selection on biotinylated Pertussis toxin$^{(R2\text{-}2)}$ | serie 1 | serie 1 |  | serie 1 |  | serie 1 | serie 1 | serie 1 |
| Expoxy-bead coupled PT |  |  | serie 1 |  | serie 2 |  |  |  |
| PT-beads saturated with a puis of biotin | yes | yes | yes | yes | no | yes | yes | yes |
| effective concentration of PT | 50 nm$^{(17\text{-}1)}$ | 50 nm$^{(17\text{-}1)}$ | 50 nm$^{(17\text{-}1)}$ | 50 nm$^{(17\text{-}3)}$ | 50 nm | 100 nm (50 nm) | 100 nm (50 nm) | 100 nm (50 nm) |
| conditions | over night at 4° C. | 60 min at RT | 90 min at RT | 60 min at RT | 90 min at RT | 90 min at RT | 90 min at RT | 90 min at RT |
| specific binding % | — | — | — | 1.2% | 0.5% | 4.2% | 2.8% | 3.5% |

From each individual clone, plasmid DNA was prepared and subjected to an automated DNA-sequencing procedure using a M13-primer 5'-TGT AAA ACG ACG GCC AGT-3' (SEQ ID NO: 25). As shown in FIGS. 3-8, a single gurmarin sequence variant begins to be significantly enriched in selection round 4 and represents >90% of all sequences after selection round 6. This clearly indicates that this variant probably binds with the highest affinity to PT. In addition to this most prominent sequence variant, a variety of other gurmarin sequences have been enriched that partially share common sequence motifs. This finding indicates that these other sequences show affinity towards PT as well.

B. PP26 Affinity Selection Against Immobilized PT

In parallel to the gurmarin selection six successive selection rounds against immobilized PT have been performed with the PP26 PROfusion™-library. Biotinylated PT immobilized to streptavidin beads has been used in these selections (Table 2). In selection round 4, a low background binding of the gurmarin pool to streptavidin beads has been observed which might indicate a starting enrichment of bead and/or streptavidin binding PP26 variants. Therefore, in the following fifth selection round two individual selections were performed using on the one hand biotin/streptavidin immobilized PT as target and on the other hand epoxy bead coupled PT. In both selections a clear background corrected enrichment of target binding have been detected (Table 2). This trend was confirmed in the sixth selection round using biotin/streptavidin immobilized PT, thus, clearly indicating an accumulation of PT-binding variants.

C. Cloning of Selected PP26 Binder Pools

The PP26 DNA-pools resulting from selection rounds R4, R5 and R6 were cloned into the pCR®2.1-TOPO®-vector using the TOPO TA Cloning® kit (Invitrogen). The PP26 DNA was ligated to the pCR®2.1-TOPO®-vector in different concentrations. For 6 µl reactions 0.5 µl/2 µl and 4 µl of the gurmarin pool DNA were used respectively. The ligation was performed according to the manufacturer's instructions. 2 µl of these ligations were transformed into 20 µl of the E. coli Top 10 F' competent cells (Invitrogen) and spread out on LB plates containing 50 µg/ml Kanamycin and 0.5% Glucose. From each of these transformations 150 single colonies were picked to a masterplate containing 50 µg/ml Kanamycin and 0.5% Glucose to repress T7 dependent protein expression and a second plate containing X-Gal and IPTG for a blue white screening. For each Transformation 96 of the colonies from the repressed masterplate corresponding to the white colonies from the blue white test were used to inoculate a 96 well LB agar plate and 500 µl liquid cultures (LB containing 50 µg/ml Kanamycin and 0.5% Glucose). The 96 well agar plates were sent out for commercial sequencing service. The liquid cultures were mixed with 500 µl 40% Glycerol, frozen in liquid nitrogen and stored at −80° C.

D. Sequencing of Individual Binder Variants

From each individual clone plasmid DNA was prepared and subjected to an automated DNA-sequencing procedure using a M13-primer 5'-TGT AAA ACG ACG GCC AGT-3' (SEQ ID NO: 25). As shown in FIGS. 9-14, two main variants have been enriched during the selection rounds. Both variants share a common conserved sequence motif. This finding indicates that the side chains of the conserved amino acids putatively establish a direct interaction with a certain PT surface region. Furthermore, at least 4 additional variants have been enriched at lesser extent. Since these variants do not comprise the above mentioned conserved sequence motif it can be concluded that these variants potentially bind to different surface regions of PT.

E. Validation of Selected PT-Binding Gurmarin- and PP26-Variants

Since the selections were performed with PROfusion™-molecules—mRNA-peptide-fusions—it is necessary in the first step of the post selection analysis to check the free peptides for their ability to bind do the target. In the next step, those variants that establish their target binding through the peptide and not the nucleic acid portion are subjected to a specificity test in the presence of AP process fluids. By this measure, those variants should be identified that are most suitable to the AP process.

1. Test of Free Peptides for Their Binding Capacity to PT

For a qualitative binding assay of free peptides of single enriched gurmarin- and PP26-binder variants the TNT T7 coupled Reticolocyte Lysat System (Promega #L5540) was used, as follows. DNA of single binder candidates was amplified by colony-PCR out of the glycerol stock of binder clones. To avoid mutations during PCR a proofreading polymerase (Pwo) was used. The PCR products were analyzed on a 2% agarose gel. 5.0 μl of PCR product were used as template for coupled in vitro transcription/translation reaction using the TNT system in a final volume of 53 μl according to the manufacturers instructions. Expressed binder candidates were subsequently purified by Ni-NTA chelat chromatography (QIAGEN). Radioactively labeled His-tag purified binder candidates (~40-70 fmol of each peptide) were incubated with biotinylated PT immobilized on streptavidin-magnetic beads for 1 h at RT. The beads were washed 3× with HBS-buffer and then resuspended in water and analyzed by liquid scintillation counting. In control experiments each candidate was incubated with streptavidin beads only (without PT). The best binder candidates of PP26 and gurmarin were identified (Tables 3 and 4, below) and were subjected to the following specificity test.

2. Specificity Test of Gurmarin and PP26 Variants in the Presence of Process Fluids For a semi-quantitative binding and specificity assay of free gurmarin and PP26 peptides in the presence of Aventis Pasteur process fluids the peptides were first produced as PROfusion™, purified to homogeneity and than transferred to free peptides by an S1-nuclease digest. For amplification of a sufficient amount of DNA of the selected binder variants (10 Gurmarin clones and 7 PP26 clones) a PCR was performed using a PCR product from TNT expression as template. After 10 cycles of PCR (94° C., 30 sec; 60° C., 30 sec; 72° C., 30 sec) the samples were analyzed on a 2% agarose gel. dsDNA (PCR product) was transcribed into RNA using the RiboMax Express In vitro transcription kit from Promega. After incubation for 45 min at 37° C., DNase I was added and the incubation at 37° C. continued for an additional 15 minutes. This mixture was subjected to a phenol/chloroform extraction. Excess of NTPs was removed by NAP-5 gel filtration (Pharmacia). RNA was analyzed on a 6%-TBU-gel.

Purified RNA was annealed (85° C. 1 min cool down to 25° C. at a ramp of 0.3° C./s) to a 1.5-fold excess of puromycin-oligonucleotide linker PEG2A18: 5'-psoralen-UAG CGG AUG C $A_{18}$ $(PEG-9)_2$ CC puromycin (nucleotides shown in italics represent 2'-O-methyl-derivatives: SEQ ID NO: 17). The covalent coupling was performed by illumination for 15 min at RT (RT) with UV-light (365 nm). The reaction product was analyzed on 6%-TBU gel. Ligated RNA was translated using the rabbit reticulocyte lysate from Promega in the presence of 15 µCi $^{35}$S-methionine (1000 Ci/mmole). After a 30 min incubation at 30° C., KCl and $MgCl_2$ were added to a final concentration of 530-mM and 150 mM respectively and a sample was analyzed on 4-20% Tris/glycine-SDS-PAGE. mRNA-protein fusions (PROfusions™) were isolated by incubation with oligo dT magnetic beads (Miltenyi) in incubation buffer (100 mM Tris-HCl pH 8.0, 10 mM EDTA, 1 mM NaCl and 0.25% Triton X-100) for 5 min at 4° C. PROfusion™ molecules were isolated by filtration through Mini-MACS-columns (Miltenyi), washing with incubation buffer and elution with water. A sample was analyzed on 4-20% Tris/glycine-SDS-PAGE.

To remove the mRNA part of the mRNA-protein fusions the oligo dT purified molecules were digested with S1-Nuclease (S1-Nuclease cleaves the DNA-part of the Puromycin linker) according to the manufacturers instructions. Samples of the PROfusion molecules before and after S1-digest were analyzed on 4-12% Bis/Tris SDS-PAGE. Streptavidin beads (M280 Dynal) were washed in HBS and incubated o/n at 4° C. Biotinylated PT (900 pmol) was incubated with 900 µl Strep-beads (preblocked in HBS buffer) for 1 h at RT. After immobilization of PT, the beads were blocked with biotin (2 mM biotin in HBS) for 1 min and immediately washed 4× with HBS buffer to remove any traces of biotin. Control beads (without PT) were blocked with biotin in the same way.

For binding analysis of the selected peptides several parallel reactions were set up, as follows: negative control only with biotin blocked Streptavidin beads; positive control with PT immobilized on Streptavidin beads; background control with biotin blocked beads in combination with ¼ volume Aventis Pasteur sample-solution C (flow through 1. AF column); mix of PT in combination with ¼ volume of sample-solution C; background control with biotin blocked beads in combination with ¼ volume of Aventis Pasteur sample-solution E (culture medium); mix of PT in combination with ¼ volume of sample-solution E; reactions 3-6 were performed to investigate the capacity of the selected peptides to bind PT specifically in the presence of samples provided by Aventis Pasteur. Binding was done for 1 h at RT in the presence of a protease inhibitor mix (complete mini™ ROCHE), to avoid degradation of the peptides. After washing with HBS solution the beads were analyzed by scintillation counting.

As shown in Table 3, three (#9, 10 19) of the ten tested gurmarin variants show a target binding to PT that is not influenced by any of the AP process fluids. These variants are the most promising candidates for affinity chromatographic applications within the AP process.

As shown in Table 4 three (#5, 6 9) of the seven tested PP26 variants show target binding to PT that is not reduced by the AP process fluids. These variants are the most promising candidates for further affinity chromatographic applications within the AP process.

TABLE 3

Post selection analysis of gurmarin-variants*

| # | seq # | peptide sequence | test 1 | test 2 | SEQ ID |
|---|---|---|---|---|---|
| 1 | 194227 | MHHHHHHSGSSSGSGCVKKDELCAGSVGHCCEPLECLRRFLNLRWCGSGSSGSS | – | n.d. | 26 |
| 2 | 194238 | MHHHHHHSGSSSGSGCVKKDELCIVMRAPCCEPLECLRRYMLKHMCGSGSSGSS | – | n.d. | 27 |
| 3 | 194239 | MHHHHHHSGSSSGSGCVKKDELCKAFRYSCCEPLECLRKWLKARFCGSGSSGSS | – | n.d. | 28 |
| 4 | 194251 | MHHHHHHSGSSSGSGCVKKDELCLRSSIDCCEPLECLYKWMQRRLCGSGSSGSS | – | n.d. | 29 |
| 5 | 194210 | MHHHHHHSGSSSGSGCVKKDELCWPRRHKCCEPLECLLEMLERKRCGSGSSGSS | – | n.d. | 30 |
| 6 | 194261 | MHHHHHHSGSSSGSGCVKKDELCMSMACVCCEPLECKYHGYFWLCGSGSSGSS | – | n.d. | 31 |
| 7 | 194214 | MHHHHHHSGSSSGSGCVKKDELCAVWFDVCCEPLECTYQSGYYWLCGSGSSGSS | – | n.d. | 32 |
| 8 | 194226 | MHHHHHHSGSSSGSGCVKKDELCEPWYWRCCEPLECVYTSGYYYSCGSGSSGSS | – | n.d. | 33 |
| 9 | 194259 | MHHHHHHSGSSSGSGCVKKDELC*ARWDLV*CCEPLEC*IYTSELYAT*CGSGSSGSS | ✓ | ✓ | 34 |
| 12 | 194297 | MHHHHHHSGSSSGSGCVKKDELCVFYFPNCCEPLECRWVNDNYGWCGSGSSGSS | ✓ | – | 35 |

TABLE 3-continued Post selection analysis of gurmarin-variants*

| # | seq # | peptide sequence | test 1 | test 2 | SEQ ID |
|---|---|---|---|---|---|
| 13 | 194330 | MHHHHHHSGSSSGSGCVKKDELCMSMACVCCEPLECKYHGYFWLCGSGSSSGSS | ✓ | — | 36 |
| 14 | 194479 | MHHHHHHSGSSSGSGCVKKDELCTTASKSCCEPLECKWTNEHFGTCGSGSSGSS | ✓ | — | 37 |
| 15 | 194511 | MHHHHHHSGSSSGSGCVKKDELCSQSVPMCCEPLECKWFNENYGICGSGSSGSS | ✓ | — | 38 |
| 16 | 194533 | MHHHHHHSGSSSGSGCVKKDELCARWDLVCCEPLECIYTSELYATCGSGSSGSS | ✓ | — | 39 |
| 17 | 194486 | MHHHHHHSGSSSGSGCVKKDELCARWDLVCCEPLECLGHGLGYAYCGSGSSGSS | — | n.d. | 40 |
| 18 | 194668 | MHHHHHHSGSSSGSGCVKKDELCMWSREVCCEPLECYYTGWYWACGSGSSGSS | — | — | 41 |
| 10 | 194264 | MHHHHHHSGSSSGSGCVKKDELC*ELAVDE*CCEPLEC*FQMGHGFKR*CGSGSSGSS | ✓ | ✓ | 42 |
| 19 | 194737 | MHHHHHHSGSSSGSGCVKKDELC*ELAVDE*CCEPLEC*TKGDLGFRK*CGSGSSGSS | ✓ | ✓ | 43 |
| 20 | 194716 | MHHHHHHSGSSSGSGCVKKDELCELAIDVCCEPLECLGHGLGYAYCGSGSSGSS | ✓ | n.d. | 44 |
| 21 | 194720 | MHHHHHHSGSSSGSGCVKKDELCELAIDVCCEPLECLGHGLGYAYCGSGSSGSS | — | — | 45 |
| 11 | 194328 | MHHHHHHSGSSSGSGCVKKDELCNWVTPMRCEPLECLGHGLGYAYCGSGSSGSS | ✓ | n.d. | 46 |

*Test 1 represents the target binding ability of free peptides (0) and test 2 represents the binding specificity of variants in the presence of AP process fluids (0). Variants that are positive in both assays are 9, 10, and 19.?

TABLE 4

Post selection analysis of PP26-variants*

| # | seq # | peptide sequence | test 1 | test 2 | SEQ ID |
|---|---|---|---|---|---|
| 1 | 197569 | MGRGSHHHHHHARSDWELSPPHVAITTRHLINCTDGPLLRDANAPKASAI | — | n.d. | 47 |
| 2 | 197536 | MGRGSHHHHHHARSLNGESTSNILTTSRKVTEWTGYTASVDANAPKASAI | — | n.d. | 48 |
| 3 | 197611 | MGRGSHHHHHHARSQVTWHHLADTVTTKNRKCTDSYIGWNXANAPKASAI | — | n.d. | 49 |
| 4 | 197530 | MGRGSHHHHHHARSIIVIHNAIQTHTPHQVSIWCPPKHNRDANAPKASAI | — | n.d. | 50 |
| 5 | 197557 | MGRGSHHHHHHARSSHCRHRNCHTITRGNMRIETPNNIRKDANAPKASAI | ✓ | ✓ | 51 |
| 6 | 197596 | MGRGSHHHHHHARSTMNTNRMDIQRLMTNHVKRDSSPGSIDANAPKASAI | ✓ | ✓ | 52 |
| 7 | 197552 | MGRGSHHHHHHARSLSALRRTERTWNTIHQGHHLEWYPPADANAPKASAI | — | n.d. | 53 |
| 8 | 197541 | MGRGSHHHHHHARSWTSMQGETLWRTDRLATTKTSMSHPPDANAPKASAI | — | n.d. | 54 |
| 9 | 197588 | MGRGSHHHHHHARSNVIPLNEVWYDTGWDRPHRSRLSIDDDANAPKASAI | ✓ | ✓ | 55 |
| 10 | 197635 | MGPGSHHHHHHARSCLATRNGFV.MNTDRGTYVKRPTVLQDANAPKASAI | ✓ | — | 56 |
| 11 | 197797 | MGRGSHHHHHHARSWGLSGTQTWKITKLATRLHHPEFETNDANAPKASAI | — | n.d. | 57 |
| 12 | 197888 | MGRGSHHHHHHARSWRWHNWGLSDTVASHPDASNSLNMMYDANAPKASAN | — | n.d. | 58 |
| 13 | 197897 | MGRGSHHHHHHHLDLWGPPSGSPRTRSTTGTSTTSSPSTPGTLTLRRHPH | — | n.d | 59 |
| 14 | 197825 | MGRGSHHHHHHARSWQPEVKMSSLVDTSQTVGAAVETRTTDANAPKASA | ✓ | — | 60 |
| 15 | 198000 | MGRGSHHHHHHARSWRDTRKLHMRHYFPLAIDSYWDHTLRDANAPKASAI | ✓ | — | 61 |
| 16 | 197983 | MGRGSHHHHHHHRSWTSMQGETLWRTDRLATTKTSMSHPPDANAPKASAI | — | n.d. | 62 |
| 17 | 197998 | MGRGSHHHHHHARSPLWYHYNCWDTICLADWLKDRPHGVYDANAPKASA | — | n.d. | 63 |
| 18 | 197947 | MGRGSHHHHHHARSVGTTIRIAQDTEHYRNVYHKLSQYSRDANAPKASAI | ✓ | — | 64 |

TABLE 4-continued

Post selection analysis of PP26-variants*

| # | seq # | peptide sequence | test 1 | test 2 | SEQ ID |
|---|---|---|---|---|---|
| 19 | 197954 | MGRGSHHHHHHARSVGTTIRIAQDTEHYRNVYHKLSQYSRDANAPKASAI | — | n.d. | 65 |
| 20 | 197971 | MGRGSHHHHHHARSNVIPLNEVWYDTGWDRPHRSRLSIDDDANAPKASAI | — | n.d. | 66 |

*Test 1 represents the target binding ability of free peptides (0) and test 2 represents the binding specificity of variants in the presence of AP process fluids (0). Variants that are positive in both assays are 5, 6 and 9.?

F. Peptide Production by Chemical Synthesis

Eight different peptides were produced by chemical synthesis in form of N-terminal biotinylated peptides. The Biotin group was spaced via a short hydrophilic linker (PEG2=8-Amino-3,6-dioxaoctanoic acid). Two of these 8 peptides (PP26-5c and gumarin-9c) were additional synthesized in form of C-terminal tagged biotinylated peptides (via an additional C-terminal Lysine). The peptides were automatically synthesized using the Fmoc/But strategy according to Sheppard, purified by HPLC and subsequently lyophilized. The quality of all purified peptides was confirmed by mass spectroscopy. The target quantity of each peptide synthesis was 5 mg purified peptide. An overview about yield and purity of the synthetic peptides after purification is given in Table 5.

TABLE 5

Peptide Synthesis of Pertussis Toxin Binding Peptides*

| Selection | Clone | Seq # | Sequence | Purity (%) | Yield (mg) | SEQ ID |
|---|---|---|---|---|---|---|
| pp26 | 5 c | 197557-1 | RSSHCRHRNCHTITRGNMRIETPNNIRKDAK | 90-95 | 7.7 | 67 |
| pp26 | 5 n | 197557-2 | RSSHCRHRNCHTITRGNMRIETPNNIRKDA | 90-95 | 7.6 | 68 |
| pp26 | 6 n | 197596-1 | RSTMNTNRMDIQRLMTNHVKRDSSPGSIDA | 90-95 | 6.3 | 69 |
| pp26 | 9 n | 197588-1 | RSNVIPLNEVWYDTGWDRPHRSRLSIDDDA | 90-95 | 5.8 | 70 |
| pp26 | 15 n | 198000-1 | RSWRDTRKLHMRHYFPLAIDSYWDHTLRDA | 90-95 | 4.8 | 71 |
| gurmarin | 9 c | 194259-1 | SGCVKKDELCARWDLVCCEPLECIYTSELYATCGK | 70 | 1.0 | 72 |
| gurmarin | 9 n | 194259-1 | SGCVKKDELCARWDLVCCEPLECIYTSELYATCG | 80-90 | 4.0 | 73 |
| gurmarin | 10 n | 194264-1 | SGCVKKDELCELAVDECCEPLECFQMGHGFKRCG | 90-95 | 4.9 | 74 |
| gurmarin | 15 n | 194511-1 | SGCVKKDELCSQSVPMCCEPLECKWFNENYGICGS | 90-95 | 6.3 | 75 |
| gurmarin | 19 n | 194737-1 | SGCVKKDELCELAIDECCEPLECTKGDLGFRKCG | 90-95 | 6.7 | 76 |

*Abbreviation c in the clone name indicates C-terminal biotinylated peptides, abbreviation n indicates N-terminal biotinylated peptides.

All pp26 peptides were dissolved in 100 mM HEPES, pH 7.4, 200 mM NaCl with a final concentration of 100 µM. All gurmarin peptides were dissolved in 100 mM HEPES, pH 7.4, 200 mM NaCl, 2 mM GSH, 1 mM GSSG with a final concentration of 100 µM and subsequently incubated under nitrogen for at least 48 hours to allow structural folding.

G. Peptide Production by Bacterial Expression

The peptides which were identified as binders to the pertussis toxin were subcloned in frame to glutathione-S-transferase (GST) and expressed bacterially. The GST-tag enhances the solubility and allows purification using Glutathione Sepharose. An enginered protease cleavage site recognized by the specific PreScission™ protease allows removal of the GST-tag releasing the peptide. The PreScission™ protease itself is a fusion protein of GST and human rhinovirus (HRV) type 14 3C protease and specifically recognizes the sequence Leu-Phe-Gln*Gly-Pro cleaving between the Gln and Gly residues. After the cleavage the uncleaved product as well as the protease can be removed from the cleavage reactions using Glutathione Sepharose.

H. Construction of Expression Vectors

1. Construction of GST Fusions for pp26-Variants

As template for PCR served the pCR2.1 vector containing the sequences of the identified pp26 binders to PT. The products obtained in a PCR using the oligonucleotides #467 (5'-CATGCCATGGGACGTGGCTCACATCATC-3'; SEQ ID NO: 77) and #468 (5'-phosphate-GGGTTAAATAGCGGATGCCTTCGGAGCGTTAGCGTC-3'; SEQ ID NO: 78) with Pwo DNA polymerase (Roche) were digested with NcoI (New England Biolobs). A modified vector (pGEX6P (Amersham/Pharmacia) containing an additional NcoI site) was digested with NcoI/SmaI (New England Biolobs) and the PCR product was directionally cloned into the NcoI/SmaI site of this vector. After transformation in TOP10 (Invitrogen) positive clones were identified by colony PCR and verified by sequencing.

2. Construction of GST Fusions for Gurmarin-Variants

As template for PCR served the pCR2.1 vector containing the sequences of the identified gurmarin binders to PT. The products obtained in a PCR using the oligonucleotides #464 (5'-GGAGATCTCATATGCACCATCACCAT-CACCATAGTG GC-3'; SEQ ID NO: 79) and #465 (5'-phosphate-GGGTTAAATAGCG GATGCTACTAGGC-3'; SEQ ID NO: 80) with Pwo DNA polymerase (Roche) were digested with NdeI (New England Biolobs). A modified vector (pGEX6P (Amersham/Pharmacia) containing an additional NdeI site) was digested with NdeI/SmaI (New England Biolobs) and the PCR product was directionally ligated into the Nde/SmaI site of this vector. After transformation in TOP10 (Invitrogen) positive clones were identified by colony PCR and verified by sequencing (Table 6).

TABLE 6

Vectors used for bacterial expression

| Plasmid number | |
|---|---|
| | pp26 |
| pS840 | pGEX6P-(His)$_6$-pp26 K5 |
| pS850 | pGEX6P-(His)$_6$-pp26K6 |
| pS841 | pGEX6P-(His)$_6$-pp26K9 |
| pS842 | pGEX6P-(His)$_6$-pp26K15 gurmarin |
| pS836 | pGEX6P-(His)$_6$-gurmarin K9 |
| pS837 | pGEX6P-(His)$_6$-gurmarin K10 |
| pS838 | pGEX6P-(His)$_6$-gurmarin K15 |
| pS839 | pGEX6P-(His)$_6$-gurmarin K19 |

3. Expression and Purification of GST-pp26 Fusions

The bacterial strain Rosetta (DE3) pLysS (Novagen) was transformed with plasmid DNA (see Table). The transfomands of the pp26 variants were grown at 37° C. 250 rpm to an OD$_{600}$ of ~0.5 and induced by the addition of 1 mM IPTG for 4 h. In case of gurmarin-GST-fusions the induction was performed for 2.5 hours using 0.33 mM IPTG. After harvesting the bacterials, cells were resuspended in PBS-KMT (10 mM Na phosphate, pH 7.5, 130 mM NaCl, 3 mM KCl, 1 mM MgCl, 0.1% Tween-20), containing 1 mM 2-Mercaptoethanol, protease inhibitors and 1 mM Lysozyme, incubated for 30 min at RT and disrupted by sonification. The soluble supernatant after centrifugation was transferred to GSH sepharose column for purification. After washing the column with 10 column volumes of 20 mM Hepes, pH 7.5, 150 mM NaCl the GST fusion protein was eluted with 20 mM GSH and analyzed on a SDS gel to confirm expression.

4. Peptide Generation by Removal of GST Tag by Cleavage with PreScission™ Protease An example for PreScission™ cleavage of one peptide from the GST-peptide fusion is shown below. The GST-tag was removed by incubation with PreScission™ Protease (Amersham Pharmacia): 2.5 mg of fusion protein was incubated with 160 U PreScission™ and digested for 16 hours at 5° C. on the sealed GSTrap FF column containing the bound GST fusion protein. After the overnight incubation a second GSTrap FF column was connected to remove the GST-tagged protease PreScission™. The sample was applied with a flow rate of 0.2 ml/min, the flow through was collected in small aliquot samples and analyzed by SDS gel electrophoresis and the amount of peptide was calculated by OD$_{280}$ measurement (ca. 700 µg).

Example 3

Affinity Purification of PT

A. Analysis of Fermentation Supernatant on Denaturing Gels

Two process fluids were considered as potential starting material for affinity chromatography process:
Sample A Concentrated culture filtrate containing 10-50 µg/ml (~0.09-0.45 µM) crude PT, fermentation supernatant
Sample B Absorption chromatography supernatant containing 9-45 µg/ml (~0.08-0.4 µM) crude PT To visualize the complexity of these process fluids, both samples were analyzed by denaturating polyacrylamid gelelectrophoresis. Mainly high molecular weight components of sample A are removed by the absorption chromatography (sample B).

B. Immobilization of Synthetic Biotinylated Core Peptides to Streptavidin Sepharose and Verification of Binding to Purified PT 1. Peptide Immobilization to Streptavidin Sepharose For binding of biotinylated peptides to streptavidin sepharose (Amersham High Performance 71-5004-40), 200 μl of 50% slurry of pre-washed streptavidin sepharose were incubated with 1 nmol peptide (10 μl of 100 μM peptide solution) in 1 ml HEPES buffer (20 mM HEPES, pH 7.5, 150 mM NaCl, 0.025% TritonX-100) at 4° C. Under the applied conditions the high binding capacity of streptavidin sepharose should allow immobilization of 100% of the biotinylated peptide (10 pmol peptide per pl packed sepharose).

2. Binding of Purified PT to Immobilized Peptides

200 μl of sepharose loaded with peptides (10% ige slurry, containing immobilized ~200 pmol peptide) were transferred to a Mobicol column (MoBiTec, 10 μm filter) and the supernatant was removed by centrifugation for 1 min at 2000 rpm. After 4 washes with HEPES buffer, the sepharose was resuspended in 200 μl HEPES buffer containing 100 pmol purified Pertussis Toxin and incubated on a rotating wheel for 1 hour at room temperature. The unbound fraction was separated by centrifugation (supernatant after binding; applied to gel analysis). Subsequently the peptide-streptavidin sepharose was washed three-times with cold HEPES buffer (each 200 μl) and resuspended in 20 μl loading buffer (30 mM Tris, pH 6.8, 1% SDS, 1% β-Mercaptoethanol, 12.5% Glycerol, 0.005% Bromphenol Blue) to elute bound PT. After 5 min incubation at 95° C. the loading buffer was collected by centrifugation and subsequently used for gel analysis (FIG. 15). As a control streptavidin sepharose without peptide was contacted with PT under identical conditions. Under the applied conditions the Pertussis toxin peptide binder clones pp26 5n, 5c, 9n, 15n and the gurmarin clones 10n, 19n, 15n, 9n show a clear binding to purified PT. All positive binder candidates were able to bind the intact hexameric PT.

C. Immobilization of Synthetic Biotinylated Core Peptides to Streptavidin Sepharose and Verification of Binding to PT out of the Fermentation Supernatant Peptide immobilization to streptavidin sepharose and binding analysis to PT out of fermentation supernatants was performed as described in chapter 0 with the exception that the peptide streptavidin sepharoses were incubated with 200 μl Sample A (fermentation supernatant) or with 200 μl Sample B (absorption chromatography supernatant column, see chapter 0) and were subsequently washed 4-times with HEPES buffer at RT. The results of the binding analysis is presented in FIG. 16. Under the applied conditions the Pertussis toxin pp26 binder clones 9n, 15n and the gurmarin clones 9n, 15n were able to bind very efficiently the intact PT hexamer out of the fermentation supernatants Sample A and Sample B. Note that under the applied conditions the pp26 binder clone 5 and the gurmarin binder clones 10 and 19 might bind PT with lower affinity. Although the PT binding to these peptides out of Sample A and Sample B were not detected under the conditions, these binders might be still qualified for application as ligand in an affinity chromatography column (a column allows retention of PT by rebinding effects and therefore would minimize the $k_{off}$ problematic).

D. Thermodynamic Data on Immobilized Peptides

For estimation of peptides binding capacity 20 pmol of sepharose-immobilized peptides were incubated with an excess of 100 pmol PT in a volume of 200 µl HEPES buffer (corresponds to 500 nM PT). After washing, the fraction of peptide-streptavidin sepharose bound PT was quantified by gel analysis. This allows directly to calculate the fraction of binding active peptide under the applied conditions (assuming the PT/peptide binding ratio is 1:1). Under the assumption that a concentration of 500 nM PT is high enough to reach $B_{max}$ for all peptides. The results of the analysis are shown in Table 7. The values presented therein are estimations for the expectable binding capacities of the peptides. An exact evaluation of binding capacity ($B_{max}$) and dissociation constant ($K_D$) of the most suitable binder may also be performed.

TABLE 7

Overview about fraction of binding active peptides under the applied experimental conditions

| Peptide name | pp26 5n | pp26 9n | pp26 15n | gurm 9n | gurm 10n | gurm 15n | gurm 19n |
|---|---|---|---|---|---|---|---|
| Fraction of binding active peptide | >5% [1] | >50% | >12.5% | >12.5% | |>5% [1] | >50% | >5% [1] |

[1] Calculation difficult because signals were near the detection limit

E. Analysis of the Stability of the Purified Pertussis Toxin Hexamer Under Defined Buffer Conditions (pH, Salt Concentration, Detergents), Using Acceptable Quality Grade Raw Materials Versus Health Authorities Requirements The Pertussis toxin hexamer stability was tested under a broad range of pH and salt conditions on a BIAcore 2000 instrument. For this purpose ~2000 RU of biotinylated PT were loaded on a streptavidin chip. Subsequently different buffers were applied to the chip immobilized PT for 2 min with a flow rate of 30 μl/min. After the end of each buffer injection the chip was equilibrated with HBS/EP running buffer (0.01 M HEPES pH 7.4, 0.15 M NaCl 3 mM EDTA 0.005% polysorbate 20 (v/v), at least 2 min with a flowrate of 30 μl/min). The difference of the measured RU signal before and after buffer injection correlates to the reduction of PT hexamer on the chip. This reduction was interpreted as loss of stability of PT hexamer under the aplied buffer conditions.

The analyzed pH range was between pH 2 and 10.5 using the following buffers: 10 mM glycin buffer (BIAcore, pH 2; 2.5; 3), 10 mM acetate buffer (BIAcore, pH 4; 4.5; 5; 5.5), 50 mM Tris/HCl (pH 8.5) and 100 mM carbonate buffer (pH 9.6 and 10.5). BIAcore sensograms demonstrating the influence of the pH on the PT hexamer stability were generated, and the results of the BIAcore analysis are summarized in Table 8. Under the applied conditions, Pertussis toxin hexamer was shown to be stable over a broad pH range between pH 2.5-10.5.

TABLE 8

Pertussis toxin hexamer stability under different pH conditions.

| pH | 2 | 2.5 | 3 | 4 | 4.5 | 5 | 5.5 | 8.5 | 9.6 | 10.5 |
|---|---|---|---|---|---|---|---|---|---|---|
| PT hexamer stability (%) | 93 | 98 | 100 | 100 | 100 | 100 | 100 | 100 | 98 | 95 |

The influence of different salt conditions on the PT hexamer stability were investigated in comparable experiments on the BIAcore 2000 instrument for NaCl, KCl and $MgCl_2$ at pH 5.0 (10 mM acetate buffer) and pH 8.5 (50 mM Tris/HCl) respectively. An overview about PT hexamer stability under the applied salt conditions is shown in Table 9. The hexamer was stable in buffer (at pH 5 and 8.5) containing up to 2.5 M NaCl or up to 2 M KCl. In case of $MgCl_2$ the PT hexamer was stable in a buffer containing up to 2 M $MgCl_2$ at pH 8.5.

TABLE 9

Pertussis toxin hexamer stability under different salt conditions

| PT hexamer stability | pH 5 | pH 8.5 |
|---|---|---|
| NaCl | 0-2.5 M stable | 0-2.5 M stable |
| KCl | 0-2.0 M stable | 0-2.0 M stable |
| $MgCl_2$ | Nd | 0-2.0 M stable |

F. Establish Defined Wash and Elution Conditions Allowing a Specific Affinity Purification of PT Out of Fermentation Supernatant (pH, Salt Concentration, Detergents)

After the determination under which conditions the Pertussis toxin hexamer is stable, the next step was to investigate the wash and elution conditions for the bound Pertussis toxin to the immobilized peptides pp26 clone 9 and 15 and gurmarin clone 9 and 15.

1. Evaluation of PT/Peptide Stability Using the BIAcore 2000 Instrument

The stability of PT/peptide complexes were investigated using the BIAcore 2000 instrument under different pH and salt conditions that were shown before not to interfere with the PT hexamer stability. 500-1000 RU of the synthetic peptides were immobilized on BIAcore streptavidin chips. To allow binding of PT to the immobilized peptides, 20 nM purified PT in HEPES buffer was injected for 1 minute. After equilibration with HBS/EP running buffer (0.01 M HEPES pH 7.4, 0.15 M NaCl 3 mM EDTA 0.005% polysorbate 20 (v/v)) the PT/peptide complexes were washed by injection of (a) 100 mM carbonate buffer at pH 10.5 and 9.5
(b) 10 mM acetate buffer at pH 5.5, 5.0, 4.5, and 4.0
(c) 10 mM glycine buffer at pH 3.0 and 2.5
(d) 0.5, 1.0, 1.5, 2.0 M NaCl in 10 mM acetate buffer buffer, pH6.0,
(e) 0.5, 1.0, 1.5, 2.0 M NaCl in 50 mM Tris/HCl buffer, pH 8.5,
(f) 0.5, 1.0, 1.5, 2.0 M KCl in 10 mM acetate buffer, pH 6.0,
(g) 0.5, 1.0, 1.5, 2.0 M KCl in 50 mM Tris/HCl buffer, pH 8.5,
(h) 0.5, 1.0, 1.5, 2.0 M NaCl in 10 mM acetate buffer, pH 6.0,
(i) 0.5, 1.0, 1.5, 2.0 M NaCl in 50 mM Tris/HCl buffer, pH 8.5.

After the end of each buffer injection, the chip was equilibrated with HBS/EP running buffer. The loss of PT hexamer on the chip under the applied buffer conditions (difference of measured RU signal before and after buffer injection) reflects the PT/peptide complex stability. An overview about the pH range stability and salt stability of all PT/peptide complexes is summarised in Table 10. All of the PT/peptide complexes were completely destabilized in the presence of 100 mM carbonate, pH 10.5 as well as 10 mM glycin, pH 2.5. For gurmarin peptide 9, buffers containing 2.5 M NaCl or at least 0.5 M $MgCl_2$ interfere with PT/peptide complex stability. PT complexes with gurmarin peptide 15 were additionally destabilized in the presence of at least 1.5 M $MgCl_2$ in 50 mM Tris/HCl, pH 8.5).

3. Evaluation of Elution Conditions for Purification of PT on Peptide Streptavidin Sepharose Elution of PT from peptide sepharose was tested under conditions that are compatible with hexamer stability.

a. Elution by $MgCl_2$

As shown above by BIAcore 2000 measurements all PT/peptide complexes were sensitive against 2 M $MgCl_2$, conditions that were shown not to be critical for PT hexamer stability. The elution efficiencies of defined $MgCl_2$ concentrations were evaluated for PT that was bound on streptavidin sepharose via one of the four immobilized synthetic peptides. 400 pmol of each peptide immobilized on 20 μl sepharose were incubated with 100 μl 50 mM Tris/HCl, pH 7.5 and 100 μl sample A to allow binding of PT. After 4 washes with 50 mM Tris/HCl, pH 7.5 (200 μl each), the bound fraction of PT was eluted using 3 consecutive 20 μl volumes of (a) 0.2 M $MgCl_2$ in 50 mM Tris/HCl, pH 8.5, or
(b) 0.5 M $MgCl_2$ in 50 mM Tris/HCl, pH 8.5, or
(c) 1.0 M $MgCl_2$ in 50 mM Tris/HCl, pH 8.5, or
(d) 1.5 M $MgCl_2$ in 50 mM Tris/HCl, pH 8.5, or
(e) 2.0 M $MgCl_2$ in 50 mM Tris/HCl, pH 8.5.

Remaining material was afterwards eluted from the peptide, streptavidin sepharose with 20 μl loading buffer (30 mM Tris, pH 6.8, 1% SDS, 1% β-Mercaptoethanol, 12.5% Glycerol, 0.005% Bromphenol Blue). All elutions were analyzed by PAGE on 12% Bis-Tris-Gels (MES running buffer) and silver staining (FIG. 19). As shown in the experiment elution with $MgCl_2$ was more efficient for the gurmarin peptides than for the pp26 peptides although a substantial amount of PT still remained on the peptide streptavidin sepharose.

b. Elution by pH-Shift

The BIAcore measurements revealed that PT was elutable from all peptides with acidic (pH of 2.5) or basic (pH of 10.5) buffer conditions that were not critical for PT hexamer stability (50 mM glycin, pH 2.5 more gentle for PT hexamer stability than 100 mM carbonat buffer, pH 10.5, see xxx). 200 pmol of each peptide immobilized on 20 μl sepharose were incubated with 100 μl 50 mM Tris/HCl, pH 7.5 and 100 μl sample A to allow binding of PT. After 4 washes with 50 mM Tris/HCl, pH 7.5 (200 μl each), PT was eluted from the peptide streptavidin sepharose by 3 consecutive 40 μl elutions

TABLE 10

Effect of different pH and salt conditions on the stability of the PT/peptide complexes

| | pp26 peptide 9 | | pp26 peptide 15 | | gurmarin peptide 9 | gurmarin peptide 15 | |
|---|---|---|---|---|---|---|---|
| pH range stability of the complex | 3-9 stable, instable at pH 2.5 or 10.5 | | 3-9 stable, instable at pH 2.5 or 10.5 | | 3-9 stable, instable at pH 2.5 or 10.5 | 3-9 stable, instable at pH 2.5 or 10.5 | |
| | pH 6 | pH 8.5 | pH 6 | pH 8.5 | pH 8.5 | pH 6 | pH 8.5 |
| NaCl stability of the complex | 2 M stable | 2 M stable | 2 M stable | 2 M stable | strong sensitive to salt | sensitive to salt | |
| KCl stability of the complex | 2 M stable | 2 M stable | 2 M stable | 2 M stable | strong sensitive to salt | sensitive to salt | |
| $MgCl_2$ stability of the complex | stable | Sensitive from 125 mM, complete elution ≧ 2 M | stable up to 2 M | Elution ≧ 1.5, but not complete | Elution ≧ 0.5 M | Elution ≧ 1 M, complete elution ≧ 2 M | Elution ≧ 1 M, complete elution ≧ 2 M |

2. Evaluation of Wash Conditions for Purification of PT on Peptide Streptavidin Sepharose Wash conditions were tried to apply close to the established conditions for pertussis toxin purification process on asialofetuin (washing with 50 mM Tris/HCl, pH 7.5, with or without 1 M NaCl). The Pertussis toxin purification protocol was optimized for the peptides pp26 clone 9 and 15 and gurmarin clone 9 and 15. 200 pmol of each peptide immobilized on 20 μl sepharose were incubated with 100 μl 50 mM Tris/HCl, pH 7.5 and 100 μl sample A or sample B to allow binding of PT. Subsequently the peptide sepharose with bound PT fraction to was washed under 3 different conditions, as shown below:

(a) 3 times with 200 μl 50 mM Tris/HCl, pH 7.5;
(b) 3 times with 200 μl 50 mM acetate pH 6.0; and,
(c) 6 times with 200 μl 50 mM acetate pH 6.0.

After washing remaining material was eluted, from the sepharose with 20 μl loading buffer (30 mM Tris, pH 6.8, 1% SDS, 1% β-Mercaptoethanol, 12.5% Glycerol, 0.005% Bromphenol Blue). All elutions were subsequently analyzed by PAGE on 12% Bis-Tris-Gels (MES running buffer) and silver staining (FIG. 17).

Washing with 50 mM acetate, pH 6.0, is more stringent and reduces the back ground of high molecular weight impurities more efficient than washing with 50 mM Tris/HCl, pH 7.5. But under these washing conditions the PT/peptide complexes are less stable, especially in case of the gurmarin peptide 9 and repeated washes with 50 mM acetate, pH 6.0 (6 washes). In contrast to 50 mM Tris/HCl, pH 7.5, the loss of peptide immobilized PT was more dramatic when washing with 50 mM acetate, pH 6.0 was repeated 10 to 20 times (as an example shown for pp26 peptide 9 in FIG. 18).

with 50 mM glycin, pH 2.5, or 100 mM carbonate buffer, pH 10.5. Remaining material was subsequently eluted from the peptide streptavidin sepharose with 20 µl loading buffer (30 mM Tris, pH 6.8, 1% SDS, 1% β-Mercaptoethanol, 12.5% Glycerol, 0.005% Bromphenol Blue). All elutions were analyzed by PAGE on 12% Bis-Tris-Gels (MES running buffer) and silver staining (FIG. 20). Nearly all of PT was elutable from the peptide streptavidin sepharose using 50 mM glycine, pH 2.5 as well as using 100 mM carbonate buffer, pH 10.5.

4. Apply Optimized Conditions for Small Scale Purification Scheme, Confirm Binding Capacity a. Purification of PT from Sample B Under Optimized Wash and Elution Conditions (4 µl Column)

Optimized wash and elution conditions were combined to allow the purification of PT on peptide streptavidin sepharoses out of Sample B. To reduce unspecific binding of PT the optimal peptide/streptavidin sepharose ratio was titrated for each peptide before. Subsequently the Sample B/peptide streptavidin sepharose ratio was optimized in respect to high recovery of PT per expectable high (moderate) input of peptide. These conditions were applied to the following small scale column purifications.

For pp26 peptide 9 and gurmarin peptide 15, the immobilization to streptavidin sepharose was performed by incubation of 16 µl streptavidin sepharose with 1600 pmol peptide. In case of pp26 peptide 15, 16 µl streptavidin sepharose was incubated with 6000 pmol peptide (pp26/15 binds with lower efficiency to the streptavidin sepharose, might be explainable by incomplete peptide biotinylation). For gurmarin peptide 9, 8000 pmol were immobilized on 80 µl streptavidin sepharose. Subsequently the washed peptide streptavidin sepharoses were equally subdivided and transferred to 4 Mobilcom columns (with 10 µM filters).

Each column (containing 4 µl sepharose with 400 pmol peptide for pp26/9 and gur/15; 4 µl with undefined amount bound peptide pp26/15; 20 µl with 2000 pmol peptide for gur/9) was incubated with 400 µl Sample B (adjusted to pH 7.0-7.5 by addition of HCl) to allow binding of PT. After 5 washes with 50 mM Tris/HCl, pH 7.5 (each 100 µl), PT was eluted from the peptide streptavidin sepharose by consecutive elutions (3 elutions for pp26/9 and gur/15; 4 elutions for pp26/15 and gur/9), as follows:

(a) with 50 mM glycine, pH 2.5 (each 20 µl) in case of column 1, or (b) with 100 mM carbonate buffer, pH 10.5 (each 20 µl) in case of column 2, or (c) with 2 M $MgCl_2$ in 50 mM Iris, pH 8.5 (each 20 µl) in case of column 3.

Remaining material on column 1-3 as well on column 4 was subsequently eluted from the peptide streptavidin sepharoses by elution with 20 µl loading buffer (30 mM Tris, pH 6.8, 1% SDS, 1% β-Mercaptoethanol, 12.5% Glycerol, 0.005% Bromphenol Blue). All elutions were analyzed by PAGE on 12% Bis-Tris-Gels (MES running buffer) and silver staining (FIGS. 21, 22). To calculate the yield of PT after purification on the peptide streptavidin sepharoses the pooled elutions 1-3 were analyzed by PAGE and silver staining and compared to defined amounts of purified PT separated on the same gel allowing an estimation (FIGS. 21B and 22B). Based on the gel estimation, the yield of purified PT was calculated as shown in Table 11.

TABLE 11

Calculation of the Pertussis Toxin yield after small scale column purification from sample B with pp26 peptide 9 or gurmarin peptide 15 as affinity ligands

| Peptide | Elution with | Estimation from FIG. 13B and 14B | Total yield of PT | Yield relative to input PT in sample B* | Yield relative to the amount of sepharose bound peptide |
|---|---|---|---|---|---|
| pp26 peptide 9 | Glycin pH 2.5 | 2 pmol PT in 3/120 of pooled elutions | 80 pmol | >48% | 20% |
| | Carbonat pH 10.5 elution | 2 pmol PT in 3/120 of pooled elutions | 80 pmol | >48% | 20% |
| | $MgCl_2$ | 1 pmol PT in 6/120 of pooled elutions | 20 pmol | >12% | 5% |
| gurmarin peptide 15 | Glycin pH 2.5 | 2 pmol PT in 3/120 of pooled elutions | 80 pmol | >48% | 20% |
| | Carbonat pH 10.5 elution | 2 pmol PT in 3/120 of pooled elutions | 80 pmol | >48% | 20% |
| | $MgCl_2$ | 1 pmol PT in 3/120 of pooled elutions | 40 pmol | >24% | 10% |

*according to the documentation related to PT, the expected PT concentration of sample B is 9-45 µg/ml, corresponding to 0.8-0.41 pmol/µl. Calculation was performed as following: 400 µl of sample B × 0.41 pmol/µl = 164 pmol input PT b. Determination of PT Yield During Affinity Purification Using Varying Peptide Densities on Streptavidin Sepharose The PT binding to peptide streptavidin sepharose was investigated in dependence of varying concentration of peptide immobilized on the streptavidin sepharose as affinity ligand. For immobilization 1 µl volume of streptavidin sepharose was incubated with increasing amounts of peptide pp26/9 or gurmarin/15 (100, 200, 300, 400, 500, 1000 pmol peptide). Unbound fractions of peptides were removed from the sepharose by 3 washes with 50 mM Tris/HCl, pH 7.5 (on column). Subsequently each peptide straptavidin matrix was incubated with 600 µl Sample A to allow binding of PT. After 80 min each matrix was washed four times with 50 mM Tris/HCl, pH 7.5 (200 µl each) and subsequently eluted with 20 µl gel loading buffer (30 mM Tris, pH 6.8, 1% SDS, 1% β-Mercaptoethanol, 12.5% glycerol, 0.005% Bromphenol blue; incubation for 10 min at 95° C.). Elutions were analyzed by PAGE on 12% Bis-Tris-Gels (MES running buffer) and silver staining (FIG. 23). Amount of PT that was bound to peptide streptavidin sepharose was calculated by densitometric evalution and plotted as a function of the amount of peptide initially used for immobilization to streptavidin sepharose (shown for pp26/9 in FIG. 23). A maximum of PT binding was reached when 300-400 pmol peptide were used for immobilization to 1 µl streptavidin sepharose. Higher amounts of peptide did not result in higher PT binding probably reflecting effects of steric hindrance of PT.

Figure 24:
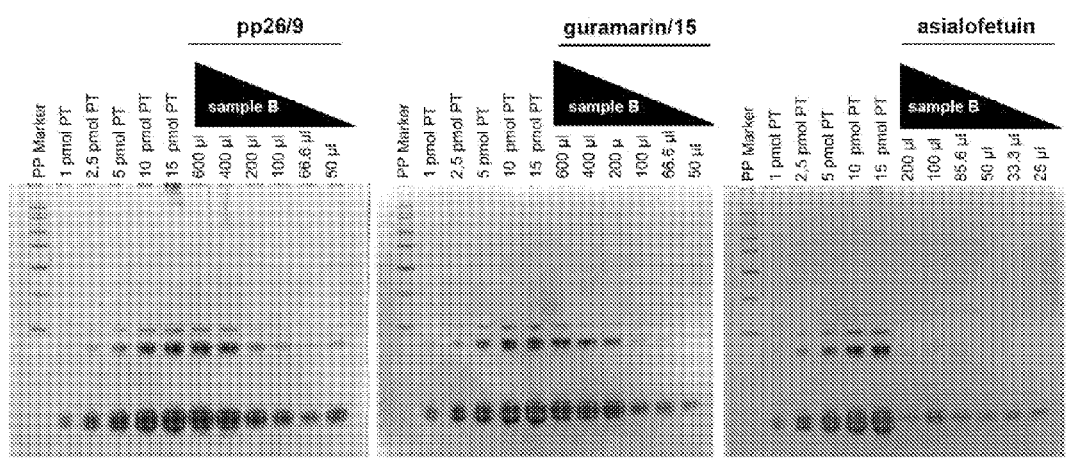

The effectively bound fraction of peptide (pp26/9 or gurmarin/15) when an input of 400 pmol peptide was used for immobilization to 1 µl streptavidin sepharose, was evaluated by PAGE on a 12% Bis-Tris-Gel (MES running buffer) and silver staining after elution with gel loading buffer (heating at 95° C. for 10 min). Amount of elutable peptide was estimated by direct comparison to defined amounts of purified PT on the same gel (data not shown): for pp26/9: 100-150 pmol; for gurmarin/15: 50 pmol.

c. Determination of PT Yield Using Varying Amounts of Sample B at Constant Concentration of Peptide Sepharose During Affinity Purification For peptide immobilization 400 pmol pp26/9 or gurmarin/15 were incubated with 1 µl streptavidin sepharose for 1 h at RT. The peptide sepharose was washed 3 times with 200 µl 50 mM Tris pH 7.5 buffer and subsequently incubated with varying amounts of Sample B (50, 66, 100, 200, 400, 600 µl, adjusted before to pH 7.0-7.5 by addition of HCl) for 1 hour at RT. The affinity matrices were washed 4 times with 100 µl 50 mM Tris/HCl, pH 7.5, and eluted by 4 consecutive elutions with 100 mM Carbonate buffer at pH 10.5 (each 20 µl). 5 µl of the pooled elutions (total 80 µl) were analyzed by PAGE on 12% Bis-Tris-Gels (MES running buffer) and silver staining. The amount of eluted PT was calculated on the basis of direct comparison to defined amounts of purified PT on the same gel as mass standard (FIG. 24, Table 12).

TABLE 12

| Input PT (pmol) | Ratio peptide:PT | Amount of PT bound (pmol) | Yield of PT relative to input amount of PT |
|---|---|---|---|
| Input peptide 16K9 (pmol) | | | |
| 100 | 300 | 1:3 | ~100 | 33% |
| 100 | 200 | 1:2 | ~88 | 44% |
| 100 | 100 | 1:1 | ~40 | 40% |
| 100 | 50 | 2:1 | ~24 | 48% |
| 100 | 33.3 | 3:1 | ~16 | 48% |
| 100 | 25 | 4:1 | ~24 | 96% |
| Input peptide 17K15 (pmol) | | | |
| 100 | 300 | 1:3 | ~80 | 27% |
| 100 | 200 | 1:2 | ~64 | 32% |
| 100 | 100 | 1:1 | ~56 | 56% |
| 100 | 50 | 2:1 | ~16 | 32% |
| 100 | 33.3 | 3:1 | ~16 | 32% |
| 100 | 25 | 4:1 | ~8 | 32% |
| Input asiaolfetuin (pmol) | | | |
| 100 | 200 | 1:2 | ~8 | 4% |
| 100 | 100 | 1:1 | ~16 | 16% |
| 100 | 85.6 | 20:17 | ~8 | 9% |
| 100 | 50 | 2:1 | ~8 | 16% |
| 100 | 33.3 | 3:1 | ~8 | 24% |
| 100 | 25 | 4:1 | ~8 | 35% |

To compare the purification efficiencies of the peptide streptavidin sepharoses with asialofetuin sepharose a titration experiment with asialofetuin sepharose was performed in parallel under comparable conditions (same amount of affinity ligand per reaction immobilized on sepharose, corresponding to ~100 pmol affinity ligand effectively bound to the sepharose). This was accomplished by incubation of 6.85 µl of asialofetuin sepharose (batch number FA 053198: density 1.1 mg/ml, 14.6 pmol/µl) with varying amounts of Sample B (50, 66, 100, 171.3, 200, 400 µl, adjusted before to pH 7.0-7.5 by addition of HCl) for 1 hour at RT. Subsequently the asialofetuin sepharose was washed and bound PT was eluted and analyzed as described above. The binding efficiency of peptide streptavidin sepharose under the applied purification conditions was significantly higher than the binding efficiency of asialofetuin sepharose.

d. Reutilization of Peptide Sepharose for Repeated PT Binding and Elution

Figure 25:
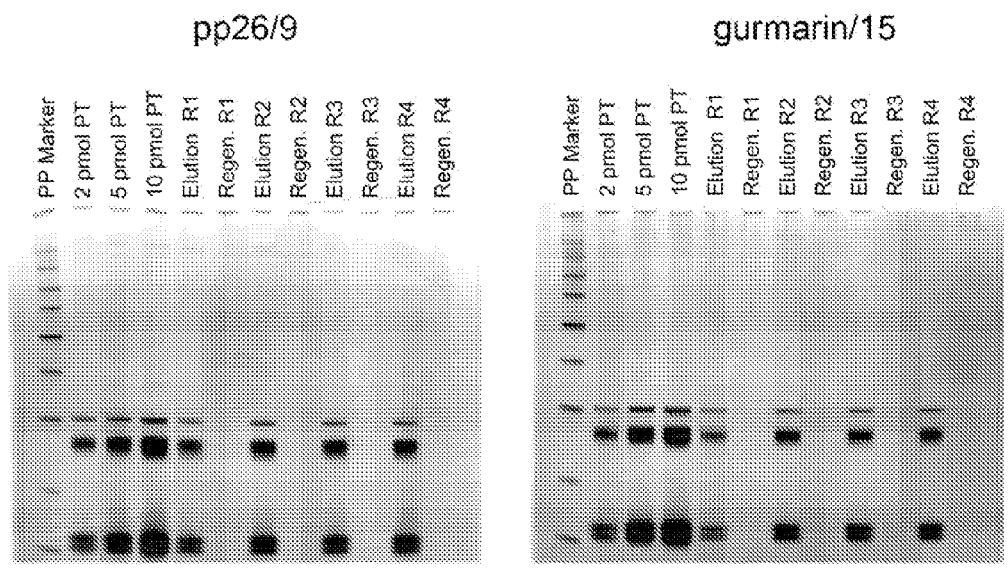

To investigate the reusability of peptide loaded sepharose (pp26/9 and gurmarin/15) for repeated binding and elution of PT the sepharoses were applied for repeated cycles of PT binding, elution and regeneration (in total 4 times). For peptide immobilization 600 pmol pp26/9 or gurmarin/15 were incubated with 2 µl streptavidin sepharose over night at RT and subsequently washed 3 times with HEPES buffer. For binding of PT each peptide streptavidin sepharose was incubated with 400 µl sample B (adjusted to pH 7.0-7.5 by addition of HCl) for 1 hour at RT and washed 4 times with 50 mM Tris/HCl, pH 7.5 (each 200 µl). PT was eluted by 4 consecutive elutions with 100 mM Carbonate buffer at pH 10.5 (each 20 µl). Subsequently the column matrices were regenerated by three washes with 10 mM HCl (1×20 µl, 2×100 µl) and afterwards neutralized by two washes with 200 µl 50 mM Tris/HCl, pH 7.5. This binding, elution and regeneration procedure was applied to the peptide sepharose for three additional times. 4 µl of the pooled elutions (in total 80 µl) and 7 µl of the first regeneration buffer from each binding/elution/regeneration cycle were analyzed by PAGE on 12% Bis-Tris-Gels (MES running buffer) and silver stained, indicating that the peptide sepharose may be re-utilized. (FIG. 25).

5. Large-Scale FPLC-Purification of PT

Optimized conditions for PT binding and elution were applied for large scale FPLC purification (0.5 ml column), as shown below:

A) Immobilization of biotinylated peptide to streptavidin-sepharose: 200 nmol peptide pp26/9 were incubated for 1 h 30 min at room temperature on a rotating wheel with 1 ml 50% Streptavidin-sepharose in volume of 10 ml (HEPES-buffer). After incubation the sepharose was washed 3× with 50 mM Tris pH 7.5.

B) Binding of PT (out of sample B): The estimated amount of peptide effectively immobilized on 500 µl sepharose was 50 nmol. The peptide-sepharose was incubated with 25 ml sample B for 1 h 30 min at room temperature in a head over tail rotator (assumed concentration of PT ~0.5 pmol/µl, corresponding to 12.5 nmol in 25 ml, corresponding to a ratio of immobilized peptide to amount of PT of 4:1).

C) FPLC-column: After incubation the sepharose was transfered to a column (Pharmacia HR 5/5) During packing of the column the sepharose was washed with 50 mM Tris pH 7.5 (2-3 ml). Subsequently the column was taken in the flow path and washed with 20 column volumes (10 ml) 50 mM Iris ph 7.5. Immobilized PT was eluted with 11 ml 100 mM carbonate buffer pH 10.5. The elution fractions were collected in 500 µl fractions (Pharmacia Fraction Collector FRAC-100) and the elution profile was evaluated by measurement of the UV absorbance at 280 nm. After elution the column was washed with 1.5 ml 50 mM Tris pH 7.5 and subsequently regenerated with 2.5 ml 10 mM HCl followed by neutralization with 10 ml 50 mM Tris pH 7.5.

Figure 26:
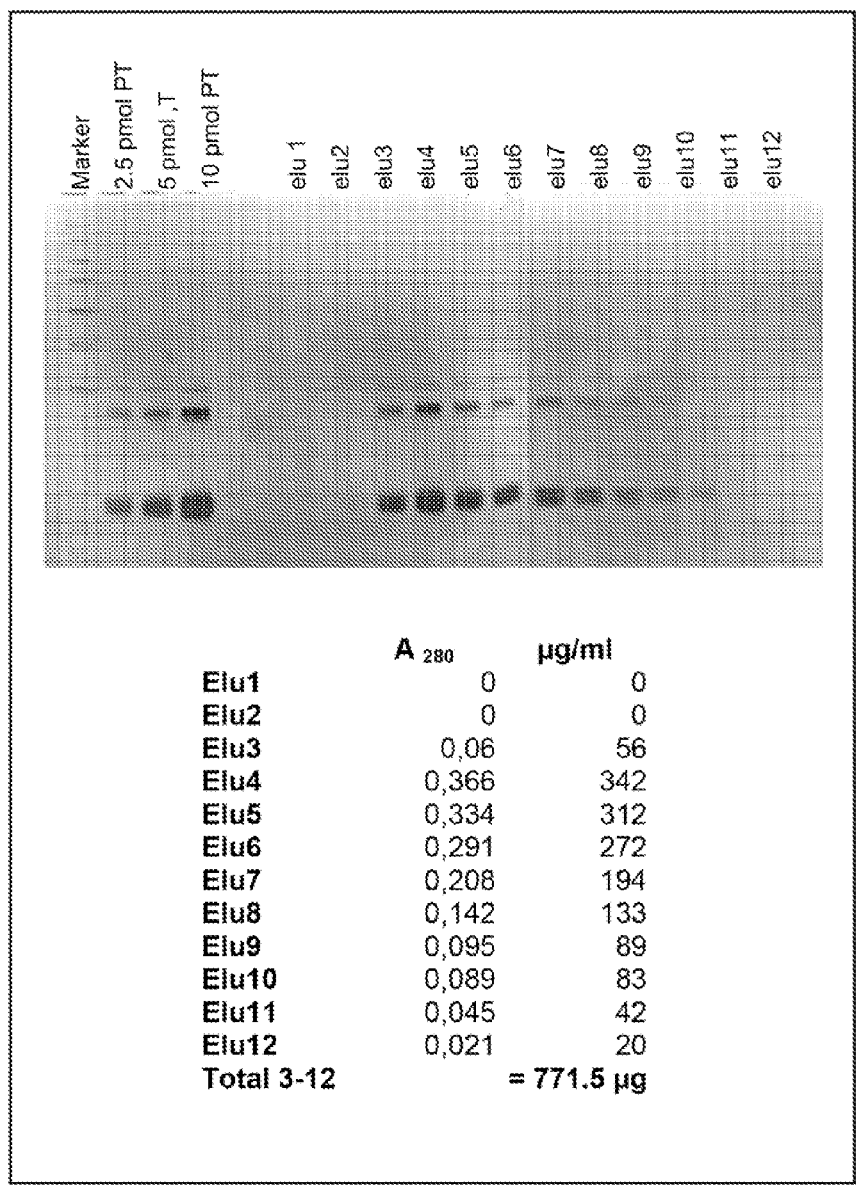

D) analysis of elution fractions and calculation of yield: The elution fractions were analyzed by PAGE (12% Bis-Tris-Gel, MES running buffer) and silver staining (FIG. 26). Concentration of PT was determined by measuring the absorbance of the elution fractions at 280 nm ($A_{280}$) and comparing these results with a calibration curve prepared with purified PT (see table in FIG. 26).

The amount of PT was additionally calculated on the basis of direct comparison to defined amounts of purified PT on the same gel as mass standard. Gel estimation leads to a yield of 8100 pmol PT. This correlates very well with the concentration determination using $A_{280}$. If it is assumed that 25 ml sample B contains 1125 µg of PT, more than 69%-72% is eluted of PT under these conditions. This result was verified by repetition of the FPLC run using the same peptide-sepharose after regeneration to bind PT out of 25 ml sample B. In this experiment, 803 µg PT was purified ($A_{280}$) (Table 13).

TABLE 13

Determination of concentration of PT in elution fraction (FPLC run #2) using $A_{280}$

| | $A_{280}$ | µg/ml |
|---|---|---|
| Elu1 | 0 | 0 |
| Elu2 | 0 | 0 |
| Elu3 | 0.091 | 85 |
| Elu4 | 0.4185 | 391 |
| Elu5 | 0.354 | 331 |
| Elu6 | 0.2835 | 265 |
| Elu7 | 0.212 | 198 |
| Elu8 | 0.148 | 138 |
| Elu9 | 0.0975 | 91 |
| Elu10 | 0.0585 | 55 |
| Elu11 | 0.0315 | 29 |
| Elu12 | 0.025 | 23 |
| Total 3-12 | | =803 µg |

TABLE 14

Summary of PT Purification Results

| | Yield PT in 12x 0.5 ml fractions (6 ml) | Relative Yield versus input amount of PT (1125 µg in 25 ml) (pmol/pmol or µg/µg) | Purity |
|---|---|---|---|
| 1. purification run | 772-813 µg | 69%-72% | Comparable to PT purified on asialofetuin sepharose, 100% |
| 2. purification run | 803 µg | 71% | Comparable to PT purified on asialofetuin sepharose, 100% |

6. Evaluation of Equilibrium and Rate Constants of the pp26 Peptide 9/Pertussis Toxin Complex Formation Equilibrium constants and rate constants for the pp26 K9/PT complex formation were evaluated using the BIAcore 2000 instrument in HBS/EP running buffer (0.01 M HEPES pH 7.4, 0.15 M NaCl, 3 mM EDTA, 0.005% (v/v) polysorbate 20) at room temperature. Binding of varying concentrations of pp26-K9 (concentartions between 2.5 nM and 100 nM) to PT immobilzed on a CM5 chip (immobilization of 6000 RU via amine coupling method) were analyzed at a flow rate of 30 µl/min. Quantitative elution of PT bound peptides were obtained by using 3 mM HCl, pH 2.5. Deducible equilibrium and rate constants were analyzed using the BIAevaluation software, the results of which are shown below:

| | |
|---|---|
| Dissociation equilibrium constant $K_D$→ | $7.5 \times 10^{-9}$ M |
| Association equilibrium constant $K_A$→ | $1.3 \times 10^{-8}$ $M^{-1}$ |
| Association rate constant $k_{on}$ → | $1.3 \times 10^{5}$ $M^{-1} \times s^{-1}$ |
| Dissociation rate constant $k_{off}$ → | $10^{-3}$ $s^{-1}$ |

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated peptide having the ability to bind pertussis toxin, the peptide being selected from the group consisting of:

(SEQ ID NO.: 67) RSSHCRHRNCHTITRGNMRIETPNNIRKDAK (SEQ ID NO.: 68) RSSHCRHRNCHTITRGNMRIETPNNIRKDA (SEQ ID NO.: 69) RSTMNTNRMDIQRLMTNHVKRDSSPGSIDA (SEQ ID NO.: 70) RSNVIPLNEVWYDTGWDRPHRSRLSIDDDA (SEQ ID NO.: 71) RSWRDTRKLHMRHYFPLAIDSYWDHTLRDA (SEQ ID NO.: 72) SGCVKKDELCARWDLVCCEPLECIYTSELYATCGK (SEQ ID NO.: 73) SGCVKKDELCARWDLVCCEPLECIYTSELYATCG (SEQ ID NO.: 74) SGCVKKDELCELAVDECCEPLECFQMGHGFKRCG (SEQ ID NO.: 75) SGCVKKDELCSQSVPMCCEPLECKWFNENYGICGS; and, (SEQ ID NO.: 76) SGCVKKDELCELAIDECCEPLECTKGDLGFRKCG.

2. The isolated peptide of claim 1 which is RSNVIPLNEVWYDTGWDRPHRSRLSIDDDA (SEQ ID NO.: 70).

3. The isolated peptide of claim 1 which is SGCVKKDELCSQSVPMCCEPLECKWFNENYGICGS (SEQ. ID NO.: 75).

4. The isolated peptide of claim 1 attached to biotin.

5. The isolated peptide of claim 1 attached to glutathione-S-transferase.

6. The isolated peptide of claim 1 attached to a solid support.

7. The peptide of claim 4 attached to a solid support.

8. The peptide of claim 7, wherein the solid support is selected from the group consisting of a column, chromatographic media, column material, bead, test tube, microtiter dish, solid particle, sepharose, agarose, microchip, silicon, silicon-glass, gold, and a membrane.

9. A complex comprising the peptide of claim 1 bound to pertussis toxin.

10. A method for purifying pertussis toxin comprising contacting a biological solution containing pertussis toxin with the peptide of claim 1 to form a pertussis toxin-peptide complex and isolating the complex.

11. The method of claim 10, further comprising the step of releasing pertussis toxin from said complex and isolating said toxin.

12. The method of claim 11, wherein said releasing step comprises altering the pH of the environment surrounding the complex.

13. The method of claim 12, wherein altering the pH comprises exposing the complex to an acidic pH.

14. The method of claim 12, wherein altering the pH comprises exposing the complex to a basic pH.

15. The method of claim 11, wherein said releasing step comprises altering the ionic strength of the environment surrounding the complex.

16. The method of claim 15, wherein altering the ionic strength of the environment comprises exposing the complex to a solution having a high concentration of one or more ionic salts.

17. The method of claim 16, wherein the ionic salt is at least one of sodium chloride or magnesium chloride.

18. The method of claim 17, wherein the ionic salt is magnesium chloride.

19. The method of claim 10, wherein the peptide is bound to a solid support.

20. The method of claim 19, wherein said solid support comprises a bead.

21. The method of claim 19, wherein said solid support comprises streptavidin sepharose.

22. The method of claim 19, wherein the peptide comprises a biotin moiety and is bound to the solid support through streptavidin.

* * * * *

SEQUENCE LISTING

<160> NUMBER OF SEQ ID NOS: 415

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Asn Gly Ser Phe Ser Gly Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Asn Gly Ser Phe Ser Gly Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Asp Gly Ser Phe Ser Gly Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: Xaa is any amino acid

<400> SEQUENCE: 4

Xaa Gly Ser Phe Ser Gly Xaa
1               5

<210> SEQ ID NO 5
<211> LENGTH: 30
<212> TYPE: PRT
<213> ORGANISM: Artificial Sequence
<220> FEATURE:
<223> OTHER INFORMATION: Synthetic

<400> SEQUENCE: 5

Arg Ser Ser His Cys Arg His Arg Asn Cys His Thr Ile Thr Arg Gly
1               5                   10                  15

Asn Met Arg Ile Glu Thr Pro Asn Asn Ile Arg Lys Asp Ala
            20                  25                  30

<210> SEQ ID NO 6
<211> LENGTH: 29
<212> TYPE: PRT

```
<213> ORGANISM: Artificial Sequence
<220> FEATURE:
<223> OTHER INFORMATION: Synthetic

<400> SEQUENCE: 6

Ser Thr Met Asn Thr Asn Arg Met Asp Ile Gln Arg Leu Met Thr Asn
1               5                   10                  15

His Val Lys Arg Asp Ser Ser Pro Gly Ser Ile Asp Ala
            20                  25

<210> SEQ ID NO 7
<211> LENGTH: 30
<212> TYPE: PRT
<213> ORGANISM: Artificial Sequence
<220> FEATURE:
<223> OTHER INFORMATION: Synthetic

<400> SEQUENCE: 7

Arg Ser Asn Val Ile Pro Leu Asn Glu Val Trp Tyr Asp Thr Gly Trp
1               5                   10                  15

Asp Arg Pro His Arg Ser Arg Leu Ser Ile Asp Asp Asp Ala
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic

<400> SEQUENCE: 8

Arg Ser Trp Arg Asp Thr Arg Lys Leu His Met Arg His Tyr Phe Pro
1               5                   10                  15

Leu Ala Ile Asp Ser Tyr Trp Asp His Thr Leu Arg Asp Ala
            20                  25                  30

<210> SEQ ID NO 9
<211> LENGTH: 34
<212> TYPE: PRT
<213> ORGANISM: Artificial Sequence
<220> FEATURE:
<223> OTHER INFORMATION: Synthetic

<400> SEQUENCE: 9

Ser Gly Cys Val Lys Lys Asp Glu Leu Cys Ala Arg Trp Asp Leu Val
1               5                   10                  15

Cys Cys Glu Pro Leu Glu Cys Ile Tyr Thr Ser Glu Leu Tyr Ala Thr
            20                  25                  30

Cys Gly

<210> SEQ ID NO 10
<211> LENGTH: 34
<212> TYPE: PRT
<213> ORGANISM: Artificial Sequence
<220> FEATURE:
<223> OTHER INFORMATION: Synthetic

<400> SEQUENCE: 10

Ser Gly Cys Val Lys Lys Asp Glu Leu Cys Glu Leu Ala Val Asp Glu
1               5                   10                  15

Cys Cys Glu Pro Leu Glu Cys Phe Gln Met Gly His Gly Phe Lys Arg
            20                  25                  30

Cys Gly
```

```
<210> SEQ ID NO 11
<211> LENGTH: 35
<212> TYPE: PRT
<213> ORGANISM: Artificial Sequence
<220> FEATURE:
<223> OTHER INFORMATION: Synthetic

<400> SEQUENCE: 11

Ser Gly Cys Val Lys Lys Asp Glu Leu Cys Ser Gln Ser Val Pro Met
1               5                   10                  15

Cys Cys Glu Pro Leu Glu Cys Lys Trp Phe Asn Glu Asn Tyr Gly Ile
            20                  25                  30

Cys Gly Ser
        35

<210> SEQ ID NO 12
<211> LENGTH: 34
<212> TYPE: PRT
<213> ORGANISM: Artificial Sequence
<220> FEATURE:
<223> OTHER INFORMATION: Synthetic

<400> SEQUENCE: 12

Ser Gly Cys Val Lys Lys Asp Glu Leu Cys Glu Leu Ala Ile Asp Glu
1               5                   10                  15

Cys Cys Glu Pro Leu Glu Cys Thr Lys Gly Asp Leu Gly Phe Arg Lys
            20                  25                  30

Cys Gly

<210> SEQ ID NO 13
<211> LENGTH: 35
<212> TYPE: PRT
<213> ORGANISM: Artificial Sequence
<220> FEATURE:
<223> OTHER INFORMATION: Synthetic

<400> SEQUENCE: 13

Gln Gln Cys Val Lys Lys Asp Glu Leu Cys Ile Pro Tyr Tyr Leu Asp
1               5                   10                  15

Cys Cys Glu Pro Leu Glu Cys Lys Lys Val Asn Trp Trp Asp His Lys
            20                  25                  30

Cys Ile Gly
        35

<210> SEQ ID NO 14
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(30)
<223> OTHER INFORMATION: Xaa is any amino acid

<400> SEQUENCE: 14

Cys Val Lys Lys Asp Glu Leu Cys Xaa Xaa Xaa Xaa Xaa Xaa Cys Cys
1               5                   10                  15

Glu Pro Leu Glu Cys Xaa Xaa Xaa Xaa Xaa Xaa Xaa Xaa Cys
            20                  25                  30

<210> SEQ ID NO 15
<211> LENGTH: 141
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (49)..(113)
<223> OTHER INFORMATION: n is a, g, t or c

<400> SEQUENCE: 15
agtggctcaa gctcaggatc aggctgcgtc aagaaagacg agctctgcnn snnsnnsnns      60
nnsnnstgct gtgagcccct cgagtgcnns nnsnnsnnsn nsnnsnnsnn snnstgcggc     120
agcggcagtt ctgggtctag c                                              141

<210> SEQ ID NO 16
<211> LENGTH: 84
<212> TYPE: DNA
<213> ORGANISM: Artificial Sequence
<220> FEATURE:
<223> OTHER INFORMATION: Synthetic

<400> SEQUENCE: 16
taatacgact cactataggg acaattacta tttacaatta caatgcacca tcaccatcac      60
catagtggct caagctcagg atca                                            84

<210> SEQ ID NO 17
<211> LENGTH: 44
<212> TYPE: DNA
<213> ORGANISM: Artificial Sequence
<220> FEATURE:
<223> OTHER INFORMATION: Synthetic

<400> SEQUENCE: 17
ttttaaatag cggatgctac taggctagac ccagaactgc cgct                      44

<210> SEQ ID NO 18
<211> LENGTH: 10
<212> TYPE: RNA
<213> ORGANISM: Artificial Sequence
<220> FEATURE:
<223> OTHER INFORMATION: Synthetic

<400> SEQUENCE: 18
uagcggaugc                                                            10

<210> SEQ ID NO 19
<211> LENGTH: 53
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (18)..(43)
<223> OTHER INFORMATION: Xaa is any amino acid

<400> SEQUENCE: 19

Thr Met Val Met Gly Arg Gly Ser His His His His His Ala Arg
1               5                   10                  15

Ser Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Asp Ala Asn Ala Pro
        35                  40                  45

Lys Ala Ser Ala Ile
    50
```

```
<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

His His His His His His
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Asp Ala Asn Ala Pro Lys
1               5

<210> SEQ ID NO 22
<211> LENGTH: 127
<212> TYPE: DNA
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (28)..(105)
<223> OTHER INFORMATION: n is a, g, t or c

<400> SEQUENCE: 22
agcggatgcc ttcggagcgt tagcgtcsnn snnsnnsnns nnsnnsnnsn nsnnsnnsnn      60
snnsnnsnns nnsnnsnnsn nsnnsnnsnn snnsnnsnns nnsnnagatc tagcatgatg     120
atgatga                                                              127

<210> SEQ ID NO 23
<211> LENGTH: 81
<212> TYPE: DNA
<213> ORGANISM: Artificial Sequence
<220> FEATURE:
<223> OTHER INFORMATION: Synthetic

<400> SEQUENCE: 23
taatacgact catagggaca attactattt acaattacaa tgggacgtgg ctcacatcat      60
catcatcatc atgctagatc t                                               81

<210> SEQ ID NO 24
<211> LENGTH: 32
<212> TYPE: DNA
<213> ORGANISM: Artificial Sequence
<220> FEATURE:
<223> OTHER INFORMATION: Synthetic

<400> SEQUENCE: 24
aattaaatag cggatgcctt cggagcgtta gc                                   32

<210> SEQ ID NO 25
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 25
tgtaaaacga cggccagt                                                    18

<210> SEQ ID NO 26
<211> LENGTH: 54
<212> TYPE: PRT
<213> ORGANISM: Artificial Sequence
<220> FEATURE:
<223> OTHER INFORMATION: Synthetic

<400> SEQUENCE: 26

Met His His His His His His Ser Gly Ser Ser Ser Gly Ser Gly Cys
1               5                   10                  15

Val Lys Lys Asp Glu Leu Cys Ala Gly Ser Val Gly His Cys Cys Glu
            20                  25                  30

Pro Leu Glu Cys Leu Arg Arg Phe Leu Asn Leu Arg Trp Cys Gly Ser
        35                  40                  45

Gly Ser Ser Gly Ser Ser
    50

<210> SEQ ID NO 27
<211> LENGTH: 54
<212> TYPE: PRT
<213> ORGANISM: Artificial Sequence
<220> FEATURE:
<223> OTHER INFORMATION: Synthetic

<400> SEQUENCE: 27

Met His His His His His His Ser Gly Ser Ser Ser Gly Ser Gly Cys
1               5                   10                  15

Val Lys Lys Asp Glu Leu Cys Ile Val Met Arg Ala Pro Cys Cys Glu
            20                  25                  30

Pro Leu Glu Cys Leu Arg Arg Tyr Met Leu Lys His Met Cys Gly Ser
        35                  40                  45

Gly Ser Ser Gly Ser Ser
    50

<210> SEQ ID NO 28
<211> LENGTH: 54
<212> TYPE: PRT
<213> ORGANISM: Artificial Sequence
<220> FEATURE:
<223> OTHER INFORMATION: Synthetic

<400> SEQUENCE: 28

Met His His His His His His Ser Gly Ser Ser Ser Gly Ser Gly Cys
1               5                   10                  15

Val Lys Lys Asp Glu Leu Cys Lys Ala Phe Arg Tyr Ser Cys Cys Glu
            20                  25                  30

Pro Leu Glu Cys Leu Arg Lys Trp Leu Lys Ala Arg Phe Cys Gly Ser
        35                  40                  45

Gly Ser Ser Gly Ser Ser
    50

<210> SEQ ID NO 29
<211> LENGTH: 54
<212> TYPE: PRT
<213> ORGANISM: Artificial Sequence
<220> FEATURE:
<223> OTHER INFORMATION: Synthetic

<400> SEQUENCE: 29
```

```
Met His His His His His Ser Gly Ser Ser Ser Gly Ser Gly Cys
1               5                   10                  15

Val Lys Lys Asp Glu Leu Cys Leu Arg Ser Ser Ile Asp Cys Cys Glu
            20                  25                  30

Pro Leu Glu Cys Leu Tyr Lys Trp Met Gln Arg Arg Leu Cys Gly Ser
        35                  40                  45

Gly Ser Ser Gly Ser Ser
    50
```

<210> SEQ ID NO 30
<211> LENGTH: 54
<212> TYPE: PRT
<213> ORGANISM: Artificial Sequence
<220> FEATURE:
<223> OTHER INFORMATION: Synthetic

<400> SEQUENCE: 30

```
Met His His His His His Ser Gly Ser Ser Ser Gly Ser Gly Cys
1               5                   10                  15

Val Lys Lys Asp Glu Leu Cys Trp Pro Arg His Lys Cys Cys Glu
            20                  25                  30

Pro Leu Glu Cys Leu Leu Glu Met Leu Glu Arg Lys Cys Gly Ser
        35                  40                  45

Gly Ser Ser Gly Ser Ser
    50
```

<210> SEQ ID NO 31
<211> LENGTH: 53
<212> TYPE: PRT
<213> ORGANISM: Artificial Sequence
<220> FEATURE:
<223> OTHER INFORMATION: Synthetic

<400> SEQUENCE: 31

```
Met His His His His His Ser Gly Ser Ser Ser Gly Ser Gly Cys
1               5                   10                  15

Val Lys Lys Asp Glu Leu Cys Met Ser Met Ala Cys Val Cys Cys Glu
            20                  25                  30

Pro Leu Glu Cys Lys Tyr His Gly Tyr Phe Trp Leu Cys Gly Ser Gly
        35                  40                  45

Ser Ser Gly Ser Ser
    50
```

<210> SEQ ID NO 32
<211> LENGTH: 54
<212> TYPE: PRT
<213> ORGANISM: Artificial Sequence
<220> FEATURE:
<223> OTHER INFORMATION: Synthetic

<400> SEQUENCE: 32

```
Met His His His His His Ser Gly Ser Ser Ser Gly Ser Gly Cys
1               5                   10                  15

Val Lys Lys Asp Glu Leu Cys Ala Val Trp Phe Asp Val Cys Cys Glu
            20                  25                  30

Pro Leu Glu Cys Thr Tyr Gln Ser Gly Tyr Tyr Trp Leu Cys Gly Ser
        35                  40                  45

Gly Ser Ser Gly Ser Ser
    50
```

<210> SEQ ID NO 33

```
<211> LENGTH: 54
<212> TYPE: PRT
<213> ORGANISM: Artificial Sequence
<220> FEATURE:
<223> OTHER INFORMATION: Synthetic

<400> SEQUENCE: 33

Met His His His His His His Ser Gly Ser Ser Ser Gly Ser Gly Cys
1               5                   10                  15

Val Lys Lys Asp Glu Leu Cys Glu Pro Trp Tyr Trp Arg Cys Cys Glu
            20                  25                  30

Pro Leu Glu Cys Val Tyr Thr Ser Gly Tyr Tyr Ser Cys Gly Ser
        35                  40                  45

Gly Ser Ser Gly Ser Ser
    50

<210> SEQ ID NO 34
<211> LENGTH: 54
<212> TYPE: PRT
<213> ORGANISM: Artificial Sequence
<220> FEATURE:
<223> OTHER INFORMATION: Synthetic

<400> SEQUENCE: 34

Met His His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Ile Tyr Thr Ser Glu Leu Tyr Ala Thr Cys Gly Ser
        35                  40                  45

Gly Ser Ser Gly Ser Ser
    50

<210> SEQ ID NO 35
<211> LENGTH: 54
<212> TYPE: PRT
<213> ORGANISM: Artificial Sequence
<220> FEATURE:
<223> OTHER INFORMATION: Synthetic

<400> SEQUENCE: 35

Met His His His His His His Ser Gly Ser Ser Ser Gly Ser Gly Cys
1               5                   10                  15

Val Lys Lys Asp Glu Leu Cys Val Phe Tyr Phe Pro Asn Cys Cys Glu
            20                  25                  30

Pro Leu Glu Cys Arg Trp Val Asn Asp Asn Tyr Gly Trp Cys Gly Ser
        35                  40                  45

Gly Ser Ser Gly Ser Ser
    50

<210> SEQ ID NO 36
<211> LENGTH: 53
<212> TYPE: PRT
<213> ORGANISM: Artificial Sequence
<220> FEATURE:
<223> OTHER INFORMATION: Synthetic

<400> SEQUENCE: 36

Met His His His His His His Ser Gly Ser Ser Ser Gly Ser Gly Cys
1               5                   10                  15

Val Lys Lys Asp Glu Leu Cys Met Ser Met Ala Cys Val Cys Cys Glu
            20                  25                  30
```

```
Pro Leu Glu Cys Lys Tyr His Gly Tyr Phe Trp Leu Cys Gly Ser Gly
        35                  40                  45

Ser Ser Gly Ser Ser
    50

<210> SEQ ID NO 37
<211> LENGTH: 54
<212> TYPE: PRT
<213> ORGANISM: Artificial Sequence
<220> FEATURE:
<223> OTHER INFORMATION: Synthetic

<400> SEQUENCE: 37

Met His His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Lys Trp Thr Asn Glu His Phe Gly Thr Cys Gly Ser
        35                  40                  45

Gly Ser Ser Gly Ser Ser
    50

<210> SEQ ID NO 38
<211> LENGTH: 54
<212> TYPE: PRT
<213> ORGANISM: Artificial Sequence
<220> FEATURE:
<223> OTHER INFORMATION: Synthetic

<400> SEQUENCE: 38

Met His His His His His His Ser Gly Ser Ser Ser Gly Ser Gly Cys
1               5                   10                  15

Val Lys Lys Asp Glu Leu Cys Ser Gln Ser Val Pro Met Cys Cys Glu
            20                  25                  30

Pro Leu Glu Cys Lys Trp Phe Asn Glu Asn Tyr Gly Ile Cys Gly Ser
        35                  40                  45

Gly Ser Ser Gly Ser Ser
    50

<210> SEQ ID NO 39
<211> LENGTH: 54
<212> TYPE: PRT
<213> ORGANISM: Artificial Sequence
<220> FEATURE:
<223> OTHER INFORMATION: Synthetic

<400> SEQUENCE: 39

Met His His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Ile Tyr Thr Ser Glu Leu Tyr Ala Thr Cys Gly Ser
        35                  40                  45

Gly Ser Ser Gly Ser Ser
    50

<210> SEQ ID NO 40
<211> LENGTH: 54
<212> TYPE: PRT
<213> ORGANISM: Artificial Sequence
<220> FEATURE:
<223> OTHER INFORMATION: Synthetic
```

```
<400> SEQUENCE: 40

Met His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser
        50

<210> SEQ ID NO 41
<211> LENGTH: 53
<212> TYPE: PRT
<213> ORGANISM: Artificial Sequence
<220> FEATURE:
<223> OTHER INFORMATION: Synthetic

<400> SEQUENCE: 41

Met His His His His His Ser Gly Ser Ser Ser Gly Ser Gly Cys
1               5                   10                  15

Val Lys Lys Asp Glu Leu Cys Met Trp Ser Arg Glu Val Cys Cys Glu
            20                  25                  30

Pro Leu Glu Cys Tyr Tyr Thr Gly Trp Tyr Trp Ala Cys Gly Ser Gly
        35                  40                  45

Ser Ser Gly Ser Ser
        50

<210> SEQ ID NO 42
<211> LENGTH: 54
<212> TYPE: PRT
<213> ORGANISM: Artificial Sequence
<220> FEATURE:
<223> OTHER INFORMATION: Synthetic

<400> SEQUENCE: 42

Met His His His His His Ser Gly Ser Ser Ser Gly Ser Gly Cys
1               5                   10                  15

Val Lys Lys Asp Glu Leu Cys Glu Leu Ala Val Asp Glu Cys Cys Glu
            20                  25                  30

Pro Leu Glu Cys Phe Gln Met Gly His Gly Phe Lys Arg Cys Gly Ser
        35                  40                  45

Gly Ser Ser Gly Ser Ser
        50

<210> SEQ ID NO 43
<211> LENGTH: 54
<212> TYPE: PRT
<213> ORGANISM: Artificial Sequence
<220> FEATURE:
<223> OTHER INFORMATION: Synthetic

<400> SEQUENCE: 43

Met His His His His His Ser Gly Ser Ser Ser Gly Ser Gly Cys
1               5                   10                  15

Val Lys Lys Asp Glu Leu Cys Glu Leu Ala Val Asp Glu Cys Cys Glu
            20                  25                  30

Pro Leu Glu Cys Thr Lys Gly Asp Leu Gly Phe Arg Lys Cys Gly Ser
        35                  40                  45

Gly Ser Ser Gly Ser Ser
        50
```

<210> SEQ ID NO 44
<211> LENGTH: 54
<212> TYPE: PRT
<213> ORGANISM: Artificial Sequence
<220> FEATURE:
<223> OTHER INFORMATION: Synthetic

<400> SEQUENCE: 44

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser
    50

<210> SEQ ID NO 45
<211> LENGTH: 54
<212> TYPE: PRT
<213> ORGANISM: Artificial Sequence
<220> FEATURE:
<223> OTHER INFORMATION: Synthetic

<400> SEQUENCE: 45

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser
    50

<210> SEQ ID NO 46
<211> LENGTH: 54
<212> TYPE: PRT
<213> ORGANISM: Artificial Sequence
<220> FEATURE:
<223> OTHER INFORMATION: Synthetic

<400> SEQUENCE: 46

Met His His His His His His Ser Gly Ser Ser Ser Gly Ser Gly Cys
1               5                   10                  15

Val Lys Lys Asp Glu Leu Cys Asn Trp Val Thr Pro Met Arg Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser
    50

<210> SEQ ID NO 47
<211> LENGTH: 50
<212> TYPE: PRT
<213> ORGANISM: Artificial Sequence
<220> FEATURE:
<223> OTHER INFORMATION: Synthetic

<400> SEQUENCE: 47

Met Gly Arg Gly Ser His His His His His His Ala Arg Ser Asp Trp
1               5                   10                  15

Glu Leu Ser Pro Pro His Val Ala Ile Thr Thr Arg His Leu Ile Asn

```
                    20                  25                  30

Cys Thr Asp Gly Pro Leu Leu Arg Asp Ala Asn Ala Pro Lys Ala Ser
        35                  40                  45

Ala Ile
    50

<210> SEQ ID NO 48
<211> LENGTH: 50
<212> TYPE: PRT
<213> ORGANISM: Artificial Sequence
<220> FEATURE:
<223> OTHER INFORMATION: Synthetic

<400> SEQUENCE: 48

Met Gly Arg Gly Ser His His His His His Ala Arg Ser Leu Asn
1               5                   10                  15

Gly Glu Ser Thr Ser Asn Ile Leu Thr Thr Ser Arg Lys Val Thr Glu
                20                  25                  30

Trp Thr Gly Tyr Thr Ala Ser Val Asp Ala Asn Ala Pro Lys Ala Ser
        35                  40                  45

Ala Ile
    50

<210> SEQ ID NO 49
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (41)..(41)
<223> OTHER INFORMATION: Xaa is any amino acid

<400> SEQUENCE: 49

Met Gly Arg Gly Ser His His His His His Ala Arg Ser Gln Val
1               5                   10                  15

Thr Trp His His Leu Ala Asp Thr Val Thr Thr Lys Asn Arg Lys Cys
                20                  25                  30

Thr Asp Ser Tyr Ile Gly Trp Asn Xaa Ala Asn Ala Pro Lys Ala Ser
        35                  40                  45

Ala Ile
    50

<210> SEQ ID NO 50
<211> LENGTH: 50
<212> TYPE: PRT
<213> ORGANISM: Artificial Sequence
<220> FEATURE:
<223> OTHER INFORMATION: Synthetic

<400> SEQUENCE: 50

Met Gly Arg Gly Ser His His His His His Ala Arg Ser Ile Ile
1               5                   10                  15

Val Ile His Asn Ala Ile Gln Thr His Thr Pro His Gln Val Ser Ile
                20                  25                  30

Trp Cys Pro Pro Lys His Asn Arg Asp Ala Asn Ala Pro Lys Ala Ser
        35                  40                  45

Ala Ile
    50

<210> SEQ ID NO 51
```

```
<211> LENGTH: 50
<212> TYPE: PRT
<213> ORGANISM: Artificial Sequence
<220> FEATURE:
<223> OTHER INFORMATION: Synthetic

<400> SEQUENCE: 51

Met Gly Arg Gly Ser His His His His His His Ala Arg Ser Ser His
1               5                   10                  15

Cys Arg His Arg Asn Cys His Thr Ile Thr Arg Gly Asn Met Arg Ile
            20                  25                  30

Glu Thr Pro Asn Asn Ile Arg Lys Asp Ala Asn Ala Pro Lys Ala Ser
        35                  40                  45

Ala Ile
    50

<210> SEQ ID NO 52
<211> LENGTH: 50
<212> TYPE: PRT
<213> ORGANISM: Artificial Sequence
<220> FEATURE:
<223> OTHER INFORMATION: Synthetic

<400> SEQUENCE: 52

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45

Ala Ile
    50

<210> SEQ ID NO 53
<211> LENGTH: 50
<212> TYPE: PRT
<213> ORGANISM: Artificial Sequence
<220> FEATURE:
<223> OTHER INFORMATION: Synthetic

<400> SEQUENCE: 53

Met Gly Arg Gly Ser His His His His His His Ala Arg Ser Leu Ser
1               5                   10                  15

Ala Leu Arg Arg Thr Glu Arg Thr Trp Asn Thr Ile His Gln Gly His
            20                  25                  30

His Leu Glu Trp Tyr Pro Pro Ala Asp Ala Asn Ala Pro Lys Ala Ser
        35                  40                  45

Ala Ile
    50

<210> SEQ ID NO 54
<211> LENGTH: 50
<212> TYPE: PRT
<213> ORGANISM: Artificial Sequence
<220> FEATURE:
<223> OTHER INFORMATION: Synthetic

<400> SEQUENCE: 54

Met Gly Arg Gly Ser His His His His His His Ala Arg Ser Trp Thr
1               5                   10                  15

Ser Met Gln Gly Glu Thr Leu Trp Arg Thr Asp Arg Leu Ala Thr Thr
            20                  25                  30
```

```
Lys Thr Ser Met Ser His Pro Pro Asp Ala Asn Ala Pro Lys Ala Ser
            35                  40                  45

Ala Ile
    50

<210> SEQ ID NO 55
<211> LENGTH: 50
<212> TYPE: PRT
<213> ORGANISM: Artificial Sequence
<220> FEATURE:
<223> OTHER INFORMATION: Synthetic

<400> SEQUENCE: 55

Met Gly Arg Gly Ser His His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
            35                  40                  45

Ala Ile
    50

<210> SEQ ID NO 56
<211> LENGTH: 49
<212> TYPE: PRT
<213> ORGANISM: Artificial Sequence
<220> FEATURE:
<223> OTHER INFORMATION: Synthetic

<400> SEQUENCE: 56

Met Gly Arg Gly Ser His His His His His His Ala Arg Ser Cys Leu
1               5                   10                  15

Ala Thr Arg Asn Gly Phe Val Met Asn Thr Asp Arg Gly Thr Tyr Val
            20                  25                  30

Lys Arg Pro Thr Val Leu Gln Asp Ala Asn Ala Pro Lys Ala Ser Ala
            35                  40                  45

Ile

<210> SEQ ID NO 57
<211> LENGTH: 50
<212> TYPE: PRT
<213> ORGANISM: Artificial Sequence
<220> FEATURE:
<223> OTHER INFORMATION: Synthetic

<400> SEQUENCE: 57

Met Gly Arg Gly Ser His His His His His His Ala Arg Ser Trp Gly
1               5                   10                  15

Leu Ser Gly Thr Gln Thr Trp Lys Ile Thr Lys Leu Ala Thr Arg Leu
            20                  25                  30

His His Pro Glu Phe Glu Thr Asn Asp Ala Asn Ala Pro Lys Ala Ser
            35                  40                  45

Ala Ile
    50

<210> SEQ ID NO 58
<211> LENGTH: 50
<212> TYPE: PRT
<213> ORGANISM: Artificial Sequence
<220> FEATURE:
<223> OTHER INFORMATION: Synthetic

<400> SEQUENCE: 58
```

```
Met Gly Arg Gly Ser His His His His His Ala Arg Ser Trp Arg
1               5                   10                  15

Trp His Asn Trp Gly Leu Ser Asp Thr Val Ala Ser His Pro Asp Ala
            20                  25                  30

Ser Asn Ser Leu Asn Met Met Tyr Asp Ala Asn Ala Pro Lys Ala Ser
        35                  40                  45

Ala Asn
    50
```

<210> SEQ ID NO 59
<211> LENGTH: 49
<212> TYPE: PRT
<213> ORGANISM: Artificial Sequence
<220> FEATURE:
<223> OTHER INFORMATION: Synthetic

<400> SEQUENCE: 59

```
Met Gly Arg Gly Ser His His His His His Leu Asp Leu Trp Gly
1               5                   10                  15

Pro Pro Ser Gly Ser Pro Arg Thr Arg Ser Thr Thr Gly Thr Ser Thr
            20                  25                  30

Thr Ser Ser Pro Ser Thr Pro Gly Thr Leu Thr Leu Arg Arg His Pro
        35                  40                  45

His
```

<210> SEQ ID NO 60
<211> LENGTH: 49
<212> TYPE: PRT
<213> ORGANISM: Artificial Sequence
<220> FEATURE:
<223> OTHER INFORMATION: Synthetic

<400> SEQUENCE: 60

```
Met Gly Arg Gly Ser His His His His His Ala Arg Ser Trp Gln
1               5                   10                  15

Pro Glu Val Lys Met Ser Ser Leu Val Asp Thr Ser Gln Thr Val Gly
            20                  25                  30

Ala Ala Val Glu Thr Arg Thr Thr Asp Ala Asn Ala Pro Lys Ala Ser
        35                  40                  45

Ala
```

<210> SEQ ID NO 61
<211> LENGTH: 50
<212> TYPE: PRT
<213> ORGANISM: Artificial Sequence
<220> FEATURE:
<223> OTHER INFORMATION: Synthetic

<400> SEQUENCE: 61

```
Met Gly Arg Gly Ser His His His His His Ala Arg Ser Trp Arg
1               5                   10                  15

Asp Thr Arg Lys Leu His Met Arg His Tyr Phe Pro Leu Ala Ile Asp
            20                  25                  30

Ser Tyr Trp Asp His Thr Leu Arg Asp Ala Asn Ala Pro Lys Ala Ser
        35                  40                  45

Ala Ile
    50
```

<210> SEQ ID NO 62
<211> LENGTH: 50

<212> TYPE: PRT
<213> ORGANISM: Artificial Sequence
<220> FEATURE:
<223> OTHER INFORMATION: Synthetic

<400> SEQUENCE: 62

Met Gly Arg Gly Ser His His His His His His Ala Arg Ser Trp Thr
1               5                   10                  15

Ser Met Gln Gly Glu Thr Leu Trp Arg Thr Asp Arg Leu Ala Thr Thr
            20                  25                  30

Lys Thr Ser Met Ser His Pro Pro Asp Ala Asn Ala Pro Lys Ala Ser
        35                  40                  45

Ala Ile
    50

<210> SEQ ID NO 63
<211> LENGTH: 50
<212> TYPE: PRT
<213> ORGANISM: Artificial Sequence
<220> FEATURE:
<223> OTHER INFORMATION: Synthetic

<400> SEQUENCE: 63

Met Gly Arg Gly Ser His His His His His His Ala Arg Ser Pro
1               5                   10                  15

Leu Trp Tyr His Tyr Asn Cys Trp Asp Thr Ile Cys Leu Ala Asp Trp
            20                  25                  30

Leu Lys Asp Arg Pro His Gly Val Tyr Asp Ala Asn Ala Pro Lys Ala
        35                  40                  45

Ser Ala
    50

<210> SEQ ID NO 64
<211> LENGTH: 50
<212> TYPE: PRT
<213> ORGANISM: Artificial Sequence
<220> FEATURE:
<223> OTHER INFORMATION: Synthetic

<400> SEQUENCE: 64

Met Gly Arg Gly Ser His His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala Ile
    50

<210> SEQ ID NO 65
<211> LENGTH: 50
<212> TYPE: PRT
<213> ORGANISM: Artificial Sequence
<220> FEATURE:
<223> OTHER INFORMATION: Synthetic

<400> SEQUENCE: 65

Met Gly Arg Gly Ser His His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser

```
                35                  40                  45

Ala Ile
    50

<210> SEQ ID NO 66
<211> LENGTH: 50
<212> TYPE: PRT
<213> ORGANISM: Artificial Sequence
<220> FEATURE:
<223> OTHER INFORMATION: Synthetic

<400> SEQUENCE: 66

Met Gly Arg Gly Ser His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
        35                  40                  45

Ala Ile
    50

<210> SEQ ID NO 67
<211> LENGTH: 31
<212> TYPE: PRT
<213> ORGANISM: Artificial Sequence
<220> FEATURE:
<223> OTHER INFORMATION: Synthetic

<400> SEQUENCE: 67

Arg Ser Ser His Cys Arg His Arg Asn Cys His Thr Ile Thr Arg Gly
1               5                   10                  15

Asn Met Arg Ile Glu Thr Pro Asn Asn Ile Arg Lys Asp Ala Lys
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Synthetic

<400> SEQUENCE: 68

Arg Ser Ser His Cys Arg His Arg Asn Cys His Thr Ile Thr Arg Gly
1               5                   10                  15

Asn Met Arg Ile Glu Thr Pro Asn Asn Ile Arg Lys Asp Ala
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: Synthetic

<400> SEQUENCE: 69

Arg Ser Thr Met Asn Thr Asn Arg Met Asp Ile Gln Arg Leu Met Thr
1               5                   10                  15

Asn His Val Lys Arg Asp Ser Ser Pro Gly Ser Ile Asp Ala
            20                  25                  30

<210> SEQ ID NO 70
<211> LENGTH: 30
<212> TYPE: PRT
<213> ORGANISM: Artificial Sequence
```

```
<220> FEATURE:
<223> OTHER INFORMATION: Synthetic

<400> SEQUENCE: 70

Arg Ser Asn Val Ile Pro Leu Asn Glu Val Trp Tyr Asp Thr Gly Trp
1               5                   10                  15

Asp Arg Pro His Arg Ser Arg Leu Ser Ile Asp Asp Ala
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Synthetic

<400> SEQUENCE: 71

Arg Ser Trp Arg Asp Thr Arg Lys Leu His Met Arg His Tyr Phe Pro
1               5                   10                  15

Leu Ala Ile Asp Ser Tyr Trp Asp His Thr Leu Arg Asp Ala
            20                  25                  30

<210> SEQ ID NO 72
<211> LENGTH: 35
<212> TYPE: PRT
<213> ORGANISM: Artificial Sequence
<220> FEATURE:
<223> OTHER INFORMATION: Synthetic

<400> SEQUENCE: 72

Ser Gly Cys Val Lys Lys Asp Glu Leu Cys Ala Arg Trp Asp Leu Val
1               5                   10                  15

Cys Cys Glu Pro Leu Glu Cys Ile Tyr Thr Ser Glu Leu Tyr Ala Thr
            20                  25                  30

Cys Gly Lys
        35

<210> SEQ ID NO 73
<211> LENGTH: 34
<212> TYPE: PRT
<213> ORGANISM: Artificial Sequence
<220> FEATURE:
<223> OTHER INFORMATION: Synthetic

<400> SEQUENCE: 73

Ser Gly Cys Val Lys Lys Asp Glu Leu Cys Ala Arg Trp Asp Leu Val
1               5                   10                  15

Cys Cys Glu Pro Leu Glu Cys Ile Tyr Thr Ser Glu Leu Tyr Ala Thr
            20                  25                  30

Cys Gly

<210> SEQ ID NO 74
<211> LENGTH: 34
<212> TYPE: PRT
<213> ORGANISM: Artificial Sequence
<220> FEATURE:
<223> OTHER INFORMATION: Synthetic

<400> SEQUENCE: 74

Ser Gly Cys Val Lys Lys Asp Glu Leu Cys Glu Leu Ala Val Asp Glu
1               5                   10                  15

Cys Cys Glu Pro Leu Glu Cys Phe Gln Met Gly His Gly Phe Lys Arg
            20                  25                  30
```

Cys Gly

<210> SEQ ID NO 75
<211> LENGTH: 35
<212> TYPE: PRT
<213> ORGANISM: Artificial Sequence
<220> FEATURE:
<223> OTHER INFORMATION: Synthetic

<400> SEQUENCE: 75

Ser Gly Cys Val Lys Lys Asp Glu Leu Cys Ser Gln Ser Val Pro Met
1               5                   10                  15
Cys Cys Glu Pro Leu Glu Cys Lys Trp Phe Asn Glu Asn Tyr Gly Ile
            20                  25                  30
Cys Gly Ser
        35

<210> SEQ ID NO 76
<211> LENGTH: 34
<212> TYPE: PRT
<213> ORGANISM: Artificial Sequence
<220> FEATURE:
<223> OTHER INFORMATION: Synthetic

<400> SEQUENCE: 76

Ser Gly Cys Val Lys Lys Asp Glu Leu Cys Glu Leu Ala Ile Asp Glu
1               5                   10                  15
Cys Cys Glu Pro Leu Glu Cys Thr Lys Gly Asp Leu Gly Phe Arg Lys
            20                  25                  30
Cys Gly

<210> SEQ ID NO 77
<211> LENGTH: 28
<212> TYPE: DNA
<213> ORGANISM: Artificial Sequence
<220> FEATURE:
<223> OTHER INFORMATION: Synthetic

<400> SEQUENCE: 77
catgccatgg gacgtggctc acatcatc                                      28

<210> SEQ ID NO 78
<211> LENGTH: 36
<212> TYPE: DNA
<213> ORGANISM: Artificial Sequence
<220> FEATURE:
<223> OTHER INFORMATION: Synthetic

<400> SEQUENCE: 78
gggttaaata gcggatgcct tcggagcgtt agcgtc                             36

<210> SEQ ID NO 79
<211> LENGTH: 38
<212> TYPE: DNA
<213> ORGANISM: Artificial Sequence
<220> FEATURE:
<223> OTHER INFORMATION: Synthetic

<400> SEQUENCE: 79
ggagatctca tatgcaccat caccatcacc atagtggc                           38

<210> SEQ ID NO 80
<211> LENGTH: 26
<212> TYPE: DNA
<213> ORGANISM: Artificial Sequence
<220> FEATURE:
<223> OTHER INFORMATION: Synthetic

<400> SEQUENCE: 80
gggttaaata gcggatgcta ctaggc                                    26

<210> SEQ ID NO 81
<211> LENGTH: 60
<212> TYPE: PRT
<213> ORGANISM: Artificial Sequence
<220> FEATURE:
<223> OTHER INFORMATION: Synthetic

<400> SEQUENCE: 81

Met His His His His His His Ser Gly Ser Ser Ser Gly Ser Gly Cys
1               5                   10                  15

Val Lys Lys Asp Glu Leu Cys Ala Gly Ser Val Gly His Cys Cys Glu
            20                  25                  30

Pro Leu Glu Cys Leu Arg Arg Phe Leu Asn Leu Arg Trp Cys Gly Ser
        35                  40                  45

Gly Ser Ser Gly Ser Ser Leu Val Ala Ser Ala Ile
    50                  55                  60

<210> SEQ ID NO 82
<211> LENGTH: 60
<212> TYPE: PRT
<213> ORGANISM: Artificial Sequence
<220> FEATURE:
<223> OTHER INFORMATION: Synthetic

<400> SEQUENCE: 82

Met His His His His His His Ser Gly Ser Ser Ser Gly Ser Gly Cys
1               5                   10                  15

Val Lys Lys Asp Glu Leu Cys Ile Val Met Arg Ala Pro Cys Cys Glu
            20                  25                  30

Pro Leu Glu Cys Leu Arg Arg Tyr Met Leu Lys His Met Cys Gly Ser
        35                  40                  45

Gly Ser Ser Gly Ser Ser Leu Val Ala Ser Ala Ile
    50                  55                  60

<210> SEQ ID NO 83
<211> LENGTH: 60
<212> TYPE: PRT
<213> ORGANISM: Artificial Sequence
<220> FEATURE:
<223> OTHER INFORMATION: Synthetic

<400> SEQUENCE: 83

Met His His His His His His Ser Gly Ser Ser Ser Gly Ser Gly Cys
1               5                   10                  15

Val Lys Lys Asp Glu Leu Cys Lys Ala Phe Arg Tyr Ser Cys Cys Glu
            20                  25                  30

Pro Leu Glu Cys Leu Arg Lys Trp Leu Lys Ala Arg Phe Cys Gly Ser
        35                  40                  45

Gly Ser Ser Gly Ser Ser Leu Val Ala Ser Ala Ile
    50                  55                  60

<210> SEQ ID NO 84
<211> LENGTH: 58
<212> TYPE: PRT
<213> ORGANISM: Artificial Sequence
<220> FEATURE:
<223> OTHER INFORMATION: Synthetic

<400> SEQUENCE: 84

Met His His His His His Ser Gly Ser Ser Ser Gly Ser Gly Cys
1               5                   10                  15

Val Lys Lys Asp Glu Leu Cys Leu Arg Ser Ser Ile Asp Cys Cys Glu
            20                  25                  30

Pro Leu Glu Cys Leu Tyr Lys Trp Met Gln Arg Arg Leu Cys Gly Ser
        35                  40                  45

Gly Ser Ser Gly Ser Ser Leu Val Ala Ser
    50                  55

<210> SEQ ID NO 85
<211> LENGTH: 60
<212> TYPE: PRT
<213> ORGANISM: Artificial Sequence
<220> FEATURE:
<223> OTHER INFORMATION: Synthetic

<400> SEQUENCE: 85

Met His His His His His Ser Gly Ser Ser Ser Gly Ser Gly Cys
1               5                   10                  15

Val Lys Lys Asp Glu Leu Cys Trp Pro Arg Arg His Lys Cys Cys Glu
            20                  25                  30

Pro Leu Glu Cys Leu Leu Glu Met Leu Glu Arg Lys Arg Cys Gly Ser
        35                  40                  45

Gly Ser Ser Gly Ser Ser Leu Val Ala Ser Ala Ile
    50                  55                  60

<210> SEQ ID NO 86
<211> LENGTH: 58
<212> TYPE: PRT
<213> ORGANISM: Artificial Sequence
<220> FEATURE:
<223> OTHER INFORMATION: Synthetic

<400> SEQUENCE: 86

Met His His His His His Ser Gly Ser Ser Ser Gly Ser Gly Cys
1               5                   10                  15

Val Lys Lys Asp Glu Leu Cys Met Ser Met Ala Cys Val Cys Cys Glu
            20                  25                  30

Pro Leu Glu Cys Lys Tyr His Gly Tyr Phe Trp Leu Cys Gly Ser Gly
        35                  40                  45

Ser Ser Gly Pro Ser Ser Ile Arg Tyr Leu
    50                  55

<210> SEQ ID NO 87
<211> LENGTH: 60
<212> TYPE: PRT
<213> ORGANISM: Artificial Sequence
<220> FEATURE:
<223> OTHER INFORMATION: Synthetic

<400> SEQUENCE: 87

Met His His His His His Ser Gly Ser Ser Ser Gly Ser Gly Cys
1               5                   10                  15

Val Lys Lys Asp Glu Leu Cys Ala Val Trp Phe Asp Val Cys Cys Glu
            20                  25                  30

Pro Leu Glu Cys Thr Tyr Gln Ser Gly Tyr Tyr Trp Leu Cys Gly Ser
        35                  40                  45

Gly Ser Ser Gly Ser Ser Leu Val Ala Ser Ala Ile
    50                  55                  60

<210> SEQ ID NO 88
<211> LENGTH: 60
<212> TYPE: PRT
<213> ORGANISM: Artificial Sequence
<220> FEATURE:
<223> OTHER INFORMATION: Synthetic

<400> SEQUENCE: 88

Met His His His His His Ser Gly Ser Ser Ser Gly Ser Gly Cys
1               5                   10                  15

Val Lys Lys Asp Glu Leu Cys Glu Pro Trp Tyr Trp Arg Cys Cys Glu
            20                  25                  30

Pro Leu Glu Cys Val Tyr Thr Ser Gly Tyr Tyr Ser Cys Gly Ser
        35                  40                  45

Gly Ser Ser Gly Ser Ser Leu Val Ala Ser Ala Ile
    50                  55                  60

<210> SEQ ID NO 89
<211> LENGTH: 55
<212> TYPE: PRT
<213> ORGANISM: Artificial Sequence
<220> FEATURE:
<223> OTHER INFORMATION: Synthetic

<400> SEQUENCE: 89

Met His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Ile Tyr Thr Ser Glu Leu Tyr Ala Thr Cys Gly Ser
        35                  40                  45

Gly Ser Ser Gly Ser Ser Gly
    50                  55

<210> SEQ ID NO 90
<211> LENGTH: 60
<212> TYPE: PRT
<213> ORGANISM: Artificial Sequence
<220> FEATURE:
<223> OTHER INFORMATION: Synthetic

<400> SEQUENCE: 90

Met His His His His His Ser Gly Ser Ser Ser Gly Ser Gly Cys
1               5                   10                  15

Val Lys Lys Asp Glu Leu Cys Val Phe Tyr Phe Pro Asn Cys Cys Glu
            20                  25                  30

Pro Leu Glu Cys Arg Trp Val Asn Asp Asn Tyr Gly Trp Cys Gly Ser
        35                  40                  45

Gly Ser Ser Gly Ser Ser Leu Val Ala Ser Ala Ile
    50                  55                  60

<210> SEQ ID NO 91
<211> LENGTH: 59
<212> TYPE: PRT
<213> ORGANISM: Artificial Sequence
<220> FEATURE:
<223> OTHER INFORMATION: Synthetic

<400> SEQUENCE: 91

Met His His His His His Ser Gly Ser Ser Ser Gly Ser Gly Cys
1               5                   10                  15

-continued

Val Lys Lys Asp Glu Leu Cys Met Ser Met Ala Cys Val Cys Cys Glu
            20                  25                  30

Pro Leu Glu Cys Lys Tyr His Gly Tyr Phe Trp Leu Cys Gly Ser Gly
            35                  40                  45

Ser Ser Gly Ser Ser Leu Val Ala Ser Ala Ile
        50                  55

<210> SEQ ID NO 92
<211> LENGTH: 60
<212> TYPE: PRT
<213> ORGANISM: Artificial Sequence
<220> FEATURE:
<223> OTHER INFORMATION: Synthetic

<400> SEQUENCE: 92

Met His His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Lys Trp Thr Asn Glu His Phe Gly Thr Cys Gly Ser
            35                  40                  45

Gly Ser Ser Gly Ser Ser Leu Val Ala Ser Ala Ile
        50                  55                  60

<210> SEQ ID NO 93
<211> LENGTH: 60
<212> TYPE: PRT
<213> ORGANISM: Artificial Sequence
<220> FEATURE:
<223> OTHER INFORMATION: Synthetic

<400> SEQUENCE: 93

Met His His His His His His Ser Gly Ser Ser Ser Gly Ser Gly Cys
1               5                   10                  15

Val Lys Lys Asp Glu Leu Cys Ser Gln Ser Val Pro Met Cys Cys Glu
            20                  25                  30

Pro Leu Glu Cys Lys Trp Phe Asn Glu Asn Tyr Gly Ile Cys Gly Ser
            35                  40                  45

Gly Ser Ser Gly Ser Ser Leu Val Ala Ser Ala Ile
        50                  55                  60

<210> SEQ ID NO 94
<211> LENGTH: 60
<212> TYPE: PRT
<213> ORGANISM: Artificial Sequence
<220> FEATURE:
<223> OTHER INFORMATION: Synthetic

<400> SEQUENCE: 94

Met His His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Ile Tyr Thr Ser Glu Leu Tyr Ala Thr Cys Gly Ser
            35                  40                  45

Gly Ser Ser Gly Ser Ser Leu Val Ala Ser Ala Ile
        50                  55                  60

<210> SEQ ID NO 95
<211> LENGTH: 60
<212> TYPE: PRT
<213> ORGANISM: Artificial Sequence

```
<220> FEATURE:
<223> OTHER INFORMATION: Synthetic

<400> SEQUENCE: 95

Met His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Leu Gly His Gly Leu Gly Tyr Ala Tyr Cys Gly Ser
            35                  40                  45

Gly Ser Ser Gly Ser Ser Leu Val Ala Ser Ala Ile
    50                  55                  60

<210> SEQ ID NO 96
<211> LENGTH: 59
<212> TYPE: PRT
<213> ORGANISM: Artificial Sequence
<220> FEATURE:
<223> OTHER INFORMATION: Synthetic

<400> SEQUENCE: 96

Met His His His His His His Ser Gly Ser Ser Ser Gly Ser Gly Cys
1               5                   10                  15

Val Lys Lys Asp Glu Leu Cys Met Trp Ser Arg Glu Val Cys Cys Glu
            20                  25                  30

Pro Leu Glu Cys Tyr Tyr Thr Gly Trp Tyr Trp Ala Cys Gly Ser Gly
            35                  40                  45

Ser Ser Gly Ser Ser Leu Val Ala Ser Ala Ile
    50                  55

<210> SEQ ID NO 97
<211> LENGTH: 57
<212> TYPE: PRT
<213> ORGANISM: Artificial Sequence
<220> FEATURE:
<223> OTHER INFORMATION: Synthetic

<400> SEQUENCE: 97

Met His His His His His His Ser Gly Ser Ser Ser Gly Ser Gly Cys
1               5                   10                  15

Val Lys Lys Asp Glu Leu Cys Glu Leu Ala Val Asp Glu Cys Cys Glu
            20                  25                  30

Pro Leu Glu Cys Phe Gln Met Gly His Gly Phe Lys Arg Cys Gly Ser
            35                  40                  45

Gly Ser Ser Gly Ser Ser Gly Ser Asn
    50                  55

<210> SEQ ID NO 98
<211> LENGTH: 60
<212> TYPE: PRT
<213> ORGANISM: Artificial Sequence
<220> FEATURE:
<223> OTHER INFORMATION: Synthetic

<400> SEQUENCE: 98

Met His His His His His His Ser Gly Ser Ser Ser Gly Ser Gly Cys
1               5                   10                  15

Val Lys Lys Asp Gly Leu Cys Trp Pro Arg Arg His Lys Cys Cys Glu
            20                  25                  30

Pro Leu Glu Cys Leu Leu Glu Met Leu Glu Arg Lys Arg Cys Gly Ser
            35                  40                  45
```

Gly Ser Ser Gly Ser Ser Leu Val Ala Ser Ala Ile
      50                  55                  60

<210> SEQ ID NO 99
<211> LENGTH: 60
<212> TYPE: PRT
<213> ORGANISM: Artificial Sequence
<220> FEATURE:
<223> OTHER INFORMATION: Synthetic

<400> SEQUENCE: 99

Met His His His His His Ser Gly Ser Ser Ser Gly Ser Gly Cys
1               5                   10                  15

Val Lys Lys Asp Glu Leu Cys Glu Leu Ala Val Asp Glu Cys Cys Glu
            20                  25                  30

Pro Leu Glu Cys Thr Lys Gly Asp Leu Gly Phe Arg Lys Cys Gly Ser
        35                  40                  45

Gly Ser Ser Gly Ser Ser Leu Val Ala Ser Ala Ile
      50                  55                  60

<210> SEQ ID NO 100
<211> LENGTH: 60
<212> TYPE: PRT
<213> ORGANISM: Artificial Sequence
<220> FEATURE:
<223> OTHER INFORMATION: Synthetic

<400> SEQUENCE: 100

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
      50                  55                  60

<210> SEQ ID NO 101
<211> LENGTH: 60
<212> TYPE: PRT
<213> ORGANISM: Artificial Sequence
<220> FEATURE:
<223> OTHER INFORMATION: Synthetic

<400> SEQUENCE: 101

Met His His His His His His Ser Gly Ser Ser Ser Gly Ser Gly Cys
1               5                   10                  15

Val Lys Lys Asp Glu Leu Cys Asn Trp Val Thr Pro Met Arg Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
      50                  55                  60

<210> SEQ ID NO 102
<211> LENGTH: 62
<212> TYPE: PRT
<213> ORGANISM: Artificial Sequence
<220> FEATURE:
<223> OTHER INFORMATION: Synthetic

<400> SEQUENCE: 102

Met His His His His His His Ser Gly Ser Ser Ser Gly Ser Gly Cys

```
1               5                  10                 15
Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
          35                  40                  45

Gly Ser Ser Gly Ser Ser Leu Val Ala Ser Ala Ser Ala Ile
        50                  55                  60
```

<210> SEQ ID NO 103
<211> LENGTH: 62
<212> TYPE: PRT
<213> ORGANISM: Artificial Sequence
<220> FEATURE:
<223> OTHER INFORMATION: Synthetic

<400> SEQUENCE: 103

```
Met His His His His His His Ser Gly Ser Ser Ser Gly Ser Gly Cys
1               5                  10                 15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
          35                  40                  45

Gly Ser Ser Gly Ser Ser Leu Val Ala Tyr Ala Ser Ala Ile
        50                  55                  60
```

<210> SEQ ID NO 104
<211> LENGTH: 50
<212> TYPE: PRT
<213> ORGANISM: Artificial Sequence
<220> FEATURE:
<223> OTHER INFORMATION: Synthetic

<400> SEQUENCE: 104

```
Met His His His His His His Ser Gly Ser Ser Ser Gly Ser Gly Cys
1               5                  10                 15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
          35                  40                  45

Gly Ile
    50
```

<210> SEQ ID NO 105
<211> LENGTH: 62
<212> TYPE: PRT
<213> ORGANISM: Artificial Sequence
<220> FEATURE:
<223> OTHER INFORMATION: Synthetic

<400> SEQUENCE: 105

```
Met His His His His His His Ser Asp Ser Ser Ser Gly Ser Gly Cys
1               5                  10                 15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
          35                  40                  45

Gly Ser Ser Gly Ser Ser Leu Val Ala Ser Ala Ser Ala Ile
        50                  55                  60
```

<210> SEQ ID NO 106
<211> LENGTH: 62

```
<212> TYPE: PRT
<213> ORGANISM: Artificial Sequence
<220> FEATURE:
<223> OTHER INFORMATION: Synthetic

<400> SEQUENCE: 106

Met His His His His His Ser Gly Ser Ser Ser Gly Ser Gly Cys
1               5                   10                  15

Val Lys Lys Asp Glu Leu Cys Glu Leu Ala Ile Asp Val Cys Arg Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ser Ala Ile
    50                  55                  60

<210> SEQ ID NO 107
<211> LENGTH: 52
<212> TYPE: PRT
<213> ORGANISM: Artificial Sequence
<220> FEATURE:
<223> OTHER INFORMATION: Synthetic

<400> SEQUENCE: 107

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly
    50

<210> SEQ ID NO 108
<211> LENGTH: 49
<212> TYPE: PRT
<213> ORGANISM: Artificial Sequence
<220> FEATURE:
<223> OTHER INFORMATION: Synthetic

<400> SEQUENCE: 108

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly

<210> SEQ ID NO 109
<211> LENGTH: 58
<212> TYPE: PRT
<213> ORGANISM: Artificial Sequence
<220> FEATURE:
<223> OTHER INFORMATION: Synthetic

<400> SEQUENCE: 109

Leu His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45
```

Gly Ser Ser Gly Ser Ser Leu Val Asp Pro
    50              55

<210> SEQ ID NO 110
<211> LENGTH: 50
<212> TYPE: PRT
<213> ORGANISM: Artificial Sequence
<220> FEATURE:
<223> OTHER INFORMATION: Synthetic

<400> SEQUENCE: 110

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Asn
    50

<210> SEQ ID NO 111
<211> LENGTH: 46
<212> TYPE: PRT
<213> ORGANISM: Artificial Sequence
<220> FEATURE:
<223> OTHER INFORMATION: Synthetic

<400> SEQUENCE: 111

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys
        35                  40                  45

<210> SEQ ID NO 112
<211> LENGTH: 54
<212> TYPE: PRT
<213> ORGANISM: Artificial Sequence
<220> FEATURE:
<223> OTHER INFORMATION: Synthetic

<400> SEQUENCE: 112

Met His His His His His His Ser Gly Ser Ser Ser Gly Ser Gly Cys
1               5                   10                  15

Val Lys Lys Asp Glu Leu Cys Glu Leu Ala Val Asp Glu Cys Cys Glu
            20                  25                  30

Pro Leu Glu Cys Phe Gln Met Gly His Gly Phe Lys Arg Cys Gly Ser
        35                  40                  45

Gly Ser Ser Gly Ser Asn
    50

<210> SEQ ID NO 113
<211> LENGTH: 48
<212> TYPE: PRT
<213> ORGANISM: Artificial Sequence
<220> FEATURE:
<223> OTHER INFORMATION: Synthetic

<400> SEQUENCE: 113

Met His His His His His His Ser Gly Ser Ser Ser Gly Ser Gly Cys
1               5                   10                  15

Val Lys Lys Asp Glu Leu Cys Phe Lys Arg Phe Ser Phe Cys Cys Glu
         20                  25                  30

Pro Leu Glu Cys Leu Gly His Gly Leu Gly Tyr Ala Tyr Cys Gly Ser
         35                  40                  45

<210> SEQ ID NO 114
<211> LENGTH: 48
<212> TYPE: PRT
<213> ORGANISM: Artificial Sequence
<220> FEATURE:
<223> OTHER INFORMATION: Synthetic

<400> SEQUENCE: 114

Met His His His His His Ser Gly Ser Ser Gly Ser Gly Cys
1               5                   10                  15

Val Lys Lys Asp Glu Leu Cys Phe Lys Arg Phe Ser Phe Cys Cys Glu
         20                  25                  30

Pro Leu Glu Cys Leu Gly His Gly Leu Gly Tyr Ala Tyr Cys Gly Asn
         35                  40                  45

<210> SEQ ID NO 115
<211> LENGTH: 62
<212> TYPE: PRT
<213> ORGANISM: Artificial Sequence
<220> FEATURE:
<223> OTHER INFORMATION: Synthetic

<400> SEQUENCE: 115

Met His His His His His Ser Gly Ser Ser Ser Gly Ser Gly Cys
1               5                   10                  15

Val Lys Lys Asp Glu Leu Cys Trp Ile Arg Phe Val Val Cys Cys Glu
         20                  25                  30

Pro Leu Glu Cys Asp Cys Gly Thr Cys Met Phe Tyr Ser Cys Gly Ser
         35                  40                  45

Gly Ser Ser Gly Ser Ser Leu Val Ala Ser Ala Ser Ala Ile
         50                  55                  60

<210> SEQ ID NO 116
<211> LENGTH: 62
<212> TYPE: PRT
<213> ORGANISM: Artificial Sequence
<220> FEATURE:
<223> OTHER INFORMATION: Synthetic

<400> SEQUENCE: 116

Met His His His His His Ser Gly Ser Ser Ser Gly Ser Gly Cys
1               5                   10                  15

Val Lys Lys Asp Glu Leu Cys Ala Val Trp Phe Asp Val Cys Cys Glu
         20                  25                  30

Pro Leu Glu Cys Thr Tyr Gln Ser Gly Tyr Tyr Trp Leu Cys Gly Ser
         35                  40                  45

Gly Ser Ser Gly Ser Ser Leu Val Ala Ser Ala Ser Ala Ile
         50                  55                  60

<210> SEQ ID NO 117
<211> LENGTH: 62
<212> TYPE: PRT
<213> ORGANISM: Artificial Sequence
<220> FEATURE:
<223> OTHER INFORMATION: Synthetic

<400> SEQUENCE: 117

Met His His His His His Ser Gly Ser Ser Ser Gly Ser Gly Cys

```
                1               5                   10                  15
Val Lys Lys Asp Glu Leu Cys Leu Thr Gln Thr Arg Ser Cys Cys Glu
                    20                  25                  30

Pro Leu Glu Cys Arg Phe Leu Arg Ser His Ala Arg Thr Cys Gly Ser
                35                  40                  45

Gly Ser Ser Gly Ser Ser Leu Val Ala Ser Ala Ser Ala Ile
            50                  55                  60
```

<210> SEQ ID NO 118
<211> LENGTH: 62
<212> TYPE: PRT
<213> ORGANISM: Artificial Sequence
<220> FEATURE:
<223> OTHER INFORMATION: Synthetic

<400> SEQUENCE: 118

```
Met His His His His His Ser Gly Ser Ser Ser Gly Ser Gly Cys
1               5                   10                  15

Val Lys Lys Asp Glu Leu Cys Arg Lys Arg Tyr Arg Val Cys Cys Glu
                    20                  25                  30

Pro Leu Glu Cys Ile Leu Gln Phe Met Asn Lys Met Phe Cys Gly Ser
                35                  40                  45

Gly Ser Ser Gly Ser Ser Leu Val Ala Ser Ala Ser Ala Ile
            50                  55                  60
```

<210> SEQ ID NO 119
<211> LENGTH: 62
<212> TYPE: PRT
<213> ORGANISM: Artificial Sequence
<220> FEATURE:
<223> OTHER INFORMATION: Synthetic

<400> SEQUENCE: 119

```
Met His His His His His Ser Gly Ser Ser Ser Gly Ser Gly Trp
1               5                   10                  15

Val Lys Lys Asp Glu Leu Cys Glu Pro Trp Tyr Trp Arg Cys Cys Glu
                    20                  25                  30

Pro Leu Glu Cys Val Tyr Thr Ser Gly Tyr Tyr Tyr Ser Cys Gly Ser
                35                  40                  45

Gly Ser Ser Gly Ser Ser Leu Val Ala Ser Ala Ser Ala Ile
            50                  55                  60
```

<210> SEQ ID NO 120
<211> LENGTH: 62
<212> TYPE: PRT
<213> ORGANISM: Artificial Sequence
<220> FEATURE:
<223> OTHER INFORMATION: Synthetic

<400> SEQUENCE: 120

```
Met His His His His His Ser Gly Ser Ser Ser Gly Ser Gly Cys
1               5                   10                  15

Val Lys Lys Asp Glu Leu Cys Ala Gly Ser Val Gly His Cys Cys Glu
                    20                  25                  30

Pro Leu Glu Cys Leu Arg Arg Phe Leu Asn Leu Arg Trp Cys Gly Ser
                35                  40                  45

Gly Ser Ser Gly Ser Ser Leu Val Ala Ser Ala Ser Ala Ile
            50                  55                  60
```

<210> SEQ ID NO 121
<211> LENGTH: 62

```
<212> TYPE: PRT
<213> ORGANISM: Artificial Sequence
<220> FEATURE:
<223> OTHER INFORMATION: Synthetic

<400> SEQUENCE: 121

Met His His His His His His Ser Gly Ser Ser Ser Gly Ser Gly Cys
1               5                   10                  15

Val Lys Lys Asp Glu Leu Cys Ala Ser Arg Ile Trp Ala Cys Cys Gly
            20                  25                  30

Pro Leu Glu Cys Leu Met Arg Phe Met Ala Lys Arg Phe Cys Gly Ser
        35                  40                  45

Gly Ser Ser Gly Ser Ser Leu Val Ala Ser Ala Ser Ala Ile
    50                  55                  60

<210> SEQ ID NO 122
<211> LENGTH: 52
<212> TYPE: PRT
<213> ORGANISM: Artificial Sequence
<220> FEATURE:
<223> OTHER INFORMATION: Synthetic

<400> SEQUENCE: 122

Met His His His His His His Ser Gly Ser Ser Ser Gly Ser Gly Cys
1               5                   10                  15

Ala Lys Lys Asp Glu Leu Cys Ser Pro Ala Arg Arg Ile Cys Cys Glu
            20                  25                  30

Pro Leu Glu Cys Leu Arg Arg Trp Tyr Glu Glu Ser Phe Cys Gly Ser
        35                  40                  45

Gly Ser Ser Gly
    50

<210> SEQ ID NO 123
<211> LENGTH: 62
<212> TYPE: PRT
<213> ORGANISM: Artificial Sequence
<220> FEATURE:
<223> OTHER INFORMATION: Synthetic

<400> SEQUENCE: 123

Met His His His His His His Ser Gly Ser Ser Ser Gly Ser Gly Cys
1               5                   10                  15

Val Lys Lys Asp Glu Leu Cys Thr Met Asn Glu Val Cys Cys Cys Glu
            20                  25                  30

Pro Leu Glu Cys Tyr Gly Asp Ile Ser Gly Glu Ala Met Cys Gly Ser
        35                  40                  45

Gly Ser Ser Gly Ser Ser Leu Val Ala Ser Ala Ser Ala Ile
    50                  55                  60

<210> SEQ ID NO 124
<211> LENGTH: 62
<212> TYPE: PRT
<213> ORGANISM: Artificial Sequence
<220> FEATURE:
<223> OTHER INFORMATION: Synthetic

<400> SEQUENCE: 124

Met His His His His His His Ser Gly Ser Ser Ser Gly Ser Gly Cys
1               5                   10                  15

Val Lys Lys Asp Glu Leu Cys Ile Val Met Arg Ala Pro Cys Cys Glu
            20                  25                  30

Pro Leu Glu Cys Leu Arg Arg Tyr Met Leu Lys His Met Cys Gly Ser
```

Gly Ser Ser Gly Ser Ser Leu Val Ala Ser Ala Ser Ala Ile
        50                  55                  60

<210> SEQ ID NO 125
<211> LENGTH: 62
<212> TYPE: PRT
<213> ORGANISM: Artificial Sequence
<220> FEATURE:
<223> OTHER INFORMATION: Synthetic

<400> SEQUENCE: 125

Met His His His His His His Ser Gly Ser Ser Gly Ser Gly Cys
1               5                   10                  15

Val Lys Lys Asp Glu Leu Cys Lys Ala Phe Arg Tyr Ser Cys Cys Glu
            20                  25                  30

Pro Leu Glu Cys Leu Arg Lys Trp Leu Lys Ala Arg Phe Cys Gly Ser
        35                  40                  45

Gly Ser Ser Gly Ser Ser Leu Val Ala Ser Ala Ser Ala Ile
        50                  55                  60

<210> SEQ ID NO 126
<211> LENGTH: 55
<212> TYPE: PRT
<213> ORGANISM: Artificial Sequence
<220> FEATURE:
<223> OTHER INFORMATION: Synthetic

<400> SEQUENCE: 126

Met His His His His His His Ser Gly Ser Ser Ser Gly Ser Gly Cys
1               5                   10                  15

Val Lys Lys Asp Glu Leu Cys Val Ser Gly Leu Met Asn Cys Cys Glu
            20                  25                  30

Pro Leu Glu Cys Leu Trp Arg Trp Met Gln Lys Gln Gln Cys Gly Ser
        35                  40                  45

Gly Ser Ser Gly Ser Ser His
        50                  55

<210> SEQ ID NO 127
<211> LENGTH: 55
<212> TYPE: PRT
<213> ORGANISM: Artificial Sequence
<220> FEATURE:
<223> OTHER INFORMATION: Synthetic

<400> SEQUENCE: 127

Met His His His His His His Ser Gly Ser Ser Ser Gly Ser Gly Cys
1               5                   10                  15

Val Lys Lys Asp Glu Leu Cys Trp Arg Pro Ala Ile Thr Cys Cys Glu
            20                  25                  30

Pro Leu Glu Cys Leu Arg Ile Tyr Met Arg Leu Trp Arg Cys Gly Ser
        35                  40                  45

Gly Ser Ser Gly Ser Ser Leu
        50                  55

<210> SEQ ID NO 128
<211> LENGTH: 56
<212> TYPE: PRT
<213> ORGANISM: Artificial Sequence
<220> FEATURE:
<223> OTHER INFORMATION: Synthetic

<400> SEQUENCE: 128

```
Met His His His His His Ser Gly Ser Ser Ser Gly Ser Gly Cys
1               5                   10                  15

Val Lys Lys Asp Glu Leu Cys Ser Gln Leu Asp Ser Ala Cys Cys Glu
                20                  25                  30

Pro Leu Glu Cys Val Trp Gln Asn Asp Asn Tyr Gly Thr Cys Gly Arg
            35                  40                  45

Ala Val Leu Gly Leu Ala His Pro
    50                  55

<210> SEQ ID NO 129
<211> LENGTH: 50
<212> TYPE: PRT
<213> ORGANISM: Artificial Sequence
<220> FEATURE:
<223> OTHER INFORMATION: Synthetic

<400> SEQUENCE: 129

Met His His His His His Ser Gly Ser Ser Ser Gly Ser Gly Cys
1               5                   10                  15

Val Lys Lys Asp Glu Leu Cys Met Ser Met Val Gln Ile Cys Cys Glu
                20                  25                  30

Pro Leu Glu Cys Phe His Ile Val Trp Cys Pro Trp Ala Cys Thr Ala
            35                  40                  45

Val His
    50

<210> SEQ ID NO 130
<211> LENGTH: 51
<212> TYPE: PRT
<213> ORGANISM: Artificial Sequence
<220> FEATURE:
<223> OTHER INFORMATION: Synthetic

<400> SEQUENCE: 130

Met His His His His His Ser Asp Ser Ser Ser Gly Ser Gly Cys
1               5                   10                  15

Val Lys Lys Asp Glu Leu Cys Leu Met Arg Val Leu Arg Cys Cys Glu
                20                  25                  30

Pro Leu Glu Cys Trp Val Gly Gly Val Cys Arg Gly Gly Cys Gly Ser
            35                  40                  45

Gly Ser Tyr
    50

<210> SEQ ID NO 131
<211> LENGTH: 62
<212> TYPE: PRT
<213> ORGANISM: Artificial Sequence
<220> FEATURE:
<223> OTHER INFORMATION: Synthetic

<400> SEQUENCE: 131

Met His His His His His Ser Gly Ser Ser Ser Gly Ser Gly Cys
1               5                   10                  15

Val Lys Lys Asp Glu Leu Cys Thr Lys Ile Phe Lys Arg Cys Cys Glu
                20                  25                  30

Pro Leu Glu Cys Ser Trp Val Trp Phe Pro Tyr Ser Cys Gly Ser
            35                  40                  45

Gly Ser Ser Gly Ser Ser Leu Val Ala Ser Ala Ser Ala Ile
    50                  55                  60
```

<210> SEQ ID NO 132
<211> LENGTH: 62
<212> TYPE: PRT
<213> ORGANISM: Artificial Sequence
<220> FEATURE:
<223> OTHER INFORMATION: Synthetic

<400> SEQUENCE: 132

Met His His His His His His Ser Gly Ser Ser Ser Gly Ser Gly Cys
1               5                   10                  15

Val Lys Lys Asp Glu Leu Cys Lys Lys Ile Asn Ala Lys Cys Cys Glu
            20                  25                  30

Pro Leu Glu Cys Leu Arg Arg Phe Leu Arg Phe Lys Phe Cys Gly Ser
        35                  40                  45

Gly Ser Ser Gly Ser Ser Leu Val Ala Ser Ala Ser Ala Ile
    50                  55                  60

<210> SEQ ID NO 133
<211> LENGTH: 62
<212> TYPE: PRT
<213> ORGANISM: Artificial Sequence
<220> FEATURE:
<223> OTHER INFORMATION: Synthetic

<400> SEQUENCE: 133

Met His His His His His His Ser Gly Ser Ser Ser Gly Ser Gly Cys
1               5                   10                  15

Val Lys Lys Asp Glu Leu Cys Leu Arg Ser Ser Ile Asp Cys Cys Glu
            20                  25                  30

Pro Leu Glu Cys Leu Tyr Lys Trp Met Gln Arg Arg Leu Cys Gly Ser
        35                  40                  45

Gly Ser Ser Gly Ser Ser Leu Val Ala Ser Ala Ser Ala Ile
    50                  55                  60

<210> SEQ ID NO 134
<211> LENGTH: 62
<212> TYPE: PRT
<213> ORGANISM: Artificial Sequence
<220> FEATURE:
<223> OTHER INFORMATION: Synthetic

<400> SEQUENCE: 134

Met His His His His His His Ser Gly Ser Ser Ser Gly Ser Gly Cys
1               5                   10                  15

Val Lys Lys Asp Glu Leu Cys Gly Leu Leu Thr Ser Val Cys Cys Glu
            20                  25                  30

Pro Leu Glu Cys Val Trp Val Leu His His Phe Val Tyr Cys Gly Ser
        35                  40                  45

Gly Ser Ser Gly Ser Ser Leu Val Ala Ser Ala Ser Ala Ile
    50                  55                  60

<210> SEQ ID NO 135
<211> LENGTH: 58
<212> TYPE: PRT
<213> ORGANISM: Artificial Sequence
<220> FEATURE:
<223> OTHER INFORMATION: Synthetic

<400> SEQUENCE: 135

Met His His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Lys Trp Thr Asn Glu His Phe Gly Thr Cys Gly Ser
            35                  40                  45

Gly Ser Ser Gly Ser Ser Leu Val Ala Tyr
        50                  55

<210> SEQ ID NO 136
<211> LENGTH: 52
<212> TYPE: PRT
<213> ORGANISM: Artificial Sequence
<220> FEATURE:
<223> OTHER INFORMATION: Synthetic

<400> SEQUENCE: 136

Met His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Ile Tyr Thr Ser Glu Leu Tyr Ala Thr Cys Gly Ser
            35                  40                  45

Gly Ser Ser Gly
        50

<210> SEQ ID NO 137
<211> LENGTH: 60
<212> TYPE: PRT
<213> ORGANISM: Artificial Sequence
<220> FEATURE:
<223> OTHER INFORMATION: Synthetic

<400> SEQUENCE: 137

Met His His His His His Ser Asp Ser Ser Ser Gly Ser Gly Cys
1               5                   10                  15

Val Lys Lys Asp Glu Leu Cys Arg Asn Val Arg Thr Pro Cys Cys Glu
            20                  25                  30

Pro Leu Glu Cys Asp Leu Phe Leu Thr Phe Leu Phe Leu Cys Gly Ser
            35                  40                  45

Gly Ser Ser Gly Ser Ser Leu Val Ala Ser Ala Asn
        50                  55                  60

<210> SEQ ID NO 138
<211> LENGTH: 57
<212> TYPE: PRT
<213> ORGANISM: Artificial Sequence
<220> FEATURE:
<223> OTHER INFORMATION: Synthetic

<400> SEQUENCE: 138

Met His His His His His Ser Gly Ser Ser Ser Gly Ser Gly Cys
1               5                   10                  15

Val Lys Lys Asp Glu Leu Cys Met Ser Met Ala Cys Val Cys Cys Glu
            20                  25                  30

Pro Leu Glu Cys Lys Tyr His Gly Tyr Phe Trp Leu Cys Gly Ser Ala
            35                  40                  45

Val Leu Gly Pro Ser Ser Ile Arg Tyr
        50                  55

<210> SEQ ID NO 139
<211> LENGTH: 56
<212> TYPE: PRT
<213> ORGANISM: Artificial Sequence
<220> FEATURE:
<223> OTHER INFORMATION: Synthetic

<400> SEQUENCE: 139

Met His His His His His His Ser Gly Ser Ser Ser Gly Ser Gly Cys
1               5                   10                  15

Val Lys Lys Asp Glu Leu Cys Phe Trp Trp Leu Thr Leu Cys Cys Glu
            20                  25                  30

Pro Leu Glu Cys Leu Arg His Ile Cys Leu Val Ser Pro Cys Gly Arg
        35                  40                  45

Ala Val Leu Gly Leu Ala His Pro
    50                  55

<210> SEQ ID NO 140
<211> LENGTH: 62
<212> TYPE: PRT
<213> ORGANISM: Artificial Sequence
<220> FEATURE:
<223> OTHER INFORMATION: Synthetic

<400> SEQUENCE: 140

Met His His His His His His Ser Gly Ser Ser Ser Gly Ser Gly Cys
1               5                   10                  15

Val Lys Lys Asp Glu Leu Arg Lys Arg Arg Asn Gly His Cys Cys Glu
            20                  25                  30

Pro Leu Glu Cys Leu Trp Trp Ala Gly Val Pro Leu Met Cys Gly Ser
        35                  40                  45

Gly Ser Ser Gly Ser Ser Leu Val Ala Ser Ala Ser Ala Ile
    50                  55                  60

<210> SEQ ID NO 141
<211> LENGTH: 62
<212> TYPE: PRT
<213> ORGANISM: Artificial Sequence
<220> FEATURE:
<223> OTHER INFORMATION: Synthetic

<400> SEQUENCE: 141

Met His His His His His His Ser Asp Ser Ser Ser Gly Ser Gly Cys
1               5                   10                  15

Val Lys Lys Asp Glu Leu Cys Val Trp Asn Ser Met Pro Cys Cys Glu
            20                  25                  30

Pro Leu Glu Cys Leu Arg His Arg Leu Leu Arg Leu Cys Gly Ser
        35                  40                  45

Gly Ser Ser Gly Ser Ser Leu Val Ala Ser Ala Ser Ala Ile
    50                  55                  60

<210> SEQ ID NO 142
<211> LENGTH: 62
<212> TYPE: PRT
<213> ORGANISM: Artificial Sequence
<220> FEATURE:
<223> OTHER INFORMATION: Synthetic

<400> SEQUENCE: 142

Met His His His His His His Ser Gly Ser Ser Ser Gly Ser Gly Cys
1               5                   10                  15

Val Lys Lys Asp Glu Leu Cys Arg Pro Glu Val Leu Ser Cys Cys Glu
            20                  25                  30

Pro Leu Glu Cys Leu Arg Arg Trp Phe Gln Lys Arg Met Cys Gly Ser
        35                  40                  45

Gly Ser Ser Gly Ser Ser Leu Val Ala Ser Ala Ser Ala Ile
    50                  55                  60

<210> SEQ ID NO 143
<211> LENGTH: 62
<212> TYPE: PRT
<213> ORGANISM: Artificial Sequence
<220> FEATURE:
<223> OTHER INFORMATION: Synthetic

<400> SEQUENCE: 143

Met His His His His His His Ser Gly Ser Ser Ser Gly Ser Gly Cys
1               5                   10                  15

Val Lys Lys Asp Glu Leu Cys Phe Ser Arg Met Phe Met Cys Cys Glu
            20                  25                  30

Pro Leu Glu Cys Asn Cys Pro Leu Ile Met Phe Ile Tyr Cys Gly Ser
        35                  40                  45

Gly Ser Ser Gly Ser Ser Leu Val Ala Ser Ala Ser Ala Ile
    50                  55                  60

<210> SEQ ID NO 144
<211> LENGTH: 62
<212> TYPE: PRT
<213> ORGANISM: Artificial Sequence
<220> FEATURE:
<223> OTHER INFORMATION: Synthetic

<400> SEQUENCE: 144

Met His His His His His His Ser Gly Ser Ser Ser Gly Ser Gly Cys
1               5                   10                  15

Val Lys Lys Asp Glu Leu Cys Trp Pro Arg Arg His Lys Cys Cys Glu
            20                  25                  30

Pro Leu Glu Cys Leu Leu Glu Met Leu Glu Arg Lys Arg Cys Gly Ser
        35                  40                  45

Gly Ser Ser Gly Ser Ser Leu Val Ala Ser Ala Ser Ala Ile
    50                  55                  60

<210> SEQ ID NO 145
<211> LENGTH: 62
<212> TYPE: PRT
<213> ORGANISM: Artificial Sequence
<220> FEATURE:
<223> OTHER INFORMATION: Synthetic

<400> SEQUENCE: 145

Met His His His His His His Ser Gly Ser Ser Ser Gly Ser Gly Cys
1               5                   10                  15

Val Lys Lys Asp Glu Leu Cys His Ala Trp Tyr Thr Phe Cys Cys Glu
            20                  25                  30

Pro Leu Glu Cys Gln Arg Lys Phe Gly Gly Tyr Trp Ala Cys Gly Ser
        35                  40                  45

Gly Ser Ser Gly Ser Ser Leu Val Ala Ser Ala Ser Ala Ile
    50                  55                  60

<210> SEQ ID NO 146
<211> LENGTH: 62
<212> TYPE: PRT
<213> ORGANISM: Artificial Sequence
<220> FEATURE:
<223> OTHER INFORMATION: Synthetic

<400> SEQUENCE: 146

Met His His His His His His Ser Gly Ser Ser Ser Gly Ser Gly Cys
1               5                   10                  15

```
Val Lys Lys Asp Glu Leu Cys Trp Glu Asp Met Thr Val Cys Cys Glu
            20                  25                  30

Pro Leu Glu Cys Pro Ala Leu Glu Ser Val Val Leu Gln Cys Gly Ser
            35                  40                  45

Gly Ser Ser Gly Ser Ser Leu Val Ala Ser Ala Ser Ala Ile
        50                  55                  60

<210> SEQ ID NO 147
<211> LENGTH: 50
<212> TYPE: PRT
<213> ORGANISM: Artificial Sequence
<220> FEATURE:
<223> OTHER INFORMATION: Synthetic

<400> SEQUENCE: 147

Met His His His His His His Ser Gly Ser Ser Ser Gly Ser Gly Cys
1               5                   10                  15

Val Lys Lys Asp Glu Leu Cys Leu Cys Trp Gln Trp Thr Cys Cys Glu
            20                  25                  30

Pro Leu Glu Cys Glu Leu Gln Trp Gly Ile Ile Arg Met Cys Gly Ser
            35                  40                  45

Gly Asn
    50

<210> SEQ ID NO 148
<211> LENGTH: 60
<212> TYPE: PRT
<213> ORGANISM: Artificial Sequence
<220> FEATURE:
<223> OTHER INFORMATION: Synthetic

<400> SEQUENCE: 148

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
            35                  40                  45

Gly Ser Ser Gly Ser Ser Leu Val Ala Ser Ala Ile
        50                  55                  60

<210> SEQ ID NO 149
<211> LENGTH: 58
<212> TYPE: PRT
<213> ORGANISM: Artificial Sequence
<220> FEATURE:
<223> OTHER INFORMATION: Synthetic

<400> SEQUENCE: 149

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Arg
            35                  40                  45

Ala Val Leu Gly Leu Ala His Pro Leu Phe
        50                  55

<210> SEQ ID NO 150
<211> LENGTH: 60
<212> TYPE: PRT
<213> ORGANISM: Artificial Sequence
```

<220> FEATURE:
<223> OTHER INFORMATION: Synthetic

<400> SEQUENCE: 150

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Phe Gly His Gly Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 151
<211> LENGTH: 59
<212> TYPE: PRT
<213> ORGANISM: Artificial Sequence
<220> FEATURE:
<223> OTHER INFORMATION: Synthetic

<400> SEQUENCE: 151

Met His His His His His Ser Gly Ser Ser Ser Gly Ser Gly Cys Val
1               5                   10                  15

Lys Lys Asp Glu Leu Cys Glu Leu Ala Ile Asp Val Cys Cys Glu Pro
            20                  25                  30

Leu Glu Cys Leu Gly His Gly Leu Gly Tyr Ala Tyr Cys Gly Ser Gly
        35                  40                  45

Ser Ser Gly Ser Ser Leu Val Ala Ser Ala Ile
    50                  55

<210> SEQ ID NO 152
<211> LENGTH: 60
<212> TYPE: PRT
<213> ORGANISM: Artificial Sequence
<220> FEATURE:
<223> OTHER INFORMATION: Synthetic

<400> SEQUENCE: 152

Met His His His His His His Ser Gly Ser Ser Ser Gly Ser Asp Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 153
<211> LENGTH: 50
<212> TYPE: PRT
<213> ORGANISM: Artificial Sequence
<220> FEATURE:
<223> OTHER INFORMATION: Synthetic

<400> SEQUENCE: 153

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Asn
    50

<210> SEQ ID NO 154
<211> LENGTH: 60
<212> TYPE: PRT
<213> ORGANISM: Artificial Sequence
<220> FEATURE:
<223> OTHER INFORMATION: Synthetic

<400> SEQUENCE: 154

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Gly
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 155
<211> LENGTH: 47
<212> TYPE: PRT
<213> ORGANISM: Artificial Sequence
<220> FEATURE:
<223> OTHER INFORMATION: Synthetic

<400> SEQUENCE: 155

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly
        35                  40                  45

<210> SEQ ID NO 156
<211> LENGTH: 46
<212> TYPE: PRT
<213> ORGANISM: Artificial Sequence
<220> FEATURE:
<223> OTHER INFORMATION: Synthetic

<400> SEQUENCE: 156

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys
        35                  40                  45

<210> SEQ ID NO 157
<211> LENGTH: 48
<212> TYPE: PRT
<213> ORGANISM: Artificial Sequence
<220> FEATURE:
<223> OTHER INFORMATION: Synthetic

<400> SEQUENCE: 157

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Arg

<210> SEQ ID NO 158
<211> LENGTH: 61
<212> TYPE: PRT
<213> ORGANISM: Artificial Sequence
<220> FEATURE:
<223> OTHER INFORMATION: Synthetic

<400> SEQUENCE: 158

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Phe Gly His Gly Leu Gly Tyr Ala Tyr Cys Gly Ser
        35                  40                  45

Gly Ser Ser Gly Ser Ser Leu Val Ala Ser Ala Ser Asn
    50                  55                  60

<210> SEQ ID NO 159
<211> LENGTH: 60
<212> TYPE: PRT
<213> ORGANISM: Artificial Sequence
<220> FEATURE:
<223> OTHER INFORMATION: Synthetic

<400> SEQUENCE: 159

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Phe Glu Cys Leu Gly His Gly Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 160
<211> LENGTH: 60
<212> TYPE: PRT
<213> ORGANISM: Artificial Sequence
<220> FEATURE:
<223> OTHER INFORMATION: Synthetic

<400> SEQUENCE: 160

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Trp Tyr Ala Tyr Cys Gly Ser
        35                  40                  45

Gly Ser Ser Gly Ser Ser Leu Val Ala Ser Ala Ile
    50                  55                  60

<210> SEQ ID NO 161
<211> LENGTH: 60
<212> TYPE: PRT
<213> ORGANISM: Artificial Sequence
<220> FEATURE:
<223> OTHER INFORMATION: Synthetic

<400> SEQUENCE: 161

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Val Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 162
<211> LENGTH: 55
<212> TYPE: PRT
<213> ORGANISM: Artificial Sequence
<220> FEATURE:
<223> OTHER INFORMATION: Synthetic

<400> SEQUENCE: 162

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser His
    50                  55

<210> SEQ ID NO 163
<211> LENGTH: 59
<212> TYPE: PRT
<213> ORGANISM: Artificial Sequence
<220> FEATURE:
<223> OTHER INFORMATION: Synthetic

<400> SEQUENCE: 163

Met His His His His His His Ser Gly Ser Ser Ser Gly Ser Gly Cys
1               5                   10                  15

Val Lys Lys Asp Arg Ser Pro Thr Leu Ser Cys Cys Glu Pro Leu Glu
            20                  25                  30

Cys Leu Arg Val Tyr Leu Glu His Trp Phe Cys Gly Ser Gly Ser Gly
        35                  40                  45

Ser Ser Leu Val Ala Ser Ala Ser Ala Ile Asn
    50                  55

<210> SEQ ID NO 164
<211> LENGTH: 60
<212> TYPE: PRT
<213> ORGANISM: Artificial Sequence
<220> FEATURE:
<223> OTHER INFORMATION: Synthetic

<400> SEQUENCE: 164

Met His His His His His His Ser Gly Ser Ser Ser Gly Ser Gly Cys
1               5                   10                  15

Val Lys Lys Asp Glu Leu Cys Gln Leu Cys Ala Leu His Cys Cys Glu
            20                  25                  30

Pro Leu Glu Cys Val Arg Met Met Phe Leu Val His Arg Cys Gly Ser
        35                  40                  45

Gly Ser Ser Gly Ser Ser Leu Val Ala Ser Ala Ile
    50                  55                  60

<210> SEQ ID NO 165
<211> LENGTH: 61
<212> TYPE: PRT

<213> ORGANISM: Artificial Sequence
<220> FEATURE:
<223> OTHER INFORMATION: Synthetic

<400> SEQUENCE: 165

Met His His His His His His Ser Gly Ser Ser Ser Gly Ser Gly Cys
1               5                   10                  15

Val Lys Lys Asp Glu Leu Cys Asn Trp Val Thr Pro Met Arg Cys Glu
            20                  25                  30

Pro Leu Glu Cys Val Leu Gly His Gly Leu Gly Tyr Ala Tyr Cys Gly
        35                  40                  45

Ser Gly Ser Ser Gly Ser Ser Leu Val Ala Ser Ala Ile
    50                  55                  60

<210> SEQ ID NO 166
<211> LENGTH: 61
<212> TYPE: PRT
<213> ORGANISM: Artificial Sequence
<220> FEATURE:
<223> OTHER INFORMATION: Synthetic

<400> SEQUENCE: 166

Met His His His His His His Ser Gly Ser Ser Ser Gly Ser Gly Cys
1               5                   10                  15

Val Lys Lys Asp Glu Leu Cys Val Phe Tyr Phe Pro Asn Cys Cys Glu
            20                  25                  30

Pro Leu Glu Cys Val Arg Trp Val Asn Asp Asn Tyr Gly Trp Cys Gly
        35                  40                  45

Ser Gly Ser Ser Gly Ser Ser Leu Val Ala Ser Ala Ile
    50                  55                  60

<210> SEQ ID NO 167
<211> LENGTH: 61
<212> TYPE: PRT
<213> ORGANISM: Artificial Sequence
<220> FEATURE:
<223> OTHER INFORMATION: Synthetic

<400> SEQUENCE: 167

Met His His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Val Lys Trp Thr Asn Glu His Phe Gly Thr Cys Gly
        35                  40                  45

Ser Gly Ser Ser Gly Ser Ser Leu Val Ala Ser Ala Ile
    50                  55                  60

<210> SEQ ID NO 168
<211> LENGTH: 58
<212> TYPE: PRT
<213> ORGANISM: Artificial Sequence
<220> FEATURE:
<223> OTHER INFORMATION: Synthetic

<400> SEQUENCE: 168

Met His His His His His His Ser Gly Ser Ser Ser Gly Ser Gly Cys
1               5                   10                  15

Val Lys Lys Asp Glu Leu Cys Met Ser Met Ala Cys Val Cys Cys Glu
            20                  25                  30

Pro Leu Glu Cys Val Lys Tyr His Gly Tyr Phe Trp Leu Cys Cys Gly
        35                  40                  45

```
Ser Gly Ser Ser Gly Ser Ser Leu Val Glu
        50                  55
```

<210> SEQ ID NO 169
<211> LENGTH: 61
<212> TYPE: PRT
<213> ORGANISM: Artificial Sequence
<220> FEATURE:
<223> OTHER INFORMATION: Synthetic

<400> SEQUENCE: 169

```
Met His His His His His Ser Gly Ser Ser Gly Ser Gly Cys
1               5                   10                  15

Val Lys Lys Asp Glu Leu Cys Ser Val Trp Tyr Arg Val Cys Cys Glu
            20                  25                  30

Pro Leu Glu Cys Val Thr Pro Asp Trp Ser Gly Ile Leu Tyr Cys Gly
        35                  40                  45

Ser Gly Ser Ser Gly Ser Ser Leu Val Ala Ser Ala Ile
        50                  55                  60
```

<210> SEQ ID NO 170
<211> LENGTH: 52
<212> TYPE: PRT
<213> ORGANISM: Artificial Sequence
<220> FEATURE:
<223> OTHER INFORMATION: Synthetic

<400> SEQUENCE: 170

```
Ser Ser Ser Gly Ser Gly Cys Val Lys Lys Asp Glu Leu Cys Glu Leu
1               5                   10                  15

Ala Ile Asp Val Cys Cys Glu Pro Leu Glu Cys Val Leu Gly His Gly
            20                  25                  30

Leu Gly Tyr Ala Tyr Cys Gly Ser Gly Ser Ser Gly Ser Ser Leu Val
        35                  40                  45

Ala Ser Ala Ile
    50
```

<210> SEQ ID NO 171
<211> LENGTH: 60
<212> TYPE: PRT
<213> ORGANISM: Artificial Sequence
<220> FEATURE:
<223> OTHER INFORMATION: Synthetic

<400> SEQUENCE: 171

```
Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
        50                  55                  60
```

<210> SEQ ID NO 172
<211> LENGTH: 60
<212> TYPE: PRT
<213> ORGANISM: Artificial Sequence
<220> FEATURE:
<223> OTHER INFORMATION: Synthetic

<400> SEQUENCE: 172

```
Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Val Ser Ser Gly Ser Ser Leu Val Ala Ser Ala Ile
    50                  55                  60
```

<210> SEQ ID NO 173
<211> LENGTH: 58
<212> TYPE: PRT
<213> ORGANISM: Artificial Sequence
<220> FEATURE:
<223> OTHER INFORMATION: Synthetic

<400> SEQUENCE: 173

```
Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ile Leu Gly Leu Ala His Pro Leu Phe
    50                  55
```

<210> SEQ ID NO 174
<211> LENGTH: 60
<212> TYPE: PRT
<213> ORGANISM: Artificial Sequence
<220> FEATURE:
<223> OTHER INFORMATION: Synthetic

<400> SEQUENCE: 174

```
Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Val Phe
    50                  55                  60
```

<210> SEQ ID NO 175
<211> LENGTH: 56
<212> TYPE: PRT
<213> ORGANISM: Artificial Sequence
<220> FEATURE:
<223> OTHER INFORMATION: Synthetic

<400> SEQUENCE: 175

```
Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Leu Gly Leu Ala His Pro
    50                  55
```

<210> SEQ ID NO 176

```
<211> LENGTH: 54
<212> TYPE: PRT
<213> ORGANISM: Artificial Sequence
<220> FEATURE:
<223> OTHER INFORMATION: Synthetic

<400> SEQUENCE: 176

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Arg
    50

<210> SEQ ID NO 177
<211> LENGTH: 53
<212> TYPE: PRT
<213> ORGANISM: Artificial Sequence
<220> FEATURE:
<223> OTHER INFORMATION: Synthetic

<400> SEQUENCE: 177

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Leu
    50

<210> SEQ ID NO 178
<211> LENGTH: 55
<212> TYPE: PRT
<213> ORGANISM: Artificial Sequence
<220> FEATURE:
<223> OTHER INFORMATION: Synthetic

<400> SEQUENCE: 178

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser His
    50                  55

<210> SEQ ID NO 179
<211> LENGTH: 54
<212> TYPE: PRT
<213> ORGANISM: Artificial Sequence
<220> FEATURE:
<223> OTHER INFORMATION: Synthetic

<400> SEQUENCE: 179

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30
```

```
Pro Leu Glu Cys Leu Gly His Gly Leu Gly Tyr Ala Tyr Cys Gly Ser
        35                  40                  45

Gly Ser Ser Gly Ser Ser
    50

<210> SEQ ID NO 180
<211> LENGTH: 54
<212> TYPE: PRT
<213> ORGANISM: Artificial Sequence
<220> FEATURE:
<223> OTHER INFORMATION: Synthetic

<400> SEQUENCE: 180

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Arg
    50

<210> SEQ ID NO 181
<211> LENGTH: 45
<212> TYPE: PRT
<213> ORGANISM: Artificial Sequence
<220> FEATURE:
<223> OTHER INFORMATION: Synthetic

<400> SEQUENCE: 181

Ser Gly Ser Ser Gly Ser Gly Cys Val Lys Lys Asp Glu Leu Cys
1               5                   10                  15

Glu Leu Ala Ile Asp Val Cys Cys Glu Pro Leu Glu Cys Leu Gly His
            20                  25                  30

Gly Leu Gly Tyr Ala Tyr Cys Gly Ser Gly Ser Ser Gly
        35                  40                  45

<210> SEQ ID NO 182
<211> LENGTH: 52
<212> TYPE: PRT
<213> ORGANISM: Artificial Sequence
<220> FEATURE:
<223> OTHER INFORMATION: Synthetic

<400> SEQUENCE: 182

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Asp
    50

<210> SEQ ID NO 183
<211> LENGTH: 51
<212> TYPE: PRT
<213> ORGANISM: Artificial Sequence
<220> FEATURE:
<223> OTHER INFORMATION: Synthetic

<400> SEQUENCE: 183

Met His His His His His His Ser Gly Ser Ser Ser Gly Ser Gly Cys
```

```
                1               5                   10                  15
Val Lys Lys Asp Glu Leu Cys Glu Leu Ala Ile Asp Val Cys Cys Glu
                    20                  25                  30

Pro Leu Glu Cys Leu Gly His Gly Leu Gly Tyr Ala Tyr Cys Gly Ser
            35                  40                  45

Gly Ser Ser
    50
```

<210> SEQ ID NO 184
<211> LENGTH: 51
<212> TYPE: PRT
<213> ORGANISM: Artificial Sequence
<220> FEATURE:
<223> OTHER INFORMATION: Synthetic

<400> SEQUENCE: 184

```
Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
                    20                  25                  30

Pro Leu Glu Cys Leu Gly His Gly Leu Gly Tyr Ala Tyr Cys Gly Ser
            35                  40                  45

Gly Ser Tyr
    50
```

<210> SEQ ID NO 185
<211> LENGTH: 51
<212> TYPE: PRT
<213> ORGANISM: Artificial Sequence
<220> FEATURE:
<223> OTHER INFORMATION: Synthetic

<400> SEQUENCE: 185

```
Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
                    20                  25                  30

Pro Leu Glu Cys Leu Gly His Gly Leu Gly Tyr Ala Tyr Cys Gly Ser
            35                  40                  45

Cys Ser Tyr
    50
```

<210> SEQ ID NO 186
<211> LENGTH: 50
<212> TYPE: PRT
<213> ORGANISM: Artificial Sequence
<220> FEATURE:
<223> OTHER INFORMATION: Synthetic

<400> SEQUENCE: 186

```
Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
                    20                  25                  30

Pro Leu Glu Cys Leu Gly His Gly Leu Gly Tyr Ala Tyr Cys Gly Ser
            35                  40                  45

Gly Arg
    50
```

<210> SEQ ID NO 187
<211> LENGTH: 49

```
<212> TYPE: PRT
<213> ORGANISM: Artificial Sequence
<220> FEATURE:
<223> OTHER INFORMATION: Synthetic

<400> SEQUENCE: 187

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Thr
        35                  40                  45

Ala

<210> SEQ ID NO 188
<211> LENGTH: 49
<212> TYPE: PRT
<213> ORGANISM: Artificial Sequence
<220> FEATURE:
<223> OTHER INFORMATION: Synthetic

<400> SEQUENCE: 188

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly

<210> SEQ ID NO 189
<211> LENGTH: 45
<212> TYPE: PRT
<213> ORGANISM: Artificial Sequence
<220> FEATURE:
<223> OTHER INFORMATION: Synthetic

<400> SEQUENCE: 189

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr
        35                  40                  45

<210> SEQ ID NO 190
<211> LENGTH: 60
<212> TYPE: PRT
<213> ORGANISM: Artificial Sequence
<220> FEATURE:
<223> OTHER INFORMATION: Synthetic

<400> SEQUENCE: 190

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Val Phe
        50                  55                  60
```

```
<210> SEQ ID NO 191
<211> LENGTH: 51
<212> TYPE: PRT
<213> ORGANISM: Artificial Sequence
<220> FEATURE:
<223> OTHER INFORMATION: Synthetic

<400> SEQUENCE: 191

Met His His His Ser Gly Ser Ser Gly Ser Gly Cys Val Lys Lys
1               5                   10                  15

Asp Glu Leu Cys Glu Leu Ala Ile Asp Val Cys Cys Glu Pro Leu Glu
            20                  25                  30

Cys Trp Leu Gly His Gly Leu Gly Tyr Ala His Cys Gly Ser Gly Ser
        35                  40                  45

Ser Gly Ser
    50

<210> SEQ ID NO 192
<211> LENGTH: 61
<212> TYPE: PRT
<213> ORGANISM: Artificial Sequence
<220> FEATURE:
<223> OTHER INFORMATION: Synthetic

<400> SEQUENCE: 192

Met His His His His His His Ser Gly Ser Ser Ser Gly Ser Gly Cys
1               5                   10                  15

Val Lys Lys Asp Glu Leu Cys Glu Leu Ala Ile Asp Glu Cys Cys Glu
            20                  25                  30

Pro Leu Glu Cys Val Thr Lys Gly Asp Leu Gly Phe Arg Lys Cys Gly
        35                  40                  45

Ser Gly Ser Ser Gly Ser Ser Leu Val Ala Ser Ala Ile
    50                  55                  60

<210> SEQ ID NO 193
<211> LENGTH: 50
<212> TYPE: PRT
<213> ORGANISM: Artificial Sequence
<220> FEATURE:
<223> OTHER INFORMATION: Synthetic

<400> SEQUENCE: 193

Met His His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Leu Gly His Gly Leu Gly Tyr Ala Tyr Cys Gly Ser
        35                  40                  45

Gly Ser
    50

<210> SEQ ID NO 194
<211> LENGTH: 50
<212> TYPE: PRT
<213> ORGANISM: Artificial Sequence
<220> FEATURE:
<223> OTHER INFORMATION: Synthetic

<400> SEQUENCE: 194

Met His His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
```

```
                    20                  25                  30

Pro Leu Glu Cys Leu Gly His Gly Leu Gly Tyr Ala Tyr Cys Gly Ser
            35                  40                  45

Gly Tyr
    50

<210> SEQ ID NO 195
<211> LENGTH: 54
<212> TYPE: PRT
<213> ORGANISM: Artificial Sequence
<220> FEATURE:
<223> OTHER INFORMATION: Synthetic

<400> SEQUENCE: 195

Met His His His His His His Ser Gly Ser Ser Ser Gly Ser Gly Cys
1               5                   10                  15

Val Lys Lys Asp Glu Leu Cys Ala Arg Trp Asp Leu Val Cys Cys Glu
            20                  25                  30

Pro Leu Glu Cys Ile Tyr Thr Ser Glu Leu Tyr Ala Thr Cys Gly Ser
            35                  40                  45

Gly Ser Ser Gly Ser Arg
    50

<210> SEQ ID NO 196
<211> LENGTH: 60
<212> TYPE: PRT
<213> ORGANISM: Artificial Sequence
<220> FEATURE:
<223> OTHER INFORMATION: Synthetic

<400> SEQUENCE: 196

Met His His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Lys Trp Thr Asn Glu His Phe Gly Thr Cys Gly Ser
            35                  40                  45

Gly Ser Ser Gly Ser Ser Leu Val Ala Ser Ala Ile
    50                  55                  60

<210> SEQ ID NO 197
<211> LENGTH: 58
<212> TYPE: PRT
<213> ORGANISM: Artificial Sequence
<220> FEATURE:
<223> OTHER INFORMATION: Synthetic

<400> SEQUENCE: 197

Met His His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Lys Trp Thr Asn Glu His Phe Gly Thr Cys Gly Thr
            35                  40                  45

Ala Val Leu Gly Leu Ala His Pro Leu Phe
    50                  55

<210> SEQ ID NO 198
<211> LENGTH: 60
<212> TYPE: PRT
<213> ORGANISM: Artificial Sequence
<220> FEATURE:
```

<223> OTHER INFORMATION: Synthetic

<400> SEQUENCE: 198

Met His His His His His Ser Gly Ser Ser Ser Gly Ser Gly Cys
1               5                   10                  15

Val Lys Lys Asp Glu Leu Cys Ser Gln Ser Val Pro Met Cys Cys Glu
            20                  25                  30

Pro Leu Glu Cys Lys Trp Phe Asn Glu Asn Tyr Gly Ile Cys Gly Ser
        35                  40                  45

Gly Ser Ser Gly Ser Ser Leu Val Ala Ser Ala Ile
    50                  55                  60

<210> SEQ ID NO 199
<211> LENGTH: 60
<212> TYPE: PRT
<213> ORGANISM: Artificial Sequence
<220> FEATURE:
<223> OTHER INFORMATION: Synthetic

<400> SEQUENCE: 199

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 200
<211> LENGTH: 60
<212> TYPE: PRT
<213> ORGANISM: Artificial Sequence
<220> FEATURE:
<223> OTHER INFORMATION: Synthetic

<400> SEQUENCE: 200

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Asp
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
    50                  55                  60

<210> SEQ ID NO 201
<211> LENGTH: 60
<212> TYPE: PRT
<213> ORGANISM: Artificial Sequence
<220> FEATURE:
<223> OTHER INFORMATION: Synthetic

<400> SEQUENCE: 201

Met His His His His His His Ser Gly Ser Ser Ser Gly Ser Gly Cys
1               5                   10                  15

Ala Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ile Arg Tyr

<210> SEQ ID NO 202
<211> LENGTH: 59
<212> TYPE: PRT
<213> ORGANISM: Artificial Sequence
<220> FEATURE:
<223> OTHER INFORMATION: Synthetic

<400> SEQUENCE: 202

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala
    50                  55

<210> SEQ ID NO 203
<211> LENGTH: 58
<212> TYPE: PRT
<213> ORGANISM: Artificial Sequence
<220> FEATURE:
<223> OTHER INFORMATION: Synthetic

<400> SEQUENCE: 203

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Ala Val Leu Gly Leu Ala His Pro Leu Phe
    50                  55

<210> SEQ ID NO 204
<211> LENGTH: 57
<212> TYPE: PRT
<213> ORGANISM: Artificial Sequence
<220> FEATURE:
<223> OTHER INFORMATION: Synthetic

<400> SEQUENCE: 204

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala
    50                  55

<210> SEQ ID NO 205
<211> LENGTH: 55
<212> TYPE: PRT
<213> ORGANISM: Artificial Sequence
<220> FEATURE:
<223> OTHER INFORMATION: Synthetic

<400> SEQUENCE: 205

Met His His His His His His Ser Gly Ser Ser Ser Gly Ser Gly Cys
1               5                   10                  15

```
Val Lys Lys Asp Glu Leu Cys Glu Leu Ala Ile Asp Val Cys Cys Glu
         20                  25                  30

Pro Leu Glu Cys Leu Gly His Gly Leu Gly Tyr Ala Tyr Cys Gly Ser
             35                  40                  45

Gly Ser Ser Gly Ser Ser His
     50                  55

<210> SEQ ID NO 206
<211> LENGTH: 60
<212> TYPE: PRT
<213> ORGANISM: Artificial Sequence
<220> FEATURE:
<223> OTHER INFORMATION: Synthetic

<400> SEQUENCE: 206

Met His His His His His Ser Gly Ser Ser Gly Ser Gly Cys
1               5                  10                  15

Val Lys Lys Asp Glu Leu Cys Glu Leu Ala Ile Asp Val Cys Cys Glu
         20                  25                  30

Pro Leu Glu Cys Leu Gly His Gly Leu Gly Tyr Ala Tyr Cys Gly Ser
             35                  40                  45

Gly Ser Ser Gly Ser Ser Pro Ser Ser Ile Arg Tyr
     50                  55                  60

<210> SEQ ID NO 207
<211> LENGTH: 58
<212> TYPE: PRT
<213> ORGANISM: Artificial Sequence
<220> FEATURE:
<223> OTHER INFORMATION: Synthetic

<400> SEQUENCE: 207

Met His His His His His Ser Gly Ser Ser Ser Gly Ser Gly Cys
1               5                  10                  15

Val Lys Lys Asp Glu Leu Cys Glu Leu Ala Ile Asp Val Cys Cys Glu
         20                  25                  30

Pro Leu Glu Cys Leu Gly His Gly Leu Gly Tyr Ala Tyr Cys Gly Thr
             35                  40                  45

Ala Val Leu Gly Leu Ala His Pro Leu Phe
     50                  55

<210> SEQ ID NO 208
<211> LENGTH: 58
<212> TYPE: PRT
<213> ORGANISM: Artificial Sequence
<220> FEATURE:
<223> OTHER INFORMATION: Synthetic

<400> SEQUENCE: 208

Met His His His His His Ser Gly Ser Ser Ser Gly Ser Gly Cys
1               5                  10                  15

Val Arg Lys Asp Glu Leu Cys Glu Leu Ala Ile Asp Val Cys Cys Glu
         20                  25                  30

Pro Leu Glu Cys Leu Gly His Gly Leu Gly Tyr Ala Tyr Cys Gly Ser
             35                  40                  45

Gly Ser Leu Gly Leu Ala His Pro Leu Phe
     50                  55

<210> SEQ ID NO 209
<211> LENGTH: 53
<212> TYPE: PRT
```

<213> ORGANISM: Artificial Sequence
<220> FEATURE:
<223> OTHER INFORMATION: Synthetic

<400> SEQUENCE: 209

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser
    50

<210> SEQ ID NO 210
<211> LENGTH: 58
<212> TYPE: PRT
<213> ORGANISM: Artificial Sequence
<220> FEATURE:
<223> OTHER INFORMATION: Synthetic

<400> SEQUENCE: 210

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Arg
        35                  40                  45

Ala Val Leu Gly Leu Ala His Pro Leu Phe
    50                  55

<210> SEQ ID NO 211
<211> LENGTH: 58
<212> TYPE: PRT
<213> ORGANISM: Artificial Sequence
<220> FEATURE:
<223> OTHER INFORMATION: Synthetic

<400> SEQUENCE: 211

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser
    50                  55

<210> SEQ ID NO 212
<211> LENGTH: 60
<212> TYPE: PRT
<213> ORGANISM: Artificial Sequence
<220> FEATURE:
<223> OTHER INFORMATION: Synthetic

<400> SEQUENCE: 212

Met His His His His His Ser Gly Ser Ser Ser Gly Ser Gly Cys
1               5                   10                  15

Val Lys Lys Asp Glu Leu Cys Thr Thr Ala Ser Lys Ser Cys Cys Glu
            20                  25                  30

Pro Leu Glu Cys Lys Trp Thr Asn Glu His Phe Gly Thr Cys Gly Ser
        35                  40                  45

Gly Ser Ser Gly Ser Ser Leu Val Ala Ser Ala Ile
        50                  55                  60

<210> SEQ ID NO 213
<211> LENGTH: 61
<212> TYPE: PRT
<213> ORGANISM: Artificial Sequence
<220> FEATURE:
<223> OTHER INFORMATION: Synthetic

<400> SEQUENCE: 213

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile Tyr
        50                  55                  60

<210> SEQ ID NO 214
<211> LENGTH: 51
<212> TYPE: PRT
<213> ORGANISM: Artificial Sequence
<220> FEATURE:
<223> OTHER INFORMATION: Synthetic

<400> SEQUENCE: 214

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Tyr
    50

<210> SEQ ID NO 215
<211> LENGTH: 57
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: Xaa is any amino acid

<400> SEQUENCE: 215

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Glu Xaa
        50                  55

<210> SEQ ID NO 216
<211> LENGTH: 61
<212> TYPE: PRT
<213> ORGANISM: Artificial Sequence
<220> FEATURE:

<223> OTHER INFORMATION: Synthetic

<400> SEQUENCE: 216

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Arg Tyr
    50                  55                  60

<210> SEQ ID NO 217
<211> LENGTH: 47
<212> TYPE: PRT
<213> ORGANISM: Artificial Sequence
<220> FEATURE:
<223> OTHER INFORMATION: Synthetic

<400> SEQUENCE: 217

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly
        35                  40                  45

<210> SEQ ID NO 218
<211> LENGTH: 56
<212> TYPE: PRT
<213> ORGANISM: Artificial Sequence
<220> FEATURE:
<223> OTHER INFORMATION: Synthetic

<400> SEQUENCE: 218

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Asp
    50                  55

<210> SEQ ID NO 219
<211> LENGTH: 54
<212> TYPE: PRT
<213> ORGANISM: Artificial Sequence
<220> FEATURE:
<223> OTHER INFORMATION: Synthetic

<400> SEQUENCE: 219

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Val Leu Gly Leu Ala
    50

```
<210> SEQ ID NO 220
<211> LENGTH: 59
<212> TYPE: PRT
<213> ORGANISM: Artificial Sequence
<220> FEATURE:
<223> OTHER INFORMATION: Synthetic

<400> SEQUENCE: 220

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala
    50                  55

<210> SEQ ID NO 221
<211> LENGTH: 61
<212> TYPE: PRT
<213> ORGANISM: Artificial Sequence
<220> FEATURE:
<223> OTHER INFORMATION: Synthetic

<400> SEQUENCE: 221

Met His His His His His His Ser Gly Ser Ser Ser Gly Ser Gly Cys
1               5                   10                  15

Val Lys Lys Asp Glu Leu Cys Glu Leu Ala Ile Asp Glu Cys Cys Glu
            20                  25                  30

Pro Leu Glu Cys Thr Lys Gly Asp Leu Gly Phe Arg Lys Cys Gly Ser
        35                  40                  45

Gly Ser Ser Gly Ser Ser Leu Val Ala Ser Ala Ile Tyr
    50                  55                  60

<210> SEQ ID NO 222
<211> LENGTH: 59
<212> TYPE: PRT
<213> ORGANISM: Artificial Sequence
<220> FEATURE:
<223> OTHER INFORMATION: Synthetic

<400> SEQUENCE: 222

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Glu Phe Trp Val Pro Ser Ser Ile Arg Tyr Leu
    50                  55

<210> SEQ ID NO 223
<211> LENGTH: 58
<212> TYPE: PRT
<213> ORGANISM: Artificial Sequence
<220> FEATURE:
<223> OTHER INFORMATION: Synthetic

<400> SEQUENCE: 223

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30
```

```
Pro Leu Glu Cys Leu Gly His Gly Leu Gly Tyr Ala Tyr Cys Gly Ser
        35                  40                  45

Gly Ser Ser Gly Ser Ser Leu Val Ala Ser
    50                  55

<210> SEQ ID NO 224
<211> LENGTH: 53
<212> TYPE: PRT
<213> ORGANISM: Artificial Sequence
<220> FEATURE:
<223> OTHER INFORMATION: Synthetic

<400> SEQUENCE: 224

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser
    50

<210> SEQ ID NO 225
<211> LENGTH: 55
<212> TYPE: PRT
<213> ORGANISM: Artificial Sequence
<220> FEATURE:
<223> OTHER INFORMATION: Synthetic

<400> SEQUENCE: 225

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser His
    50                  55

<210> SEQ ID NO 226
<211> LENGTH: 58
<212> TYPE: PRT
<213> ORGANISM: Artificial Sequence
<220> FEATURE:
<223> OTHER INFORMATION: Synthetic

<400> SEQUENCE: 226

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Ala Val Leu Gly Leu Ala His Pro Leu Phe
    50                  55

<210> SEQ ID NO 227
<211> LENGTH: 54
<212> TYPE: PRT
<213> ORGANISM: Artificial Sequence
<220> FEATURE:
<223> OTHER INFORMATION: Synthetic
```

<400> SEQUENCE: 227

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ile Leu Gly Leu Ala
    50

<210> SEQ ID NO 228
<211> LENGTH: 60
<212> TYPE: PRT
<213> ORGANISM: Artificial Sequence
<220> FEATURE:
<223> OTHER INFORMATION: Synthetic

<400> SEQUENCE: 228

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Asn
    50                  55                  60

<210> SEQ ID NO 229
<211> LENGTH: 57
<212> TYPE: PRT
<213> ORGANISM: Artificial Sequence
<220> FEATURE:
<223> OTHER INFORMATION: Synthetic

<400> SEQUENCE: 229

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala
    50                  55

<210> SEQ ID NO 230
<211> LENGTH: 52
<212> TYPE: PRT
<213> ORGANISM: Artificial Sequence
<220> FEATURE:
<223> OTHER INFORMATION: Synthetic

<400> SEQUENCE: 230

Met His His His His His Ser Gly Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Asp
    50

<210> SEQ ID NO 231
<211> LENGTH: 60
<212> TYPE: PRT
<213> ORGANISM: Artificial Sequence
<220> FEATURE:
<223> OTHER INFORMATION: Synthetic

<400> SEQUENCE: 231

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Phe
    50                  55                  60

<210> SEQ ID NO 232
<211> LENGTH: 56
<212> TYPE: PRT
<213> ORGANISM: Artificial Sequence
<220> FEATURE:
<223> OTHER INFORMATION: Synthetic

<400> SEQUENCE: 232

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val
    50                  55

<210> SEQ ID NO 233
<211> LENGTH: 58
<212> TYPE: PRT
<213> ORGANISM: Artificial Sequence
<220> FEATURE:
<223> OTHER INFORMATION: Synthetic

<400> SEQUENCE: 233

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Leu Ala His Pro Leu Phe
    50                  55

<210> SEQ ID NO 234
<211> LENGTH: 60
<212> TYPE: PRT
<213> ORGANISM: Artificial Sequence
<220> FEATURE:
<223> OTHER INFORMATION: Synthetic

<400> SEQUENCE: 234

Met His His His His His His Ser Gly Ser Ser Ser Gly Ser Gly Cys
1               5                   10                  15

-continued

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Asn
    50                  55                  60

<210> SEQ ID NO 235
<211> LENGTH: 50
<212> TYPE: PRT
<213> ORGANISM: Artificial Sequence
<220> FEATURE:
<223> OTHER INFORMATION: Synthetic

<400> SEQUENCE: 235

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Arg
    50

<210> SEQ ID NO 236
<211> LENGTH: 58
<212> TYPE: PRT
<213> ORGANISM: Artificial Sequence
<220> FEATURE:
<223> OTHER INFORMATION: Synthetic

<400> SEQUENCE: 236

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Tyr
    50                  55

<210> SEQ ID NO 237
<211> LENGTH: 59
<212> TYPE: PRT
<213> ORGANISM: Artificial Sequence
<220> FEATURE:
<223> OTHER INFORMATION: Synthetic

<400> SEQUENCE: 237

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala
    50                  55

<210> SEQ ID NO 238
<211> LENGTH: 60
<212> TYPE: PRT
<213> ORGANISM: Artificial Sequence -continued

```
<220> FEATURE:
<223> OTHER INFORMATION: Synthetic

<400> SEQUENCE: 238

Met His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Asn
    50                  55                  60

<210> SEQ ID NO 239
<211> LENGTH: 59
<212> TYPE: PRT
<213> ORGANISM: Artificial Sequence
<220> FEATURE:
<223> OTHER INFORMATION: Synthetic

<400> SEQUENCE: 239

Met His His His His His His Ser Gly Ser Ser Ser Gly Ser Gly Cys
1               5                   10                  15

Val Lys Lys Gly Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala
    50                  55

<210> SEQ ID NO 240
<211> LENGTH: 55
<212> TYPE: PRT
<213> ORGANISM: Artificial Sequence
<220> FEATURE:
<223> OTHER INFORMATION: Synthetic

<400> SEQUENCE: 240

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu
    50                  55

<210> SEQ ID NO 241
<211> LENGTH: 58
<212> TYPE: PRT
<213> ORGANISM: Artificial Sequence
<220> FEATURE:
<223> OTHER INFORMATION: Synthetic

<400> SEQUENCE: 241

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45
```

Gly Ser Leu Gly Leu Ala His Pro Leu Tyr
        50                  55

<210> SEQ ID NO 242
<211> LENGTH: 60
<212> TYPE: PRT
<213> ORGANISM: Artificial Sequence
<220> FEATURE:
<223> OTHER INFORMATION: Synthetic

<400> SEQUENCE: 242

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Ala Ile
        50                  55                  60

<210> SEQ ID NO 243
<211> LENGTH: 60
<212> TYPE: PRT
<213> ORGANISM: Artificial Sequence
<220> FEATURE:
<223> OTHER INFORMATION: Synthetic

<400> SEQUENCE: 243

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val Ala Ser Arg Tyr
        50                  55                  60

<210> SEQ ID NO 244
<211> LENGTH: 56
<212> TYPE: PRT
<213> ORGANISM: Artificial Sequence
<220> FEATURE:
<223> OTHER INFORMATION: Synthetic

<400> SEQUENCE: 244

Met His His His His His His Ser Gly Ser Ser Ser Gly Ser Gly Cys
1               5                   10                  15

Val Lys Lys Asp Glu Leu Cys Glu Leu Ala Ile Asp Val Cys Cys Glu
            20                  25                  30

Pro Leu Glu Cys Leu Gly His Gly Leu Gly Tyr Ala Tyr Cys Gly Ser
        35                  40                  45

Gly Ser Ser Gly Ser Ser Leu Val
        50                  55

<210> SEQ ID NO 245
<211> LENGTH: 60
<212> TYPE: PRT
<213> ORGANISM: Artificial Sequence
<220> FEATURE:
<223> OTHER INFORMATION: Synthetic

<400> SEQUENCE: 245

Met His His His His His His Ser Gly Ser Ser Ser Gly Ser Gly Cys

```
                1               5                  10                 15
Val Lys Lys Asp Glu Leu Cys Met Trp Ser Arg Glu Val Cys Cys Glu
                    20                  25                  30

Leu Leu Glu Cys Tyr Tyr Thr Gly Trp Tyr Trp Ala Cys Gly Ser Gly
                    35                  40                  45

Ser Ser Gly Ser Ser Leu Val Ala Ser Ala Ile Tyr
        50                  55                  60

<210> SEQ ID NO 246
<211> LENGTH: 58
<212> TYPE: PRT
<213> ORGANISM: Artificial Sequence
<220> FEATURE:
<223> OTHER INFORMATION: Synthetic

<400> SEQUENCE: 246

Met His His His His His Ser Gly Ser Ser Ser Gly Ser Ala Ala
1               5                  10                  15

Ser Arg Lys Thr Ser Ser Ala Ser Trp Arg Ser Thr Cys Ala Val Ser
                    20                  25                  30

Pro Ser Ser Ala Trp Gly Thr Ala Trp Gly Thr Arg Thr Ala Ala Ala
                    35                  40                  45

Ala Val Leu Gly Leu Ala His Pro Leu Phe
        50                  55

<210> SEQ ID NO 247
<211> LENGTH: 59
<212> TYPE: PRT
<213> ORGANISM: Artificial Sequence
<220> FEATURE:
<223> OTHER INFORMATION: Synthetic

<400> SEQUENCE: 247

Met His His His His His Ser Gly Ser Ser Ser Gly Ser Ala Ala
1               5                  10                  15

Ser Arg Lys Thr Ser Ser Ala Ser Trp Arg Ser Thr Cys Ala Val Ser
                    20                  25                  30

Pro Ser Ser Ala Trp Gly Thr Ala Trp Gly Thr Arg Thr Ala Ala Ala
                    35                  40                  45

Ala Val Leu Gly Leu Ala His Pro Pro Ile Tyr
        50                  55

<210> SEQ ID NO 248
<211> LENGTH: 56
<212> TYPE: PRT
<213> ORGANISM: Artificial Sequence
<220> FEATURE:
<223> OTHER INFORMATION: Synthetic

<400> SEQUENCE: 248

Met His His His His His Ser Gly Ser Ser Ser Gly Ser Ala Ala
1               5                  10                  15

Ser Arg Lys Thr Ser Ser Ala Ser Trp Arg Ser Thr Cys Ala Val Ser
                    20                  25                  30

Pro Ser Ser Ala Trp Gly Thr Ala Trp Gly Thr Arg Thr Ala Ala Ala
                    35                  40                  45

Ala Val Leu Gly Leu Ala His His
        50                  55

<210> SEQ ID NO 249
<211> LENGTH: 57
```

```
<212> TYPE: PRT
<213> ORGANISM: Artificial Sequence
<220> FEATURE:
<223> OTHER INFORMATION: Synthetic

<400> SEQUENCE: 249

Met His His His His His Ser Gly Lys Leu Arg Ile Leu Arg Gln
1               5                   10                  15

Glu Arg Arg Ala Leu Arg Ala Gly Asp Arg Arg Val Leu Ala Pro Arg
            20                  25                  30

Val Leu Gly Ala Arg Pro Gly Val Arg Val Leu Arg Gln Arg Gln Phe
        35                  40                  45

Trp Val Pro Ser Ser Ile Arg Tyr Leu
    50                  55

<210> SEQ ID NO 250
<211> LENGTH: 58
<212> TYPE: PRT
<213> ORGANISM: Artificial Sequence
<220> FEATURE:
<223> OTHER INFORMATION: Synthetic

<400> SEQUENCE: 250

Met His His His His His His Ser Gly Ser Thr Gln Asp Gln Ala Ala
1               5                   10                  15

Ser Arg Lys Thr Ser Ser Ala Ser Trp Arg Ser Thr Cys Ala Val Ser
            20                  25                  30

Pro Ser Ser Ala Trp Gly Thr Ala Trp Gly Thr Arg Thr Ala Ala Ala
        35                  40                  45

Ala Val Leu Gly Leu Ala His Pro Leu Phe
    50                  55

<210> SEQ ID NO 251
<211> LENGTH: 54
<212> TYPE: PRT
<213> ORGANISM: Artificial Sequence
<220> FEATURE:
<223> OTHER INFORMATION: Synthetic

<400> SEQUENCE: 251

Met His His His His His Gln Val Ala Gln Leu Arg Ile Arg Leu Arg
1               5                   10                  15

Gln Glu Arg Arg Ala Leu Arg Ala Gly Asp Arg Arg Val Leu Ala Pro
            20                  25                  30

Arg Val Leu Gly Ala Arg Pro Gly Val Arg Val Leu Arg Gln Arg Gln
        35                  40                  45

Phe Trp Val Pro Ser Ser
    50

<210> SEQ ID NO 252
<211> LENGTH: 59
<212> TYPE: PRT
<213> ORGANISM: Artificial Sequence
<220> FEATURE:
<223> OTHER INFORMATION: Synthetic

<400> SEQUENCE: 252

Met His His His His His His Ser Gly Ser Ser Ser Gly Ser Gly Cys
1               5                   10                  15

Val Lys Lys Asp Glu Leu Cys Met Trp Ser Arg Glu Val Cys Cys Glu
            20                  25                  30

Leu Leu Glu Cys Tyr Tyr Thr Gly Trp Tyr Trp Ala Cys Gly Ser Gly
```

-continued

```
                35                  40                  45
Ser Ser Gly Ser Ser Leu Val Ala Ser Ala Ile
        50                  55

<210> SEQ ID NO 253
<211> LENGTH: 50
<212> TYPE: PRT
<213> ORGANISM: Artificial Sequence
<220> FEATURE:
<223> OTHER INFORMATION: Synthetic

<400> SEQUENCE: 253

Met Gly Arg Gly Ser His His His His His Ala Arg Ser Asn Val
1               5                   10                  15

Ile Pro Leu Asn Glu Val Trp Tyr Asp Thr Gly Trp Asp Arg Pro His
                20                  25                  30

Arg Ser Arg Leu Ser Ile Asp Asp Ala Asn Ala Pro Lys Ala Ser
        35                  40                  45

Ala Ile
    50

<210> SEQ ID NO 254
<211> LENGTH: 50
<212> TYPE: PRT
<213> ORGANISM: Artificial Sequence
<220> FEATURE:
<223> OTHER INFORMATION: Synthetic

<400> SEQUENCE: 254

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
                20                  25                  30

His Lys Leu Ser Gln Tyr Ser Arg Asp Ala Asn Ala Pro Lys Ala Ser
        35                  40                  45

Ala Ile
    50

<210> SEQ ID NO 255
<211> LENGTH: 50
<212> TYPE: PRT
<213> ORGANISM: Artificial Sequence
<220> FEATURE:
<223> OTHER INFORMATION: Synthetic

<400> SEQUENCE: 255

Met Gly Arg Gly Ser His His His His His Ala Arg Ser Trp Arg
1               5                   10                  15

Asp Thr Arg Lys Leu His Met Arg His Tyr Phe Pro Leu Ala Ile Asp
                20                  25                  30

Ser Tyr Trp Asp His Thr Leu Arg Asp Ala Asn Ala Pro Lys Ala Ser
        35                  40                  45

Ala Ile
    50

<210> SEQ ID NO 256
<211> LENGTH: 50
<212> TYPE: PRT
<213> ORGANISM: Artificial Sequence
<220> FEATURE:
<223> OTHER INFORMATION: Synthetic

<400> SEQUENCE: 256
```

```
Met Gly Arg Gly Ser His His His His His Ala Arg Ser Trp Thr
1               5                   10                  15

Ser Met Gln Gly Glu Thr Leu Trp Arg Thr Asp Arg Leu Ala Thr Thr
                20                  25                  30

Lys Thr Ser Met Ser His Pro Pro Asp Ala Asn Ala Pro Lys Ala Ser
            35                  40                  45

Ala Ile
    50
```

<210> SEQ ID NO 257
<211> LENGTH: 50
<212> TYPE: PRT
<213> ORGANISM: Artificial Sequence
<220> FEATURE:
<223> OTHER INFORMATION: Synthetic

<400> SEQUENCE: 257

```
Met Gly Arg Gly Ser His His His His His Ala Arg Ser Pro
1               5                   10                  15

Leu Trp Tyr His Tyr Asn Cys Trp Asp Thr Ile Cys Leu Ala Asp Trp
                20                  25                  30

Leu Lys Asp Arg Pro His Gly Val Tyr Asp Ala Asn Ala Pro Lys Ala
            35                  40                  45

Ser Ala
    50
```

<210> SEQ ID NO 258
<211> LENGTH: 50
<212> TYPE: PRT
<213> ORGANISM: Artificial Sequence
<220> FEATURE:
<223> OTHER INFORMATION: Synthetic

<400> SEQUENCE: 258

```
Met Gly Arg Gly Ser His His His His His Ala Arg Ser Cys Leu
1               5                   10                  15

Ala Thr Arg Asn Gly Phe Val Gln Met Asn Thr Asp Arg Gly Thr Tyr
                20                  25                  30

Val Lys Arg Pro Thr Val Leu Gln Asp Ala Asn Ala Pro Lys Ala Ser
            35                  40                  45

Ala Ile
    50
```

<210> SEQ ID NO 259
<211> LENGTH: 50
<212> TYPE: PRT
<213> ORGANISM: Artificial Sequence
<220> FEATURE:
<223> OTHER INFORMATION: Synthetic

<400> SEQUENCE: 259

```
Met Gly Arg Gly Ser His His His His His Ala Arg Ser Leu Ser
1               5                   10                  15

Ala Leu Arg Arg Thr Glu Arg Thr Trp Asn Thr Ile His Gln Gly His
                20                  25                  30

His Leu Glu Trp Tyr Pro Pro Ala Asp Ala Asn Ala Pro Lys Ala Ser
            35                  40                  45

Ala Ile
    50
```

```
<210> SEQ ID NO 260
<211> LENGTH: 50
<212> TYPE: PRT
<213> ORGANISM: Artificial Sequence
<220> FEATURE:
<223> OTHER INFORMATION: Synthetic

<400> SEQUENCE: 260

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45

Ala Ile
    50

<210> SEQ ID NO 261
<211> LENGTH: 50
<212> TYPE: PRT
<213> ORGANISM: Artificial Sequence
<220> FEATURE:
<223> OTHER INFORMATION: Synthetic

<400> SEQUENCE: 261

Met Gly Arg Gly Ser His His His His His His Ala Arg Ser Asp Trp
1               5                   10                  15

Glu Leu Ser Pro Pro His Val Ala Ile Thr Thr Arg His Leu Ile Asn
            20                  25                  30

Cys Thr Asp Gly Pro Leu Leu Arg Asp Ala Asn Ala Pro Lys Ala Ser
        35                  40                  45

Ala Ile
    50

<210> SEQ ID NO 262
<211> LENGTH: 50
<212> TYPE: PRT
<213> ORGANISM: Artificial Sequence
<220> FEATURE:
<223> OTHER INFORMATION: Synthetic

<400> SEQUENCE: 262

Met Gly Arg Gly Ser His His His His His His Ala Arg Ser Leu Asn
1               5                   10                  15

Gly Glu Ser Thr Ser Asn Ile Leu Thr Thr Ser Arg Lys Val Thr Glu
            20                  25                  30

Trp Thr Gly Tyr Thr Ala Ser Val Asp Ala Asn Ala Pro Lys Ala Ser
        35                  40                  45

Ala Ile
    50

<210> SEQ ID NO 263
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (41)..(41)
<223> OTHER INFORMATION: Xaa is any amino acid

<400> SEQUENCE: 263

Met Gly Arg Gly Ser His His His His His His Ala Arg Ser Gln Val
```

```
                1               5                   10                  15
Thr Trp His His Leu Ala Asp Thr Val Thr Thr Lys Asn Arg Lys Cys
                    20                  25                  30

Thr Asp Ser Tyr Ile Gly Trp Asn Xaa Ala Asn Ala Pro Lys Ala Ser
            35                  40                  45

Ala Ile
    50

<210> SEQ ID NO 264
<211> LENGTH: 50
<212> TYPE: PRT
<213> ORGANISM: Artificial Sequence
<220> FEATURE:
<223> OTHER INFORMATION: Synthetic

<400> SEQUENCE: 264

Met Gly Arg Gly Ser His His His His His His Ala Arg Ser Ile Ile
1               5                   10                  15

Val Ile His Asn Ala Ile Gln Thr His Thr Pro His Gln Val Ser Ile
                    20                  25                  30

Trp Cys Pro Pro Lys His Asn Arg Asp Asp Ala Asn Ala Pro Lys Ala
            35                  40                  45

Ser Ala
    50

<210> SEQ ID NO 265
<211> LENGTH: 50
<212> TYPE: PRT
<213> ORGANISM: Artificial Sequence
<220> FEATURE:
<223> OTHER INFORMATION: Synthetic

<400> SEQUENCE: 265

Met Gly Arg Gly Ser His His His His His His Ala Arg Ser Ser His
1               5                   10                  15

Cys Arg His Arg Asn Cys His Thr Ile Thr Arg Gly Asn Met Arg Ile
                    20                  25                  30

Glu Thr Pro Asn Asn Ile Arg Lys Asp Ala Asn Ala Pro Lys Ala Ser
            35                  40                  45

Ala Ile
    50

<210> SEQ ID NO 266
<211> LENGTH: 50
<212> TYPE: PRT
<213> ORGANISM: Artificial Sequence
<220> FEATURE:
<223> OTHER INFORMATION: Synthetic

<400> SEQUENCE: 266

Met Gly Arg Gly Ser His His His His His His Ala Arg Ser Trp Gly
1               5                   10                  15

Leu Ser Gly Thr Gln Thr Trp Lys Ile Thr Lys Leu Ala Thr Arg Leu
                    20                  25                  30

His His Pro Glu Phe Glu Thr Asn Asp Ala Asn Ala Pro Lys Ala Ser
            35                  40                  45

Ala Ile
    50

<210> SEQ ID NO 267
<211> LENGTH: 50
```

```
<212> TYPE: PRT
<213> ORGANISM: Artificial Sequence
<220> FEATURE:
<223> OTHER INFORMATION: Synthetic

<400> SEQUENCE: 267

Met Gly Arg Gly Ser His His His His His Ala Arg Ser Trp Arg
1               5                   10                  15

Trp His Asn Trp Gly Leu Ser Asp Thr Val Ala Ser His Pro Asp Ala
            20                  25                  30

Ser Asn Ser Leu Asn Met Met Tyr Asp Ala Asn Ala Pro Lys Ala Ser
        35                  40                  45

Ala Asn
    50

<210> SEQ ID NO 268
<211> LENGTH: 49
<212> TYPE: PRT
<213> ORGANISM: Artificial Sequence
<220> FEATURE:
<223> OTHER INFORMATION: Synthetic

<400> SEQUENCE: 268

Met Gly Arg Gly Ser His His His His His Leu Asp Leu Trp Gly
1               5                   10                  15

Pro Pro Ser Gly Ser Pro Arg Thr Arg Ser Thr Thr Gly Thr Ser Thr
            20                  25                  30

Thr Ser Ser Pro Ser Thr Pro Gly Thr Leu Thr Leu Arg Arg His Pro
        35                  40                  45

His

<210> SEQ ID NO 269
<211> LENGTH: 49
<212> TYPE: PRT
<213> ORGANISM: Artificial Sequence
<220> FEATURE:
<223> OTHER INFORMATION: Synthetic

<400> SEQUENCE: 269

Met Gly Arg Gly Ser His His His His His His Ala Arg Ser Trp Gln
1               5                   10                  15

Pro Glu Val Lys Met Ser Ser Leu Val Asp Thr Ser Gln Thr Val Gly
            20                  25                  30

Ala Ala Val Glu Thr Arg Thr Thr Asp Ala Asn Ala Pro Lys Ala Ser
        35                  40                  45

Ala

<210> SEQ ID NO 270
<211> LENGTH: 50
<212> TYPE: PRT
<213> ORGANISM: Artificial Sequence
<220> FEATURE:
<223> OTHER INFORMATION: Synthetic

<400> SEQUENCE: 270

Met Gly Arg Gly Ser His His His His His His Ala Arg Ser Trp Thr
1               5                   10                  15

Ser Met Gln Gly Glu Thr Leu Trp Arg Thr Asp Arg Leu Ala Thr Thr
            20                  25                  30

Lys Thr Ser Met Ser His Pro Pro Asp Ala Asn Ala Pro Lys Ala Ser
        35                  40                  45
```

Ala Ile
    50

<210> SEQ ID NO 271
<211> LENGTH: 50
<212> TYPE: PRT
<213> ORGANISM: Artificial Sequence
<220> FEATURE:
<223> OTHER INFORMATION: Synthetic

<400> SEQUENCE: 271

Met Gly Arg Gly Ser His His His His His Ala Arg Ser Leu Ser
1               5                   10                  15

Ala Leu Arg Arg Thr Glu Arg Thr Trp Asn Thr Ile His Gln Gly His
            20                  25                  30

His Leu Glu Trp Tyr Pro Pro Ala Asp Ala Asn Ala Pro Lys Ala Ser
        35                  40                  45

Ala Ile
    50

<210> SEQ ID NO 272
<211> LENGTH: 50
<212> TYPE: PRT
<213> ORGANISM: Artificial Sequence
<220> FEATURE:
<223> OTHER INFORMATION: Synthetic

<400> SEQUENCE: 272

Met Gly Arg Gly Ser His His His His His Ala Arg Ser Leu Ser
1               5                   10                  15

Ala Leu Arg Arg Thr Glu Arg Thr Trp Asn Thr Ile His Gln Gly His
            20                  25                  30

His Leu Glu Trp Tyr Pro Thr Ala Asp Ala Asn Ala Pro Lys Ala Ser
        35                  40                  45

Ala Ile
    50

<210> SEQ ID NO 273
<211> LENGTH: 50
<212> TYPE: PRT
<213> ORGANISM: Artificial Sequence
<220> FEATURE:
<223> OTHER INFORMATION: Synthetic

<400> SEQUENCE: 273

Met Gly Arg Gly Ser His His His His His Ala Arg Ser Lys Asp
1               5                   10                  15

Thr Ala Arg Thr Thr Ala Thr Leu Leu Thr Asn Asp Glu Asp Arg Lys
            20                  25                  30

Thr His Trp Arg Met Phe Tyr Pro Asp Ala Asn Ala Pro Lys Ala Ser
        35                  40                  45

Ala Ile
    50

<210> SEQ ID NO 274
<211> LENGTH: 50
<212> TYPE: PRT
<213> ORGANISM: Artificial Sequence
<220> FEATURE:
<223> OTHER INFORMATION: Synthetic

<400> SEQUENCE: 274

Met Gly Arg Gly Ser His His His His Tyr His Ala Arg Ser Lys Asp

```
                1               5                  10                 15
Thr Ala Arg Thr Thr Ala Thr Leu Leu Thr Asn Asp Glu Asp Arg Lys
                20                 25                 30
Thr His Trp Arg Met Phe Tyr Pro Asp Ala Asn Ala Pro Lys Ala Ser
            35                 40                 45
Ala Ile
    50

<210> SEQ ID NO 275
<211> LENGTH: 50
<212> TYPE: PRT
<213> ORGANISM: Artificial Sequence
<220> FEATURE:
<223> OTHER INFORMATION: Synthetic

<400> SEQUENCE: 275

Met Gly Arg Gly Ser His His His His His His Ala Arg Ser Thr Pro
1               5                  10                 15
Arg Leu Arg Lys Val Tyr Asp Leu Thr Val Thr Thr Ser Ser Gln
            20                 25                 30
Ile Asp Lys Leu Gln Pro Ser Arg Asp Ala Asn Ala Pro Lys Ala Ser
        35                 40                 45
Ala Ile
    50

<210> SEQ ID NO 276
<211> LENGTH: 50
<212> TYPE: PRT
<213> ORGANISM: Artificial Sequence
<220> FEATURE:
<223> OTHER INFORMATION: Synthetic

<400> SEQUENCE: 276

Met Gly Arg Gly Ser His His His His His His Ala Arg Ser Ser His
1               5                  10                 15
Cys Arg His Arg Asn Cys His Thr Ile Thr Arg Gly Asn Met Arg Ile
            20                 25                 30
Glu Thr Pro Asn Asn Ile Arg Lys Asp Ala Asn Ala Pro Lys Ala Ser
        35                 40                 45
Ala Ile
    50

<210> SEQ ID NO 277
<211> LENGTH: 50
<212> TYPE: PRT
<213> ORGANISM: Artificial Sequence
<220> FEATURE:
<223> OTHER INFORMATION: Synthetic

<400> SEQUENCE: 277

Met Gly Arg Gly Ser His His His His His His Ala Arg Ser Asp Trp
1               5                  10                 15
Glu Leu Ser Pro Pro His Val Ala Ile Thr Thr Arg His Leu Ile Asn
            20                 25                 30
Cys Thr Asp Gly Pro Leu Leu Arg Asp Ala Asn Ala Pro Lys Ala Ser
        35                 40                 45
Ala Ile
    50

<210> SEQ ID NO 278
<211> LENGTH: 50
```

```
<212> TYPE: PRT
<213> ORGANISM: Artificial Sequence
<220> FEATURE:
<223> OTHER INFORMATION: Synthetic

<400> SEQUENCE: 278

Met Gly Arg Gly Ser His His His His His His Ala Arg Ser Ile Ser
1               5                   10                  15

Leu Ala Gln Tyr Tyr Trp Thr Ala Gln Arg Asp Met His Leu Leu Ile
            20                  25                  30

Met His Lys Phe Met Asp Met Pro Asp Ala Asn Ala Pro Lys Ala Ser
        35                  40                  45

Ala Ile
    50

<210> SEQ ID NO 279
<211> LENGTH: 50
<212> TYPE: PRT
<213> ORGANISM: Artificial Sequence
<220> FEATURE:
<223> OTHER INFORMATION: Synthetic

<400> SEQUENCE: 279

Met Gly Arg Gly Ser His His His His His His Ala Arg Ser Ile Ile
1               5                   10                  15

Val Ile His Asn Ala Ile Gln Thr His Thr Pro His Gln Val Ser Ile
            20                  25                  30

Trp Cys Pro Pro Lys His Asn Arg Asp Ala Asn Ala Pro Lys Ala Ser
        35                  40                  45

Ala Ile
    50

<210> SEQ ID NO 280
<211> LENGTH: 50
<212> TYPE: PRT
<213> ORGANISM: Artificial Sequence
<220> FEATURE:
<223> OTHER INFORMATION: Synthetic

<400> SEQUENCE: 280

Met Gly Arg Gly Ser His His His His His His Ala Arg Ser Lys Phe
1               5                   10                  15

Arg Gln Ile Trp Glu Asn Glu Arg Lys Ala His Arg Met Val Met His
            20                  25                  30

Gln Phe Tyr Gln Val Ile Arg Pro Asp Ala Asn Ala Pro Lys Ala Ser
        35                  40                  45

Ala Ile
    50

<210> SEQ ID NO 281
<211> LENGTH: 50
<212> TYPE: PRT
<213> ORGANISM: Artificial Sequence
<220> FEATURE:
<223> OTHER INFORMATION: Synthetic

<400> SEQUENCE: 281

Met Gly Arg Gly Ser His His His His His His Ala Arg Ser Val Ile
1               5                   10                  15

Val Cys Val Cys Thr Thr Ala Gly Asn Tyr Asn His His Asp Gly Phe
            20                  25                  30

Phe Lys Arg Tyr Asp Asn Ser Tyr Asp Ala Asn Ala Pro Lys Ala Ser
```

```
                    35                  40                  45
Ala Ile
    50

<210> SEQ ID NO 282
<211> LENGTH: 50
<212> TYPE: PRT
<213> ORGANISM: Artificial Sequence
<220> FEATURE:
<223> OTHER INFORMATION: Synthetic

<400> SEQUENCE: 282

Met Gly Arg Gly Ser His His His His His Ala Arg Ser Leu Asn
1               5                   10                  15

Gly Glu Ser Thr Ser Asn Ile Leu Thr Thr Ser Arg Lys Val Thr Glu
            20                  25                  30

Trp Thr Gly Tyr Thr Ala Ser Val Asp Ala Asn Ala Pro Lys Ala Ser
        35                  40                  45

Ala Ile
    50

<210> SEQ ID NO 283
<211> LENGTH: 50
<212> TYPE: PRT
<213> ORGANISM: Artificial Sequence
<220> FEATURE:
<223> OTHER INFORMATION: Synthetic

<400> SEQUENCE: 283

Ile Gly Arg Gly Ser His His His His His Ala Arg Ser Ser Tyr
1               5                   10                  15

Pro Asp His Gly Arg Tyr Arg Asn Gln Ile Glu Arg Gly Thr Ile Glu
            20                  25                  30

Met Thr Tyr Ile Asp Thr His Tyr Asp Ala Asn Ala Pro Lys Ala Ser
        35                  40                  45

Ala Ile
    50

<210> SEQ ID NO 284
<211> LENGTH: 49
<212> TYPE: PRT
<213> ORGANISM: Artificial Sequence
<220> FEATURE:
<223> OTHER INFORMATION: Synthetic

<400> SEQUENCE: 284

Met Gly Arg Gly Ser His His His His His Ala Arg Ser Gly Ala Glu
1               5                   10                  15

Pro Gly Met Ser Gly Lys Pro Lys Val Thr Thr Trp His His Lys Arg
            20                  25                  30

Tyr Arg Arg Phe Met Thr His Asp Ala Asn Ala Pro Lys Ala Ser Ala
        35                  40                  45

Ile

<210> SEQ ID NO 285
<211> LENGTH: 46
<212> TYPE: PRT
<213> ORGANISM: Artificial Sequence
<220> FEATURE:
<223> OTHER INFORMATION: Synthetic

<400> SEQUENCE: 285
```

Met Gly Arg Gly Ser His His His His His His Ala Arg Ser Asp Ile
1               5                   10                  15

Asp Thr Ala Glu Val Asn Arg Trp Glu Ser Asn Leu Lys Ser Tyr Leu
            20                  25                  30

Tyr Asn Met Thr Asp Ala Asn Ala Pro Lys Ala Ser Ala Ile
        35                  40                  45

<210> SEQ ID NO 286
<211> LENGTH: 50
<212> TYPE: PRT
<213> ORGANISM: Artificial Sequence
<220> FEATURE:
<223> OTHER INFORMATION: Synthetic

<400> SEQUENCE: 286

Met Gly Arg Gly Ser His His His His His His Ala Arg Ser Val Leu
1               5                   10                  15

Thr Gly Gln Ser Leu Tyr Tyr Gln Phe Met Ser Arg Ala Phe Phe Thr
            20                  25                  30

Leu Gln Lys Phe Thr Gln Asn Leu Asp Ala Asn Ala Pro Lys Ala Ser
        35                  40                  45

Ala Ile
    50

<210> SEQ ID NO 287
<211> LENGTH: 50
<212> TYPE: PRT
<213> ORGANISM: Artificial Sequence
<220> FEATURE:
<223> OTHER INFORMATION: Synthetic

<400> SEQUENCE: 287

Met Gly Arg Gly Ser His His His His His His Ala Arg Ser Lys Ile
1               5                   10                  15

Ala Glu Tyr Trp Leu Thr Glu Arg Met Met His Leu Arg Ala Met Met
            20                  25                  30

Lys Leu Leu Asn Lys His Ala His Asp Ala Asn Ala Pro Lys Ala Ser
        35                  40                  45

Ala Ile
    50

<210> SEQ ID NO 288
<211> LENGTH: 50
<212> TYPE: PRT
<213> ORGANISM: Artificial Sequence
<220> FEATURE:
<223> OTHER INFORMATION: Synthetic

<400> SEQUENCE: 288

Met Gly Arg Gly Ser His His His His His His Ala Arg Ser His Ser
1               5                   10                  15

Ala Leu Met His Asp Lys Asp Ser Ser Thr Ser Thr Tyr Tyr Pro Gln
            20                  25                  30

Tyr Ala Asn Ser Pro Ser Val Gly Asp Ala Asn Ala Pro Lys Ala Ser
        35                  40                  45

Ala Ile
    50

<210> SEQ ID NO 289
<211> LENGTH: 50
<212> TYPE: PRT
<213> ORGANISM: Artificial Sequence
<220> FEATURE:
<223> OTHER INFORMATION: Synthetic

<400> SEQUENCE: 289

Met Gly Arg Gly Ser His His His His His His Ala Arg Ser His Leu
1               5                   10                  15

Asp Pro Cys Ala Asp Leu Asn Val Thr Gln Gln Arg Thr Thr Arg Glu
            20                  25                  30

Thr His Ser Asp Asn Glu Asn His Asp Ala Asn Ala Pro Lys Ala Ser
        35                  40                  45

Ala Ile
    50

<210> SEQ ID NO 290
<211> LENGTH: 50
<212> TYPE: PRT
<213> ORGANISM: Artificial Sequence
<220> FEATURE:
<223> OTHER INFORMATION: Synthetic

<400> SEQUENCE: 290

Met Gly Arg Gly Ser His His His His His His Ala Arg Ser Pro Leu
1               5                   10                  15

Tyr Gln Gly Glu Thr Leu Asn Ala Tyr Ala Pro Gln Ser Met Val Lys
            20                  25                  30

Ile Ser Lys Asp Tyr Val Leu His Asp Ala Asn Ala Pro Lys Ala Ser
        35                  40                  45

Ala Ile
    50

<210> SEQ ID NO 291
<211> LENGTH: 50
<212> TYPE: PRT
<213> ORGANISM: Artificial Sequence
<220> FEATURE:
<223> OTHER INFORMATION: Synthetic

<400> SEQUENCE: 291

Met Gly Arg Gly Ser His His His His His His Ala Arg Ser Tyr Met
1               5                   10                  15

Ala Arg Trp His Pro Met Thr His Asn His Met Lys Glu Thr Leu Phe
            20                  25                  30

Ala Ala Glu Pro His Val Cys Thr Asp Ala Asn Ala Pro Lys Ala Ser
        35                  40                  45

Ala Ile
    50

<210> SEQ ID NO 292
<211> LENGTH: 50
<212> TYPE: PRT
<213> ORGANISM: Artificial Sequence
<220> FEATURE:
<223> OTHER INFORMATION: Synthetic

<400> SEQUENCE: 292

Met Gly Arg Gly Ser His His His His His His Ala Arg Pro Arg Phe
1               5                   10                  15

His Pro Pro Phe Leu Arg Asp Arg Ser Val Asn Arg Met Ile Met Asn
            20                  25                  30

Glu His Arg Pro Arg Tyr Ser His Asp Ala Asn Ala Pro Lys Ala Ser
        35                  40                  45

Ala Ile
    50

<210> SEQ ID NO 293
<211> LENGTH: 50
<212> TYPE: PRT
<213> ORGANISM: Artificial Sequence
<220> FEATURE:
<223> OTHER INFORMATION: Synthetic

<400> SEQUENCE: 293

Met Gly Arg Gly Ser His His His His His Ala Arg Ser Ser Pro
1               5                   10                  15

Arg Tyr Ala Tyr Cys Gly Ser Arg Trp Asn Gly Ser Arg Met His Asn
            20                  25                  30

Asn Lys Phe Thr Pro Ser Thr Arg Asp Ala Asn Ala Pro Lys Ala Ser
        35                  40                  45

Ala Ile
    50

<210> SEQ ID NO 294
<211> LENGTH: 49
<212> TYPE: PRT
<213> ORGANISM: Artificial Sequence
<220> FEATURE:
<223> OTHER INFORMATION: Synthetic

<400> SEQUENCE: 294

Met Gly Arg Gly Ser His His His His His Ala Arg Ser Asn Met
1               5                   10                  15

Asn Gln Met Thr Asn Ala Leu Asn Leu Arg Arg Arg Ser Arg Thr Trp
            20                  25                  30

Val Ala Thr Phe Arg Ser Glu Asp Ala Asn Ala Pro Lys Ala Ser Ala
        35                  40                  45

Ile

<210> SEQ ID NO 295
<211> LENGTH: 50
<212> TYPE: PRT
<213> ORGANISM: Artificial Sequence
<220> FEATURE:
<223> OTHER INFORMATION: Synthetic

<400> SEQUENCE: 295

Met Gly Arg Gly Ser His His His His His Ala Arg Ser Met Asn
1               5                   10                  15

Gly Leu Asp Met Gly Ser Pro Ile Trp Tyr Asn Met Gln Leu Lys Leu
            20                  25                  30

Ile Tyr Phe Ser Cys Asn Trp Asn Asp Ala Asn Ala Pro Lys Ala Ser
        35                  40                  45

Ala Ile
    50

<210> SEQ ID NO 296
<211> LENGTH: 50
<212> TYPE: PRT
<213> ORGANISM: Artificial Sequence
<220> FEATURE:
<223> OTHER INFORMATION: Synthetic

<400> SEQUENCE: 296

Met Gly Arg Gly Ser His His His His His Ala Arg Ser Arg Val
1               5                   10                  15

```
Arg Asp Pro Asp Ser Gly Arg Thr His Gln Ile Arg Ser His Leu Lys
            20                  25                  30

His Tyr Ser Asn Phe Pro Val Ala Asp Ala Asn Ala Pro Lys Ala Ser
        35                  40                  45

Ala Ile
    50

<210> SEQ ID NO 297
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (41)..(41)
<223> OTHER INFORMATION: Xaa is any amino acid

<400> SEQUENCE: 297

Met Gly Arg Gly Ser His His His His His Ala Arg Ser Gln Val
1               5                   10                  15

Thr Trp His His Leu Ala Asp Thr Val Thr Thr Lys Asn Arg Lys Cys
            20                  25                  30

Thr Asp Ser Tyr Ile Gly Trp Asn Xaa Ala Asn Ala Pro Lys Ala Ser
        35                  40                  45

Ala Ile
    50

<210> SEQ ID NO 298
<211> LENGTH: 48
<212> TYPE: PRT
<213> ORGANISM: Artificial Sequence
<220> FEATURE:
<223> OTHER INFORMATION: Synthetic

<400> SEQUENCE: 298

Met Gly Arg Gly Ser His His His His His Ala Arg Ser Ile Leu
1               5                   10                  15

Asp Val Asn Asp Glu Lys Arg Pro Pro Gly Trp Tyr Arg Thr Asn Ile
            20                  25                  30

Ile Asp Ser Pro Ser Gly Asp Ala Asn Ala Pro Lys Ala Ser Ala Ile
        35                  40                  45

<210> SEQ ID NO 299
<211> LENGTH: 50
<212> TYPE: PRT
<213> ORGANISM: Artificial Sequence
<220> FEATURE:
<223> OTHER INFORMATION: Synthetic

<400> SEQUENCE: 299

Met Gly Arg Gly Ser His His His His His Ala Arg Ser Arg Arg
1               5                   10                  15

Tyr Arg Asp Gly Ile Phe Arg Arg Met Arg Ser Asx Thr Asn Ala Arg
            20                  25                  30

Gly Ala Arg His Ala Asp Leu Tyr Asp Ala Asn Ala Pro Lys Ala Ser
        35                  40                  45

Ala Ile
    50

<210> SEQ ID NO 300
<211> LENGTH: 50
```

```
<212> TYPE: PRT
<213> ORGANISM: Artificial Sequence
<220> FEATURE:
<223> OTHER INFORMATION: Synthetic

<400> SEQUENCE: 300

Met Gly Arg Gly Ser His His His His His His Ala Arg Ser Lys Cys
1               5                   10                  15

His Val Arg Arg Lys Glu Ser Ala Ser Ser Lys Asn Arg His Asn His
            20                  25                  30

Thr Trp His Asp Ser Asn Leu Tyr Asp Ala Asn Ala Pro Lys Ala Ser
        35                  40                  45

Ala Ile
    50

<210> SEQ ID NO 301
<211> LENGTH: 50
<212> TYPE: PRT
<213> ORGANISM: Artificial Sequence
<220> FEATURE:
<223> OTHER INFORMATION: Synthetic

<400> SEQUENCE: 301

Met Gly Arg Gly Ser His His His His His Ala Arg Ser Arg Thr
1               5                   10                  15

Leu Leu Ile Arg Leu Tyr Pro Pro Asp Arg Phe Gly Ser Ser Arg Gln
            20                  25                  30

Met Ala Thr Arg Asp Ser Phe Thr Asp Ala Asn Ala Pro Lys Ala Ser
        35                  40                  45

Ala Ile
    50

<210> SEQ ID NO 302
<211> LENGTH: 50
<212> TYPE: PRT
<213> ORGANISM: Artificial Sequence
<220> FEATURE:
<223> OTHER INFORMATION: Synthetic

<400> SEQUENCE: 302

Met Gly Arg Gly Ser His His His His His His Ala Arg Ser Ser Gly
1               5                   10                  15

Met Tyr Val Val Ser Lys Pro Ala Ser Asp Ser Trp Thr Thr Cys Ala
            20                  25                  30

Pro Tyr Thr Tyr Gly Thr Met Val Asp Ala Asn Ala Pro Lys Ala Ser
        35                  40                  45

Ala Ile
    50

<210> SEQ ID NO 303
<211> LENGTH: 50
<212> TYPE: PRT
<213> ORGANISM: Artificial Sequence
<220> FEATURE:
<223> OTHER INFORMATION: Synthetic

<400> SEQUENCE: 303

Met Gly Arg Gly Ser His His His His His His Ala Arg Ser Asn Leu
1               5                   10                  15

Ser Thr Ile Arg Asx Met Asn Arg His Leu Thr Asp Arg Arg Leu Thr
            20                  25                  30

Ala Phe Arg Asn Gln Val Val Phe Asp Ala Asn Ala Pro Lys Ala Ser
```

-continued

```
                35                  40                  45
Ala Ile
    50

<210> SEQ ID NO 304
<211> LENGTH: 50
<212> TYPE: PRT
<213> ORGANISM: Artificial Sequence
<220> FEATURE:
<223> OTHER INFORMATION: Synthetic

<400> SEQUENCE: 304

Met Gly Arg Gly Ser His His His His His His Ala Arg Ser Ile Asn
1               5                   10                  15

Ala Trp Trp Tyr His Ile Gln Ser His Leu His Gln Trp Arg Arg His
            20                  25                  30

Arg Leu Tyr Thr Ala Asn Gln Trp Asp Ala Asn Ala Pro Lys Ala Ser
        35                  40                  45

Ala Ile
    50

<210> SEQ ID NO 305
<211> LENGTH: 50
<212> TYPE: PRT
<213> ORGANISM: Artificial Sequence
<220> FEATURE:
<223> OTHER INFORMATION: Synthetic

<400> SEQUENCE: 305

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45

Ala Ile
    50

<210> SEQ ID NO 306
<211> LENGTH: 50
<212> TYPE: PRT
<213> ORGANISM: Artificial Sequence
<220> FEATURE:
<223> OTHER INFORMATION: Synthetic

<400> SEQUENCE: 306

Met Gly Arg Gly Ser His His His His His His Ala Arg Pro Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Asp Ala Asn Ala Pro Lys Ala Ser
        35                  40                  45

Ala Ile
    50

<210> SEQ ID NO 307
<211> LENGTH: 50
<212> TYPE: PRT
<213> ORGANISM: Artificial Sequence
<220> FEATURE:
<223> OTHER INFORMATION: Synthetic

<400> SEQUENCE: 307
```

```
Met Gly Arg Gly Ser His His His His Ala Arg Ser Asn Val
1               5                   10                  15

Ile Pro Leu Asn Glu Val Trp Tyr Asp Thr Gly Trp Asp Arg Pro His
                20              25                  30

Arg Ser Arg Leu Ser Ile Asp Asp Ala Asn Ala Pro Lys Ala Ser
            35              40                  45

Ala Ile
    50
```

<210> SEQ ID NO 308
<211> LENGTH: 50
<212> TYPE: PRT
<213> ORGANISM: Artificial Sequence
<220> FEATURE:
<223> OTHER INFORMATION: Synthetic

<400> SEQUENCE: 308

```
Met Gly Arg Gly Ser His His His His Arg Ala Arg Ser Asn Val
1               5                   10                  15

Ile Pro Leu Ser Glu Val Trp Tyr Asp Thr Gly Trp Asp Arg Pro His
                20              25                  30

Arg Ser Arg Leu Ser Ile Asp Asp Asp Ala Asn Ala Pro Lys Ala Thr
            35              40                  45

Ala Ile
    50
```

<210> SEQ ID NO 309
<211> LENGTH: 50
<212> TYPE: PRT
<213> ORGANISM: Artificial Sequence
<220> FEATURE:
<223> OTHER INFORMATION: Synthetic

<400> SEQUENCE: 309

```
Ile Glu Arg Gly Ser Gln His His His His Ala Arg Ser Asn Val
1               5                   10                  15

Ile Thr Leu Asn Glu Val Trp Tyr Asp Thr Gly Trp Asp Arg Pro His
                20              25                  30

Arg Ser Arg Leu Ser Ile Asp Asp Asp Ala Asn Ala Pro Lys Ala Thr
            35              40                  45

Ala Ile
    50
```

<210> SEQ ID NO 310
<211> LENGTH: 49
<212> TYPE: PRT
<213> ORGANISM: Artificial Sequence
<220> FEATURE:
<223> OTHER INFORMATION: Synthetic

<400> SEQUENCE: 310

```
Met Gly Arg Gly Ser His His His His His Ala Arg Ser Asn Val
1               5                   10                  15

Ile Thr Leu Ser Glu Val Trp Asp Thr Gly Trp Asn Arg Pro Leu Arg
                20              25                  30

Gln Arg Cys Arg Ser Glu Thr Asp Asp Asn Ala Gln Lys Ala Asn Asp
            35              40                  45

Ile
```

<210> SEQ ID NO 311

```
<211> LENGTH: 50
<212> TYPE: PRT
<213> ORGANISM: Artificial Sequence
<220> FEATURE:
<223> OTHER INFORMATION: Synthetic

<400> SEQUENCE: 311

Met Gly Arg Gly Ser His His His His His Arg Ala Arg Ser Asn Val
1               5                   10                  15

Ile Pro Leu Ser Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
        35                  40                  45

Ala Ile
    50

<210> SEQ ID NO 312
<211> LENGTH: 50
<212> TYPE: PRT
<213> ORGANISM: Artificial Sequence
<220> FEATURE:
<223> OTHER INFORMATION: Synthetic

<400> SEQUENCE: 312

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala Ile
    50

<210> SEQ ID NO 313
<211> LENGTH: 50
<212> TYPE: PRT
<213> ORGANISM: Artificial Sequence
<220> FEATURE:
<223> OTHER INFORMATION: Synthetic

<400> SEQUENCE: 313

Met Gly Arg Gly Ser Tyr His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala Ile
    50

<210> SEQ ID NO 314
<211> LENGTH: 51
<212> TYPE: PRT
<213> ORGANISM: Artificial Sequence
<220> FEATURE:
<223> OTHER INFORMATION: Synthetic

<400> SEQUENCE: 314

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30
```

His Lys Leu Ser Gln Tyr Ser Arg Asp Asn Ala Asn Ala Pro Lys Ala
        35                  40                  45

Ser Ala Ile
    50

<210> SEQ ID NO 315
<211> LENGTH: 50
<212> TYPE: PRT
<213> ORGANISM: Artificial Sequence
<220> FEATURE:
<223> OTHER INFORMATION: Synthetic

<400> SEQUENCE: 315

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asn Ala Asn Ala Pro Lys Ala Thr
        35                  40                  45

Ala Ile
    50

<210> SEQ ID NO 316
<211> LENGTH: 50
<212> TYPE: PRT
<213> ORGANISM: Artificial Sequence
<220> FEATURE:
<223> OTHER INFORMATION: Synthetic

<400> SEQUENCE: 316

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Cys Arg Asn Ala Asn Ala Pro Lys Ala Thr
        35                  40                  45

Ala Ile
    50

<210> SEQ ID NO 317
<211> LENGTH: 50
<212> TYPE: PRT
<213> ORGANISM: Artificial Sequence
<220> FEATURE:
<223> OTHER INFORMATION: Synthetic

<400> SEQUENCE: 317

Met Gly Arg Gly Ser His His His His His Ala Arg Ser Trp Thr
1               5                   10                  15

Ser Met Gln Gly Glu Thr Leu Trp Arg Thr Asp Arg Leu Ala Thr Thr
            20                  25                  30

Lys Thr Ser Met Ser His Pro Pro Asp Ala Asn Ala Pro Lys Ala Ser
        35                  40                  45

Ala Ile
    50

<210> SEQ ID NO 318
<211> LENGTH: 50
<212> TYPE: PRT
<213> ORGANISM: Artificial Sequence
<220> FEATURE:
<223> OTHER INFORMATION: Synthetic

```
<400> SEQUENCE: 318

Met Gly Arg Gly Ser His His His His Leu Ala Arg Ser Trp Thr
1               5                   10                  15

Ser Met Gln Gly Glu Thr Leu Trp Arg Thr Asp Arg Leu Ala Thr Thr
                20                  25                  30

Lys Thr Ser Met Ser His Pro Pro Asp Ala Asn Ala Pro Lys Ala Ser
            35                  40                  45

Ala Ile
    50

<210> SEQ ID NO 319
<211> LENGTH: 51
<212> TYPE: PRT
<213> ORGANISM: Artificial Sequence
<220> FEATURE:
<223> OTHER INFORMATION: Synthetic

<400> SEQUENCE: 319

Met Gly Arg Gly Ser His His His His His Ala Arg Ser Trp
1               5                   10                  15

Thr Ser Met Gln Gly Glu Thr Leu Trp Arg Thr Asp Arg Leu Ala Ala
                20                  25                  30

Thr Lys Thr Ser Met Ser His Pro Pro Asp Ala Asn Ala Pro Lys Ala
            35                  40                  45

Ser Ala Ile
    50

<210> SEQ ID NO 320
<211> LENGTH: 50
<212> TYPE: PRT
<213> ORGANISM: Artificial Sequence
<220> FEATURE:
<223> OTHER INFORMATION: Synthetic

<400> SEQUENCE: 320

Met Gly Arg Gly Ser His His His His His Ala Arg Ser Leu Ser
1               5                   10                  15

Ala Leu Arg Arg Thr Glu Arg Thr Trp Asn Thr Ile His Gln Gly His
                20                  25                  30

His Leu Glu Trp Tyr Pro Pro Asp Ala Asn Ala Pro Lys Ala Ser
            35                  40                  45

Ala Ile
    50

<210> SEQ ID NO 321
<211> LENGTH: 49
<212> TYPE: PRT
<213> ORGANISM: Artificial Sequence
<220> FEATURE:
<223> OTHER INFORMATION: Synthetic

<400> SEQUENCE: 321

Met Gly Arg Gly Ser His His His His His Ala Arg Ser Leu Ser Ala
1               5                   10                  15

Leu Arg Arg Thr Glu Arg Thr Trp Asn Thr Ile His Gln Gly His His
                20                  25                  30

Leu Glu Trp Tyr Pro Pro Ala Asp Ala Asn Ala Pro Lys Ala Ser Ala
            35                  40                  45

Ile
```

-continued

<210> SEQ ID NO 322
<211> LENGTH: 50
<212> TYPE: PRT
<213> ORGANISM: Artificial Sequence
<220> FEATURE:
<223> OTHER INFORMATION: Synthetic

<400> SEQUENCE: 322

Met Gly Arg Gly Ser His His His His His His Ala Arg Ser Cys Leu
1               5                   10                  15

Ala Thr Arg Asn Gly Phe Val Gln Met Asn Thr Asp Arg Gly Thr Tyr
            20                  25                  30

Val Lys Arg Pro Tyr Val Leu Gln Asp Ala Asn Ala Pro Lys Ala Ser
        35                  40                  45

Ala Ile
    50

<210> SEQ ID NO 323
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (37)..(37)
<223> OTHER INFORMATION: Xaa is any amino acid

<400> SEQUENCE: 323

Met Gly Arg Gly Ser His His His His His His Ala Arg Ser Lys Val
1               5                   10                  15

Asn Pro Met Arg Glu Val Arg Cys Asn Ala Arg Cys Ile Arg Lys His
            20                  25                  30

Arg Phe Arg Leu Xaa Ile Arg Asp Asp Ala Asn Ala Pro Lys Ala Ser
        35                  40                  45

Ala Ile
    50

<210> SEQ ID NO 324
<211> LENGTH: 50
<212> TYPE: PRT
<213> ORGANISM: Artificial Sequence
<220> FEATURE:
<223> OTHER INFORMATION: Synthetic

<400> SEQUENCE: 324

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45

Ala Ile
    50

<210> SEQ ID NO 325
<211> LENGTH: 50
<212> TYPE: PRT
<213> ORGANISM: Artificial Sequence
<220> FEATURE:
<223> OTHER INFORMATION: Synthetic

<400> SEQUENCE: 325

Met Gly Arg Gly Ser His His His His His His Ala Arg Ser Met Leu

```
                 1               5                  10                 15
Leu Leu Asn Glu Thr Tyr Arg Arg Tyr Arg Ser Trp Asp Glu Tyr Arg
                20                 25                 30

Asn Asp Ile Gly Ser Asn Leu Asp Asp Ala Asn Ala Pro Lys Ala Ser
         35                 40                 45

Ala Ile
    50

<210> SEQ ID NO 326
<211> LENGTH: 50
<212> TYPE: PRT
<213> ORGANISM: Artificial Sequence
<220> FEATURE:
<223> OTHER INFORMATION: Synthetic

<400> SEQUENCE: 326

Met Gly Arg Gly Ser His His His His His His Ala Arg Ser Gly His
1               5                  10                 15

Arg Glu Ser Asn Arg Val Asn Ser Asn Tyr Ala Asp Gln Leu His Ser
                20                 25                 30

Thr Pro Ile Leu Asn Thr Trp Asn Asp Ala Asn Ala Pro Lys Ala Ser
         35                 40                 45

Ala Ile
    50

<210> SEQ ID NO 327
<211> LENGTH: 50
<212> TYPE: PRT
<213> ORGANISM: Artificial Sequence
<220> FEATURE:
<223> OTHER INFORMATION: Synthetic

<400> SEQUENCE: 327

Met Gly Arg Gly Ser His His His His His His Ala Arg Ser Ser Gly
1               5                  10                 15

Gln Ile Pro Tyr Lys Tyr Gly Asp Ala Ile Pro Ser Met Leu Thr His
                20                 25                 30

Asn Ala Glu Asn Gln Pro His Asp Ala Asn Ala Pro Lys Ala Ser
         35                 40                 45

Ala Ile
    50

<210> SEQ ID NO 328
<211> LENGTH: 50
<212> TYPE: PRT
<213> ORGANISM: Artificial Sequence
<220> FEATURE:
<223> OTHER INFORMATION: Synthetic

<400> SEQUENCE: 328

Met Gly Arg Gly Ser His His His His His His Ala Arg Ser Thr Pro
1               5                  10                 15

Arg Leu Arg Lys Val Tyr Asp Leu Thr Val Thr Thr Thr Ser Ser Gln
                20                 25                 30

Ile Asp Lys Leu Gln Pro Ser Arg Asp Ala Asn Ala Pro Lys Ala Ser
         35                 40                 45

Ala Ile
    50

<210> SEQ ID NO 329
<211> LENGTH: 50
```

```
<212> TYPE: PRT
<213> ORGANISM: Artificial Sequence
<220> FEATURE:
<223> OTHER INFORMATION: Synthetic

<400> SEQUENCE: 329

Met Gly Arg Gly Ser His His His His His Ala Arg Ser Glu Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala Ile
    50

<210> SEQ ID NO 330
<211> LENGTH: 50
<212> TYPE: PRT
<213> ORGANISM: Artificial Sequence
<220> FEATURE:
<223> OTHER INFORMATION: Synthetic

<400> SEQUENCE: 330

Met Gly Arg Gly Ser His His His His His Ala Arg Ser Met Arg
1               5                   10                  15

Pro Ile Leu Val Val Lys Tyr Pro Pro Tyr Leu Gln Thr Leu Asp Asn
            20                  25                  30

Lys Arg Asp Ile Arg Gln Met Asp Asp Ala Asn Ala Pro Lys Ala Ser
        35                  40                  45

Ala Ile
    50

<210> SEQ ID NO 331
<211> LENGTH: 50
<212> TYPE: PRT
<213> ORGANISM: Artificial Sequence
<220> FEATURE:
<223> OTHER INFORMATION: Synthetic

<400> SEQUENCE: 331

Met Gly Arg Gly Ser His His His His His Ala Arg Ser Lys Asn
1               5                   10                  15

Asn Thr Lys His Tyr Thr Val Val Thr Trp Cys Tyr Leu Glu Arg Lys
            20                  25                  30

Asn Gln Asn Leu Thr Ser His Thr Asp Ala Asn Ala Pro Lys Ala Ser
        35                  40                  45

Ala Ile
    50

<210> SEQ ID NO 332
<211> LENGTH: 50
<212> TYPE: PRT
<213> ORGANISM: Artificial Sequence
<220> FEATURE:
<223> OTHER INFORMATION: Synthetic

<400> SEQUENCE: 332

Met Gly Arg Gly Ser His His His His His Ala Arg Ser Ile Leu
1               5                   10                  15

Arg Ser Ala Ser Cys Ser Ala Leu Thr Asp His Lys Arg Val Ala Tyr
            20                  25                  30

Ala Cys Thr His Thr Glu Tyr Lys Asp Ala Asn Ala Pro Lys Ala Ser
```

-continued

```
                35                  40                  45

Ala Ile
    50

<210> SEQ ID NO 333
<211> LENGTH: 50
<212> TYPE: PRT
<213> ORGANISM: Artificial Sequence
<220> FEATURE:
<223> OTHER INFORMATION: Synthetic

<400> SEQUENCE: 333

Met Gly Arg Asp Ser His His His His His Ala Arg Ser Ile Ala
1               5                   10                  15

Asn Met Tyr Gln Leu Trp Ser Met Asn Arg Ser Asp His Asn Leu Val
                20                  25                  30

Ile Lys Lys Gln Met Ser Leu Leu Asp Ala Asn Ala Pro Lys Ala Ser
        35                  40                  45

Ala Ile
    50

<210> SEQ ID NO 334
<211> LENGTH: 50
<212> TYPE: PRT
<213> ORGANISM: Artificial Sequence
<220> FEATURE:
<223> OTHER INFORMATION: Synthetic

<400> SEQUENCE: 334

Met Gly Arg Gly Ser His His His His His Ala Arg Ser Met Leu
1               5                   10                  15

Leu Leu Asn Glu Thr Tyr Arg Arg Tyr Arg Ser Trp Asn Glu Tyr Arg
                20                  25                  30

Asn Asp Ile His Ser Asn Leu Asp Asp Ala Asn Ala Pro Lys Ala Ser
        35                  40                  45

Ala Ile
    50

<210> SEQ ID NO 335
<211> LENGTH: 50
<212> TYPE: PRT
<213> ORGANISM: Artificial Sequence
<220> FEATURE:
<223> OTHER INFORMATION: Synthetic

<400> SEQUENCE: 335

Met Gly Arg Gly Ser His His His His His Thr Arg Ser Glu Glu
1               5                   10                  15

Asn Arg Gln Trp Arg Asn Glu Gly Ser Thr Pro Phe Ser Ser Leu Ile
                20                  25                  30

Ser Asp Met Ser Lys Pro Ile Val Asp Ala Asn Ala Pro Lys Ala Ser
        35                  40                  45

Ala Ile
    50

<210> SEQ ID NO 336
<211> LENGTH: 50
<212> TYPE: PRT
<213> ORGANISM: Artificial Sequence
<220> FEATURE:
<223> OTHER INFORMATION: Synthetic

<400> SEQUENCE: 336
```

```
Met Gly Arg Gly Ser His His His His His Ala Arg Ser Leu Val
1               5                   10                  15

Thr Arg Leu Leu Arg Thr His Arg Glu Glu Lys Val Phe Glu Pro Ser
            20                  25                  30

Pro Thr Gly Pro Ser Glu Lys His Asp Ala Asn Ala Pro Lys Ala Ser
        35                  40                  45

Ala Ile
    50

<210> SEQ ID NO 337
<211> LENGTH: 49
<212> TYPE: PRT
<213> ORGANISM: Artificial Sequence
<220> FEATURE:
<223> OTHER INFORMATION: Synthetic

<400> SEQUENCE: 337

Met Gly Arg Gly Ser His His His His His Ala Arg Ser Asp Met Asp
1               5                   10                  15

Leu Trp Asp Leu Pro Ala Leu Ala Pro Gln Ser Thr Thr Met Gln Met
            20                  25                  30

His Ser Phe Thr His Met Lys Asp Ala Asn Ala Pro Lys Ala Ser Ala
        35                  40                  45

Ile

<210> SEQ ID NO 338
<211> LENGTH: 50
<212> TYPE: PRT
<213> ORGANISM: Artificial Sequence
<220> FEATURE:
<223> OTHER INFORMATION: Synthetic

<400> SEQUENCE: 338

Met Arg Arg Gly Ser His His His His His Ala Arg Ser Arg Arg
1               5                   10                  15

Val Thr Thr Glu Gly Gly Pro Lys Trp Ile Pro Gly His His Met Arg
            20                  25                  30

Asp Asn Ile Pro Glu Ile Ala Asn Asp Ala Asn Ala Pro Lys Ala Ser
        35                  40                  45

Ala Ile
    50

<210> SEQ ID NO 339
<211> LENGTH: 50
<212> TYPE: PRT
<213> ORGANISM: Artificial Sequence
<220> FEATURE:
<223> OTHER INFORMATION: Synthetic

<400> SEQUENCE: 339

Met Gly Arg Gly Ser His His His His His Ala Arg Ser Trp Gly
1               5                   10                  15

Leu Ser Gly Thr Gln Thr Trp Lys Ile Thr Lys Leu Ala Thr Arg Leu
            20                  25                  30

His His Pro Glu Phe Glu Thr Asn Asp Ala Asn Ala Pro Lys Ala Ser
        35                  40                  45

Ala Ile
    50

<210> SEQ ID NO 340
```

<211> LENGTH: 49
<212> TYPE: PRT
<213> ORGANISM: Artificial Sequence
<220> FEATURE:
<223> OTHER INFORMATION: Synthetic

<400> SEQUENCE: 340

Met Gly Arg Gly Ser His His His His His Ala Arg Ser Thr Trp Asn
1               5                   10                  15

Gly Arg Pro Leu His His Leu Asp His Gln Trp Tyr Pro Asp Glu Ala
            20                  25                  30

Arg Leu His Ala Ile His Asn Asp Ala Asn Ala Pro Lys Ala Ser Ala
        35                  40                  45

Ile

<210> SEQ ID NO 341
<211> LENGTH: 50
<212> TYPE: PRT
<213> ORGANISM: Artificial Sequence
<220> FEATURE:
<223> OTHER INFORMATION: Synthetic

<400> SEQUENCE: 341

Met Gly Arg Gly Ser His His His His His Ala Arg Ser Thr Asn
1               5                   10                  15

Arg Gly Val Asn His Thr Gly Gln Met Arg Thr Met Pro Pro Ala Pro
            20                  25                  30

Thr Val Glu Arg Ala Leu Asn Tyr Asp Ala Asn Ala Pro Lys Ala Ser
        35                  40                  45

Ala Ile
    50

<210> SEQ ID NO 342
<211> LENGTH: 45
<212> TYPE: PRT
<213> ORGANISM: Artificial Sequence
<220> FEATURE:
<223> OTHER INFORMATION: Synthetic

<400> SEQUENCE: 342

Thr Gly Arg Gly Ser His His His His His Ala Arg Ser Pro Leu
1               5                   10                  15

Glu Leu Tyr Val Ile Thr Arg Asp Ala Arg Thr Asp Thr Gly Pro Ser
            20                  25                  30

Ser Leu Arg Asp Ala Asn Ala Pro Lys Ala Ser Ala Ile
        35                  40                  45

<210> SEQ ID NO 343
<211> LENGTH: 50
<212> TYPE: PRT
<213> ORGANISM: Artificial Sequence
<220> FEATURE:
<223> OTHER INFORMATION: Synthetic

<400> SEQUENCE: 343

Met Gly Arg Gly Ser His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Pro Arg Leu Ser Ile Asp Asp Ala Asn Ala Pro Lys Ala Ser
        35                  40                  45

Ala Ile

<210> SEQ ID NO 344
<211> LENGTH: 49
<212> TYPE: PRT
<213> ORGANISM: Artificial Sequence
<220> FEATURE:
<223> OTHER INFORMATION: Synthetic

<400> SEQUENCE: 344

Met Gly Arg Gly Ser His His His His His Ala Arg Ser Asn Val Ile
1               5                   10                  15

Pro Leu Asn Glu Val Trp Tyr Asp Thr Gly Trp Asp Arg Pro His Arg
            20                  25                  30

Ser Ser Leu Ser Ile Asp Asp Asp Ala Asn Ala Pro Lys Ala Ser Ala
        35                  40                  45

Ile

<210> SEQ ID NO 345
<211> LENGTH: 50
<212> TYPE: PRT
<213> ORGANISM: Artificial Sequence
<220> FEATURE:
<223> OTHER INFORMATION: Synthetic

<400> SEQUENCE: 345

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala Ile
    50

<210> SEQ ID NO 346
<211> LENGTH: 50
<212> TYPE: PRT
<213> ORGANISM: Artificial Sequence
<220> FEATURE:
<223> OTHER INFORMATION: Synthetic

<400> SEQUENCE: 346

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asn Ala Asn Ala Pro Lys Ala Ser
        35                  40                  45

Ala Ile
    50

<210> SEQ ID NO 347
<211> LENGTH: 49
<212> TYPE: PRT
<213> ORGANISM: Artificial Sequence
<220> FEATURE:
<223> OTHER INFORMATION: Synthetic

<400> SEQUENCE: 347

Met Gly Arg Gly Ser His His His His His Ala Arg Ser Val Gly Thr
1               5                   10                  15

```
Thr Ile Arg Ile Ala Gln Asp Thr Glu His Tyr Arg Asn Val Tyr His
            20                  25                  30

Lys Leu Ser Gln Tyr Ser Arg Asp Ala Asn Ala Pro Lys Ala Ser Ala
            35                  40                  45

Ile

<210> SEQ ID NO 348
<211> LENGTH: 49
<212> TYPE: PRT
<213> ORGANISM: Artificial Sequence
<220> FEATURE:
<223> OTHER INFORMATION: Synthetic

<400> SEQUENCE: 348

Met Gly Arg Gly Ser His His His His Ala Arg Ser Val Gly Thr
1               5                   10                  15

Thr Ile Arg Ile Ala Gln Asp Thr Glu His Tyr Arg Asn Val Tyr His
            20                  25                  30

Lys Leu Ser His Tyr Ser Arg Asp Ala Asn Ala Pro Lys Ala Ser Ala
            35                  40                  45

Ile

<210> SEQ ID NO 349
<211> LENGTH: 50
<212> TYPE: PRT
<213> ORGANISM: Artificial Sequence
<220> FEATURE:
<223> OTHER INFORMATION: Synthetic

<400> SEQUENCE: 349

Met Gly Arg Gly Ser His His His His His Ala Arg Ser Trp Thr
1               5                   10                  15

Ser Met Gln Gly Glu Thr Leu Trp Arg Thr Asp Arg Leu Ala Thr Thr
            20                  25                  30

Lys Thr Ser Met Ser His Pro Pro Asp Ala Asn Ala Pro Lys Ala Ser
            35                  40                  45

Ala Ile
    50

<210> SEQ ID NO 350
<211> LENGTH: 49
<212> TYPE: PRT
<213> ORGANISM: Artificial Sequence
<220> FEATURE:
<223> OTHER INFORMATION: Synthetic

<400> SEQUENCE: 350

Met Gly Arg Gly Ser His His His His Ala Arg Ser Pro Leu Trp
1               5                   10                  15

Tyr His Tyr Asn Cys Trp Asp Thr Ile Cys Leu Ala Asp Trp Leu Lys
            20                  25                  30

Asp Arg Pro His Gly Val Tyr Asp Ala Asn Ala Pro Lys Ala Ser Ala
            35                  40                  45

Ile

<210> SEQ ID NO 351
<211> LENGTH: 50
<212> TYPE: PRT
<213> ORGANISM: Artificial Sequence
<220> FEATURE:
<223> OTHER INFORMATION: Synthetic
```

<400> SEQUENCE: 351

Met Gly Arg Gly Ser His His His His His Ala Arg Ser Leu Ser
1               5                   10                  15

Ala Leu Met Arg Thr Glu Arg Thr Trp Asn Thr Ile His Gln Gly His
            20                  25                  30

His Leu Glu Trp Tyr Pro Pro Ala Asp Ala Asn Ala Pro Lys Ala Ser
        35                  40                  45

Ala Ile
    50

<210> SEQ ID NO 352
<211> LENGTH: 50
<212> TYPE: PRT
<213> ORGANISM: Artificial Sequence
<220> FEATURE:
<223> OTHER INFORMATION: Synthetic

<400> SEQUENCE: 352

Met Gly Arg Gly Ser His His His His His Ala Arg Ser Leu Ser
1               5                   10                  15

Ala Leu Arg Arg Thr Glu Arg Thr Trp Asn Thr Ile His Gln Gly His
            20                  25                  30

His Leu Glu Trp Tyr Pro Pro Ala Asp Ala Asn Ala Pro Lys Ala Ser
        35                  40                  45

Ala Ile
    50

<210> SEQ ID NO 353
<211> LENGTH: 49
<212> TYPE: PRT
<213> ORGANISM: Artificial Sequence
<220> FEATURE:
<223> OTHER INFORMATION: Synthetic

<400> SEQUENCE: 353

Met Gly Arg Gly Ser His His His His Ala Arg Ser Leu Ser Ala
1               5                   10                  15

Leu Arg Arg Thr Glu Arg Thr Trp Asn Thr Ile His Gln Gly His His
            20                  25                  30

Leu Glu Trp Tyr Pro Pro Ala Asp Ala Asn Ala Pro Lys Ala Ser Ala
        35                  40                  45

Ile

<210> SEQ ID NO 354
<211> LENGTH: 49
<212> TYPE: PRT
<213> ORGANISM: Artificial Sequence
<220> FEATURE:
<223> OTHER INFORMATION: Synthetic

<400> SEQUENCE: 354

Met Gly Arg Gly Ser His His His His His Ala Arg Ser Cys Leu
1               5                   10                  15

Ala Thr Arg Asn Gly Phe Val Met Asn Thr Asp Arg Gly Thr Tyr Val
            20                  25                  30

Lys Arg Pro Thr Val Leu Gln Asp Ala Asn Ala Pro Lys Ala Ser Ala
        35                  40                  45

Ile

<210> SEQ ID NO 355

```
<211> LENGTH: 50
<212> TYPE: PRT
<213> ORGANISM: Artificial Sequence
<220> FEATURE:
<223> OTHER INFORMATION: Synthetic

<400> SEQUENCE: 355

Met Gly Arg Gly Ser His His His His His His Ala Arg Ser Cys Leu
1               5                   10                  15

Ala Thr Arg Asn Gly Phe Val Gln Met Asn Thr Asp Arg Gly Thr Tyr
            20                  25                  30

Val Lys Arg Pro Thr Val Leu Gln Asp Ala Asn Ala Pro Lys Ala Ser
        35                  40                  45

Ala Ile
    50

<210> SEQ ID NO 356
<211> LENGTH: 50
<212> TYPE: PRT
<213> ORGANISM: Artificial Sequence
<220> FEATURE:
<223> OTHER INFORMATION: Synthetic

<400> SEQUENCE: 356

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45

Ala Ile
    50

<210> SEQ ID NO 357
<211> LENGTH: 50
<212> TYPE: PRT
<213> ORGANISM: Artificial Sequence
<220> FEATURE:
<223> OTHER INFORMATION: Synthetic

<400> SEQUENCE: 357

Met Gly Arg Gly Ser His His His His His His Ala Arg Ser Ser Phe
1               5                   10                  15

Asn Lys Val Gly Arg Val Asp Ser Glu Phe Gly Thr Lys Ala Asn Ser
            20                  25                  30

His Gln Ile Pro Ser Gly Glu Leu Asp Ala Asn Ala Pro Lys Ala Ser
        35                  40                  45

Ala Ile
    50

<210> SEQ ID NO 358
<211> LENGTH: 50
<212> TYPE: PRT
<213> ORGANISM: Artificial Sequence
<220> FEATURE:
<223> OTHER INFORMATION: Synthetic

<400> SEQUENCE: 358

Met Gly Arg Gly Ser His His His His His His Ala Arg Ser Ile Lys
1               5                   10                  15

Tyr Trp Met Ile Pro Ser Trp Asn Leu Tyr Pro Trp Leu Leu Met Tyr
            20                  25                  30
```

Asp Thr Leu Ile His Pro Thr Met Asp Ala Asn Ala Pro Lys Ala Ser
        35                  40                  45

Ala Ile
    50

<210> SEQ ID NO 359
<211> LENGTH: 50
<212> TYPE: PRT
<213> ORGANISM: Artificial Sequence
<220> FEATURE:
<223> OTHER INFORMATION: Synthetic

<400> SEQUENCE: 359

Met Gly Arg Gly Ser His His His His His Ala Arg Ser Trp Trp
1               5                   10                  15

Thr Arg Met Gln Ile Pro Thr Ser Trp Tyr Trp Tyr Thr Tyr Trp Ile
            20                  25                  30

Asn His Leu Gln Lys His Asp Ile Asp Ala Asn Ala Pro Lys Ala Ser
        35                  40                  45

Ala Ile
    50

<210> SEQ ID NO 360
<211> LENGTH: 50
<212> TYPE: PRT
<213> ORGANISM: Artificial Sequence
<220> FEATURE:
<223> OTHER INFORMATION: Synthetic

<400> SEQUENCE: 360

Met Gly Arg Gly Ser His His His His His Ala Arg Ser Trp Arg
1               5                   10                  15

Trp His Asn Trp Gly Leu Ser Asp Thr Val Ala Ser His Pro Asp Ala
            20                  25                  30

Ser Asn Ser Leu Asn Met Met Tyr Asp Ala Asn Ala Pro Lys Ala Ser
        35                  40                  45

Ala Ile
    50

<210> SEQ ID NO 361
<211> LENGTH: 50
<212> TYPE: PRT
<213> ORGANISM: Artificial Sequence
<220> FEATURE:
<223> OTHER INFORMATION: Synthetic

<400> SEQUENCE: 361

Met Gly Arg Gly Ser His His His His His Asp Ala Arg Ser Ser His
1               5                   10                  15

Trp Ser Asn Ala Asp His Ile Gly Pro Ser Arg Cys Leu Gly Cys Thr
            20                  25                  30

Met Thr Thr Leu Ile Arg Leu Pro Asp Ala Asn Ala Pro Lys Ala Ser
        35                  40                  45

Ala Ile
    50

<210> SEQ ID NO 362
<211> LENGTH: 50
<212> TYPE: PRT
<213> ORGANISM: Artificial Sequence
<220> FEATURE:
<223> OTHER INFORMATION: Synthetic -continued

```
<400> SEQUENCE: 362

Met Gly Arg Gly Ser His His His His His Ala Arg Ser Arg Ser
1               5                   10                  15

Ile Pro Val Arg Ile Gln Gly Asn Pro Gly Asn Ser His Tyr Arg Leu
            20                  25                  30

Met Gly Ala Ser Met Val His Gly Asp Ala Asn Ala Pro Lys Ala Ser
        35                  40                  45

Ala Ile
    50

<210> SEQ ID NO 363
<211> LENGTH: 50
<212> TYPE: PRT
<213> ORGANISM: Artificial Sequence
<220> FEATURE:
<223> OTHER INFORMATION: Synthetic

<400> SEQUENCE: 363

Met Gly Arg Asp Ser His His His His Ala Arg Ser Ile Ala
1               5                   10                  15

Asn Met Tyr Gln Leu Trp Ser Met Asn Arg Ser Asp His Asn Leu Val
            20                  25                  30

Ile Lys Lys Gln Met Ser Leu Leu Asp Ala Asn Ala Pro Lys Ala Ser
        35                  40                  45

Ala Ile
    50

<210> SEQ ID NO 364
<211> LENGTH: 48
<212> TYPE: PRT
<213> ORGANISM: Artificial Sequence
<220> FEATURE:
<223> OTHER INFORMATION: Synthetic

<400> SEQUENCE: 364

Met Gly Arg Ser His His His His His Ala Arg Ser Gly Lys Phe Arg
1               5                   10                  15

His Glu Ile Tyr Asn Met Glu Trp Pro Leu Ala Leu Glu Arg Tyr Trp
            20                  25                  30

Asp Tyr His Gly Glu Pro Asp Ala Asn Ala Pro Lys Ala Ser Ala Ile
        35                  40                  45

<210> SEQ ID NO 365
<211> LENGTH: 50
<212> TYPE: PRT
<213> ORGANISM: Artificial Sequence
<220> FEATURE:
<223> OTHER INFORMATION: Synthetic

<400> SEQUENCE: 365

Met Gly Arg Gly Ser His His His His His Ala Arg Ser Leu Glu
1               5                   10                  15

Thr Thr Thr Thr Ser Leu Met Asn Glu Glu Asp Ala Trp Asn Trp Thr
            20                  25                  30

Ile Glu Lys Ser Arg His Ile Glu Asp Ala Asn Ala Pro Lys Ala Ser
        35                  40                  45

Ala Ile
    50

<210> SEQ ID NO 366
<211> LENGTH: 50
```

```
<212> TYPE: PRT
<213> ORGANISM: Artificial Sequence
<220> FEATURE:
<223> OTHER INFORMATION: Synthetic

<400> SEQUENCE: 366

Met Gly Arg Gly Ser His His His His His Ala Arg Ser Ile Met
1               5                   10                  15

Tyr Met His Trp Gln Trp Ala Val Asn Arg Met Gly His Ala Thr Ala
            20                  25                  30

Met Ser Thr Leu Ala Asn Ala Tyr Asp Ala Asn Ala Pro Lys Ala Ser
        35                  40                  45

Ala Ile
    50

<210> SEQ ID NO 367
<211> LENGTH: 49
<212> TYPE: PRT
<213> ORGANISM: Artificial Sequence
<220> FEATURE:
<223> OTHER INFORMATION: Synthetic

<400> SEQUENCE: 367

Met Gly Arg Gly Ser His His His His His Ala Arg Ser Asn Asp
1               5                   10                  15

Ile Pro Leu Asn Val Trp Tyr Asp Thr Gly Trp Asp Arg Pro His Arg
            20                  25                  30

Ser Arg Leu Thr Ile Asp Asp Asp Ala Asn Ala Pro Lys Ala Ser Ala
        35                  40                  45

Ile

<210> SEQ ID NO 368
<211> LENGTH: 49
<212> TYPE: PRT
<213> ORGANISM: Artificial Sequence
<220> FEATURE:
<223> OTHER INFORMATION: Synthetic

<400> SEQUENCE: 368

Met Gly Arg Gly Ser His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
        35                  40                  45

Ala

<210> SEQ ID NO 369
<211> LENGTH: 49
<212> TYPE: PRT
<213> ORGANISM: Artificial Sequence
<220> FEATURE:
<223> OTHER INFORMATION: Synthetic

<400> SEQUENCE: 369

Met Gly Arg Gly Ser His His His His His Arg Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Asp Ala Asn Ala Pro Lys Ala Ser
        35                  40                  45
```

Ala

<210> SEQ ID NO 370
<211> LENGTH: 49
<212> TYPE: PRT
<213> ORGANISM: Artificial Sequence
<220> FEATURE:
<223> OTHER INFORMATION: Synthetic

<400> SEQUENCE: 370

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala

<210> SEQ ID NO 371
<211> LENGTH: 49
<212> TYPE: PRT
<213> ORGANISM: Artificial Sequence
<220> FEATURE:
<223> OTHER INFORMATION: Synthetic

<400> SEQUENCE: 371

Met Gly Arg Gly Ser His His His His His Thr Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser
        35                  40                  45

Ala

<210> SEQ ID NO 372
<211> LENGTH: 48
<212> TYPE: PRT
<213> ORGANISM: Artificial Sequence
<220> FEATURE:
<223> OTHER INFORMATION: Synthetic

<400> SEQUENCE: 372

Met Gly Arg Gly Ser His His His Gln His Asn Ala Arg Ser Val Ala
1               5                   10                  15

Thr Thr Ile Pro Asp Arg Pro Gly His Gly Thr Leu Pro Glu Arg Leu
            20                  25                  30

Pro Gln Ala Leu Pro Glu Leu Pro Gly Arg Arg Ser Glu Gly Ile Arg
        35                  40                  45

<210> SEQ ID NO 373
<211> LENGTH: 49
<212> TYPE: PRT
<213> ORGANISM: Artificial Sequence
<220> FEATURE:
<223> OTHER INFORMATION: Synthetic

<400> SEQUENCE: 373

Met Gly Arg Gly Ser His His His His His Ala Arg Ser Val Gly
1               5                   10                  15

Thr Thr Ile Arg Ile Ala Gln Asp Thr Glu His Tyr Arg Asn Val Tyr
            20                  25                  30

His Lys Leu Ser Gln Tyr Ser Arg Asp Ala Asn Ala Pro Lys Ala Ser

```
                  35                   40                  45
Ala

<210> SEQ ID NO 374
<211> LENGTH: 49
<212> TYPE: PRT
<213> ORGANISM: Artificial Sequence
<220> FEATURE:
<223> OTHER INFORMATION: Synthetic

<400> SEQUENCE: 374

Met Gly Arg Gly Ser His Tyr His His His Ala Arg Ser Val Gly
1               5                   10                  15

Thr Thr Ile Arg Ile Ala Gln Asp Thr Glu His Tyr Arg Asn Val Tyr
                20                  25                  30

His Lys Leu Ser Gln Tyr Ser Arg Asp Ala Asn Ala Pro Lys Ala Ser
            35                  40                  45

Ala

<210> SEQ ID NO 375
<211> LENGTH: 48
<212> TYPE: PRT
<213> ORGANISM: Artificial Sequence
<220> FEATURE:
<223> OTHER INFORMATION: Synthetic

<400> SEQUENCE: 375

Met Gly Arg Gly Ser His His His His Ala Arg Ser Val Gly Thr
1               5                   10                  15

Thr Ile Arg Ile Ala Gln Asp Thr Glu His Tyr Arg Asn Val Tyr His
                20                  25                  30

Lys Leu Ser Gln Tyr Ser Arg Asp Ala Asn Ala Pro Lys Ala Ser Ala
            35                  40                  45

<210> SEQ ID NO 376
<211> LENGTH: 49
<212> TYPE: PRT
<213> ORGANISM: Artificial Sequence
<220> FEATURE:
<223> OTHER INFORMATION: Synthetic

<400> SEQUENCE: 376

Met Gly Arg Gly Ser His His His His His Ala Arg Ser Trp Thr
1               5                   10                  15

Ser Met Gln Gly Glu Thr Leu Trp Arg Thr Asp Arg Leu Ala Thr Thr
                20                  25                  30

Lys Thr Ser Met Ser His Pro Pro Asp Ala Asn Ala Pro Lys Ala Ser
            35                  40                  45

Ala

<210> SEQ ID NO 377
<211> LENGTH: 49
<212> TYPE: PRT
<213> ORGANISM: Artificial Sequence
<220> FEATURE:
<223> OTHER INFORMATION: Synthetic

<400> SEQUENCE: 377

Met Gly Arg Gly Ser His His His His His Ala Arg Ser Trp Gln
1               5                   10                  15

Pro Glu Val Lys Met Ser Ser Leu Val Asp Thr Ser Gln Thr Val Gly
                20                  25                  30
```

Ala Ala Val Glu Thr Arg Thr Thr Asp Ala Asn Ala Pro Lys Ala Ser
        35                  40                  45

Ala

<210> SEQ ID NO 378
<211> LENGTH: 49
<212> TYPE: PRT
<213> ORGANISM: Artificial Sequence
<220> FEATURE:
<223> OTHER INFORMATION: Synthetic

<400> SEQUENCE: 378

Met Gly Arg Gly Ser His His His His His His Ala Arg Ser Leu Ser
1               5                   10                  15

Ala Leu Arg Arg Thr Glu Arg Thr Trp Asn Thr Ile His Gln Gly His
            20                  25                  30

His Leu Glu Trp Tyr Pro Pro Ala Asp Ala Asn Ala Pro Lys Ala Ser
        35                  40                  45

Ala

<210> SEQ ID NO 379
<211> LENGTH: 49
<212> TYPE: PRT
<213> ORGANISM: Artificial Sequence
<220> FEATURE:
<223> OTHER INFORMATION: Synthetic

<400> SEQUENCE: 379

Met Gly Arg Gly Ser His His His His His His Ala Arg Ser Cys Leu
1               5                   10                  15

Ala Thr Arg Asn Gly Phe Val Gln Met Asn Thr Asp Arg Gly Thr Tyr
            20                  25                  30

Val Lys Arg Pro Thr Val Leu Gln Asp Ala Asn Ala Pro Lys Ala Ser
        35                  40                  45

Ala

<210> SEQ ID NO 380
<211> LENGTH: 49
<212> TYPE: PRT
<213> ORGANISM: Artificial Sequence
<220> FEATURE:
<223> OTHER INFORMATION: Synthetic

<400> SEQUENCE: 380

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45

Ala

<210> SEQ ID NO 381
<211> LENGTH: 49
<212> TYPE: PRT
<213> ORGANISM: Artificial Sequence
<220> FEATURE:
<223> OTHER INFORMATION: Synthetic

<400> SEQUENCE: 381

Met Gly Arg Gly Ser His His His His His His Ala Arg Ser Gln Val

```
                1               5                   10                  15
Thr Trp His His Leu Ala Asp Thr Val Thr Thr Lys Asn Arg Lys Cys
                    20                  25                  30

Thr Asp Ser Tyr Ile Gly Trp Asn Glu Leu Thr Leu Arg Arg His Pro
            35                  40                  45

Leu

<210> SEQ ID NO 382
<211> LENGTH: 49
<212> TYPE: PRT
<213> ORGANISM: Artificial Sequence
<220> FEATURE:
<223> OTHER INFORMATION: Synthetic

<400> SEQUENCE: 382

Met Gly Arg Gly Ser His His His His His Ala Arg Ser Thr Gly
1               5                   10                  15

Gly Pro Thr Gly Thr Ser Ala Ser Ala Gly Pro Thr Ser Ala Thr Arg
                20                  25                  30

Ser Pro Pro Gly Gly Pro Arg Arg Thr Leu Thr Leu Arg Arg His Pro
            35                  40                  45

Leu

<210> SEQ ID NO 383
<211> LENGTH: 43
<212> TYPE: PRT
<213> ORGANISM: Artificial Sequence
<220> FEATURE:
<223> OTHER INFORMATION: Synthetic

<400> SEQUENCE: 383

Met Gly Arg Gly Ser His His His His His Ala Arg Ser Gly Lys
1               5                   10                  15

Val Arg Gly His Thr Lys Glu Thr Pro Pro Thr Glu Phe Gly Leu Ser
                20                  25                  30

Leu Met Asp Ala Asn Ala Pro Lys Ala Ser Ala
            35                  40

<210> SEQ ID NO 384
<211> LENGTH: 49
<212> TYPE: PRT
<213> ORGANISM: Artificial Sequence
<220> FEATURE:
<223> OTHER INFORMATION: Synthetic

<400> SEQUENCE: 384

Met Gly Arg Gly Ser His His His His His Leu Asp Leu Trp Gly
1               5                   10                  15

Pro Pro Ser Gly Ser Pro Arg Thr Arg Ser Thr Thr Gly Thr Ser Thr
                20                  25                  30

Thr Ser Ser Pro Ser Thr Pro Gly Thr Leu Thr Leu Arg Arg His Pro
            35                  40                  45

His

<210> SEQ ID NO 385
<211> LENGTH: 49
<212> TYPE: PRT
<213> ORGANISM: Artificial Sequence
<220> FEATURE:
<223> OTHER INFORMATION: Synthetic

<400> SEQUENCE: 385
```

```
Met Gly Arg Gly Ser His His His His His Ala Arg Ser Pro Thr
1               5                   10                  15

Met Arg Arg His Ile Arg Arg Ala Leu Tyr Pro Tyr Ser Thr Arg Arg
                20                  25                  30

Ser Leu Leu Thr Ser Ala Pro Val Asp Ala Asn Ala Pro Lys Ala Ser
            35                  40                  45

Ala
```

<210> SEQ ID NO 386
<211> LENGTH: 49
<212> TYPE: PRT
<213> ORGANISM: Artificial Sequence
<220> FEATURE:
<223> OTHER INFORMATION: Synthetic

<400> SEQUENCE: 386

```
Met Gly Arg Gly Ser His His His His His Ala Arg Ser Ser Val
1               5                   10                  15

His Trp Ser Tyr Cys Gly Ala Glu Val Lys Lys Asp Trp Tyr Gln His
                20                  25                  30

Thr Ala Trp Thr Lys Asn His Tyr Asp Ala Asn Ala Pro Lys Ala Ser
            35                  40                  45

Ala
```

<210> SEQ ID NO 387
<211> LENGTH: 49
<212> TYPE: PRT
<213> ORGANISM: Artificial Sequence
<220> FEATURE:
<223> OTHER INFORMATION: Synthetic

<400> SEQUENCE: 387

```
Met Gly Arg Gly Ser His His His His His Ala Arg Ser Asn Met
1               5                   10                  15

Asn Thr Arg Arg Met Asp Ile Arg Asn Leu Ile Thr Lys Arg Val Lys
                20                  25                  30

Lys Asp Tyr Ser Pro Gly Ser Lys Asp Ala Asn Ala Pro Lys Ala Ser
            35                  40                  45

Ala
```

<210> SEQ ID NO 388
<211> LENGTH: 49
<212> TYPE: PRT
<213> ORGANISM: Artificial Sequence
<220> FEATURE:
<223> OTHER INFORMATION: Synthetic

<400> SEQUENCE: 388

```
Met Gly Arg Gly Ser His His His His His Ala Arg Ser Val Asp
1               5                   10                  15

Asp Thr Gly His Leu Leu His Thr Gly Arg Leu Met Arg Thr Pro Ser
                20                  25                  30

Thr Asn Ser Trp His Thr Leu Asn Asp Ala Asn Ala Pro Lys Ala Ser
            35                  40                  45

Ala
```

<210> SEQ ID NO 389
<211> LENGTH: 49
<212> TYPE: PRT
<213> ORGANISM: Artificial Sequence
<220> FEATURE:
<223> OTHER INFORMATION: Synthetic

<400> SEQUENCE: 389

Met Gly Arg Gly Ser His His His His His His Ala Arg Ser Ser Leu
1               5                   10                  15

Asn Lys Val Gly Arg Val Asp Ser Glu Phe Gly Thr Lys Ala Asn Ser
            20                  25                  30

His Gln Ile Pro Ser Gly Glu Leu Asp Ala Asn Ala Pro Lys Ala Ser
        35                  40                  45

Ala

<210> SEQ ID NO 390
<211> LENGTH: 49
<212> TYPE: PRT
<213> ORGANISM: Artificial Sequence
<220> FEATURE:
<223> OTHER INFORMATION: Synthetic

<400> SEQUENCE: 390

Met Gly Arg Gly Ser His His His His His His Ala Arg Ser His Ser
1               5                   10                  15

Arg His Glu Trp Thr Ser Thr Pro Arg Arg Arg Ser Thr Gly Pro
            20                  25                  30

Gly Ser Arg Trp Ala Ser Gly Thr Asp Ala Asn Ala Pro Lys Ala Ser
        35                  40                  45

Ala

<210> SEQ ID NO 391
<211> LENGTH: 49
<212> TYPE: PRT
<213> ORGANISM: Artificial Sequence
<220> FEATURE:
<223> OTHER INFORMATION: Synthetic

<400> SEQUENCE: 391

Met Gly Arg Gly Ser His His His His His His Ala Arg Ser Gly Arg
1               5                   10                  15

Tyr His Arg Asp Arg Trp Leu Ala Thr Met Arg Tyr Pro Asp Pro Ser
            20                  25                  30

Gln Val Trp Ser Arg Tyr Val Pro Asp Ala Asn Ala Pro Lys Ala Ser
        35                  40                  45

Ala

<210> SEQ ID NO 392
<211> LENGTH: 49
<212> TYPE: PRT
<213> ORGANISM: Artificial Sequence
<220> FEATURE:
<223> OTHER INFORMATION: Synthetic

<400> SEQUENCE: 392

Met Gly Arg Gly Ser His His His His His His Ala Arg Ser Trp Arg
1               5                   10                  15

Trp His Asn Trp Gly Leu Ser Asp Thr Val Ala Ser His Pro Asp Ala
            20                  25                  30

Ser Asn Ser Leu Asn Met Met Tyr Asp Ala Asn Ala Pro Lys Ala Ser
        35                  40                  45

Ala

```
<210> SEQ ID NO 393
<211> LENGTH: 49
<212> TYPE: PRT
<213> ORGANISM: Artificial Sequence
<220> FEATURE:
<223> OTHER INFORMATION: Synthetic

<400> SEQUENCE: 393

Met Gly Arg Gly Ser His His His His His Ala Arg Ser Pro Leu
1               5                   10                  15

Trp Tyr His Tyr Asn Cys Trp Asp Thr Ile Cys Leu Ala Asp Trp Leu
                20                  25                  30

Lys Asp Arg Pro His Gly Val Tyr Asp Ala Asn Ala Pro Lys Ala Ser
            35                  40                  45

Ala

<210> SEQ ID NO 394
<211> LENGTH: 49
<212> TYPE: PRT
<213> ORGANISM: Artificial Sequence
<220> FEATURE:
<223> OTHER INFORMATION: Synthetic

<400> SEQUENCE: 394

Met Gly Arg Gly Ser His His His His His Ala Arg Ser Asn Val Ile
1               5                   10                  15

Pro Leu Asn Glu Val Trp Tyr Asp Thr Gly Trp Asp Arg Pro His Arg
                20                  25                  30

Ser Arg Leu Ser Ile Asp Asp Asp Ala Asn Ala Pro Lys Ala Ser Ala
            35                  40                  45

Ile

<210> SEQ ID NO 395
<211> LENGTH: 48
<212> TYPE: PRT
<213> ORGANISM: Artificial Sequence
<220> FEATURE:
<223> OTHER INFORMATION: Synthetic

<400> SEQUENCE: 395

Met Gly Leu Leu His His His His Ala Arg Ser Asn Val Ile Pro
1               5                   10                  15

Leu Asn Glu Val Trp Tyr Asp Thr Gly Trp Asp Arg Pro His Arg Ser
                20                  25                  30

Arg Leu Ser Ile Asp Asp Asp Ala Asn Ala Pro Lys Ala Ser Ala Ile
            35                  40                  45

<210> SEQ ID NO 396
<211> LENGTH: 50
<212> TYPE: PRT
<213> ORGANISM: Artificial Sequence
<220> FEATURE:
<223> OTHER INFORMATION: Synthetic

<400> SEQUENCE: 396

Met Gly Arg Ser Ser His His His His His Ala Arg Ser Asn Val
1               5                   10                  15

Ile Pro Leu Asn Glu Val Trp Tyr Asp Thr Gly Trp Asp Arg Pro His
                20                  25                  30

Arg Ser Arg Leu Ser Ile Asp Asp Asp Ala Asn Ala Pro Lys Ala Ser
            35                  40                  45

Ala Ile
```

<210> SEQ ID NO 397
<211> LENGTH: 50
<212> TYPE: PRT
<213> ORGANISM: Artificial Sequence
<220> FEATURE:
<223> OTHER INFORMATION: Synthetic

<400> SEQUENCE: 397

Met Gly Arg Gly Ser His His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
        35                  40                  45

Ala Ile
    50

<210> SEQ ID NO 398
<211> LENGTH: 49
<212> TYPE: PRT
<213> ORGANISM: Artificial Sequence
<220> FEATURE:
<223> OTHER INFORMATION: Synthetic

<400> SEQUENCE: 398

Met Gly Arg Gly Ser His His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
        35                  40                  45

Asn

<210> SEQ ID NO 399
<211> LENGTH: 50
<212> TYPE: PRT
<213> ORGANISM: Artificial Sequence
<220> FEATURE:
<223> OTHER INFORMATION: Synthetic

<400> SEQUENCE: 399

Met Gly Arg Gly Ser His His His His His His Ala Arg Ser Asn Val
1               5                   10                  15

Ile Pro Leu Asn Glu Val Trp Tyr Asp Thr Gly Trp Asp Arg Pro His
            20                  25                  30

Arg Ser Arg Leu Ser Ile Asp Asp Ala Asn Ala Pro Lys Ala Ser
        35                  40                  45

Ala Ile
    50

<210> SEQ ID NO 400
<211> LENGTH: 49
<212> TYPE: PRT
<213> ORGANISM: Artificial Sequence
<220> FEATURE:
<223> OTHER INFORMATION: Synthetic

<400> SEQUENCE: 400

Met Gly Arg Ser His His His His His His Ala Arg Ser Asn Val Ile
1               5                   10                  15

```
Pro Leu Asn Glu Val Trp Tyr Asp Thr Gly Trp Asp Arg Pro His Arg
            20                  25                  30

Ser Arg Leu Ser Ile Asp Asp Ala Asn Ala Pro Lys Ala Ser Ala
            35                  40                  45

Ile

<210> SEQ ID NO 401
<211> LENGTH: 45
<212> TYPE: PRT
<213> ORGANISM: Artificial Sequence
<220> FEATURE:
<223> OTHER INFORMATION: Synthetic

<400> SEQUENCE: 401

Met Gly Arg Ser His His His His His Ala Arg Ser Asn Val Ile
1               5                   10                  15

Pro Leu Asn Glu Val Trp Tyr Asp Thr Gly Trp Asp Arg Pro His Arg
            20                  25                  30

Ser Arg Leu Ser Ile Asp Asp Ala Asn Ala Pro Arg
            35                  40                  45

<210> SEQ ID NO 402
<211> LENGTH: 50
<212> TYPE: PRT
<213> ORGANISM: Artificial Sequence
<220> FEATURE:
<223> OTHER INFORMATION: Synthetic

<400> SEQUENCE: 402

Met Gly Arg Gly Ser His His His His His Ala Arg Ser Val Gly
1               5                   10                  15

Thr Thr Ile Arg Ile Ala Gln Asp Thr Glu His Thr Arg Asn Val Tyr
            20                  25                  30

His Lys Leu Ser Gln Tyr Ser Arg Asp Ala Asn Ala Pro Lys Ala Ser
            35                  40                  45

Ala Ile
    50

<210> SEQ ID NO 403
<211> LENGTH: 44
<212> TYPE: PRT
<213> ORGANISM: Artificial Sequence
<220> FEATURE:
<223> OTHER INFORMATION: Synthetic

<400> SEQUENCE: 403

Met Gly Arg Gly Ser His His His His His Ala Arg Ser Val Gly
1               5                   10                  15

Thr Thr Ile Arg Ile Ala Gln Asp Thr Glu His Thr Arg Asn Val Tyr
            20                  25                  30

His Lys Leu Ser Gln Tyr Ser Arg Asp Ala Asn Ala
            35                  40

<210> SEQ ID NO 404
<211> LENGTH: 50
<212> TYPE: PRT
<213> ORGANISM: Artificial Sequence
<220> FEATURE:
<223> OTHER INFORMATION: Synthetic

<400> SEQUENCE: 404

Met Gly Arg Gly Ser His His His His His Ala Arg Ser Val Gly
1               5                   10                  15
```

```
Thr Thr Ile Arg Ile Ala Gln Asp Thr Glu His Thr Arg Asn Val Tyr
        20                  25                  30

His Lys Leu Ser Gln Tyr Ser Arg Asp Ala Asn Ala Pro Lys Ala Ser
        35                  40                  45

Ala Ile
    50

<210> SEQ ID NO 405
<211> LENGTH: 50
<212> TYPE: PRT
<213> ORGANISM: Artificial Sequence
<220> FEATURE:
<223> OTHER INFORMATION: Synthetic

<400> SEQUENCE: 405

Met Gly Arg Gly Ser His His His His His Ala Arg Ser Trp Thr
1               5                   10                  15

Ser Met Gln Gly Glu Thr Leu Trp Arg Thr Asp Arg Leu Ala Thr Thr
        20                  25                  30

Lys Thr Ser Met Ser His Pro Pro Asp Ala Asn Ala Pro Lys Ala Ser
        35                  40                  45

Ala Ile
    50

<210> SEQ ID NO 406
<211> LENGTH: 50
<212> TYPE: PRT
<213> ORGANISM: Artificial Sequence
<220> FEATURE:
<223> OTHER INFORMATION: Synthetic

<400> SEQUENCE: 406

Met Gly Arg Gly Ser His His His His His Ala Arg Ser Cys Leu
1               5                   10                  15

Ala Thr Arg Asn Gly Phe Glu Gln Met Asn Thr Asp Arg Gly Thr Tyr
        20                  25                  30

Val Lys Arg Thr Thr Val Leu Gln Asp Ala Asn Ala Pro Lys Ala Ser
        35                  40                  45

Ala Ile
    50

<210> SEQ ID NO 407
<211> LENGTH: 50
<212> TYPE: PRT
<213> ORGANISM: Artificial Sequence
<220> FEATURE:
<223> OTHER INFORMATION: Synthetic

<400> SEQUENCE: 407

Met Gly Arg Gly Ser His His His His His Ala Arg Ser Trp Arg
1               5                   10                  15

Asp Thr Arg Lys Leu His Met Arg His Tyr Phe Pro Leu Ala Ile Asp
        20                  25                  30

Ser Tyr Trp Asp His Thr Leu Arg Asp Ala Asn Ala Pro Lys Ala Ser
        35                  40                  45

Ala Ile
    50

<210> SEQ ID NO 408
<211> LENGTH: 50
<212> TYPE: PRT
```

```
<213> ORGANISM: Artificial Sequence
<220> FEATURE:
<223> OTHER INFORMATION: Synthetic

<400> SEQUENCE: 408

Met Gly Arg Gly Ser His His His His His His Ala Arg Ser Ser Pro
1               5                   10                  15

Leu Trp Tyr His Tyr Asn Cys Trp Asp Thr Ile Cys Leu Ala Asp Trp
            20                  25                  30

Leu Lys Asp Arg Pro His Gly Val Asp Ala Asn Ala Pro Lys Ala Ser
        35                  40                  45

Ala Ile
    50

<210> SEQ ID NO 409
<211> LENGTH: 51
<212> TYPE: PRT
<213> ORGANISM: Artificial Sequence
<220> FEATURE:
<223> OTHER INFORMATION: Synthetic

<400> SEQUENCE: 409

Met Gly Arg Gly Ser His His His His His His Ala Arg Ser Pro
1               5                   10                  15

Leu Trp Tyr His Tyr Asn Cys Trp Asp Thr Ile Cys Leu Ala Asp Trp
            20                  25                  30

Leu Lys Asp Arg Pro His Gly Val Tyr Asp Ala Asn Ala Pro Lys Ala
        35                  40                  45

Ser Ala Ile
    50

<210> SEQ ID NO 410
<211> LENGTH: 50
<212> TYPE: PRT
<213> ORGANISM: Artificial Sequence
<220> FEATURE:
<223> OTHER INFORMATION: Synthetic

<400> SEQUENCE: 410

Met Gly Arg Gly Ser His His His His His His Ala Arg Ser Gly Arg
1               5                   10                  15

Tyr His Arg Asp Arg Trp Leu Ala Thr Met Arg Tyr Pro Asp Pro Ser
            20                  25                  30

Gln Val Trp Ser Arg Tyr Val Pro Asp Ala Asn Ala Pro Lys Ala Ser
        35                  40                  45

Ala Ile
    50

<210> SEQ ID NO 411
<211> LENGTH: 50
<212> TYPE: PRT
<213> ORGANISM: Artificial Sequence
<220> FEATURE:
<223> OTHER INFORMATION: Synthetic

<400> SEQUENCE: 411

Met Gly Arg Gly Ser His His His His His His Ala Arg Ser Thr Met
1               5                   10                  15

Asn Thr Asn Arg Met Asp Ile Gln Arg Leu Met Thr Asn His Val Lys
            20                  25                  30

Arg Asp Ser Ser Pro Gly Ser Ile Asp Ala Asn Ala Pro Lys Ala Ser
        35                  40                  45
```

```
Ala Ile
    50

<210> SEQ ID NO 412
<211> LENGTH: 50
<212> TYPE: PRT
<213> ORGANISM: Artificial Sequence
<220> FEATURE:
<223> OTHER INFORMATION: Synthetic

<400> SEQUENCE: 412

Met Gly Arg Gly Ser His His His His His Ala Arg Ser Asn Leu
1               5                   10                  15

Tyr Ile Thr Gly Glu Phe Lys Arg Gln Thr Asp Asn Asn Gly Ser Glu
            20                  25                  30

Leu Arg Arg Met Ser Arg Pro Arg Asp Ala Asn Ala Pro Lys Ala Ser
        35                  40                  45

Ala Ile
    50

<210> SEQ ID NO 413
<211> LENGTH: 50
<212> TYPE: PRT
<213> ORGANISM: Artificial Sequence
<220> FEATURE:
<223> OTHER INFORMATION: Synthetic

<400> SEQUENCE: 413

Met Gly Arg Gly Ser His His His His His Ala Arg Ser Asn Cys
1               5                   10                  15

Leu Ile Ser Leu Thr Ala Glu Glu Lys Ala Leu Asn Arg Met Met Asn
            20                  25                  30

Val Ser Val Pro Arg Val Met Thr Asp Ala Asn Ala Pro Lys Ala Ser
        35                  40                  45

Ala Ile
    50

<210> SEQ ID NO 414
<211> LENGTH: 50
<212> TYPE: PRT
<213> ORGANISM: Artificial Sequence
<220> FEATURE:
<223> OTHER INFORMATION: Synthetic

<400> SEQUENCE: 414

Met Gly Arg Asp Ser His His His His His Ala Arg Ser Ile Ala
1               5                   10                  15

Asn Met Tyr Gln Leu Trp Ser Met Asn Arg Ser Asp His Asn Leu Val
            20                  25                  30

Ile Lys Lys Gln Met Ser Leu Leu Asp Ala Asn Ala Pro Lys Ala Ser
        35                  40                  45

Ala Ile
    50

<210> SEQ ID NO 415
<211> LENGTH: 50
<212> TYPE: PRT
<213> ORGANISM: Artificial Sequence
<220> FEATURE:
<223> OTHER INFORMATION: Synthetic

<400> SEQUENCE: 415
```

-continued

```
Met Gly Arg Gly Ser His His His His His His Ala Arg Ser Leu Ser
1               5                   10                  15

Arg Leu Ala Thr Val Leu Asp Glu Pro Asp Arg Ser Leu Gln Thr Arg
            20                  25                  30

Thr Asn Arg Pro His Arg Met Ile Asp Ala Asn Ala Pro Lys Ala Ser
        35                  40                  45

Ala Ile
    50
```